US012662657B2

(12) United States Patent
Meissner et al.

(10) Patent No.: US 12,662,657 B2
(45) Date of Patent: ***Jun. 23, 2026

(54) UNIVERSAL DONOR STEM CELLS AND RELATED METHODS

(71) Applicant: President and Fellows of Harvard College, Cambridge, MA (US)

(72) Inventors: Torsten B. Meissner, Cambridge, MA (US); Leonardo M.R. Ferreira, Cambridge, MA (US); Jack L. Strominger, Cambridge, MA (US); Chad A. Cowan, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,385

(22) Filed: May 8, 2024

(65) Prior Publication Data

US 2024/0368540 A1 Nov. 7, 2024

Related U.S. Application Data

(60) Continuation of application No. 17/993,674, filed on Nov. 23, 2022, now Pat. No. 12,031,154, which is a continuation of application No. 17/148,556, filed on Jan. 13, 2021, now Pat. No. 11,618,881, which is a division of application No. 15/572,776, filed as application No. PCT/US2016/031551 on May 9, 2016, now Pat. No. 10,968,426.

(60) Provisional application No. 62/158,999, filed on May 8, 2015.

(51) Int. Cl.
| | |
|---|---|
| *C12N 5/0735* | (2010.01) |
| *A61K 39/00* | (2006.01) |
| *C12N 5/074* | (2010.01) |
| *C12N 15/86* | (2006.01) |
| *C12N 15/90* | (2006.01) |

(52) U.S. Cl.
CPC .......... *C12N 5/0606* (2013.01); *A61K 39/001* (2013.01); *C12N 5/0696* (2013.01); *C12N 15/86* (2013.01); *C12N 15/907* (2013.01); *C12N 2310/20* (2017.05); *C12N 2501/50* (2013.01); *C12N 2501/599* (2013.01); *C12N 2501/998* (2013.01); *C12N 2510/00* (2013.01)

(58) Field of Classification Search
CPC .................................................. C12N 5/0606
See application file for complete search history.

(56) References Cited

U.S. PATENT DOCUMENTS

| | | | |
|---|---|---|---|
| 5,272,082 A | 12/1993 | Santoli et al. |
| 5,674,722 A | 10/1997 | Mulligan et al. |
| 6,986,887 B2 | 1/2006 | Lawman et al. |
| 7,413,904 B2 | 8/2008 | Gold et al. |
| 7,452,718 B2 | 11/2008 | Gold et al. |
| 7,674,620 B2 | 3/2010 | Totey et al. |
| 7,875,273 B2 | 1/2011 | Messina et al. |
| 7,951,925 B2 | 5/2011 | Ando et al. |
| 8,013,143 B2 | 9/2011 | Mcswiggen et al. |
| 8,105,831 B2 | 1/2012 | Russell et al. |
| 8,236,771 B2 | 8/2012 | Cicciarelli et al. |
| 8,420,395 B2 | 4/2013 | Calos |
| 8,697,359 B1 | 4/2014 | Zhang |
| 8,771,945 B1 | 7/2014 | Zhang |
| 8,795,965 B2 | 8/2014 | Zhang |
| 8,808,687 B2 | 8/2014 | Humayun et al. |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,927,280 B2 | 1/2015 | Melton et al. |
| 8,932,814 B2 | 1/2015 | Cong et al. |
| 8,945,839 B2 | 2/2015 | Zhang |
| 9,062,289 B2 | 6/2015 | Gold et al. |
| 9,157,062 B2 | 10/2015 | Chen et al. |
| 9,181,527 B2 | 11/2015 | Sentman |

(Continued)

FOREIGN PATENT DOCUMENTS

| | | |
|---|---|---|
| JP | 2016/520308 A | 7/2016 |
| WO | WO-2001/073002 A2 | 10/2001 |

(Continued)

OTHER PUBLICATIONS

Qu et al. (2022, Biomarker Res., vol. 10(20), pp. 1-18) (Year: 2022).*

(Continued)

*Primary Examiner* — Anoop K Singh
*Assistant Examiner* — David A Montanari
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are universal donor stem cells and related methods of their use and production. The universal donor stem cells disclosed herein are useful for overcoming the immune rejection in cell-based transplantation therapies. In certain embodiments, the universal donor stem cells disclosed herein do not express one or more MHC-I and MHC-II human leukocyte antigens. Similarly, in certain embodiments, the universal donor stem cells disclosed herein do not express one or more human leukocyte antigens (e.g., HLA-A, HLA-B and/or HLA-C) corresponding to MHC-I and MHC-II human leukocyte antigens, thereby rendering such cells hypoimmunogenic.

21 Claims, 134 Drawing Sheets

Specification includes a Sequence Listing.

(56) References Cited

U.S. PATENT DOCUMENTS

| | | | |
|---|---|---|---|
| 9,273,283 | B2 | 3/2016 | Sentman |
| 9,597,357 | B2 | 3/2017 | Gregory et al. |
| 9,738,908 | B2 | 8/2017 | Wu et al. |
| 9,822,370 | B2 | 11/2017 | Musunuru et al. |
| 9,885,033 | B2 | 2/2018 | Joung et al. |
| 10,208,319 | B2 | 2/2019 | Musunuru et al. |
| 10,968,426 | B2 | 4/2021 | Meissner et al. |
| 11,203,758 | B2 | 12/2021 | Zhao et al. |
| 11,208,661 | B2 | 12/2021 | Zhao et al. |
| 11,492,591 | B2 | 11/2022 | Meissner et al. |
| 12,031,154 | B2 | 7/2024 | Meissner et al. |
| 12,031,155 | B2 | 7/2024 | Meissner et al. |
| 12,110,500 | B2 | 10/2024 | Meissner et al. |
| 12,180,263 | B2 | 12/2024 | Cowan et al. |
| 12,421,493 | B2 | 9/2025 | Meissner et al. |
| 12,497,590 | B2 | 12/2025 | Meissner et al. |
| 2002/0012660 | A1 | 1/2002 | Colman et al. |
| 2002/0106742 | A1 | 8/2002 | Samson et al. |
| 2002/0188963 | A1 | 12/2002 | Loring |
| 2004/0053836 | A1 | 3/2004 | Mayer-Kuckuk et al. |
| 2005/0048069 | A1 | 3/2005 | Gorczynski et al. |
| 2006/0024819 | A1 | 2/2006 | Finney |
| 2007/0274967 | A1 | 11/2007 | Cao |
| 2007/0283452 | A1 | 12/2007 | Liu et al. |
| 2008/0182328 | A1 | 7/2008 | Snyder et al. |
| 2008/0188000 | A1 | 8/2008 | Reik et al. |
| 2010/0062003 | A1 | 3/2010 | Murphy et al. |
| 2010/0076057 | A1 | 3/2010 | Sontheimer et al. |
| 2010/0093617 | A1 | 4/2010 | Barrangou et al. |
| 2010/0135992 | A1 | 6/2010 | Rother et al. |
| 2010/0227805 | A1 | 9/2010 | Karin et al. |
| 2011/0110897 | A1 | 5/2011 | Schwarz et al. |
| 2011/0262406 | A1 | 10/2011 | Del Campo et al. |
| 2011/0300538 | A1 | 12/2011 | Barrangou et al. |
| 2012/0088676 | A1 | 4/2012 | Weill et al. |
| 2012/0142062 | A1 | 6/2012 | Doyon et al. |
| 2012/0192298 | A1 | 7/2012 | Weinstein et al. |
| 2012/0225927 | A1 | 9/2012 | Sah et al. |
| 2012/0251618 | A1 | 10/2012 | Schrum et al. |
| 2012/0282174 | A1 | 11/2012 | Weissman et al. |
| 2012/0321667 | A1 | 12/2012 | Sentman |
| 2013/0122591 | A1 | 5/2013 | Cost et al. |
| 2013/0156849 | A1 | 6/2013 | de Fougerolles et al. |
| 2013/0177577 | A1 | 7/2013 | Kobayashi et al. |
| 2013/0288251 | A1 | 10/2013 | Horvath et al. |
| 2013/0330778 | A1 | 12/2013 | Zainer et al. |
| 2014/0030240 | A1 | 1/2014 | Gregory et al. |
| 2014/0065667 | A1 | 3/2014 | Guschin et al. |
| 2014/0080216 | A1 | 3/2014 | Cost et al. |
| 2014/0093913 | A1 | 4/2014 | Cost et al. |
| 2014/0106449 | A1 | 4/2014 | June et al. |
| 2014/0120622 | A1 | 5/2014 | Gregory et al. |
| 2014/0134143 | A1 | 5/2014 | Baylink et al. |
| 2014/0134195 | A1 | 5/2014 | Russell |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang et al. |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273230 | A1 | 9/2014 | Chen et al. |
| 2014/0273231 | A1 | 9/2014 | Zhang |
| 2014/0273232 | A1 | 9/2014 | Zhang et al. |
| 2014/0273233 | A1 | 9/2014 | Chen et al. |
| 2014/0273234 | A1 | 9/2014 | Zhang et al. |
| 2014/0287938 | A1 | 9/2014 | Zhang et al. |
| 2014/0295556 | A1 | 10/2014 | Joung et al. |
| 2014/0295557 | A1 | 10/2014 | Joung et al. |
| 2014/0301990 | A1 | 10/2014 | Gregory et al. |
| 2014/0302563 | A1 | 10/2014 | Doudna et al. |
| 2014/0310830 | A1 | 10/2014 | Zhang et al. |
| 2014/0315985 | A1 | 10/2014 | May et al. |
| 2014/0335620 | A1 | 11/2014 | Zhang et al. |
| 2014/0336133 | A1 | 11/2014 | Miller et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0349405 | A1 | 11/2014 | Sontheimer et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357530 | A1 | 12/2014 | Zhang et al. |
| 2014/0377868 | A1 | 12/2014 | Joung et al. |
| 2015/0017136 | A1 | 1/2015 | Galetto et al. |
| 2015/0020223 | A1 | 1/2015 | Zhang et al. |
| 2015/0031132 | A1 | 1/2015 | Church et al. |
| 2015/0031133 | A1 | 1/2015 | Church et al. |
| 2015/0031134 | A1 | 1/2015 | Zhang et al. |
| 2015/0044191 | A1 | 2/2015 | Liu et al. |
| 2015/0044192 | A1 | 2/2015 | Liu et al. |
| 2015/0056225 | A1 | 2/2015 | Russell |
| 2015/0056705 | A1 | 2/2015 | Conway et al. |
| 2015/0071889 | A1 | 3/2015 | Musunuru et al. |
| 2015/0110760 | A1 | 4/2015 | Zhang et al. |
| 2015/0110762 | A1 | 4/2015 | Holmes et al. |
| 2015/0139994 | A1 | 5/2015 | Xu |
| 2015/0152436 | A1 | 6/2015 | Musunuru et al. |
| 2015/0166969 | A1 | 6/2015 | Takeuchi et al. |
| 2015/0176013 | A1 | 6/2015 | Musunuru et al. |
| 2015/0283178 | A1 | 10/2015 | June et al. |
| 2015/0344912 | A1 | 12/2015 | Kim et al. |
| 2016/0009813 | A1 | 1/2016 | Themeli et al. |
| 2016/0024524 | A1 | 1/2016 | Joung et al. |
| 2016/0046724 | A1 | 2/2016 | Brogdon et al. |
| 2016/0068814 | A1 | 3/2016 | Palecek et al. |
| 2016/0143953 | A1 | 5/2016 | Gregory et al. |
| 2016/0168594 | A1 | 6/2016 | Zhang et al. |
| 2016/0185861 | A1 | 6/2016 | Bedoya et al. |
| 2016/0311907 | A1 | 10/2016 | Brogdon et al. |
| 2016/0348073 | A1 | 12/2016 | Meissner et al. |
| 2016/0362472 | A1 | 12/2016 | Bitter et al. |
| 2017/0175128 | A1 | 6/2017 | Welstead et al. |
| 2018/0141992 | A1 | 5/2018 | Cowan et al. |
| 2018/0155717 | A1 | 6/2018 | Valamehr et al. |
| 2018/0249688 | A1 | 9/2018 | Ayares et al. |
| 2018/0362975 | A1 | 12/2018 | Chen et al. |
| 2019/0015487 | A1 | 1/2019 | Bhoumik et al. |
| 2019/0032049 | A1 | 1/2019 | Naldini et al. |
| 2019/0262309 | A1 | 8/2019 | Alici et al. |
| 2019/0376045 | A1 | 12/2019 | Schrepfer et al. |
| 2021/0161971 | A1 | 6/2021 | Nagy et al. |
| 2021/0261916 | A1 | 8/2021 | Meissner et al. |
| 2022/0333119 | A1 | 10/2022 | Musunuru et al. |
| 2023/0303968 | A1 | 9/2023 | Meissner et al. |
| 2023/0303969 | A1 | 9/2023 | Meissner et al. |
| 2023/0323288 | A1 | 10/2023 | Meissner et al. |
| 2024/0141288 | A1 | 5/2024 | Meissner et al. |
| 2024/0368539 | A1 | 11/2024 | Meissner et al. |
| 2025/0333473 | A1 | 10/2025 | Cowan et al. |

FOREIGN PATENT DOCUMENTS

| | | |
|---|---|---|
| WO | WO-2002102997 A2 | 12/2002 |
| WO | WO-2003050247 A2 | 6/2003 |
| WO | WO-2003100018 A2 | 12/2003 |
| WO | WO-2004042346 A2 | 5/2004 |
| WO | WO-2005/113805 A2 | 12/2005 |
| WO | WO-2008/052770 A2 | 5/2008 |
| WO | WO-2008060785 A2 | 5/2008 |
| WO | WO-2008/102274 A2 | 8/2008 |
| WO | WO-2009/019528 A1 | 2/2009 |
| WO | WO-2009124404 A1 | 10/2009 |
| WO | WO-2010/015899 A2 | 2/2010 |
| WO | WO-2010/143917 A2 | 12/2010 |
| WO | WO-2010141801 A2 | 12/2010 |
| WO | WO-2011146862 A1 | 11/2011 |

(56) References Cited

FOREIGN PATENT DOCUMENTS

| | | | |
|---|---|---|---|
| WO | WO-2012/145384 A1 | 10/2012 |
| WO | WO-2013/016446 A2 | 1/2013 |
| WO | 2013/074916 A1 | 5/2013 |
| WO | WO-2013/126794 A1 | 8/2013 |
| WO | WO-2013/158292 A1 | 10/2013 |
| WO | WO-2013/176915 A1 | 11/2013 |
| WO | WO-2013/176916 A1 | 11/2013 |
| WO | WO-2014/065596 A1 | 5/2014 |
| WO | WO-2014/093622 A2 | 6/2014 |
| WO | WO-2014/150624 A1 | 9/2014 |
| WO | WO-2014/151994 A1 | 9/2014 |
| WO | WO-2014/153115 A2 | 9/2014 |
| WO | WO-2014/153470 A2 | 9/2014 |
| WO | WO-2014/165825 A2 | 10/2014 |
| WO | WO-2014165663 A1 | 10/2014 |
| WO | WO-2014/184741 A1 | 11/2014 |
| WO | WO-2014/184744 A1 | 11/2014 |
| WO | WO-2014/191128 A1 | 12/2014 |
| WO | WO-2014/204726 A1 | 12/2014 |
| WO | WO-2015/006498 A2 | 1/2015 |
| WO | WO-2015/057976 A1 | 4/2015 |
| WO | WO-2015/113063 A1 | 7/2015 |
| WO | WO-2015164740 A1 | 10/2015 |
| WO | WO-2016/057821 A2 | 4/2016 |
| WO | WO-2016/057835 A2 | 4/2016 |
| WO | WO-2016/063264 A1 | 4/2016 |
| WO | WO-2016/073955 A2 | 5/2016 |
| WO | WO-2016/112779 A1 | 7/2016 |
| WO | WO-2016/160721 A1 | 10/2016 |
| WO | WO-2016/183041 A2 | 11/2016 |
| WO | WO-2017/079673 A1 | 5/2017 |
| WO | WO-2018/132783 A1 | 7/2018 |

OTHER PUBLICATIONS

Murata et al. (2014, J. Biochem., vol. 155(6), pp. 335-344) (Year: 2014).*

Barclay et al. (2009, Curr. Opin. Immunol., vol. 21(1), pp. 47-52) (Year: 2009).*

Sneddon et al., 2018, Cell Stem Cell, vol. 22(6), pp. 810-823 (Year: 2018).*

Chen et al. (2020, Stem Cell Res. and Therapy, vol. 11(275) pp. 1-13) (Year: 2020).*

Principles of Anatomy and Physiology, 2006, Wiley, 11th Ed., pp. 99-100 and 689-690. (Year: 2006).*

Lorscheider et al. (2021, Ther. Deliv., vol. 12(1), pp. 55-76) (Year: 2021).*

Zugazagoitia et al., 2016, Clin. Therapeutics, vol. 38, pp. 1551-1566 (Year: 2016).*

Non-Final Office Action for U.S. Appl. No. 15/818,710, dated Sep. 29, 2024.

Notice of Allowance for U.S. Appl. No. 17/993,659, dated Oct. 10, 2024.

Alignment—16278645 SEQ 815 vs. Kmiec SEQ ID No. 473 (2021).

Brandl, et al., "Creation of Targeted Genomic Deletions Using TALEN or CRISPR/Cas Nuclease Pairs in One-Cell Mouse Embryos," *FEBS Open Bio.*, 5:26-35, (2015).

Canver, et al. "Characterization of Genomic Deletion Efficiency Mediated by Clustered Regularly Interspaced Palindromic Repeats (CRISPR)/Cas9 Nuclease System in Mammalian Cells," *Journal of Biological Chemistry*, 289(31):21312-21324, (Aug. 2014).

Carroll, "A CRISPR Approach to Gene Targeting," Molecular Therapy 20.9 (2012): 1658-1660.

Chiba et al., "Genome Editing in Human Pluripotent Stem Cells Using Site-Specific Nucleases," *Methods in Molecular Biology*, 1239:267-280, (2015).

Chitra, et al., "Beta-2 Microglobulin as an Immunological Marker to Assess the Progression of Human Immunodeficiency Virus Infected Patients on Highly Active Antiretroviral Therapy," *Clinica Chimica Acta*, 412:1151-1154, (2011).

Cho, et al., "Analysis of off-target effects of CRISPR/Cas-derived RNA-guided endonucleases and nickases," Genome Research (24): 132-141 (2014).

Cho, et al., "Targeted Genome Engineering in Human Cells with RNA-Guided Endonucleases," *Supplementary Information, Nature Biotechnology*, pp. 1-11, (2013).

Cho, et al., "Targeted genome engineering in human cells with the Cas9 RNA-guided endonuclease," Nature Biotechnology, 31:230-232, 2013.

Christian, et al., "Treating DNA Double-Strand Breaks with TAL Effector Nucleases," Genetics 757-761 (2010).

Christianson, et al., "Enhanced human CD4+ T cell engraftment in beta2-microglobulin-deficient NOD-scid mice." Journal of Immunology (Baltimore, Md.: 1950) 158.8 (1997): 3578-3586.

Cong, et al., "Multiplex Genome Engineering Using CRISPR/Cas Systems," Science 339: 819-823 (2013).

Cowan, "Human Cell-Based Models of Primary Adipocyte Disorders," National Institutes of Health Grant No. DK095384 (Funding Start Date Apr. 1, 2012), Abstract.

Cowan, "Integrating Lipid Genotypes and Phenotypes in IPS Derived Hepatocytes/Adipocytes," National Institutes of Health Grant No. HL107440 (Funding Start Date Jul. 5, 2011), Abstract.

Cowan, "Isogenic Human Pluripotent Stem Cell-Based Models of Human Disease Mutations." National Institutes of Health Grant No. DK097768 (Funding Start Date Sep. 25, 2012), Abstract.

Cradick, et al., "CRISPR/Cas9 Systems Targeting B-Globin and CCR5 Genes Have Substantial Off-Target Activity," *Nucleic Acids Research*, pp. 1-9, (2013).

Davis, et al., "Micro-Injection-Mediated Hematopoietic Stem Cell Gene Therapy," *Current Opinion in Molecular Therapeutics*, 2(4):412-419, (2000).

Desphande, et al., "Clustered Regularly Interspaced Short Palindromic Repeats/Cas9 Genetic Engineering: A Novel Therapeutic Approach in Colon Carcinomas," *American Journal of Robotic Surgery*, 1:1-4, (2014).

Ding, et al., "A TALEN genome editing system to generate human stem cell-based disease models," Cell Stem Cell 12(2): 238-251 (2013).

Ding, et al., "Enhanced Efficiency of Human Pluripotent Stem Cell Genome Editing through Replacing TALENs with CRISPRs," Cell Stem Cell 12: 393-394; plus supplemental materials (2013) (published online on Apr. 4, 2013).

DiTomaso, et al., "Immunobiological Characterization of Cancer Stem Cells Isolated from Glioblastoma Patients," *Human Cancer Biology*, 16(3):800-831, (Jan. 26, 2010).

Doudna et al., "The new frontier of genome engineering with CRISPR-Cas9," *Science*, 346(6213):1077, 1258096-1 through 1258096-9, (2014).

Edelstein, et al., "Gene Therapy Clinical Trials Worldwide 1989-2004—An Overview," *The Journal of Gene Medicine*, 6:597-602, (2004).

Extended European Search Report from European Application 14779492.9, dated Nov. 29, 2016.

Extended European Search Report from European Application 14822545.1, dated Oct. 24, 2016.

Final Office Action for U.S. Appl. No. 14/485,288, dated Apr. 26, 2017.

Final Office Action for U.S. Appl. No. 14/485,288, dated Aug. 24, 2015.

Final Office Action for U.S. Appl. No. 14/509,787, dated Mar. 1, 2019.

Final Office Action for U.S. Appl. No. 14/509,787, dated Mar. 22, 2021.

Final Office Action for U.S. Appl. No. 14/509,787, dated May 24, 2018.

Final Office Action for U.S. Appl. No. 14/509,924, dated Feb. 14, 2017.

Final Office Action for U.S. Appl. No. 14/809,787 dated Dec. 2, 2016.

Final Office Action for U.S. Appl. No. 15/083,021, dated Jan. 10, 2019.

Final Office Action for U.S. Appl. No. 15/083,021, dated Mar. 4, 2021.

(56)     References Cited

OTHER PUBLICATIONS

Final Office Action for U.S. Appl. No. 15/524,968, dated Oct. 19, 2023.
Final Office Action for U.S. Appl. No. 15/818,710, dated Apr. 20, 2021.
Final Office Action for U.S. Appl. No. 15/818,710, dated Apr. 22, 2019.
Final Office Action for U.S. Appl. No. 15/818,710, dated Feb. 21, 2023.
Final Office Action for U.S. Appl. No. 15/818,710, dated Mar. 6, 2024.
Final Office Action for U.S. Appl. No. 16/278,645, dated Feb. 4, 2021.
Final Office Action for U.S. Appl. No. 16/908,618, dated Sep. 7, 2022.
Final Office Action for U.S. Appl. No. 17/327,606, dated Dec. 12, 2022.
Final Office Action for U.S. Appl. No. 17/327,620, dated Feb. 3, 2022.
Final Office Action for U.S. Appl. No. 17/327,620, dated Jan. 6, 2023.
Final Office Action for U.S. Appl. No. 17/327,625 dated Mar. 27, 2023.
Final Office Action for U.S. Appl. No. 17/327,625, dated Dec. 24, 2021.
Final Office Action for U.S. Appl. No. 17/525,644, dated Sep. 9, 2023.
Final Office Action for U.S. Appl. No. 17/728,927, dated May 29, 2024.
Gaj, et al., "ZFN, TALEN, and CRISPR/Cas-Based Methods for Genome Engineering," *Trends in Biotechnology*, 31(7):397-405, (2013).
Gargett, et al, "The inducible caspase-9 suicide gene system as a "safety switch" to limit on-target, off-tumor toxicities of chimeric antigen receptor T cells," *Front. Pharmacol.*, 5(235):1-7, (Oct. 28, 2014).
GenBank AY136510.1 Kutlar, et al., "A new hemoglobin, beta chain . . . " Jul. 26, 2002 Kutlar, et al., A New Hemoglobin, Beta Chain Variant 'Hb S-Wake' Confirmed to be on the Same Chromosome with Hemoglobin S Mutation, Detected in an African-American Family: GenBank: AY13651 0.1. Jul. 26, 2002 [Retrieved on Dec. 23, 2015]. Retrieved from the Internet: URL:http://www.ncbi.nlm.nih.gov/nucleotide/23268448.
GenBank M13792.1 Human Adenosine Deaminase (ADA) Gene, Complete cds [online] Oct. 4, 1995 [retrieved Oct. 25, 2014]. Available on the internet: <URL: http://www.ncbi.nlm.nih.gov/nuccore/M13792>. Especially p. 17 n\35125-35147 and nt 35090-35112.
GenBank M137921.1 Human adenosine deaminase . . . p. 17n/35125-35147 and nt 35090-35112.
GenBank: AY136510.1, Kutlar, et al., "A New Hemoglobin, Beta Chain Variant 'Hb S-Wake' Confirmed to be on the Same Chromosome With Hemoglobin S Mutation, Detected in an African-American Family," Retrieved from the internet on Dec. 23, 2015 < http://www.ncbi.nlm.nih.govlnucleotide/23268448?report=genbanl<&log$=nuclalign&blast_rank=2&RID=7NNHZVRH014>.
GenBank: AY692262.1, Rieder, et al., *Homo sapiens* Interleukin 2 Receptor, Gamma (Severe Combined ; Immunodeficiency) (IL2RG) Gene, Complete cds: GenBank: AY692262.1. Jul. 21, 2004 [Retrieved on Mar. 3, 2016]. Retrieved from the Internet: <URL:; http://www.ncbi.nlm.nih.gov/nucleotide/50897 469>; pp. 1-4.
GenBank: EF150856.1, Kutlar, et al., "*Homo sapiens* beta-globin (HBB) gene, HBB-Hb sickle-Monroe allele, exons 1, 2 and partial cds," Retrieved from the internet on Feb. 22, 2016.http://www.ncbi.nlm.nih.gov/nuccore/EF150856>.
Geurts, et al., "Knockout Rats via Embryo Microinjection of Zinc-Finger Nucleases," Science 325:433 (2009).
Goh, "CRISPR—What Can go Wrong and How to Deal with it," *SiTOOLs Biotech Blog*, pp. 1-9, (Apr. 11, 2017).

Gonzalez et al., "An iCRISPR Platform for Rapid, Multiplexable, and Inducible Genome Editing in Human Pluripotent Stem Cells," *Cell Stem Cell*, 15:215-226, (2014).
Graham, et al. "Resources for the Design of CRISPR Gene Editing Experiments." Genome biology 16.1 (2015): 1-21.
Gussow, et al., "The Human Beta 2-Microglobulin Gene. Primary Structure and Definition of the Transcriptional Unit," *Journal of Immunology*, 139(9):3132-3138, (Nov. 1, 1987), GenBank Supplement pp. 1-5.
Han, et al., "Generation of Hypoimmunogenic Human Pluripotent Stem Cells," *Proceedings of the National Academy of Sciences*, 116(21):10441-10446, (2019).
Harrer, et al., "Generation of Stem Cell-Derived Hypoimmunogenic b Cells That Circumvent Immune Detection," Master's Thesis. Degree Program Tissue Engineering and Regenerative Medicine University of Applied Sciences, Vienna. Sep. 2018. Retrieved from the internet <URL: https://static1.squarespace.com/static/559921a3e4b02c1d7480f8f4/t/5c790ded24a69426265feb35/1551437298166/Harrer+Jacqueline_852 _.pdf>.
Hendel, et al., "Quantifying Genome-Editing Outcomes at Endogenous Loci with SMRT Sequencing," Cell Reports 7: 293-305 (2014).
High, et al., "DNA-Cleaving Enzymes Trigger a Repair Process That Can Now be Harnessed to Correct Mutations in the Human Genome in vitro. This Represents Another Step Towards Gene-Correction Strategies for Treating Human Disease," *Nature*, 435:577 & 579, (2005).
Holt, et al., "Human Hematopoietic Stem/Progenitor Cells Modified by Zinc-Finger Nucleases Targeted to CCRG Control HIV-1 in vivo," *Nature Biotechnology*, 28.8:839-847, (2010).
Hruscha, et al., "Efficient CRISPR/Cas9 genome editing with low off-target effects in zebrafish," Development (140):4982-4987 (2013).
Hsu, et al., "Development and Applications of CRISPR-Cas9 for Genome Engineering," *Cell*, 157:1262-1278, (2014).
Hsu, et al., "DNA targeting specificity of RNA-guided Cas9 nucleases." Nature biotechnology 31.9 (2013): 827-832.
Hu, et al., "Generation of Hypoimmunogenic Induced Pluripotent Stem Cells for Allogeneic Cell and Tissue Transplantation," *Transplantation*, 101(5S-3: p. S2, (May 2017).
Hwang, et al., "Efficient Genome Editing in Zebrafish Using a CRISPR-Cas System," *Nature Biotechnology*, 31(3):227-229, (Mar. 2013).
Integrated Breeding Platform (IBP), "Breeding Genetically Modified Animals for Food Production—Symposium Summary," Swedish University of Agriculture Sciences, pp. 1-3, (2014).
International Preliminary Report on Patentability for International Application PCT/US2014/46034, mailed Jan. 21, 2016.
International Search Report for International Application PCT/US2014/033082, dated Nov. 4, 2014.
International Search Report for International Application PCT/US2014/46034, dated Jan. 23, 2015.
International Search Report for International Application PCT/US2015/054747, dated Apr. 29, 2016.
International Search Report for International Application PCT/US2015/054762, dated Mar. 11, 2016.
International Search Report for International Application PCT/US2015/59621, dated Jun. 3, 2016.
International Search Report for International Application PCT/US2016/024554, dated Aug. 25, 2016.
International Search Report from International Application PCT/US2016/031551, dated Nov. 30, 2016.
International Search Report from International Application PCT/US2020/018467, dated Sep. 17, 2020.
Jaiswal, et al., "CD47 is Upregulated on Circulating Hematopoietic Stem Cells and Leukemia Cells to Avoid Phagocytosis," Cell, 138:271-285, (Jul. 24, 2009).
Jiang, et al., "RNA-Guided Editing of Bacterial Genomes Using CRISPR-Cas Systems," *Nature Biotechnology*, 31(3):233-239, (Mar. 2013).
Jinek, et al., "A programmable Dual-RNA-Guided DNA Endonuclease in Adaptive Bacterial Immunity," Science 337: 816-821 (2012).
Jinek, et al., "RNA-Programmed Genome Editing in Human Cells," eLife Research Article, pp. 1-9, (2013).

(56)                    References Cited

OTHER PUBLICATIONS

Johnson-Salbia, et al., "Gene Therapy: Optimising DNA Delivery to the Nucleus," Current Drug Targets 2: 371-399 (2001).

Jun et al., "CRISPR/Cas: a novel way of RNA-guided genome editing," *Hereditas*, 35(11):1265-1273, (2013), English Abstract.

Kariko et al., "Incorporation of Pseudouridine Into mRNA Yields Superior Nonimmunogenic Vector With Increased Translational Capacity and Biological Stability," *Molecular Therapy*, 16(11):1833-1840, (2008).

Khalili et al., "Genome editing strategies: potential tools for eradicating HIV-1/AIDS," *J. Neurovirol*, 21(3):310-321, (2015).

Koller, et al., "Normal Development of Mice Deficient in ß2M, MHC Class I Proteins, and CD8+ T Cells," *Science*, 248:1227-1230, Jun. 8, 1990).

Lagresle-Peyrou, et al., "Human adenylate kinase 2 deficiency causes a profound hematopoietic defect associated with sensorineural deafness," Nat Genet 41(1): 106-111 (2009).

Late Breaking Abstracts: Presented at the American Society of Gene & Cell Therapy's 16th Annual Meeting, May 15-18, 2013, Salt Lake City, Utah (56 pages).

Li, et al., "In vivo genome editing restores hemostasis in a mouse model of hemophilia," Nature 475: 217-221 (2011).

Li, et al., "MAGeCK Enables Robust Identification of Essential Genes From Genome-Scale CRISPR/Cas9 Knockout Screens," *Genome Biology*, 15:1-12, (2014).

Lin, et al., "CRISPR/Cas9 systems have off-target activity with insertions or Deletions Between Target DNA and Guide RNA Sequences," *Nucleic Acids Research*, pp. 1-13, (2014).

Lin, et al., "Enhanced Homology-Directed Human Genome Engineering by Controlled Timing of CRISPR/Cas9 Delivery," *Elife*, DOI:10.7554:1-13, (2014).

Lloyd et al., "Beyond the antigen receptor: editing the genome of T-Cells for cancer adoptive cellular therapies," *Frontiers in Immunology*, 4(221):1-7, (2013).

Lombardo, et al., "Gene Editing in Human Stem Cells Using Zinc Finger Nucleases and Integrase-Defective Lentiviral Vector Delivery," Nature Biotechnology, 25(11):1298-1306, (2007).

Lu, et al., "Generating Hypoimmunogenic Human Embryonic Stem Cells by the Disruption of Beta 2-Microglobulin," *Stem Cell Rev.*, 9(6):806-813, (Aug. 10, 2013).

Luo, et al., "Synthetic DNA delivery systems," Nature Biotechnology 18: 33-37 (2000).

Ma, et al., "Heritable Multiplex Genetic Engineering in Rats Using CRISPR/Cas9," *PLOS One*, 9(3):e89413:pp. 1-8, (2014).

Maier, et al., "Efficient Clinical Scale Gene Modification via Zinc Finger Nuclease-Targeted Disruption of the HIV Co-receptor CCR5," *Human Gene Therapy*, 24:245-258, (Mar. 2013).

Mali, et al., "RNA-Guided Human Genome Engineering via Cas9," Science 339: 823-826 (2013); and Supplemental Material.

Mandal, et al., "Efficient Ablation of Genes in Human Hematopoietic Stem and Effector Cells using CRISPR/Cas9," *Cell Stem Cell*, 15:643-652, (Nov. 6, 2014).

Mandal, et al., "Reprogramming Human Fibroblasts to Pluripotency Using Modified mRNA," *Nature Protocols*, 8(3):568-582, (2013).

Masquelier, et al., "A Novel 24-Base Pair Deletion in the Coding Region of CCR5 in an African Population," *AIDS*, 21(1):111-122, (2007).

Mattapally, et al., "Human Leukocyte Antigen Class I and II Knockout Human Induced Pluripotent Stem Cell-Derived Cells: Universal Donor for Cell Therapy," *Journal of American Heart Association*, 2018(7):1-13, (Nov. 29, 2018).

Meissner, et al., "Genome Editing for Human Gene Therapy," Methods in Enzymology, 256: pp. 273-295, 2014.

Meissner, et al., "The Universal Donor Stem Cell: Removing the Immune Barrier to Transplantation Using CRISPR/Cas9 (TRAN1P. 946)," *The Journal of Immunology*, pp. 1-5, (Dec. 10, 2021).

Merkle et al., "Modeling Human Disease with Pluripotent Stem Cells: from Genome Association to Function," *Cell Stem Cell*, 12:656-668, (2013).

Micklefield, "Backbone Modification of Nucleic Acids: Synthesis, Structure and Therapeutic Applications," Current Medicinal Chemistry, 8:1157-1179, 2001.

Musunuru, "Genetic and Functional Analysis of a Novel Locus Associated with LDL-C and MI," National Institutes of Health Grant No. HL098364, (Funding Start Date May 3, 2010), Abstract.

Musunuru, "Stem Cell Models of Familial Combined Hypolipidemia," National Institutes of Health Grant No. HL118744 (Funding Start Date Feb. 1, 2013), Abstract.

NCBI Accession No. NG012920.1, "*Homo sapiens* Beta-2-microglobulin (B2M), RefSeqGene on Chromosome 15." NCBI, Jul. 8, 2013. Accessed Apr. 24, 2019 (6 pages).

Non-Final Office Action for U.S. Appl. No. 14/485,288, dated Mar. 26, 2015.

Non-Final Office Action for U.S. Appl. No. 14/485,288, dated Sep. 6, 2016.

Non-Final Office Action for U.S. Appl. No. 14/509,787, dated Apr. 11, 2016.

Non-Final Office Action for U.S. Appl. No. 14/509,787, dated Jul. 28, 2020.

Non-Final Office Action for U.S. Appl. No. 14/509,787, dated Oct. 25, 2021.

Non-Final Office Action for U.S. Appl. No. 14/509,924, dated Jul. 29, 2016.

Non-Final Office Action for U.S. Appl. No. 14/509,924, dated Mar. 12, 2018.

Non-Final Office Action for U.S. Appl. No. 15/083,021, dated Apr. 2, 2018.

Non-Final Office Action for U.S. Appl. No. 15/083,021, dated Jun. 2, 2020.

Non-Final Office Action for U.S. Appl. No. 15/524,968, dated Apr. 5, 2023.

Non-Final Office Action for U.S. Appl. No. 15/572,776, dated Apr. 1, 2020.

Non-Final Office Action for U.S. Appl. No. 15/818,710, dated Aug. 3, 2023.

Non-Final Office Action for U.S. Appl. No. 15/818,710, dated Jul. 27, 2020.

Non-Final Office Action for U.S. Appl. No. 15/818,710, dated Jun. 8, 2022.

Non-Final Office Action for U.S. Appl. No. 15/818,710, dated Sep. 13, 2018.

Non-Final Office Action for U.S. Appl. No. 16/278,645, dated Aug. 19, 2021.

Non-Final Office Action for U.S. Appl. No. 16/278,645, dated Jul. 17, 2020.

Non-Final Office Action for U.S. Appl. No. 16/908,618, dated Dec. 17, 2021.

Non-Final Office Action for U.S. Appl. No. 17/148,556, dated Jan. 21, 2022.

Non-Final Office Action for U.S. Appl. No. 17/148,556, dated May 31, 2022.

Non-Final Office Action for U.S. Appl. No. 17/327,606, dated May 27, 2022.

Non-Final Office Action for U.S. Appl. No. 17/327,620, dated Oct. 18, 2021.

Non-Final Office Action for U.S. Appl. No. 17/327,625, dated Sep. 3, 2021.

Non-Final Office Action for U.S. Appl. No. 17/327,625, dated Oct. 5, 2023.

Non-Final Office Action for U.S. Appl. No. 17/497,927, dated Feb. 17, 2022.

Non-Final Office Action for U.S. Appl. No. 17/525,644, dated Apr. 3, 2023.

Non-Final Office Action for U.S. Appl. No. 17/525,644, dated Nov. 25, 2022.

Non-Final Office Action for U.S. Appl. No. 17/728,927, dated Sep. 13, 2023.

Non-Final Office Action for U.S. Appl. No. 17/993,659, dated May 24, 2024.

Non-Final Office Action for U.S. Appl. No. 17/993,667, dated Nov. 24, 2023.

(56)        References Cited

OTHER PUBLICATIONS

Non-Final Office Action for U.S. Appl. No. 17/993,674, dated Nov. 9, 2023.
Non-Final Office Action for U.S. Appl. No. 17/993,680, dated Nov. 24, 2023.
Notice of Allowance for U.S. Appl. No. 14/485,288, dated Jul. 14, 2017).
Notice of Allowance for U.S. Appl. No. 14/509,924, dated Oct. 10, 2018.
Notice of Allowance for U.S. Appl. No. 15/572,776, dated Sep. 16, 2020.
Notice of Allowance for U.S. Appl. No. 17/148,556, dated Oct. 27, 2022.
Notice of Allowance for U.S. Appl. No. 17/497,927, dated Jun. 23, 2022.
Notice of Allowance for U.S. Appl. No. 17/993,667, dated Mar. 20, 2024.
Notice of Allowance for U.S. Appl. No. 17/993,674, dated Mar. 25, 2024.
Notice of Allowance for U.S. Appl. No. 17/993,680, dated Mar. 26, 2024.
Palu, et al., "In pursuit of new developments for gene therapy of human diseases," Journal of Biotechnology 68:1-13 (1999).
Papapetrou, et al., "Genomic Safe Harbors Permit High β-Globin Transgene Expression in Thalassemia Induced Pluripotent Stem Cells," *Nature Biotechnology*, 29(1):73-81, (Jan. 2011).
Pavel-Dinu, et al. "Gene correction for SCID-X1 in long-term hematopoietic stem cells." Nature communications 10.1 (2019): 1634.
Pelletier et al., "Mouse Genome Engineering via CRISPR-Cas9 for Study of Immune Function," *Cell Press*, 42:18-27, (2015).
Pfeifer, et al., "Gene Therapy: Promises and Problems," Annu. Rev. Genomics Hum. Genet. 2: 177-211 (2001).
Porteus, et al., "Gene targeting using zinc finger nucleases," Nature Biotechnology 23(8): 967-973 (2005).
Ramalingam, et al., "A CRISPR Way to Engineer the Human Genome," *Genome Biology*, 14(107):1-4, (2013).
Ramirez, et al., "Unexpected failure rates for modular assembly of engineered zinc fingers," Nature Methods 5(5): 374-375 (2008).
Ran, et al., "Double Nicking by RNA-Guided CRISPR Cas9 for Enhanced Genome Editing Specificity," Cell 154: 1380-1389 (2013).
Randau, "RNA processing in the minimal organism Nanoarchaeum equitans," Genome Biol 13.7 : 6 (2012).
Rebmann, et al., "HLA-G as a Tolerogenic Molecule in Transplantation and Pregnancy," *Journal of Immunology Research*, 2014:1-16, (2014).
Ren, et al., "Multiplex Genome Editing to Generate Universal CAR T Cells Resistant to PD1 Inhibition," *Clin. Cancer Res.*, 23(9):2255-2266, (May 1, 2017).
Rieder, et al., *Homo sapiens* Interleukin 2 Receptor, Gamma (Severe Combined Immunodeficiency) (IL2RG) Gene, Complete cds: GenBank: AY692262.1. Jul. 21, 2004 [Retrieved on Mar. 3, 2016]. Retrieved from the Internet: <URL: http://www.ncbi.nlm.nih.gov/nucleotide/ 50897 469>; pp. 1-4.
Riolobos, et al., "HLA Engineering of Human Pluripotent Stem Cells," *Molecular Therapy*, 21(6):1232-1241, (Jun. 2013).
Romieu-Mourez, et al., "Regulation of MHC Class II Expression and Antigen Processing in Murine and Human Mesenchymal Stromal Cells by IFN-gamma, TGF-beta, and Cell Density," *The Journal of Immunology*, 179:1549-1558, (2007).
Rong, et al., "An Effective Approach to Prevent Immune Rejection of Human ESC-Derived Allograts," *Cell Stem Cell*, 14(1):121-130, (Jan. 2, 2014).
Sadelain, et al., "Safe Harbours for the Integration of new DNA in the Human Genome," *Nature Reviews Cancer*, 12:51-58, (2012).
Schwank, et al., "Functional Repair of CFTR by CRISPR/Cas9 in Intestinal Stem Cell Organoids of Cystic Fibrosis Patients," Cell Stem Cell 13: 653-658 (2013).

Sequence alignment between NCBI accession No. NG-012920.2 and SEQ ID No. 1, pp. 1-3. (Year: 2018). Retrieved Mar. 31, 2023, from GenCore version 6.4.2. (5 pages).
Shalem, et al., "Genome-scale CRISPR-Cas9 knockout screening in human cells," *Science* 343, 84-87 (2014).
Shen, et al., "Generation of Gene-Modified Mice via Cas9/RNA-Mediated Gene Targeting," *Cell Research*, 23:720-723, (2013).
Shoji, et al., "Current Status of Delivery Systems to Improve Target Efficacy of Oligonucleotides," Current Pharmaceutical Design 10: 785-796 (2004).
Simon, et al., "Recent advances in synthetic biosafety [version 1; peer review: 2 approved]," *F1000Research*, 5(F1000 Faculty Rev):2118:1-8 (Aug. 31, 2016).
Skardal, "Bioprinting Essentials of Cell and Protein Viability," Essentials of 3D Biofabrication and Translation, Chapter 1, 17 pages, 2015.
Smithies, et al., "Insertion of DNA Sequences Into the Human Chromosomal β-Globin Locus by Homologous Recombination," Nature, 317(19):230-234, (Sep. 1985).
STIC Alignment 16278645 SEQ 814 vs WO2001/73002 SEQ485 and 465 (2020).
STIC Alignment 16278645 SEQ814 vs WO2001/73002 SEQ481 (2020).
Talkowski, et al., "Next-Generation Sequencing Strategies Enable Routine Detection of Balanced Chromosome Rearrangements for Clinical Diagnostics and Genetic Research," The American Journal of Human Genetics (88): 469-481 (2011).
Tasher, et al., "The Genetic Basis of Severe Combined Immunodeficiency and its Variants," The Application of Clinical Genetics 5: 67-80 (2012).
Tebas, et al., "Gene Editing of CCR5 in Autologous CD4 T Cells of Persons Infection with HIV," *The New England Journal of Medicine*, 370(10):901-910, (Mar. 6, 2014).
Tena, et al., "Transgenic Expression of Human CD47 Markedly Increases Engraftment in a Murine Model of Pig-to-Human Hematopoietic Cell Transplantation," American Journal of Transplantation, 14:2713-2722, (2014).
Third Party Observation for PCT Application PCT/US2014/033082, made/submitted Aug. 3, 2015.
Third Party Submission Under 37 CFR 1.290 for U.S. Appl. No. 14/485,288, made/submitted Jul. 14, 2015.
Timmermans, et al. "Generation of T Cells from Human Embryonic Stem Cell-Derived Hematopoietic Zones," *J. Immunology*, 182:6879-6888, (2009).
Toriaki, et al., "A Foundation for Universal T-Cell Based Immunotherapy: T Cells Engineered to Express a CD19-Specific Chimeric-Antigen-Receptor and Eliminate Expression of Endogenous TCR," *Blood*, 119(24):5697-5705, (Jun. 14, 2012).
Van den Berg, et al., "Innate Immune "Self" Recognition: A Role for CD47-SIRPalpha Interactions in Hematopoietic Stem Cell Transplantation," *Trends in Immunology*, 29(5):203-206, (Apr. 3, 2008).
Van Lith, et al., "HLA-DP, HLA-DQ, and HLA-DR Have Different Requirements for Invariant Chain and HLA-DM," J. Biol. Chem., 285(52): 40800-40808, 2010.
Verma, et al., "Modified Oligonucleotides: Synthesis and Strategy for Users," Annu. Rev. Biochem., 67:99-134, 1998.
Wang et al., "One-Step Generation of Mice Carrying Mutations in Multiple Genes by CRISPR/Cas-Mediated Genome Engineering," *Cell*, 153:910-918, (2013).
Wang, et al., "Genetic screens in human cells using the CRISPR-Cas9 system," *Science* 343, 80-84 (2014).
Wiginton, et al., "Complete Sequence and Structure of the Gene for Human Adenosine Deaminase," Biochemistry 25(25): 8234-8244. Abstract (1986).
Wilen, et al., "Engineering HIV-Resistant Human CD4+ T Cells With CXCR4-Specific Zinc-Finger Nucleases," *PLoS Pathogens*, 7(4):1-15, (Apr. 2011).
Woodbine, et al., PRKDC Mutations in a SCID Patient with Profound Neurological Abnormalities. The Journal of Clinical Investigation 123(7): 2969-2980. (2013).
Wu et al., "Target specificity of the CRISPR-Cas9 system," *Quantitative Biology*, 2(2):59-70, (2014).

(56)        References Cited

OTHER PUBLICATIONS

Xie et al., "Seamless gene correction of β-thalassemia mutations in patient-specific iPSCs using CRISPR/Cas9 and piggyBac," *Genome Research*, 24:1526-1533, (2014).
Zetsche, et al., "Cpf1 is a single RNA-guided endonuclease of a class 2 CRISPR-Cas system." Cell 163.3 (2015): 759-771.
Zhang et al., "CRISPR/Cas9 for genome editing: progress, implications and challenges," *HMG Advance Access*, Published Mar. 20, 2014 pp. 1-21.
Abraches, et al., "Neural Differentiation of Embryonic Stem Cells In Vitro: A Road Map to Neurogenesis in the Embryo," PLoS ONE 4(7), 2009.
Apostolou, et al., "Stem cells: IPS cells under attack," Nature, vol. 474, pp. 165-166 (2011).
Asgari, et at, "Differentiation and Transplantation of Human Induced Pluripotent Stem Cell-derived Hepatocyte-like Cells," Stem Cell Rev and Rep, DOI 10.1007/s12015-011-9330-y, 2011.
Atkins et al., "Endothelial Differentiation," Arteriosclerosis, Thrombosis, and Vascular Biology, 31(7), 1476-1484, 2011.
Barclay, et al., "The Interaction Between Signal Regulatory Protein Alpha and CD47: and Structure, Function, and Therapeutic Target," Annual Review of Immunology, vol. 32, No. 1, pp. 25-50, Mar. 2014.
Bjorklund, et al., "Embryonic stem cells develop into functional dopaminergic neurons after transplantation in a Parkinson rat model," PNAS, 99(4), 2344-2349, 2002.
Buchholz, et al., "Rapid and Efficient Directed Differentiation of Human Pluripotent Stem Cells Into Retinal Pigmented Epithelium," Stem Cells Trans Med, 2(5): 384-393, (2013).
Burridge, et al., "A Universal System for Highly Efficient Cardiac Differentiation of Human Induced Pluripotent Stem Cells That Eliminates Interline Variability," PLoS One, vol. 6, Issue 4, (2011).
Burridge, et al., "Production of De Novo Cardiomyocytes: Human Pluripotent Stem Cell Differentiation and Direct Reprogramming," Cell Stem Cell, 10:16-28, 2012.
Cannon, et al., "CCR5 Knockout Strategies," Curr. Opin. HIV AIDS; 6(1):74-79, 2011.
Chao, et al., "The CD47-SIRPa Pathway in Cancer Immune Evasion and Potential Therapeutic Implications," NIH Public Access Author Manuscript, pp. 1-13, 2012.
Chen, et al., "Development of a scalable suspension culture for cardiac differentiation from human pluripotent stem cells," Stem Cell Res, 15(2):365-375, 2015.
Chen, et al., "Functional disruption of human leukocyte antigen II in human embryonic stem cell," Biol Res., 48:59, 2015.
Cho, et al., "Highly efficient and large-scale generation of functional dopamine neurons from human embryonic stem cells," PNAS, 105:3392-3397, 2008.
Chong et al., "Human Embryonic Stem Cell-Derived Cardiomyocytes Regenerate Non-Human Primate Hearts," Nature, 510(7504):273-7, 2014.
Cowan, et. al., "Derivation of Embryonic Stem-Cell Lines from Human Blastocysts," New England J. Med., 350:13, 2004.
Di Stasi, et al., "Inducible Apoptosis as a Safety Switch for Adoptive Cell Therapy," The New England Journal of Medicine, 365:1673-83 (2011).
Diecke, et al., "Novel codon-optimized mini-intronic plasmid for efficient, inexpensive, and xeno-free induction of Pluripotency," Sci Rep. 5:8081, 2015.
Final Office Action for U.S. Appl. No. 17/728,927, dated May 23, 2025.
Focosi et al., "Effect of Induced Pluripotent Stem Cell Technology in Blood Banking," Stem Cells Translational Medicine, 5:269-274, 2016.
Food and Drug Administration, Guidance for Industry, "Eligibility Determination for Donors of Human Cells, Tissues, and Cellular and Tissue-Based Products (HCT/Ps)," Aug. 2007.
Hosoya et al., "Preparation of pancreatic beta-cells from human iPS cells with small molecules," Islets, 4:3, pp. 249-252, eo12, 2012.

Huang, et al., "Differentiation of human embryonic stem cells into smooth muscle cells in adherent monolayer culture," Biochem Biophys Res Commun 351(2)321-7, 2006.
Huangfu, et al., "Induction of pluripotent stem cells by defined factors is greatly improved by small molecule compounds," Nature Biotechnol, 26 (7): 795-797, 2008.
Idelson, et al., "Directed Differentiation of Human Embryonic Stem Cells into Functional Retinal Pigment Epithelium Cells," Cell Stem Cell, 5(4): 396-408 (2009).
IPSC transplantation clinical trials; World Wide Web at clinicaltrials. gov/ct2/results?cond=transplantation&term=iPSC&cntry=&state= &city=&dist=; Last update 2021.
Kamao, et al., "Characterization of Human Induced Pluripotent Stem Cell-Derived Retinal Pigment Epithelium Cell Sheets Aiming for Clinical Application," Stem Cell Reports 2:205-18, 2014.
Kattman, et al., "Stage-Specific Optimization of Activin/Nodal and BMP Signaling Promotes Cardiac Differentiation of Mouse and Human Pluripotent Stem Cell Lines," Cell Stem Cell 8:228-240, 2011.
Kawamura et al., "Cardiomyocytes Derived from MHC-Homozygous Induced Pluripotent Stem Cells Exhibit Reduced Allogeneic Immunogenicity in MHC-Matched Non-human Primates," Stem Cell Reports 6(3): 312-320, 2016.
Kim, et al., "Association of CD47 with Natural Killer Cell-Mediated Cytotoxicity of Head-and-Neck Squamous Cell Carcinoma Lines," Tumor Biology, vol. 29, pp. 28-34, 2008.
Kim, et al., "Dopamine neurons derived from embryonic stem cells function in an animal model of Parkinson's disease," Nature, 418, 50-56 (2002).
Kurmann, et al., "Regeneration of thyroid function by transplantation of differentiated pluripotent stem cells," 17(5): 527-542, 2015.
Lakshmipathy, et al., "Pluripotent Stem Cells Methods and Protocols," Spring Protocols, Humana Press (2013).
Lamba, et al., "Efficient generation of retinal progenitor cells from human embryonic stem cells," PNAS, 2006, 103(34):12769-12774.
Lee et al., "Evaluation of 28 Human Embryonic Stem Cell Lines for Use as Unrelated Donors in Stem Cell Therapy: Implications of HLA and ABO Genotypes," Cell Transplantation, vol. 19, pp. 1383-1395, 2010.
Lee, et al., "Down-regulation of MHC class I expression in human neuronal stem cells using viral stealth mechanism," Biochemical and biophysical research communications 326,4: 825-835, 2005.
Li, et al., "Cardiomyocyte Transplantation Improves Heart Function," Ann. Thorac. Surg. 62:654-61, (1996).
Li, et al., "How far are stem-cell-derived erythrocytes from the clinical arena?", BioScience, vol. 63(8), pp. 632-643, Aug. 2013.
Liu, et al., "Efficient Differentiation of Mouse Embryonic Stem Cells into Insulin-Producing Cells," Exp. Diabetes Res, vol. 2012, Article ID 201295, 2012.
Lowry, et al., "Generation of human induced pluripotent stem cells from dermal fibroblasts," PNAS, 105:2883-2888, 2008.
Mallon, et al., "Comparison of the molecular profiles of human embryonic and induces pluripotent stem cells of isogenic origin," Stem Cell Research, 12:376-386, 2014.
Maruyama, Y., "Session I Considerations for Screening/ Transferring Cells for Further Manufacturing," Pharmaceuticals and Medical Devices Agency, 2016.
Mohit, et al., "Biological delivery approaches for gene therapy: Strategies to potentiate efficacy and enhance specificity," Molecular immunology, 56(4), 599-611, 2013.
Molne, et al., "Blood Group ABO Antigen Expression in Human Embryonic Stem Cells and in Differentiated Hepatocyte- and Cardiomyocyte-Like Cells," Transplantation, 86(10):1407-13, 2008.
Nakagawa, et al., "Generation of induced pluripotent stem cells without Myc from mouse and human fibroblasts," Nature Biotechnology, 26:101-106, 2008.
Non-Final Office Action for U.S. Appl. No. 17/540,968, dated Apr. 24, 2025.
Pagliuca, et al., "Generation of Functional Human Pancreatic Beta Cells In Vitro," Cell, 159, 428-439, 2014.
Prasain, et al., "Differentiation of human pluripotent stem cells to cells similar to cord-blood endothelial colony-forming cells," Nat. Biotechnol., 32(11): 1151-1157, 2014.

(56) References Cited

OTHER PUBLICATIONS

Regateiro, et al., "TGF-Beta in transplantation tolerance," Current Opinion in Immunology, 23: 660-669, 2011.

Reijo, et al., "Gene expression profiles of human inner cell mass cells and embryonic stem cells," Differentiation, vol. 78, pp. 18-23, 2009.

Reubinoff, et al., "Embryonic stem cell lines from human bastocysts: somatic differentiation in vitro," Nature Biotechnology, vol. 18, pp. 399-404, Apr. 2000.

Rowland, et al., "Pluripotent Human Stem Cells for the Treatment of Retinal Disease," Journal of Cellular Physiology, 227(2):457-466 (2012).

Ryan, et al., "POU domain family values: flexibility, partnerships, and developmental codes," Genes & Dev. 11:1207-1225, 1997.

Sakai, et al., "Autologous Heart Cell Transplantation Improves Cardiac Function After Myocardial Injury," Ann. Thorac. Surg. 8:2074-81, (1999).

Sakai, et al., "Fetal Cell Transplantation: A Comparison of Three Cell Types," The Journal of Thoracic and Cardiovascular Surgery, 118:715-725, 1999.

Seki, et al., "Methods of induced pluripotent stem cells for clinical application," World J. Stem Cells, 7(1):116-125, 2015.

Sharma, et al., "Derivation of Highly Purified Cardiomyocytes from Human Induced Pluripotent Stem Cells Using Small Molecule-modulated Differentiation and Subsequent Glucose Starvation," Journal of Visualized Experiments, 2015.

Shiba, et al., "hESC-Derived Cardiomyocytes Electrically Couple and Suppress Arrhythmias in Injured Hearts," Nature, 189 (7415):322-5, 2012.

Shiina, et al., "The HLA genomic loci map: expression, interaction, diversity and disease," Journal of Human Genetics, 54:15-39 (2009).

Singh, et al., "Redirecting Specificity of T-Cell Populations for CD19 Using the Sleeping Beauty System," Cancer Res., 68(8), 2008.

Si-Tayeb, et al., "Highly Efficient Generation of Human Hepatocyte-Like Cells from Induced Pluripotent Stem Cells," Hepatology 51:297-305, 2010.

Snykers, et al., "Hepatic Differentiation of Mesenchymal Stem Cells: In Vitro Strategies," Methods in Molecular Biology, 698:305-314, 2011.

Takahashi, et al., "Induction of Pluripotent Stem Cells from Mouse Embryonic and Adult Fibroblast Cultures by Defined Factors," Cell, 126:663-676, 2006.

Taylor, et al., "Immunological considerations for embryonic and induced pluripotent stem cell banking," Phil. Trans. R. Soc. B, 366, 2312-2322, 2011.

Teraoka, et al., "Expression of recipient CD47 on rat insulinoma cell xenografts prevents macrophage-mediated rejection through SIRPa inhibitory signaling in mice," PloS one, 8(3), e58359, 2013.

Tey, et al., "Inducible Caspase 9 Suicide Gene to Improve the Safety of Allodepleted T Cells after Haploidentical Stem Cell Transplantation," Biology of Blood and Marrow Transplantation, 13:913-924, (2007).

Themeli, et al., "Generation of tumor-targeted human T lymphocytes from induced pluripotent stem cells for cancer therapy," Nature Biotechnology, vol. 31, No. 10, 2013.

Thomson, et al., "Embryonic stem cell lines derived from human blastocysts," Science, 282, 1145, 1998.

Ueda, et al., "Pluripotent stem cells as a source for T cell research and clinical application," Jpn. J. Clin. Immunol., 38(2) 101-108, 2015.

Vegas, et al., "Long term Glycemic Control Using Polymer Encapsulated, Human Stem-Cell Derived beta-cells in Immune Competent mice," Nat. Med. 22(3): 306-311, 2016.

Wang, et al., "Targeted Disruption of the Beta2-Microglobulin Gene Minimizes the Immunogenicity of Human Embryonic Stem Cells," Stem Cells Translational Medicine, 4:1234-1245, 2015.

Watanabe, et al., "Cardiomyocyte Transplantation in a Porcine Myocardia Infarcion Model," Cell Transplantation, 7:239, 1998.

Woltjen, et al., "piggyBac transposition reprograms fibroblasts to induced pluripotent stem cells," Nature, 458 (7239): 766-770, 2009.

Wrana, J., "TGF-Beta Receptors and Signalling Mechanisms," Miner. Electrolyte Metab., 24, 120-130, 1998.

Wu, et al., "Development of an inducible caspase-9 safety switch for pluripotent stem cell-based therapies," Molecular Therapy—Methods & Clinical Development, 1, 14053, 2014.

Xu, et al., "Cardiac Bodies: A Novel Culture Method for Enrichment of Cardiomyocytes Derived from Human Embryonic Stem Cells," Stem Cells and Development, 15: 631-9, 2006.

Zhou, et al., "Adenoviral Gene Delivery Can Reprogram Human Fibroblasts to Induced Pluripotent Stem Cells," Stem Cells, 27 (11): 2667-74, 2009.

Zhou, et al., "Generation of Induced Pluripotent Stem Cells Using Recombinant Proteins," Cell Stem Cell 8:381-384, 2009.

Rebres, et al., "Membrane Raft Association of CD47 Is Necessary for Actin Polymerization and Protein Kinase C 0 Translocation in Its Synergistic Activation of T Cells," The Journal of Biological Chemistry, 276(10):7672-7680, 2001.

Ticchioni, et al., "Integrin-associated protein (CD47/IAP) contributes to T cell arrest on inflammatory vascular endothelium under flow," The FASEB Journal, vol. 15, 2001.

Drozina, et al., "Expression of MHC II Genes," CTMI, 290:147-170, 2005.

Nishimura, et al., "Generation of Rejuvenated Antigen-Specific T Cells by Reprogramming to Pluripotency and Redifferentiation," Cell Stem Cell, 12, 114-126, 2013.

Zschoke, J., "Dominant versus recessive: Molecular mechanisms in metabolic disease," J. Internit. Metab. Dis., 31:599-618, 2008.

Non-Final Office Action for U.S. Appl. No. 18/658,343, dated Jan. 29, 2025.

Non-Final Office Action for U.S. Appl. No. 17/728,927, dated Dec. 30, 2024.

Aussel, et al., "The hidden risks of CRISPR/Cas: structural variations and genome integrity," Nature Communications, 16:7208, 2025.

Barclay, et al., "The SIRP family of receptors and immune regulation," Nature Reviews, vol. 6, 2006.

D'Ydewalle, et al., "Spinal Muscular Atrophy Therapeutics: Where do we Stand?" Neurotherapeutics, 12:303-316, 2015.

Ellwanger, et al., "Beyond HIV infection: Neglected and varied impacts of CCR5 and CCR532 on viral diseases," Virus Research, 286(2020).

Final Office Action for U.S. Appl. No. 15/818,710, dated Dec. 9, 2025.

Frederiksen, et al., "CRISPR-Cas9 immune-evasive hESCs are rejected following transplantation into immunocompetent mice," Frontiers in Genome Editing, 2024.

Frock, et al., "Genome-wide detection of DNA double-stranded breaks induced by engineered nucleases," Nature Biotechnology, 33(2), Feb. 2015.

Han, et al., "The role of B2M in cancer immunotherapy resistance: function, resistance mechanism, and reversal strategies," Frontiers in Immunology, Mar. 2025.

Hayflick, L., "The Limited in Vitro Lifetime of Human Diploid Cell Strains," Experimental Cell Research, 37, 614-636, 1965.

Hunt, et al., "Unintended CRISPR-Cas9 editing outcomes: a review of the detection and prevalence of structural variants generated by gene-editing in human cells," Human Genetics, 142:705-720, 2023.

Kajiho, et al., "SIRPa interacts with nephrin at the podocyte slit diaphragm," The FEBS Journal, 279, 3010-3021, 2012.

Kalter, et al., "Off-target effects in CRISPR-Cas genome editing for human therapeutics: Progress and challenges," Molecular Therapy: Nucleic Acids, vol. 36, Sep. 2025.

Madireddy, et al., "Sclerosis, Huntington's Disease, and Parkinson's Diseases, through the Mitigation of Reactive Oxygen Species," Journal of Neuroscience and Neurological Disorder, 2019.

Meissner, et al., "Genome Editing for Human Gene Therapy," Methods of Enzymology, 546:273-295, (2014).

Non-Final Office Action for U.S. Appl. No. 17/728,927, dated Nov. 3, 2025.

Non-Final Office Action for U.S. Appl. No. 18/949,619, dated Nov. 5, 2025.

(56) References Cited

OTHER PUBLICATIONS

Notice of Allowance for U.S. Appl. No. 15/524,968, dated Aug. 15, 2024.

Notice of Allowance for U.S. Appl. No. 18/658,343, dated Aug. 18, 2025.

Oh, et al., "Characteristics of primary and immortalized fibroblast cells derived from the miniature and domestic pigs," BMC Cell Biology, 8:20, 2007.

Salahudeen, et al., "An overview of pharmacodynamic modelling, ligand-binding approach and its application in clinical practice," Saudi Pharmaceutical Journal, 25, 165-175, 2017.

Sun, et al., "Cutting Edge: Viral Infection Breaks NK Cell Tolerance to "Missing Self" 1," The Journal of Immunology, 2008.

Yao, et al., "Thrombospondin-1 Activation of Signal-Regulatory Protein-alpha Stimulates Reactive Oxygen Species Production and Promotes Renal Ischemia Reperfusion Injury," J. Am. Soc. Nephrol., 25(6):1171-1186, 2014.

Zetsche, et al., "Cpf1 is a Single RNA-Guided Endonuclease of a Class 2 CRISPR-Cas System," Cell, 163, 759-771, 2015.

* cited by examiner

The HLA Barrier in Transplantation

2 A

2 B

10 A

SEQ ID NO: 817985

SEQ ID NO: 817986

10 B

SEQ ID NO: 817987
SEQ ID NO: 817988
SEQ ID NO: 817989
SEQ ID NO: 817990
SEQ ID NO: 817991
SEQ ID NO: 817992
SEQ ID NO: 817993
SEQ ID NO: 817994
SEQ ID NO: 817995
SEQ ID NO: 817996
SEQ ID NO: 817997
SEQ ID NO: 817998
SEQ ID NO: 817999
SEQ ID NO: 818000
SEQ ID NO: 818001
SEQ ID NO: 818002
SEQ ID NO: 818003

```
  1 MDKKYSIGLD IGTNSVGWAV ITDEYKVPSK KFKVLGNTDR HSIKKNLIGA LLFDSGETAE

61 ATRLKRTARR RYTRRKNRIC YLQEIFSNEM AKVDDSFFHR LEESFLVEED KKHERHPIFG

121 NIVDEVAYHE KYPTIYHLRK KLVDSTDKAD LRLIYLALAH MIKFRGHFLI EGDLNPDNSD

181 VDKLFIQLVQ TYNQLFEENP INASGVDAKA ILSARLSKSR RLENLIAQLP GEKKNGLFGN

241 LIALSLGLTP NFKSNFDLAE DAKLQLSKDT YDDDLDNLLA QIGDQYADLF LAAKNLSDAI

301 LLSDILRVNT EITKAPLSAS MIKRYDEHHQ DLTLLKALVR QQLPEKYKEI FFDQSKNGYA

361 GYIDGGASQE EFYKFIKPIL EKMDGTEELL VKLNREDLLR KQRTFDNGSI PHQIHLGELH

421 AILRRQEDFY PFLKDNREKI EKILTFRIPY YVGPLARGNS RFAWMTRKSE ETITPWNFEE

481 VVDKGASAQS FIERMTNFDK NLPNEKVLPK HSLLYEYFTV YNELTKVKYV TEGMRKPAFL

541 SGEQKKAIVD LLFKTNRKVT VKQLKEDYFK KIECFDSVEI SGVEDRFNAS LGTYHDLLKI

601 IKDKDFLDNE ENEDILEDIV LTLTLFEDRE MIEERLKTYA HLFDDKVMKQ LKRRRYTGWG

661 RLSRKLINGI RDKQSGKTIL DFLKSDGFAN RNFMQLIHDD SLTFKEDIQK AQVSGQGDSL

721 HEHIANLAGS PAIKKGILQT VKVVDELVKV MGRHKPENIV IEMARENQTT QKGQKNSRER

781 MKRIEEGIKE LGSQILKEHP VENTQLQNEK LYLYYLQNGR DMYVDQELDI NRLSDYDVDH

841 IVPQSFLKDD SIDNKVLTRS DKNRGKSDNV PSEEVVKKMK NYWRQLLNAK LITQRKFDNL

901 TKAERGGLSE LDKAGFIKRQ LVETRQITKH VAQILDSRMN TKYDENDKLI REVKVITLKS

961 KLVSDFRKDF QFYKVREINN YHHAHDAYLN AVVGTALIKK YPKLESEFVY GDYKVYDVRK

1021 MIAKSEQEIG KATAKYFFYS NIMNFFKTEI TLANGEIRKR PLIETNGETG EIVWDKGRDF

1081 ATVRKVLSMP QVNIVKKTEV QTGGFSKESI LPKRNSDKLI ARKKDWDPKK YGGFDSPTVA

1141 YSVLVVAKVE KGKSKKLKSV KELLGITIME RSSFEKNPID FLEAKGYKEV KKDLIIKLPK

1201 YSLFELENGR KRMLASAGEL QKGNELALPS KYVNFLYLAS HYEKLKGSPE DNEQKQLFVE

1261 QHKHYLDEII EQISEFSKRV ILADANLDKV LSAYNKHRDK PIREQAENII HLFTLTNLGA

1321 PAAFKYFDTT IDRKRYTSTK EVLDATLIHQ SITGLYETRI DLSQLGGD   (SEQ ID NO: 1)
```

FIG. 12

Comparison of the MHC-II and MHC-I Enhanceosomes

Meissner et al., 2011 Microbes&Infection

HLA-B and HLA-C knock-out strategy

Human HLA complex

Centromere — B C E A H G F — Telomere

HLA-B    HLA-C

1 + #2    #3 + #4

E    A

CRISPR sgRNA sequences:

sgRNA #1: ATCCCTAAATATGGTGTCCC    SEQ ID NO: 818004
sgRNA #2: TCCCTAAATATGGTGTCCCT    SEQ ID NO: 818005 sgRNA #3: GTGATCCGGGTATGGGCAGT    SEQ ID NO: 818006
sgRNA #4: TGATCCGGGTATGGGCAGTG    SEQ ID NO: 818007

PCR screening confirms clone 1D as a homozygous knock-out clone

Sequence confirmation of HLA-B, -C deletion in 1D KO clone

RT-PCR confirms loss of HLA-B and HLA-C mRNA expression in HuES8

Sequence confirmation of HLA-B RT-PCR bands obtained from WT and clone 1D

HLA-A knockout strategy using the dual sgRNA approach

CRISPR sgRNA sequences:

sgRNA #5: AGCGCAAGTGGGAGGGCGGC     SEQ ID NO: 818017 sgRNA #6: CGGCTCGTGGGCTGCATGTG     SEQ ID NO: 818018

On-target cutting efficiency of HLA-A sgRNAs using TIDE

Sequencing confirms successful deletion of HLA-A in HuES8

TALEN-induced CIITA mutations in BJ-RIPSCs

Figure 15C:
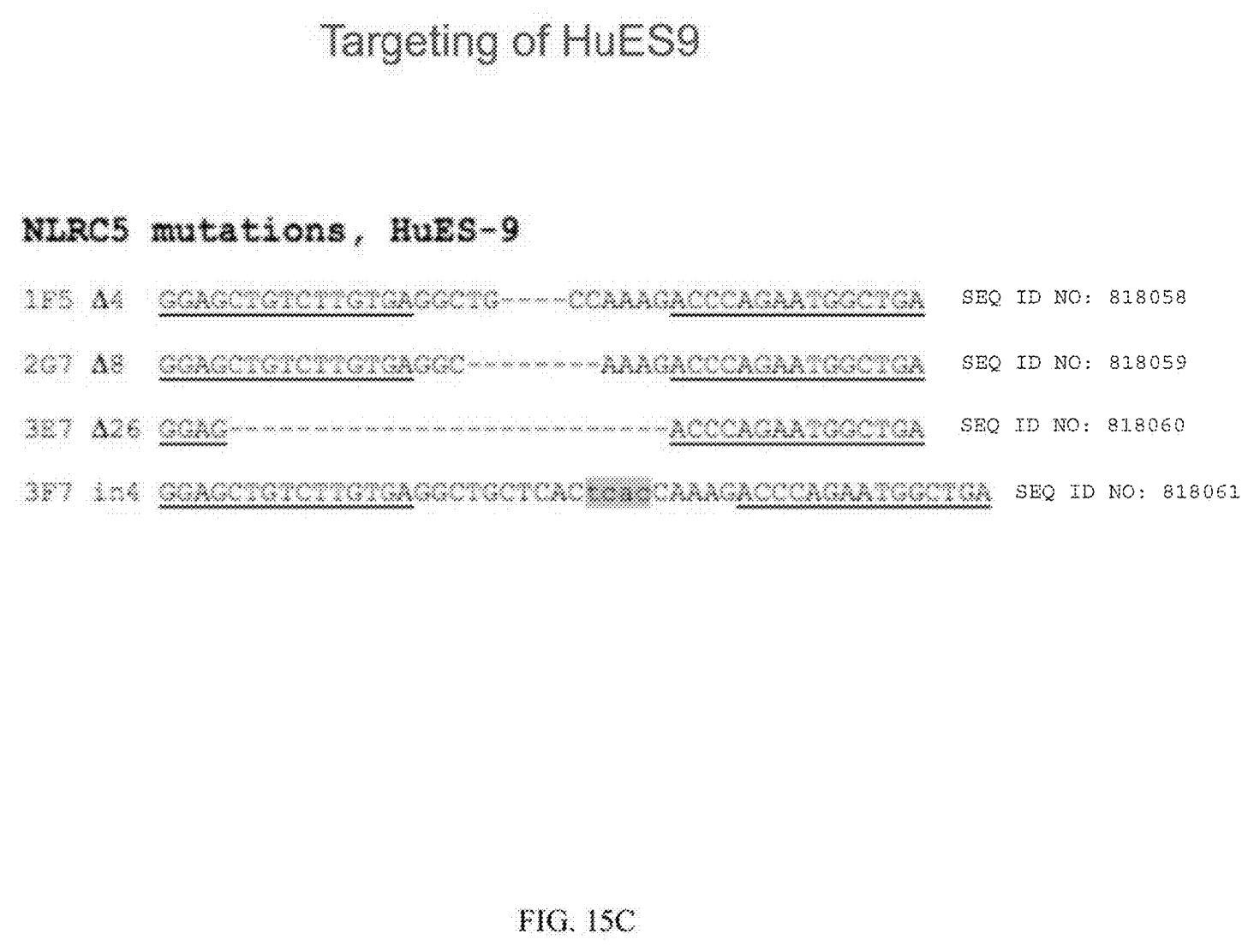

Targeting of HuES9

NlRC5 mutations, HuES-9

1F5 A4    GCAGCGTCGTGACCCG----------CCAAAGACCCAGAATGCCTGA    SEQ ID NO: 818058

2C7 A8    GCAGCGTCGTGTGACCC----------AAAGACCCAGAAGTGCCTGA    SEQ ID NO: 818059

3E7 A26   GCGAG---------ACCCACAAGTGCCTGA    SEQ ID NO: 818060

3F7 1C4   GCGAGCGTCGTGTGACCCTGTCTAGCCCCCCCAC---TGCCCAAAGACCCAGAATGCCTGA    SEQ ID NO: 818061

Lentiviral Transduction of Thp-1

Dual-vector lentiviral GeCKO system lentiCas9-Blast psi+ RRE | EFS | SpCas9 | Flag | P2A | Blast | WPRE | cPPT lentiGuide-Puro psi+ RRE | U6 | sgRNA | EF1a | Puro | WPRE | cPPT 2 component system Lenti-Cas9-Blasticidin [establish stable Thp-1 Cas9 cell line]

Lenti-Guide-puro [bring in guide]

Sanjana at al., 2014 Nat Methods

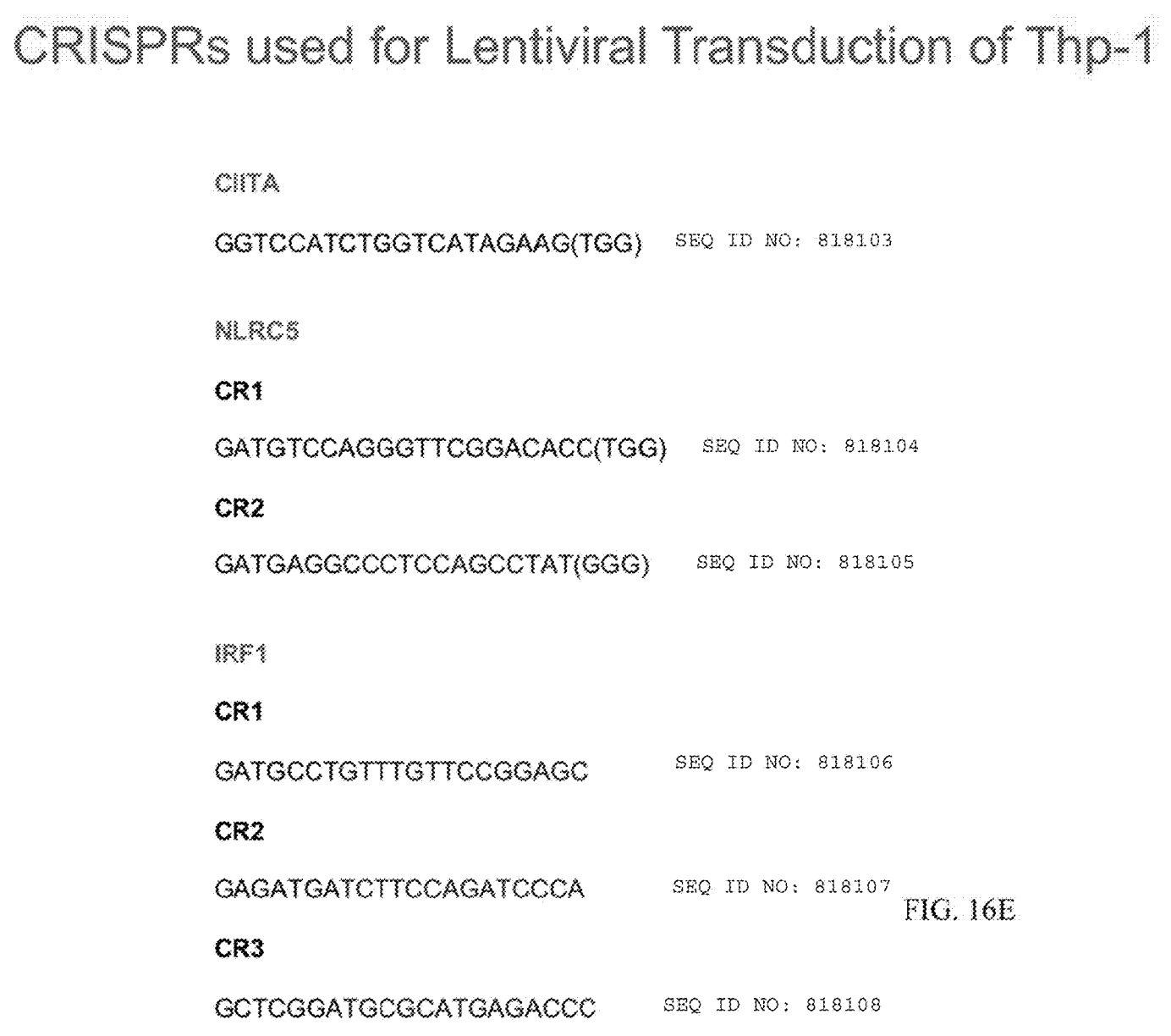

CRISPRs used for Lentiviral Transduction of Thp-1

CIITA

GGTCCATCTGGTCATAGAAG(TGG)    SEQ ID NO: 818103

NLRC5

CR1

GATGTCCAGGGTTCGGACACC(TGG)    SEQ ID NO: 818104

CR2

GATGAGGCCCTCCAGCCTAT(GGG)    SEQ ID NO: 818105

IRF1

CR1

GATGCCTGTTTGTTCCGGAGC    SEQ ID NO: 818106

CR2

GAGATGATCTTCCAGATCCCA    SEQ ID NO: 818107

CR3

GCTCGGATGGCATGAGACCC    SEQ ID NO: 818108

FIG. 16E

CIITA and NLRC5 act independently on MHC-II and MHC-I, respectively

Dual CRISPR Strategy targeting the *IRF1* locus

*IRF1* gene locus – Chr. 5q31.1

CR1   GCTCATGGCGCATCCGAGTGAT    SEQ ID NO: 818109

CR2   GAGATGATCTTCCAGATCCCA    SEQ ID NO: 818110

CR3   GCTCGGGATGCGCATGAGACCC    SEQ ID NO: 818111

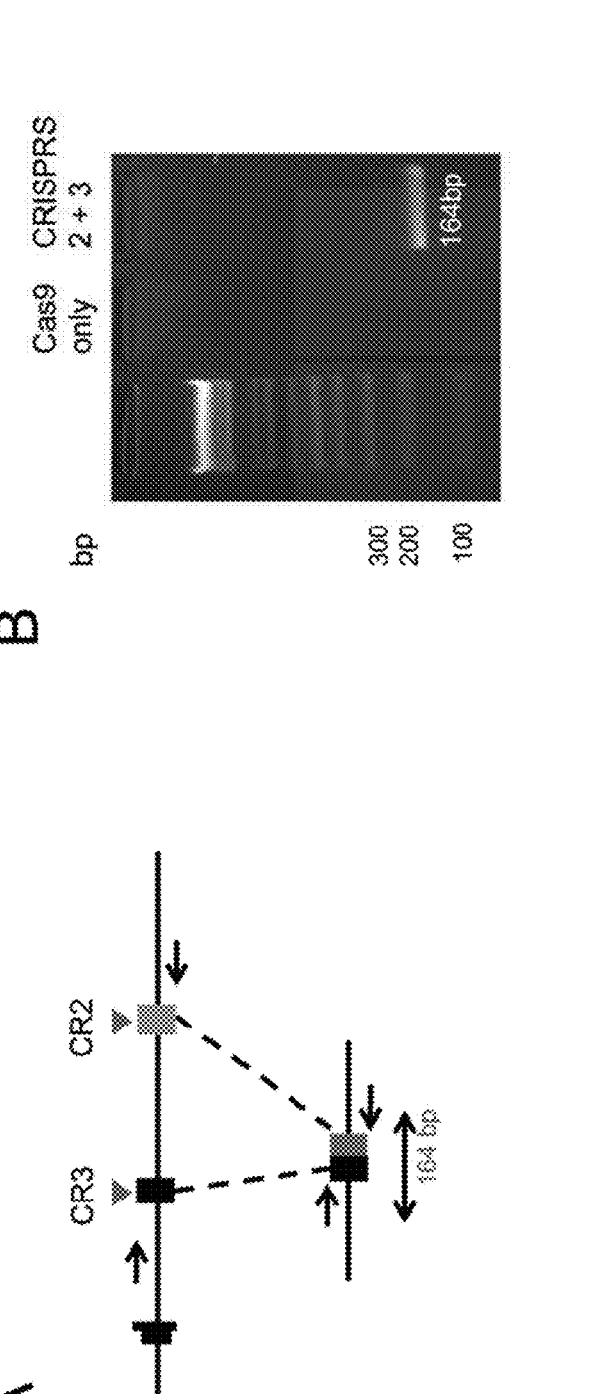
'Dual guide strategy' for the targeted deletion of *IRF1*
293T cells
FIG. 17C

SEQUENCE CONFIRMATION OF *IRF-1* CRISPR INDUCED DELETION

Screening of *IRF1*-targeted HuES9

Dual CRISPR strategy using CRISPRs #2 and #3

RECONFIRMATION OF IRF-1 CLONES

SEQUENCE CONFIRMATION OF IRF-1 CRISPR INDUCED DELETION IN CLONE 12

WILDTYPE  cagGAGGAGATGATCTTCCAGATCCCATGGAAGCATGCTGCCAAGC   SEQ ID NO: 818115

12  cagGAGGAGATGATCTTCCA                 TGGAAGCATGCTGCCAAGC   SEQ ID NO: 818116

SEQ ID NO: 818117

HuES9

SEQUENCE CONFIRMATION OF IRF-1 CRISPR INDUCED DELETION IN CLONE 17

SEQUENCE CONFIRMATION OF IRF-1 CRISPR INDUCED INSERTION IN CLONE 21

WILDTYPE    cagGAGGAGATGATCTTCCAGATC-------CCATGGAAGCATGCTGCCAAGC
SEQ ID NO: 818121

21    cagGAGGAGATGATCTTCCAGATCATGCTGCCATGGAAGCATGCTGCCAAGC
SEQ ID NO: 818122

HuES9

Impaired MHC class I Induction in IRF1-/- HuES9 clones following IFNγ treatment
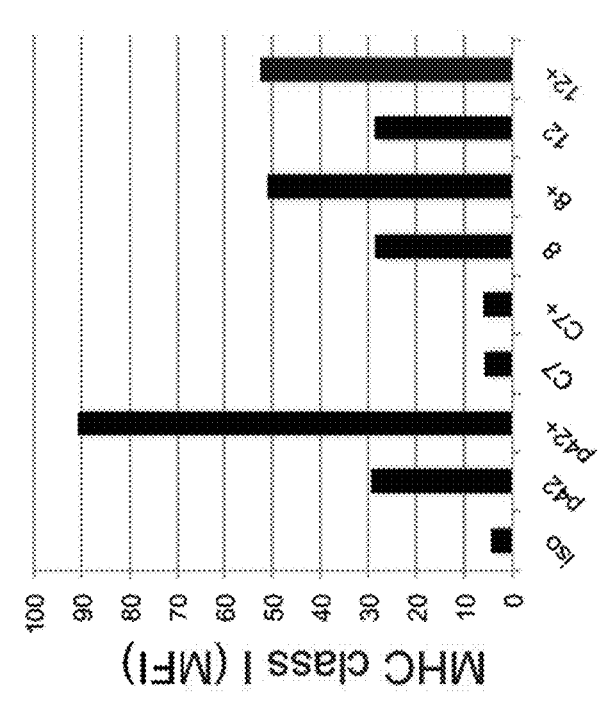
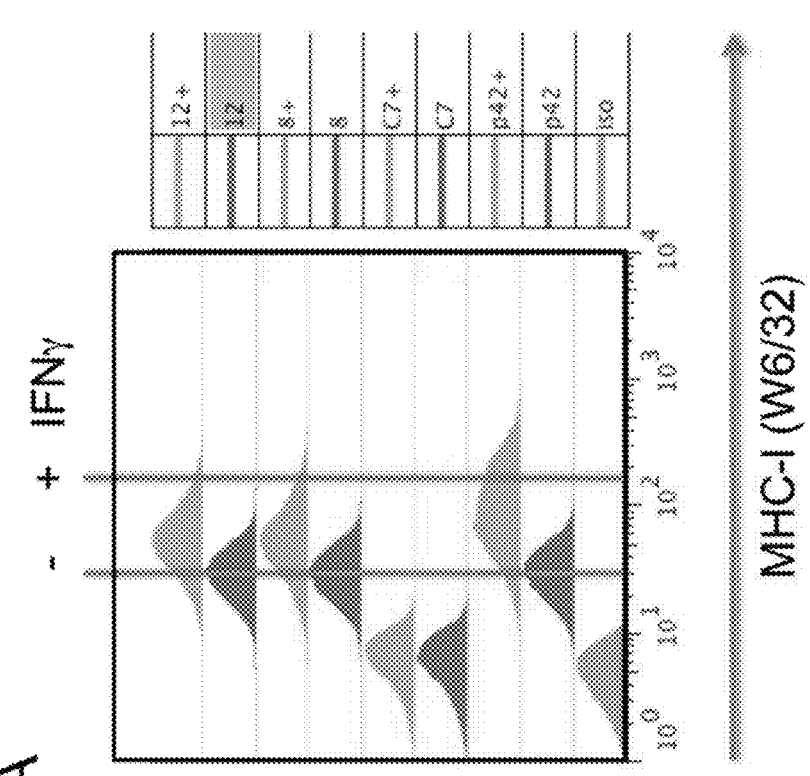
FIG. 17K

Dual Guide Targeting of RFX5 in 293T Cells

SEQ ID NO: 818124 CRISPR Pair #1: GTCTTGGGGCCTTAGCATC

SEQ ID NO: 818125 CRISPR Pair #2: ACCCTTCTTCAGAGGCTCCG

SEQ ID NO: 818126 CRISPR Pair #3: GGGCTAGAATTGAGAGGGAC

SEQ ID NO: 818127 CRISPR Pair #4: GGAGTGCCCTGGGGCCTTCT

Targeting of RFX5 results in reduced MHC class I expression
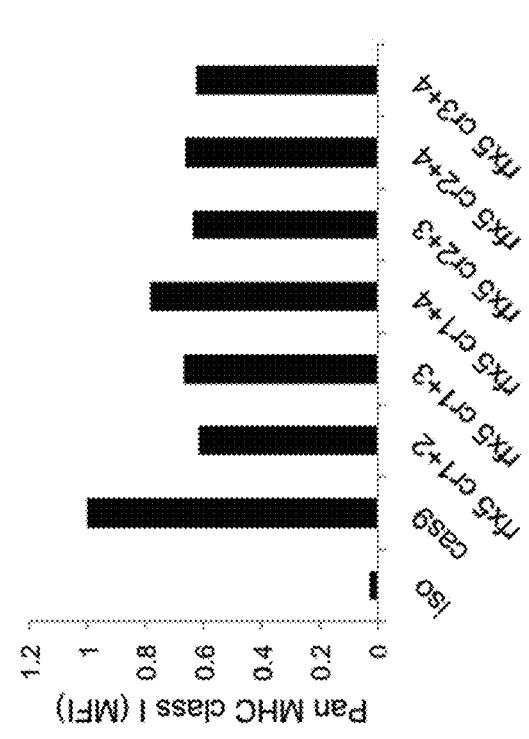
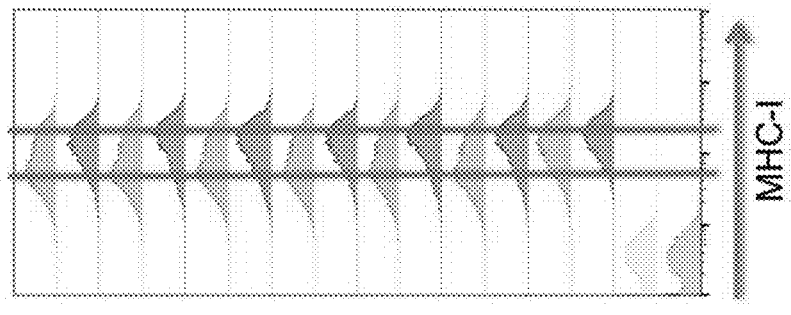
FIG. 18B Dual Guide Targeting of RFX-ANK in 293T Cells CRISPR Pair #1: GCAGGCTGGGTAAGCTCCAT
SEQ ID NO: 818128

CRISPR Pair #2: TGCAAGGCTAGGTATGCAGT
SEQ ID NO: 818129

CRISPR Pair #3: GACCCCTGCCTCAGAACTTG
SEQ ID NO: 818130

CRISPR Pair #4: CTGTGAGGGTGGGTAAACTG
SEQ ID NO: 818131

Targeting RFX5 and RFX-ANK Results in Reduced MHC class I Expression
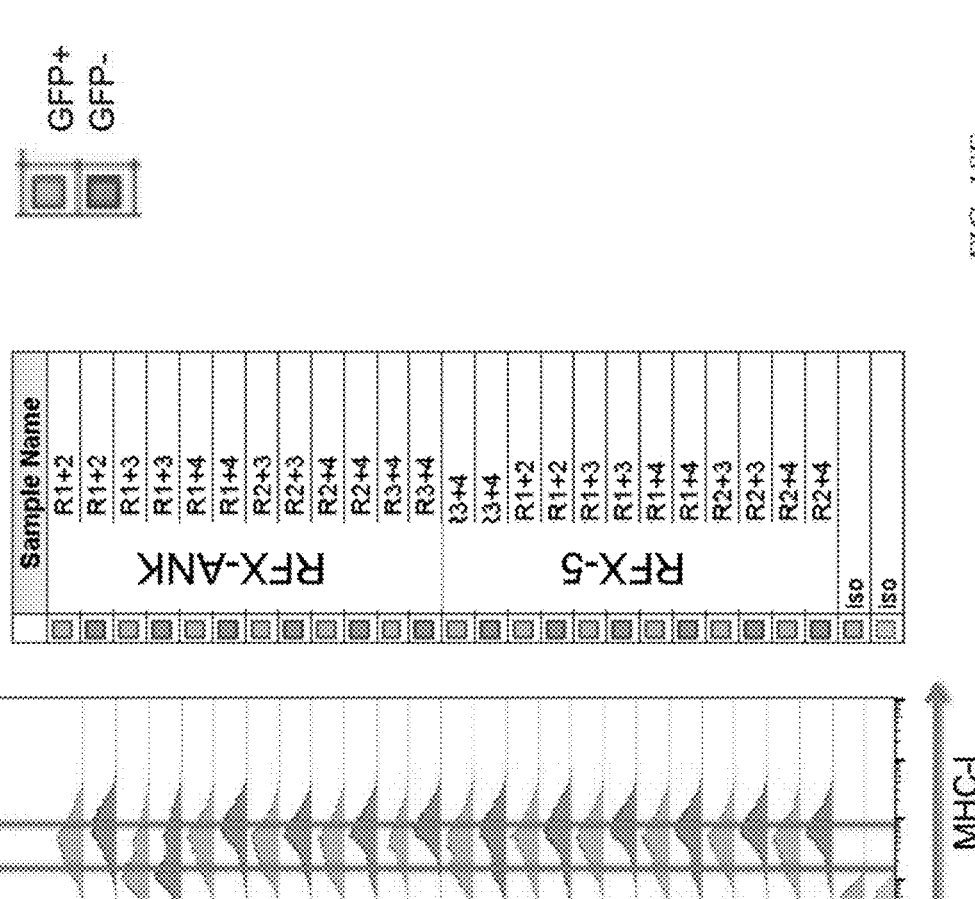
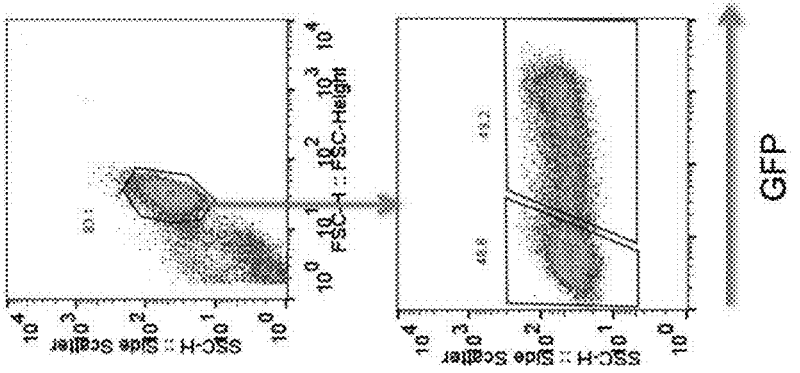
FIG. 18E Dual Guide Targeting of RFX-AP in 293T Cells CRISPR Pair #1: TTGGTTCGCGAAGTGCCGTT  SEQ ID NO: 818132

CRISPR Pair #2: ACTTGGCGAACCAAAGACTC  SEQ ID NO: 818133

CRISPR Pair #3: CGCGGGGTGGGGCACGCCGC  SEQ ID NO: 818134

CRISPR Pair #4: ACCGAGGCTGGCGCCAAGGT  SEQ ID NO: 818135

Targeting of RFX-AP results in reduced MHC class I expression
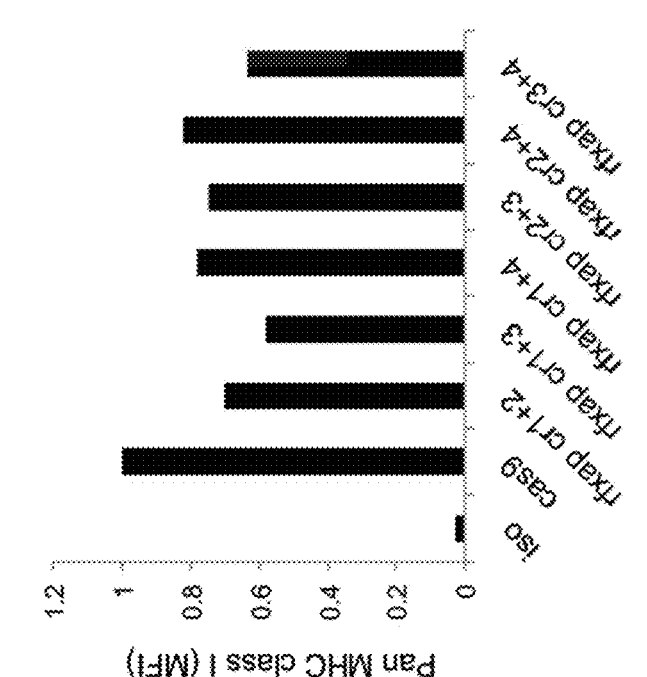
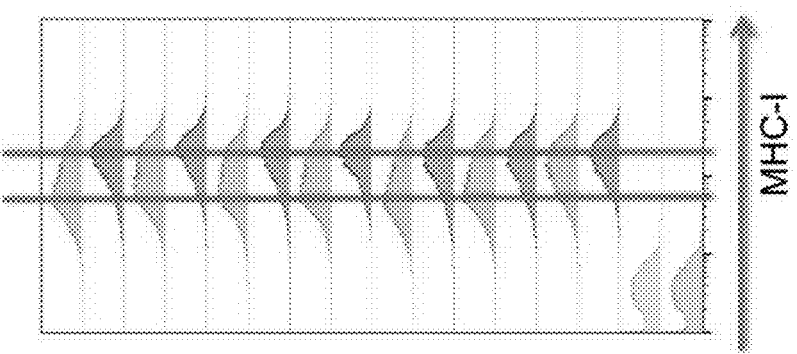
FIG. 18H Dual Guide Targeting of NFY-A in 293T Cells CRISPR Pair #1: AGTGTACCTCACAGCCTTCT    SEQ ID NO: 818136

CRISPR Pair #2: GACAGAGCAGATTGTTGTCC    SEQ ID NO: 818137

CRISPR Pair #3: AGTGAGATTCCTGTCCACTC    SEQ ID NO: 818138

CRISPR Pair #4: GACAGATTCAGCAGCAGGTA    SEQ ID NO: 818139

Dual Guide Targeting of NFY-C in 293T Cells

CR3+CR4
CR4+CR3
CR2+CR4
CR3+CR2
CR1+CR4
CR1+CR3
CR1+CR2
Mock 531   476   397   503   453   446   367   bp

FIG. 19B

CRISPR Pair #1: AGCAAAGCCTACAGTCGTTC    SEQ ID NO: 818140
CRISPR Pair #2: GTTGTCGAGATGTCCACAGA    SEQ ID NO: 818141
CRISPR Pair #3: TCAGACTTCTGTCCAGATT     SEQ ID NO: 818142
CRISPR Pair #4: TCCTCACCACTGTTAAATTC    SEQ ID NO: 818143

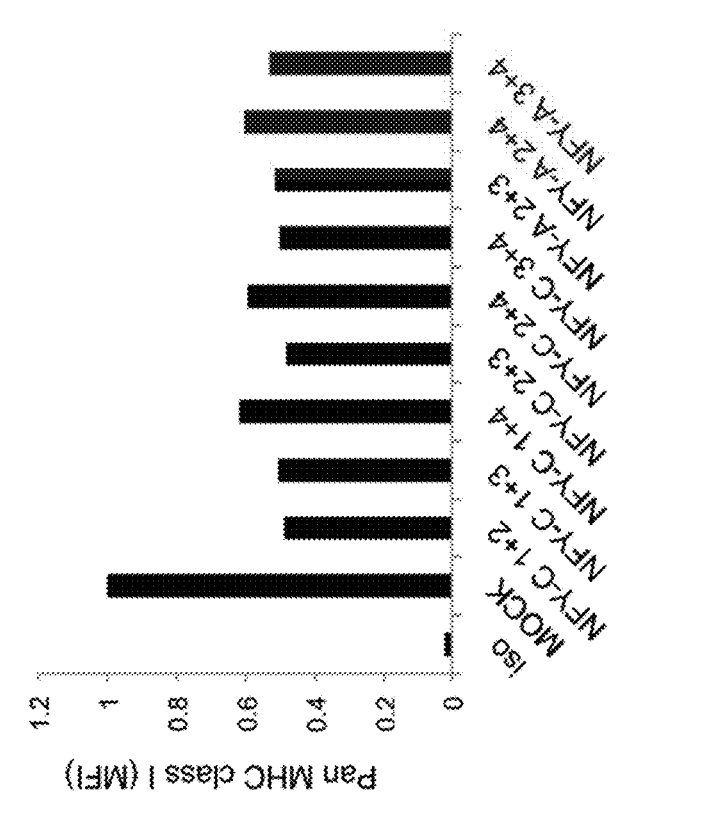
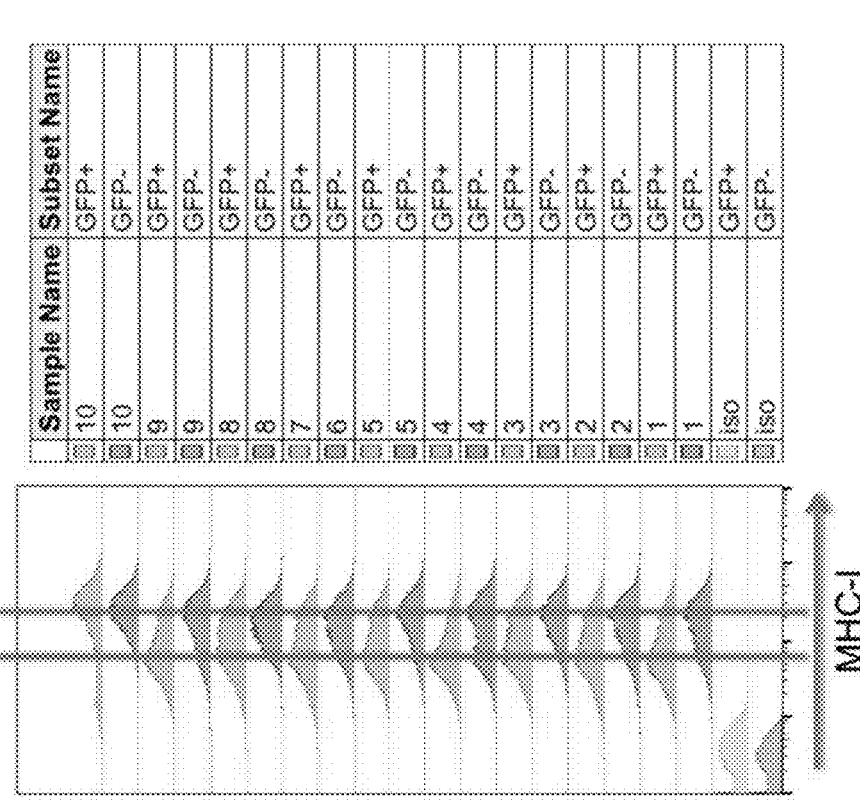
FIG. 19C

Dual Guide Targeting of NFY-B in 293T Cells

CRISPR Pair #1: GTGAGCGCTTAGTATTTACC SEQ ID NO: 818144

CRISPR Pair #2: ACCAGCACATAGCATGAACC SEQ ID NO: 818145

CRISPR Pair #3: GTAGCTGTCAACAACAGACA SEQ ID NO: 818146

CRISPR Pair #4: ACCAGGTTCATGCTATGTGC SEQ ID NO: 818147

Targeting NFY-B Results in Reduced MHC class I Expression
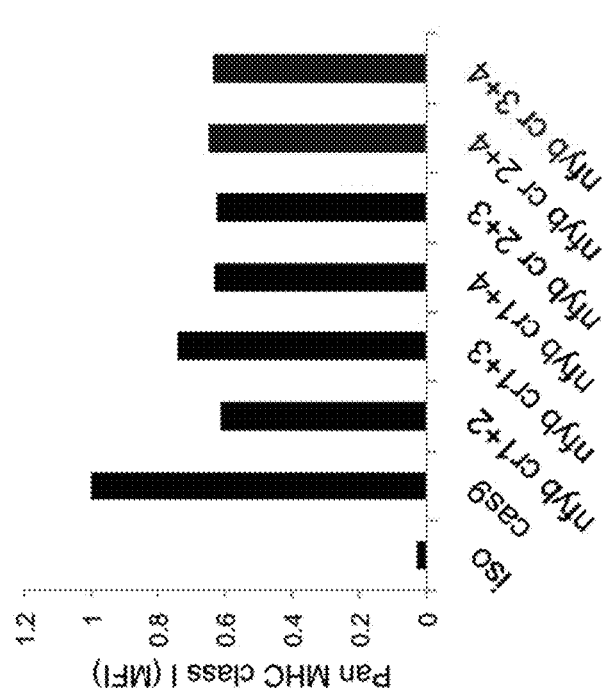
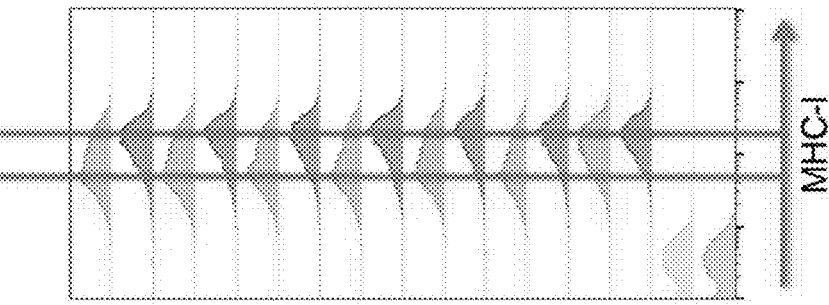
FIG. 19E

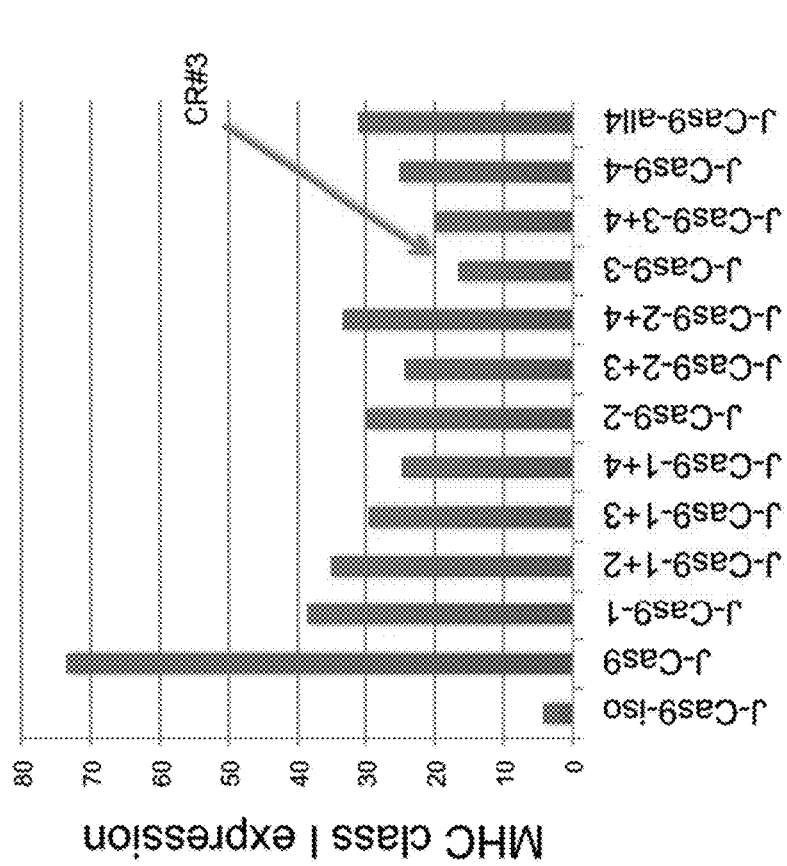
TAP1 CRISPR expression reduces MHC-I surface expression in Jurkat T cells
TAP1
CR#1  TTGGCACTCGGACGCCGTCC(CGG)
SEQ ID NO: 818148
CR#2  TCGGCGGTACCCGGAGCTTC(AGG)
SEQ ID NO: 818149
CR#3  CCCGGTCCGCGGATAGCCACC(AGG)
SEQ ID NO: 818150
CR#4  TGGTGCTATCCGCGGACCCG(GGG)
SEQ ID NO: 818151
FIG. 20A TAP1 CRISPR expression reduces MHC-I surface expression in Jurkat T cells 48 hrs IFNg, W6/32 1:200

Eliminating HLA surface expression in Jurkat (Cas9) T cells

Eliminating HLA surface expression in Jurkat (Cas9) T cells

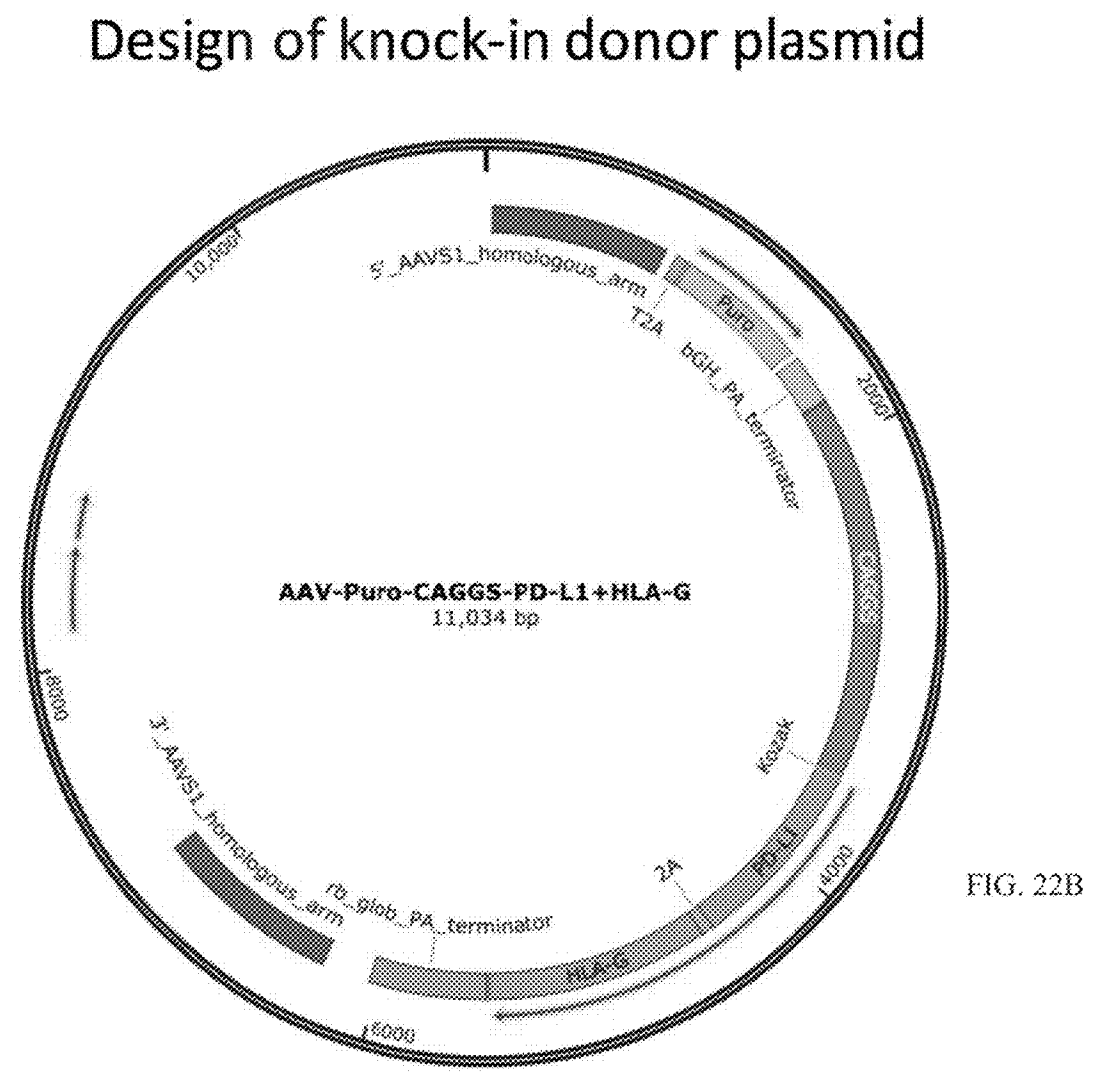

Design of knock-in donor plasmid

AAV-Puro-CAGGS-PD-L1+HLA-G
11,034 bp

5'_AAVS1_homologous_arm
Puro
T2A
bGH_PA_terminator
Kozak
rb_glob_PA_terminator
3'_AAVS1_homologous_arm

FIG. 22B

Ectopic PD-L1 and HLA-G expression in 293T cells

Ectopic HLA-G expression in JEG-3 cells

Transfected with PD-L1-HLA-G donor plasmid

Untransfected

HLA-G

FSC-H :: FSC-Height

PCR screening confirms 1G as a heterozygous KI clone for PD-L1/HLA-G
HuES8
KI primers #1
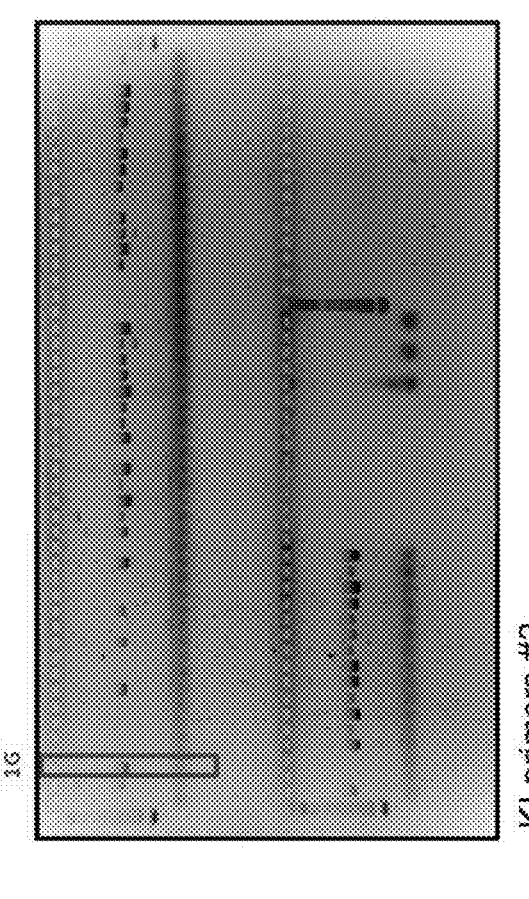
KI primers #2
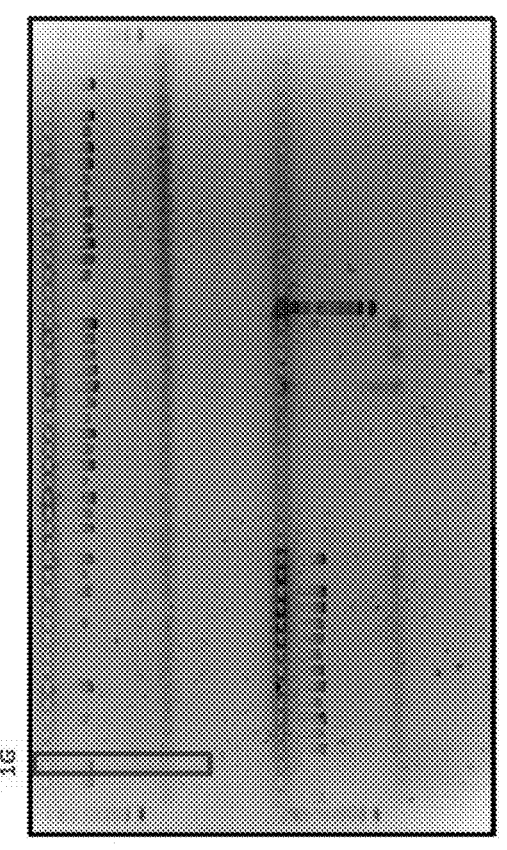
WT primers
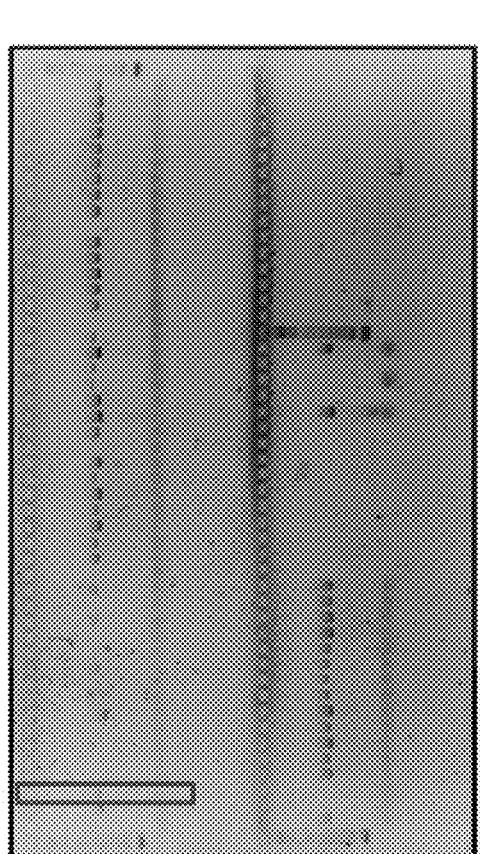
FIG. 22E Stable PD-L1 and HLA-G expression from safe harbor locus in HuES8

Ectopic CD47 Expression in 293T and hPSCs

Deletion of TRAC and TRBC in HuES9 to disrupt TCR Expression

TRAC       SEQ ID NO: 818164

CR1 AGAGCAACAGTGCTGTGGCCTGG)

CR2 TGGAATAATGCTGTTGTTGA(AGG)
            SEQ ID NO: 818165

TRBC       SEQ ID NO: 818166

CR1 CGCTGTCAAGTCCAGTTCTA(CGG)

CR2 GGCTCTCGGAGAATGACGAG(TGG)
            SEQ ID NO: 818167

**TCRA KO in HuES9

*TCRB KO in HuES9

***TCRA KO in HuES9 B2M-/-CIITA-/-, in fact this is now a triple knock-out stem cell line for B2M-/-, CIITA-/-, TCR-/-, which upon differentiation into T cells will be devoid of MHC-I and –II and no TCR surface expression; the perfect blank canvas for introducing a Chimeric Antigen Receptor (CAR). Additional modifications such as deletion of the inhibitory receptors PD-1 and CTLA4, will make this cells powerful tools for cancer immunotherapy.

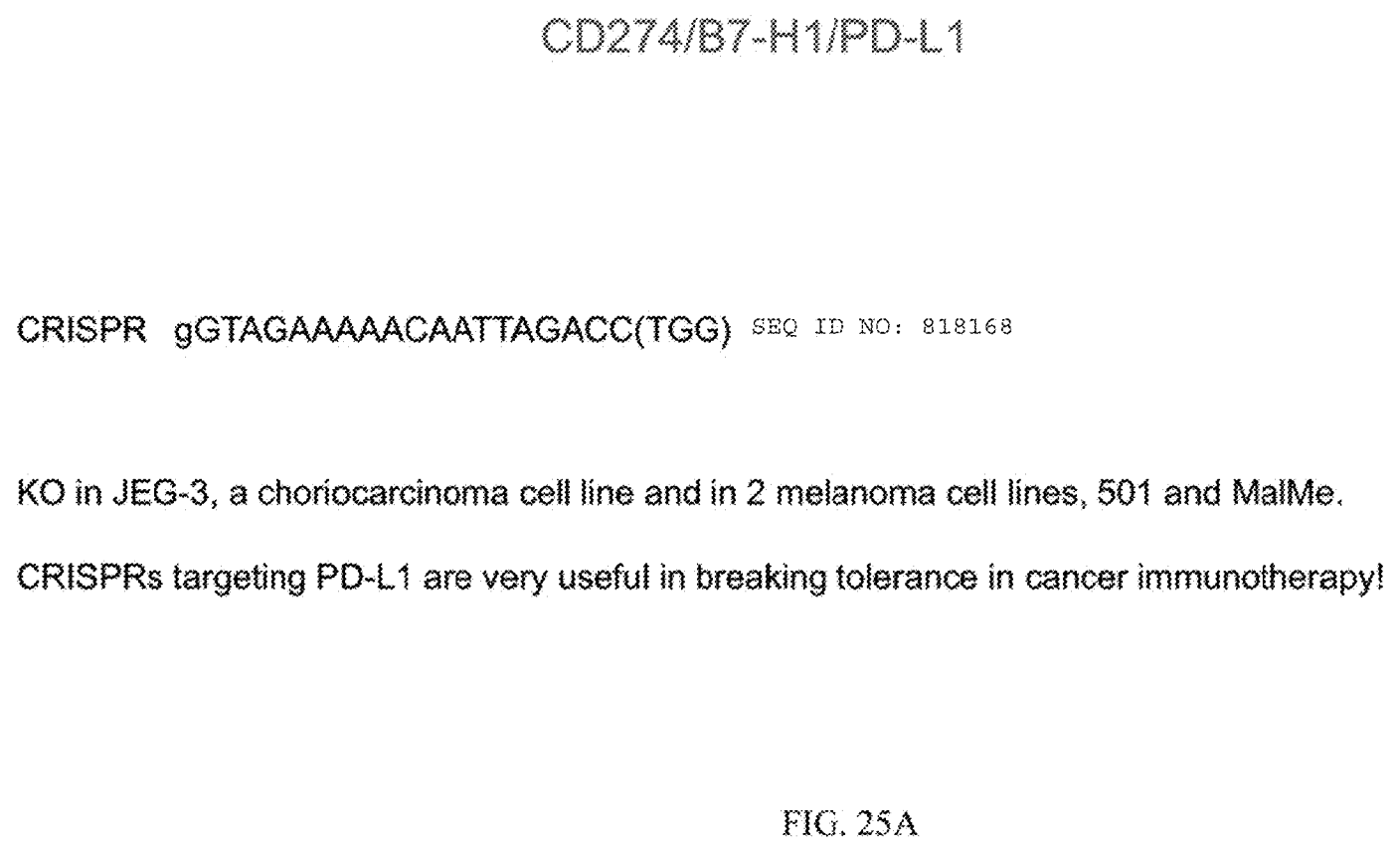

CRISPR gGTAGAAAAACAATTAGACC(TGG) SEQ ID NO: 818168

KO in JEG-3, a choriocarcinoma cell line and in 2 melanoma cell lines, 501 and MalMe.

CRISPRs targeting PD-L1 are very useful in breaking tolerance in cancer immunotherapy!

FIG. 25A

Screening of targeted B7-H1 colonies

CRISPR Cutting Efficiency: 22/265 => 8.3%
JEG-3 cells

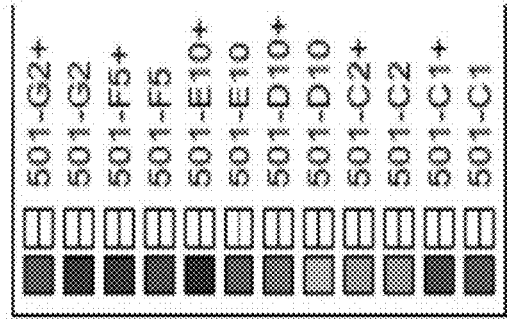
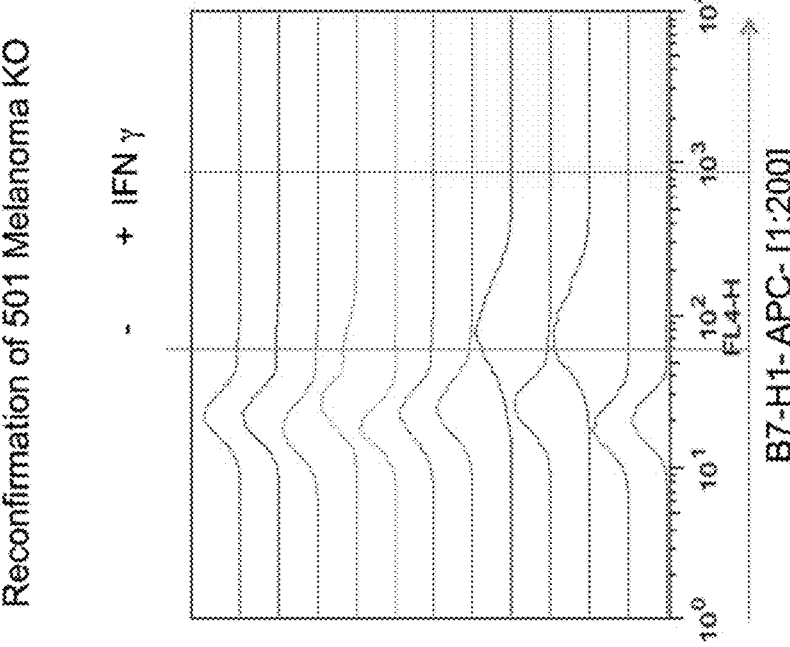
FIG. 25C

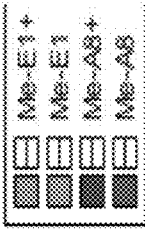
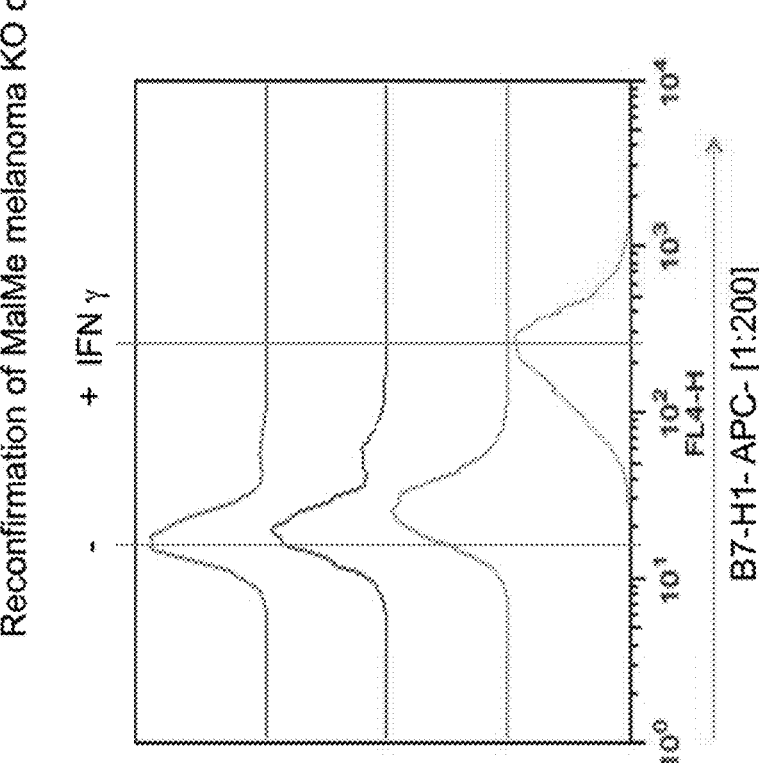
FIG. 25D

Co-Stimulatory/Inhibitory Molecules and their Receptors on T cells

Chen and Files, Nat Immunol 2013

Dual Guide Targeting of TIGIT in 293T Cells

All 4 CRs work!!!

CR3+CR4   CR2+CR4   CR2+CR3   CR1+CR4   CR1+CR3   CR1+CR2   Mock 300   266   174   166   141   133   292 bp

CRISPR #1: GTAGCCGACTGCAGATAGGA
SEQ ID NO: 818169

CRISPR #2: CCTCTGAGAAAGACGGTCT
SEQ ID NO: 818170

CRISPR #3: TCAGGCCTTACCTGAGGCGA
SEQ ID NO: 818171

CRISPR #4: GGCTCCCTCGCCTCAGGTA
SEQ ID NO: 818172

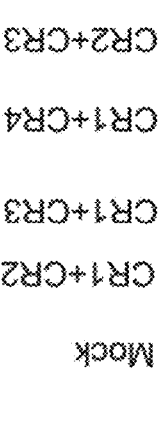
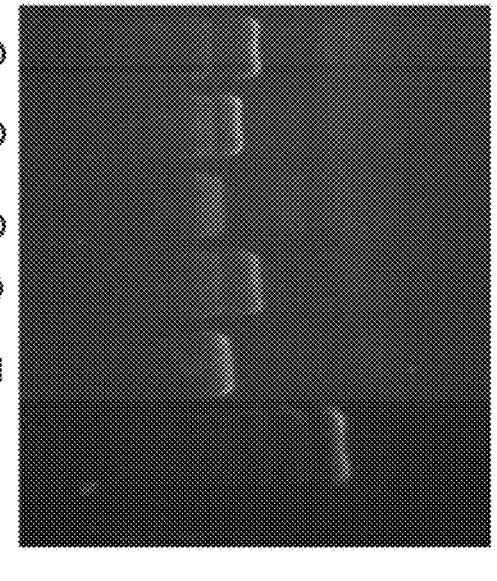
Dual Guide Targeting of TIM3 in 293T Cells
All 4 CRs work!!!
SEQ ID NO: 818173 CRISPR #1: CTTACAAGTAAGTCTCGGCA
SEQ ID NO: 818174 CRISPR #2: GAAGAAGTACCCAGTCCATT
SEQ ID NO: 818175 CRISPR #3: GACATAATGGTGCTGTACAG
SEQ ID NO: 818176 CRISPR #4: GTTAAAACTGTGCCTAACAG
Mock   CR1+CR2   CR1+CR3   CR1+CR4   CR2+CR3
412 283 378 309 249 bp
FIG. 26C Dual Guide Targeting of HVEM in 293T Cells All 4 CRs work!!!

SEQ ID NO: 818177    CRISPR #1: AGCCTCAAGACGTCGGTTTT

SEQ ID NO: 818178    CRISPR #2: AGCTCGGGAACCCAGCTAGC

SEQ ID NO: 818179    CRISPR #3: GGATCTGCCGAGCAGACGGAG

SEQ ID NO: 818180    CRISPR #4: GGAACTCAGCGGCCATTGCTG

Dual Guide Targeting of 2B4/CD244 in 293T Cells

All 4 CRs work!!!

307 134 273 166 169 276 200 bp

SEQ ID NO: 818181   CRISPR #1: CCAGTCAGCAAGAGGACGAT
SEQ ID NO: 818182   CRISPR #2: AAGGAGGTCCTACCTGGCGT

SEQ ID NO: 818183   CRISPR #3: ACCAGACTCTCTGCCGTGCA
SEQ ID NO: 818184   CRISPR #4: CCTGCTCCTCAAGGTGTATC

Dual Guide Targeting of CD28 in 293T Cells

CR1, 2, 3 work!!!

338 306 223 290 192 258 192 bp

CRISPR #1: TTGGAACCCTAGCCCATCGTC
SEQ ID NO: 818185
CRISPR #2: CTCACACTTCGGGTTCCTCG
SEQ ID NO: 818186

CRISPR #3: ATTTTTTGAGGTCTTCCAAT
SEQ ID NO: 818187
CRISPR #4: TACCTGTTACTTGAATTGAA
SEQ ID NO: 818188

CR 1, 2 and 4 work!!!

Dual Guide Targeting of OX40 in 293T Cells 355 225 327 253  bp

SEQ ID NO: 818189  CRISPR #1: CCTTGCGGGGGTGTGTGGCTATA
SEQ ID NO: 818190  CRISPR #2: TGGGGCTGAGCACCGTGACG

SEQ ID NO: 818191  CRISPR #3: GCAGAGCCGCACACGGCCCG
SEQ ID NO: 818192  CRISPR #4: TCTCTGCTGTCGCCAGAGTC

FIG. 26H

Dual Guide Targeting of CD226 in 293T Cells
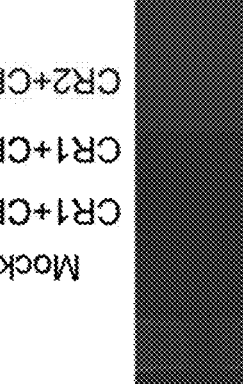
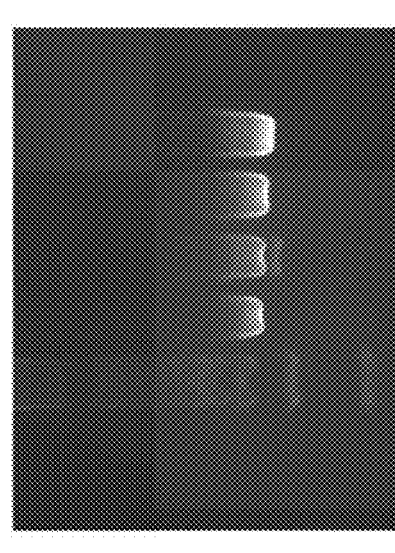
SEQ ID NO: 818197  CRISPR #1: GCTCTTCTTCATGTATACAG
SEQ ID NO: 818198  CRISPR #2: CACGACTGATAACATCTGAG
SEQ ID NO: 818199  CRISPR #3: GAAGGAAACTGCATTGTGCT
SEQ ID NO: 818200  CRISPR #4: GGATTATCCTACTTTACTTT
CR1 and 2 work!!!
341 200 319 223 bp
Mock
CR1+CR2
CR1+CR4
CR2+CR4
FIG. 26I Dual Guide Targeting of CD2 in 293T Cells CR1, 2, 3 work!!!

CRISPR #1: GGCACGTGGTTAAGCTCTCG
SEQ ID NO: 818201
CRISPR #2: TTGACTCTTATGCTTACCTT
SEQ ID NO: 818202

CRISPR #3: TACATGGAAAGCTCATCTTA
SEQ ID NO: 818203
CRISPR #4: AGTTACTGAGAGTCACTTTC
SEQ ID NO: 818204

CR 2, 3 work!!!
Dual Guide Targeting of LAG3 in 293T Cells
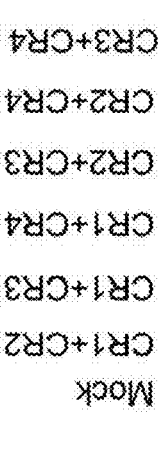
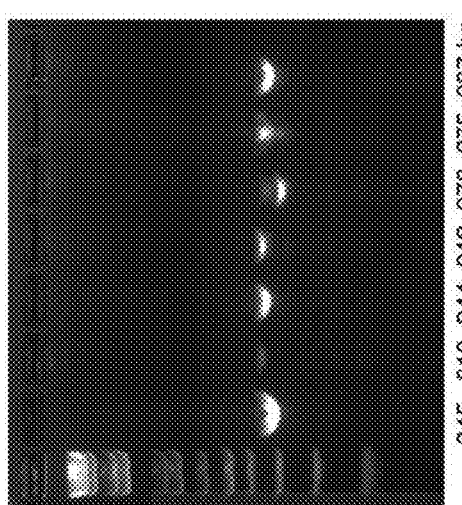
FIG. 26K
SEQ ID NO: 818205    CRISPR #1: CCTTTTGGAGGGCTCAGCGC
SEQ ID NO: 818206    CRISPR #2: GACCATAGGAGAGAGATGTGGG
SEQ ID NO: 818207    CRISPR #3: GGGTGGCTCCAGgtaaaacg
SEQ ID NO: 818208    CRISPR #4: CCCGCCATCCCGTTTTACC All 4 CRs work!!!

Dual Guide Targeting of BTLA in 293T Cells 322 141 156 238 307 227 242 bp

Mock
CR1+CR2
CR1+CR3
CR1+CR4
CR2+CR3
CR2+CR4
CR3+CR4

CRISPR #1: GGTCAGTTTACCTACCCCAG
SEQ ID NO: 818209
CRISPR #2: TTTCCATCACTGATATGTGC
SEQ ID NO: 818210

CRISPR #3: CCTAAGCAGGTGCCTTACCA
SEQ ID NO: 818211
CRISPR #4: TAATCCCATATCTGGACATC
SEQ ID NO: 818212

Dual Guide Targeting of ICOS in 293T Cells

SEQ ID NO: 818213    CRISPR #1: GAAGACACCCTTACCTGTAC
SEQ ID NO: 818214    CRISPR #2: CAGTCACTCATCAAGGTAAA

SEQ ID NO: 818215    CRISPR #3: GTTCAATGACAACATCATTC
SEQ ID NO: 818216    CRISPR #4: TAGAACAGAGATCACAAGAC

Dual Guide Targeting of CD27 in 293T Cells

CR 1 +2 works!!

Mock CR1+CR2 CR1+CR3 CR1+CR4 CR2+CR3 CR3+CR4

376   174   232   364   345   250 bp

SEQ ID NO: 818217   CRISPR #1: ATTGGCTTTTGTGTGCAAAAAA
SEQ ID NO: 818218   CRISPR #2: CCTGCTATTCTAGTGTATAC
SEQ ID NO: 818219   CRISPR #3: TTCTGAAATTGTAGCGAAGA
SEQ ID NO: 818220   CRISPR #4: ACATACTCATTTTCTCAAAT

Dual Guide Targeting of ST2 in 293T Cells

All CRs works!!

SEQ ID NO: 818221   CRISPR #1: TCACTGGCATACGACAGTGA

SEQ ID NO: 818222   CRISPR #2: TCGTATGCCAGTGACTCATC

SEQ ID NO: 818223   CRISPR #3: CTTACTAAACTTTGCTGCTG

SEQ ID NO: 818224   CRISPR #4: TGATAAACAGAATGGGGTTT

Dual Guide Targeting of GITR in 293T Cells

CR 1 + 3 work!!

CRISPR #1: CGGGGGCGATGGGCGCGTTTC
SEQ ID NO: 818225

CRISPR #2: TGACCTGAGAATCCCGACCC
SEQ ID NO: 818226

CRISPR #3: GGGGACGGGGCGTGTCCAAC
SEQ ID NO: 818227

CRISPR #4: TGAGCGCGCACAGCAGCGCC
SEQ ID NO: 818228

316 182 260 296 240 164 240 bp

Various Cell Lines Tested

| | HLA | | | | | |
| | HLA-A | HLA-B/C | NLRC5 | CIITA | B2M | IRF1 |
|---|---|---|---|---|---|---|
| HuES8 | + | + | | | | |
| HuES9 | | | + | + | + | + |
| BJ-RiPSCs | | | + | + | | |
| Thp1 | | | + | + | + | + |
| Jurkat | | | | | + | + |
| Primary T cells | + | + | + | + | + | + |
| HEK293T | | | | | | |

HuES8 and HuES9 are human ES cell lines
BJ-RiPSCs is an iPSC line

All other enhanceosome components (RFX and NFY) were only tested in HEK293T cells at this point

FIG. 27

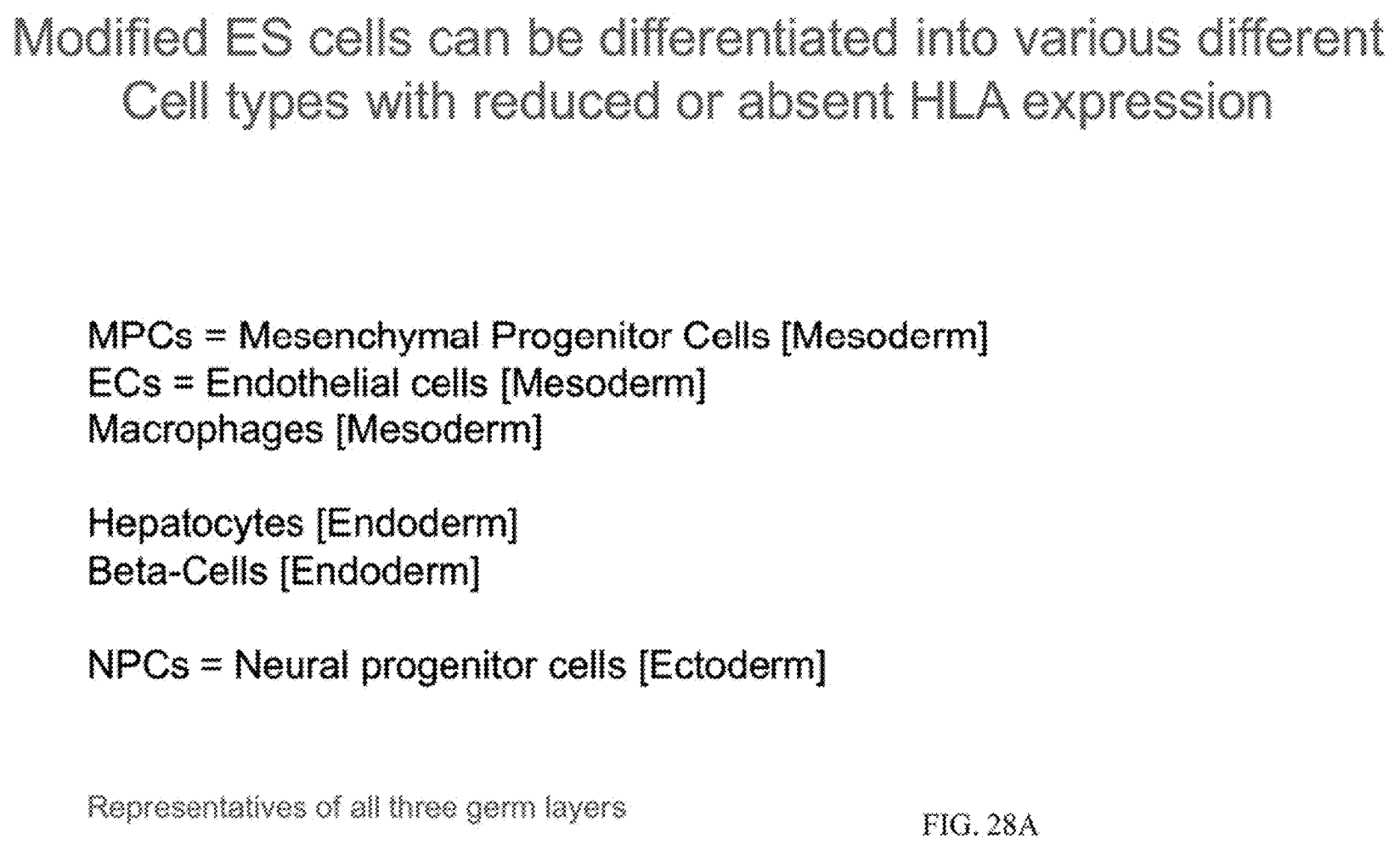

Modified ES cells can be differentiated into various different
Cell types with reduced or absent HLA expression MPCs = Mesenchymal Progenitor Cells [Mesoderm]
ECs = Endothelial cells [Mesoderm]
Macrophages [Mesoderm]

Hepatocytes [Endoderm]
Beta-Cells [Endoderm]

NPCs = Neural progenitor cells [Ectoderm]

Representatives of all three germ layers

FIG. 28A

Reduced MHC-I Expression in NLRC5-/- Human ES Cells

MHC-I expression (%max)

iso WT NLRC5-/- CITTA-/-

48 hrs IFNγ

- Low basal MHC-I expression in stem cells
- Can be increased by IFNγ stimulation
- ~50% reduction in IFNγ-treated NLRC5-/- cells Reduced MHC-I Expression in NLRC5-/- Human MPCs Data combined:
two independent experiments using 3x WT, 4x NLRC5-/-

Reduced MHC- I expression in stem cell-derived NLRC5-/- ECs

ECs – Similar Differentiation Efficiency
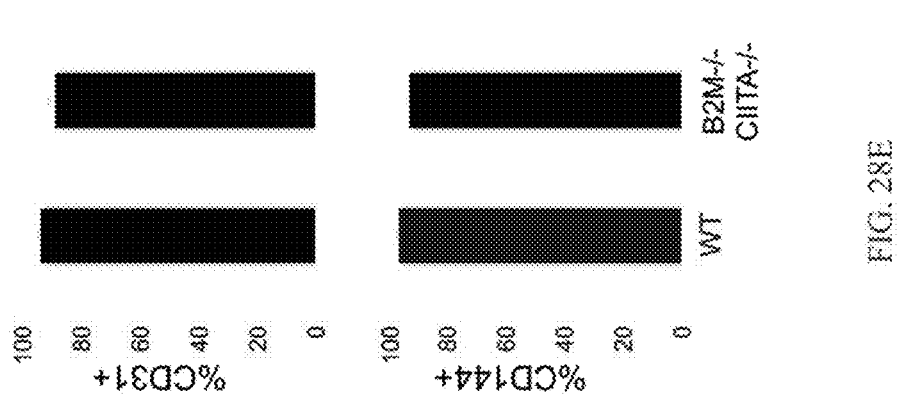
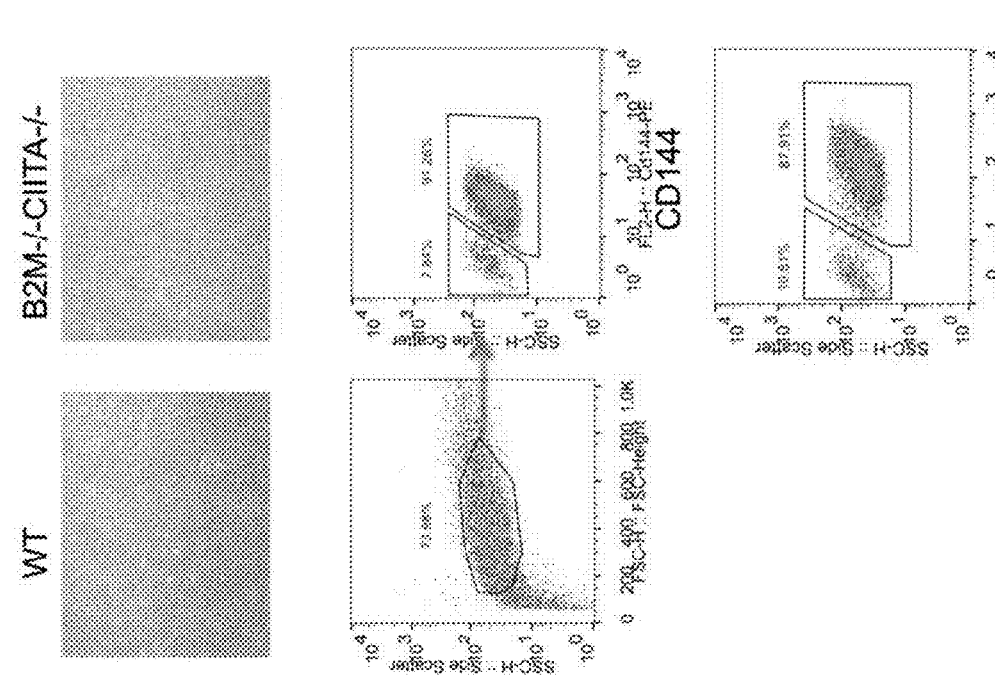
FIG. 28E

Adaptation to Spin Culture for beta-Cell Differentiation
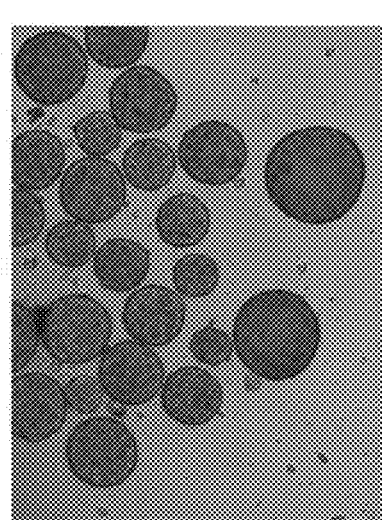
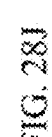
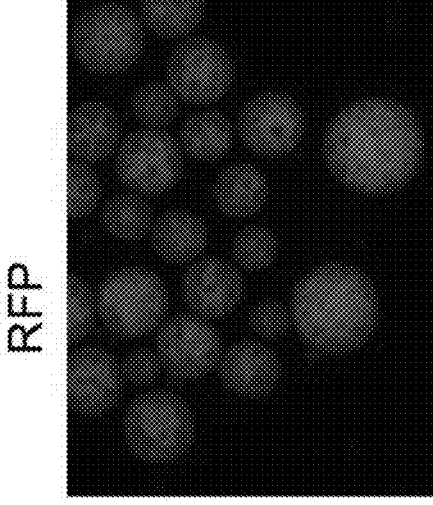
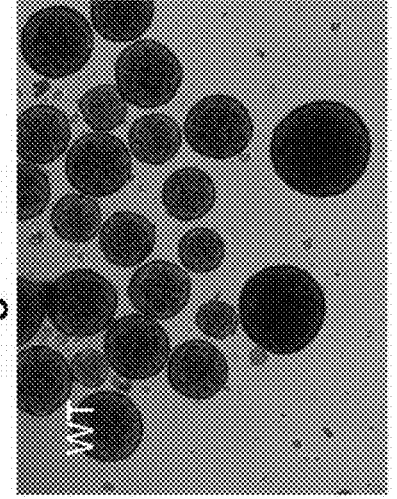
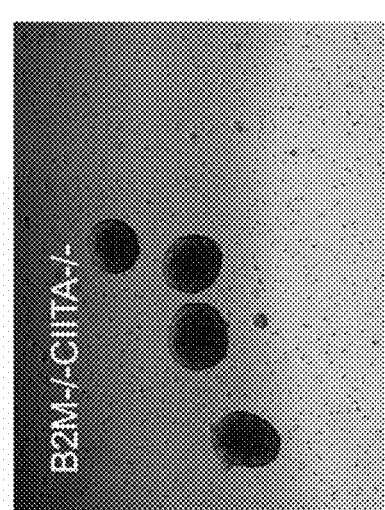
Merge
RFP
Bright field
HuES9-RFP
WT
B2M-/-CIITA-/-
FIG. 28J 'Hypoimmunogenic' DKO Cell Lines Generated

| HuESO | MHC-I | MHC-II |
|---|---|---|
| WT | yes | yes |
| NLRC5-/- C2TA-/- | reduced | no |
| B2M-/- C2TA-/- | no | no |

FIG. 29A

CRISPR Targeting of B7-H3 in JEG-3 cells

GCTGACAGATACCAAACAGC (TGG)    SEQ ID NO: 818229

FIG. 30A

Screening of targeted B7-H3 colonies

CRISPR Cutting Efficiency: 15/80 => 18.7%
in JEG-3 cells

Confirmation of B7-H3 Knock-Outs through Sequencing

WT   CACAGCTCAACCTCATCTGGCACAGATACCAAACAGCTGGTGCACAGCTTT   SEQ ID NO: 818230

C11   Δ16   CACAGCTCAACCTNATCTGGCAG————————————————AGCTGGTGCACAGCTTT   SEQ ID NO: 818231

G6   Δ26   CACAGCTCAACCTCATCTGG————TG-C————————————ACAG————————TTT   SEQ ID NO: 818232

293T cells, 12-wells, 48 h post-transfection

B2M C1 and C2 Cpf1 crRNAs bind to first exon
B2M C3 binds to first intron

C1 sequence: [TTTA]ATAAAGTGGAGGCGTCGCG
                    SEQ ID NO: 818239

C2 sequence: [TTTC]TGGCCTGGAGGCTATCCAGC
                    SEQ ID NO: 818240

C3 sequence: [TTTA]ATGTTATGAAAAAATCAGG
                    SEQ ID NO: 818241

Surveyor assay:
C1 expected bands: 50 and 450 bp
C2 expected bands: 150 and 350 bp
C3 expected bands: 125 and 375 bp

Cpf1 cuts - Surveyor

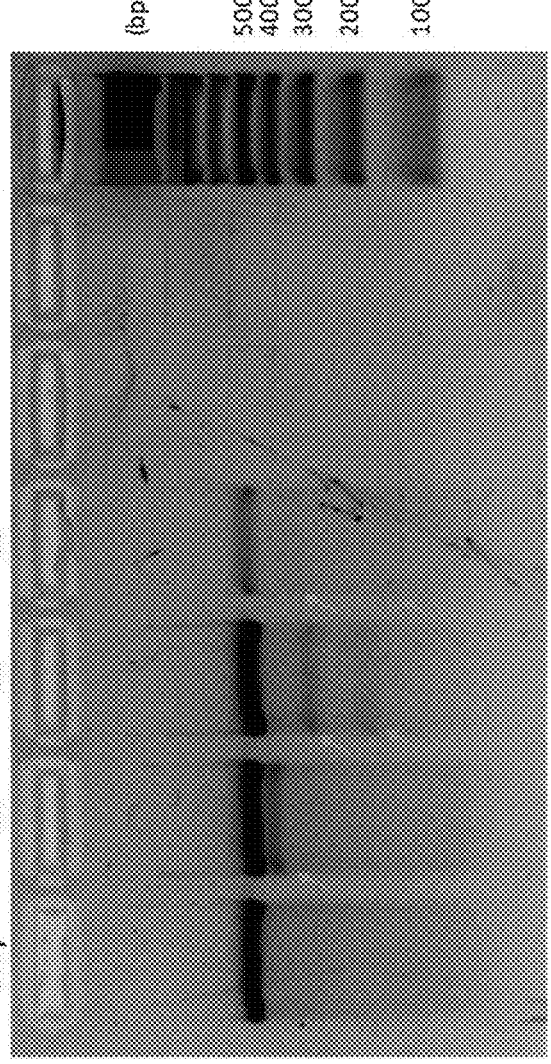

Blue arrows indicate Surveyor nuclease cleavage bands

FIG. 36

Cpf1 crRNA design and cloning

Express guides (crRNAs) as U6 promoter-direct repeat seq – 20 nt guide PCR product1

Fw primer (binding U6 promoter)

GAGGGCCTATTTCCCATGATTCCT    (24 nt)    (SEQ ID NO: 42546)

Rev primers: rev comp target seq (20 nt)-rev comp direct repeat seq-rev comp end U6 P Rev primer example: AsCpf1 DNMT1 GUIDE 4 (63 nt)

CCTTTATTTAGCTGAAGTGAAAAGTGAGAAGTGTGAAATAGGATTTTGGCTTTCTCAATTCCACAAG (SEQ ID NO: 42547)

Cells transfected with Cpf1 DNA (either As or Lb) and crRNA PCR product generated using Lentiguide-puro plasmid as template (for hU6 promoter) and guide specific reverse primers

FIG. 39

Design of B2M TALEN and induced mutations

Primary human
T Cells

CD3 surface expression

UNIVERSAL DONOR STEM CELLS AND RELATED METHODS

CROSS-REFERENCE TO RELATED APPLICATIONS

This application is a continuation application of U.S. application Ser. No. 17/993,674, filed Nov. 23, 2022, which is a continuation application of U.S. application Ser. No. 17/148,556, (now U.S. Pat. No. 11,618,881), filed Jan. 13, 2021, which is a divisional application of U.S. application Ser. No. 15/572,776, (now U.S. Pat. No. 10,968,426), filed Nov. 8, 2017, which is a national stage filing under 35 U.S.C. 371 of International Application No. PCT/US2016/031551, filed May 9, 2016, which claims the benefit of U.S. Provisional Application No. 62/158,999, filed on May 8, 2015, the contents of which are hereby incorporated by reference in their entirety. International Application No. PCT/US2016/031551 was published under PCT Article 21 (2) in English.

SEQUENCE LISTING

The Sequence Listing associated with this application is provided in .xml format on compact disk in lieu of a paper copy and is hereby incorporated by reference into the specification. The name of the .xml file containing the Sequence Listing is HRVY-073-306X.XML. The xml file is 1,040,736,512 bytes in size and was created on May 17, 2023.

BACKGROUND OF THE INVENTION

Degenerative diseases pose a disproportionate threat to human health. Often age-related, these diseases result in the progressive deterioration of affected tissues and organs and, ultimately, disability and death of the affected subject. The promise of regenerative medicine is to replace diseased or missing cells with new healthy cells. Over the past five years, a new paradigm for regenerative medicine has emerged—the use of human pluripotent stem cells (hPSCs) to generate any adult cell type for transplantation into patients. In principle, hPSC-based cell therapies have the potential to treat most if not all degenerative illnesses, however the success of such therapies may be limited by a subject's immune response.

Strategies that have been considered to overcome the immune rejection include HLA-matching (e.g. identical twin or umbilical cord banking), the administration of immunosuppressive drugs to the subject, blocking antibodies, bone marrow suppression/mixed chimerism, HLA-matched stem cell repositories and autologous stem cell therapy. Needed are novel approaches, compositions and methods for overcoming immune rejection associated with cell replacement therapies.

SUMMARY OF THE INVENTION

Disclosed herein are efficient strategies to overcome immune rejection in cell-based transplantation therapies by the creation of universal donor stem cell lines that, as quality-controlled cell-based products, will form the base for regenerative cell therapies.

The present inventors have successfully employed genome editing tools such as a TALEN and/or CRISPR system in human pluripotent stem cells to reduce expression or knock out the highly polymorphic classical MHC-I genes (HLA-A, HLA-B and HLA-C) and/or MHC-II genes. In certain aspects, such reduced expression or knock out of the MHC-I and/or MHC-II genes is accomplished by directly and/or indirectly targeting the NLRC5, B2M and CIITA genes and other components of the MHC enhanceosome (e.g., transcriptional regulators of MHC-I or MHC-II).

Disclosed herein are methods of preparing hypoimmunogenic stem cells, the method comprising modulating expression of one or more MHC-I and MHC-II human leukocyte antigens by the stem cell and thereby preparing the hypoimmunogenic stem cell. Also disclosed are methods of modulating expression of one or more MHC-I and MHC-II human leukocyte antigens by a stem cell, comprising deleting one or more genes encoding one or more transcriptional regulators of MHC-I or MHC-II from at least one allele of the cell and thereby modulating expression of the one or more MHC-I and MHC-II human leukocyte antigens.

In certain aspects, modulating expression of the one or more MHC-I and MHC-II human leukocyte antigens comprises reducing, inhibiting and/or interfering with the expression of the one or more MHC-I and MHC-II human leukocyte antigens. In certain embodiments, modulating expression of the one or more MHC-I and MHC-II human leukocyte antigens comprises deleting one or more genes encoding one or more transcriptional regulators of MHC-I or MHC-II from at least one allele of the cell. For example, in certain embodiments such methods comprise deleting one or more genes encoding one or more of the transcriptional regulators of MHC-I or MHC-II selected from the group consisting of NLRC5, CIITA, B2M and combinations thereof.

In certain aspects, the methods disclosed herein further comprise modulating expression of one or more tolerogenic factors by the stem cell. Modulating expression of the tolerogenic factors may comprises increasing the expression of the tolerogenic factors. Such tolerogenic factors may be inserted into a safe harbor locus (e.g., the AAVS1 locus) of at least one allele of the cell. In certain embodiments, such tolerogenic factors inhibit immune rejection. In certain embodiments, such tolerogenic factors are selected from the group consisting of HLA-C, HLA-E, HLA-G, PD-L1, CTLA-4-Ig, CD47, C1-inhibitor, and IL-35.

Also disclosed herein are methods of preparing a hypoimmunogenic stem cell, the method comprising modulating expression of one or more tolerogenic factors by the stem cell and thereby preparing the hypoimmunogenic stem cell. In certain embodiments, modulating expression of the tolerogenic factors comprises increasing the expression of the tolerogenic factors. Such tolerogenic factors may be inserted into a safe harbor locus (e.g., the AAVS1 locus) of at least one allele of the cell. In certain embodiments, such tolerogenic factors are selected from the group consisting of HLA-C, HLA-E, HLA-G, PD-L1, CTLA-4-Ig, CD47, C1-inhibitor, and IL-35. In certain embodiments, such tolerogenic factors inhibit immune rejection of the stem cell or of a differentiated stem cell prepared therefrom.

In certain aspects, the methods disclosed further comprise modulating expression of one or more MHC-I and MHC-II human leukocyte antigens by the cell, for example, by deleting one or more genes encoding one or more transcriptional regulators of MHC-I or MHC-II from at least one allele of the cell. In certain embodiments, transcriptional regulators of MHC-I or MHC-II from are selected from the group consisting of NLRC5, CIITA, B2M and combinations thereof.

Also disclosed herein are human stem cells that do not express NLRC5 (e.g., a NLRC5−/− knockout mutant stem cell). Similarly, also disclosed are human stem cells that do not express CIITA (e.g., a CIITA–/– knockout mutant stem cell). Also disclosed are human stem cells that do not express B2M (e.g., a B2M–/– knockout mutant stem cell). In certain embodiments, also provided are human stem cells that do not express one or more of NLRC5, CIITA and B2M. In still other embodiments, also disclosed are human stem cells that do not express one or more of HLA-A, HLA-B and HLA-C.

In certain embodiments, the stem cells disclosed herein expresses one or more tolerogenic factors (e.g., one or more tolerogenic factors that inhibit immune rejection). In certain aspects, such tolerogenic factors are inserted into a safe harbor locus (e.g., the AAVS1 locus) of at least one allele of the cell. In certain embodiments, the tolerogenic factors are selected from the group consisting of HLA-C, HLA-E, HLA-G, PD-L1, CTLA-4-Ig, CD47, C1-inhibitor, and IL-35.

In some embodiments, the cell is an embryonic stem cell. In certain embodiments, the cell is a pluripotent stem cell. In certain embodiments, the stem cell is hypoimmunogenic.

In some embodiments, the cell has reduced MHC-I expression relative to the original genotype or relative to a wild-type human stem cell. In certain embodiments, the cell has reduced MHC-II expression relative to the original genotype or relative to a wild-type human stem cell. For example, such cells may have reduced expression of one or more of HLA-A, HLA-B and HLA-C relative to the original genotype or relative to a wild-type human stem cell.

Also disclosed herein are human stem cells that have been altered such that they comprise one or more tolerogenic factors inserted into a safe harbor locus (e.g., the AAVS1 locus) of at least one allele of the cell. In certain embodiments, such tolerogenic factors inhibit immune rejection. In certain embodiments, the tolerogenic factors are selected from the group consisting of HLA-C, HLA-E, HLA-G, PD-L1, CTLA-4-Ig, CD47, C1-inhibitor, and IL-35. In certain aspects, such cells do not express one or more of NLRC5, CIITA and B2M. In certain aspects, such cells do not express one or more of HLA-A, HLA-B and HLA-C. In certain embodiments, such cells have reduced expression of one or more of HLA-A, HLA-B and HLA-C relative to a wild-type human stem cell.

Also disclosed herein are methods of using the hypoimmunogenic cells disclosed herein for cell replacement therapy. For example, the universal stem cells disclosed herein may be incubated under appropriate conditions and differentiated into hypoimmunogenic cardiomyocytes, endothelial cells, hepatocytes or pancreatic beta cells.

Also disclosed herein are methods for producing hypoimmunogenic stem cells, the method comprising contacting a stem cell with a Cas protein or a nucleic acid sequence encoding the Cas protein and a first pair of ribonucleic acids having sequences selected from the group consisting of SEQ ID NOs: 36353-81239, thereby editing the NLRC5 gene to reduce or eliminate NLRC5 surface expression and/or activity in the cell.

Also disclosed are methods for producing hypoimmunogenic stem cells, the method comprising contacting a stem cell with a Cas protein or a nucleic acid sequence encoding the Cas protein and a first pair of ribonucleic acids having sequences selected from the group consisting of SEQ ID NOs: 5184-36352, thereby editing the CIITA gene to reduce or eliminate CIITA surface expression and/or activity in the cell.

Also disclosed are methods for producing hypoimmunogenic stem cells, the method comprising contacting a stem cell with a Cas protein or a nucleic acid sequence encoding the Cas protein and a first pair of ribonucleic acids having sequences selected from the group consisting of SEQ ID NOs: 81240-85644, thereby editing the B2M gene to reduce or eliminate B2M surface expression and/or activity in the cell.

Also disclosed herein are methods for producing a hypoimmunogenic stem cell, the method comprising: (a) contacting a stem cell with a Cas protein or a nucleic acid sequence encoding the Cas protein and a first pair of ribonucleic acids having sequences selected from the group consisting of SEQ ID NOs: 36353-81239, thereby editing the NLRC5 gene to reduce or eliminate NLRC5 surface expression and/or activity in the cell; (b) contacting a stem cell with a Cas protein or a nucleic acid sequence encoding the Cas protein and a second pair of ribonucleic acids having sequences selected from the group consisting of SEQ ID NOs: 5184-36352, thereby editing the CIITA gene to reduce or eliminate CIITA surface expression and/or activity in the cell; and/or (c) contacting a stem cell with a Cas protein or a nucleic acid sequence encoding the Cas protein and a third pair of ribonucleic acids having sequences selected from the group consisting of SEQ ID NOs: 81240-85644, thereby editing the B2M gene to reduce or eliminate B2M surface expression and/or activity in the cell.

Also disclosed are methods for producing hypoimmunogenic stem cells, the method comprising contacting a stem cell with a Cas protein or a nucleic acid sequence encoding the Cas protein and a first ribonucleic acid having a sequence selected from the group consisting of SEQ ID NOs: 36353-81239, thereby editing the NLRC5 gene to reduce or eliminate NLRC5 surface expression and/or activity in the cell.

Also disclosed are methods for producing hypoimmunogenic stem cells, the method comprising contacting a stem cell with a Cas protein or a nucleic acid sequence encoding the Cas protein and a first ribonucleic acid having a sequence selected from the group consisting of SEQ ID NOs: 5184-36352, thereby editing the CIITA gene to reduce or eliminate CIITA surface expression and/or activity in the cell.

Also disclosed are methods for producing hypoimmunogenic stem cells, the method comprising contacting a stem cell with a Cas protein or a nucleic acid sequence encoding the Cas protein and a first ribonucleic acid having a sequence selected from the group consisting of SEQ ID NOs: 81240-85644, thereby editing the B2M gene to reduce or eliminate B2M surface expression and/or activity in the cell.

Also disclosed herein are methods for producing hypoimmunogenic stem cells, the method comprising: (a) contacting a stem cell with a Cas protein or a nucleic acid sequence encoding the Cas protein and a first ribonucleic acid having a sequence selected from the group consisting of SEQ ID NOs: 36353-81239, thereby editing the NLRC5 gene to reduce or eliminate NLRC5 surface expression and/or activity in the cell; (b) contacting a stem cell with a Cas protein or a nucleic acid sequence encoding the Cas protein and a second ribonucleic acid having a sequence selected from the group consisting of SEQ ID NOs: 5184-36352, thereby editing the CIITA gene to reduce or eliminate CIITA surface expression and/or activity in the cell; and/or (c) contacting a stem cell with a Cas protein or a nucleic acid sequence encoding the Cas protein and a third ribonucleic acid having a sequence selected from the group consisting of SEQ ID NOs: 81240-85644, thereby editing the B2M gene to reduce or eliminate B2M surface expression and/or activity in the cell.

Also disclosed herein are hypoimmunogenic stem cells comprising a modified genome comprising a first genomic modification in which the NLRC5 gene has been edited to reduce or eliminate NLRC5 surface expression and/or activity in the cell by contacting the cell with a Cas protein or a nucleic acid encoding a Cas protein and a ribonucleic acid having a sequence selected from the group consisting of SEQ ID NOs: 36353-81239.

Also disclosed are hypoimmunogenic stem cells comprising a modified genome comprising a first genomic modification in which the CIITA gene has been edited to reduce or eliminate CIITA surface expression and/or activity in the cell by contacting the cell with a Cas protein or a nucleic acid encoding a Cas protein and a ribonucleic acid having a sequence selected from the group consisting of SEQ ID NOs: 5184-36352.

Also disclosed are hypoimmunogenic stem cells comprising a modified genome comprising a first genomic modification in which the B2M gene has been edited to reduce or eliminate B2M surface expression and/or activity in the cell by contacting the cell with a Cas protein or a nucleic acid encoding a Cas protein and a ribonucleic acid having a sequence selected from the group consisting of SEQ ID NOs: 81240-85644.

Also disclosed herein are hypoimmunogenic stem cells comprising a modified genome comprising: (a) a first genomic modification in which the NLRC5 gene has been edited to reduce or eliminate NLRC5 surface expression and/or activity in the cell by contacting the cell with a Cas protein or a nucleic acid encoding a Cas protein and a ribonucleic acid having a sequence selected from the group consisting of SEQ ID NOs: 36353-81239; (b) a second genomic modification in which the CIITA gene has been edited to reduce or eliminate CIITA surface expression and/or activity in the cell by contacting the cell with a Cas protein or a nucleic acid encoding a Cas protein and a ribonucleic acid having a sequence selected from the group consisting of SEQ ID NOs: 5184-36352; and/or (c) a third genomic modification in which the B2M gene has been edited to reduce or eliminate B2M surface expression and/or activity in the cell by contacting the cell with a Cas protein or a nucleic acid encoding a Cas protein and a ribonucleic acid having a sequence selected from the group consisting of SEQ ID NOs: 81240-85644.

Also disclosed are hypoimmunogenic stem cells comprising a modified genome comprising a first genomic modification in which the NLRC5 gene has been edited to delete a first contiguous stretch of genomic DNA, thereby reducing or eliminating NLRC5 surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 36353-81239.

Also disclosed are hypoimmunogenic stem cells comprising a modified genome comprising a first genomic modification in which the CIITA gene has been edited to delete a first contiguous stretch of genomic DNA, thereby reducing or eliminating CIITA surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 5184-36352.

Also disclosed are hypoimmunogenic stem cells comprising a modified genome comprising a first genomic modification in which the B2M gene has been edited to delete a first contiguous stretch of genomic DNA, thereby reducing or eliminating B2M surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 81240-85644.

Also disclosed herein are hypoimmunogenic stem cells comprising a modified genome comprising: (a) a first genomic modification in which the NLRC5 gene has been edited to delete a first contiguous stretch of genomic DNA, thereby reducing or eliminating NLRC5 surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 36353-81239; (b) a second genomic modification in which the CIITA gene has been edited to delete a first contiguous stretch of genomic DNA, thereby reducing or eliminating CIITA surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 5184-36352; and/or (c) a third genomic modification in which the B2M gene has been edited to delete a first contiguous stretch of genomic DNA, thereby reducing or eliminating B2M surface expression and/or activity in the cell, wherein the first contiguous stretch of genomic DNA has been deleted by contacting the cell with a Cas protein or a nucleic acid encoding a Cas protein and a first pair of ribonucleic acids having sequences selected from the group consisting of SEQ ID NOs: 81240-85644.

The above discussed, and many other features and attendant advantages of the present inventions will become better understood by reference to the following detailed description of the invention.

BRIEF DESCRIPTION OF THE DRAWINGS

FIG. 2A graphically illustrates MHC-I and MHC-II surface molecules that define donor compatibility during organ transplant. FIG. 2B illustrates the HLA region 6p21.1-21.3.

FIG. 3A illustrates a model of the MHC-II enhanceosome. FIG. 3B depicts a model of the NLRC5 enhanceosome at the MHC-I promoter.

FIG. 5A depicts a time line of macrophage differentiation.

FIG. 5B shows a bright-field image of stem cell-derived macrophages on day 5 of M-CSF medium. FIG. 5C shows MHC-II expression in induced macrophages, as assessed by qPCR 48 hrs. post stimulation with IFNγ, and evidences reduced MHC-II expression relative to wild-type cells. As illustrated in FIG. 5C, MHC-II expression can be efficiently abrogated by targeting the first coding exon of the CIITA gene depicted in FIGS. 10A-10B.

FIGS. 8A and 8B illustrate immunostaining of teratoma-infiltrating CD3+ lymphocytes. FIG. 8C illustrates co-staining of CD8 and Ki67, which is a proliferation marker, and highlights proliferating CD8+ T cells (white arrows). Nuclear DAPI staining is shown in blue.

FIG. 9A illustrates the NLRC5 locus. FIG. 9B shows targeting of the NLRC5 locus to abrogate NLRC5 expression. FIGS. 9C-9D illustrate reduced MHC-I expression in NLTC5$^{-/-}$ HLCs.

FIG. 10A depicts the CIITA locus. FIG. 10B shows the targeting of the CIITA locus to abrogate MHC-II expression.

FIG. 12 shows an exemplary amino acid sequence of a Cas protein. Yellow highlights indicate Ruv-C-like domain. Underlining indicates HNH nuclease domain.

FIG. 14A depicts an HLA-B and HLA-C knock-out strategy. Two short guide RNAs (sgRNAs) were designed upstream of the HLA-B locus and downstream of HLA-C, which allow excision of the HLA-B and HLA-C genes. sgRNA #1 and sgRNA #2 target the HLA-B upstream region, and sgRNA #3 and sgRNA #4 target HLA-C the downstream region. FIG. 14B shows that PCR screening confirms clone 1D as a homozygous knock-out clone. FIG. 14B includes a schematic showing the PCR verification strategy for successful deletion of HLA-B and HLA-C. Two pairs of wild-type (WT) primers were designed flanking each cutting site, with predicted amplicon sizes of 545 bp and 472 bp. Clone 1D was identified as a homozygous knock-out clone by the presence of about 680 bp PCR band generated with KO primers and the absence of bands using the two different sets of WT primers. Genomic DNA was isolated from the indicated targeted HuES8 clones. FIG. 14C provides a schematic showing sequence confirmation of HLA-B, HLA-C deletion in 1D KO clone. The sequencing results of 1D PCR product demonstrated successful deletion of HLA-B and HLA-C genes in HuES8. FIG. 14D shows that RT-PCR confirms the loss of HLA-B and HLA-C mRNA expression in HuES8 cells. RT-PCR with HLA-B and HLA-C specific primers demonstrated the mRNA expressions of HLA-B and HLA-C in clone 1D are eliminated. GAPDH, TOP1 and HPRT1 were used as internal controls. FIG. 14E provides a schematic showing sequence confirmation of HLA-B RT-PCR bands obtained from WT and clone 1D. WT and 1D RT-PCR products amplified with HLA-B primers were sequenced and identified as HLA-B and HLA-A mRNAs, respectively using BLAST. These results demonstrated that in the absence of the HLA-B gene, the HLA-B specific primers will amplify HLA-A mRNA in HuES8 clone 1D. FIG. 14F shows the karyotyping of HuES8 clone 1D by NanoString nCounter. HuES8 clone 1D displays a normal karyotype as assessed by NanoString nCounter set. FIG. 14G provides a schematic showing HLA-A knockout strategy using the dual sgRNA approach. The schematic shows the positions of the two sgRNAs (sgRNA #5 and sgRNA #6) that were designed to bind upstream and downstream of HLA-A. FIG. 14H shows the on-target cutting efficiency of HLA-A sgRNA using TIDE. The cutting efficiency of sgRNA #5 and sgRNA #6 was determined in 293T cells using TIDE. FIG. 14I demonstrates that PCR screening confirmed clone 4E as a heterozygous HLA-A knockout clone. PCR screening strategy confirmed deletion of HLA-A in HuES8. KO primers were designed with one primer annealing upstream and one primer annealing downstream of the cutting sites. Upon HLA-A deletion, the resulting amplicon is observed as 220 bp on a 2% agarose gel. Two pairs of WT primers were designed flanking each cutting site, with predicted amplicons sizes of 589 bp and 571 bp. Clone 4E was identified as heterozygous clone due to the presence of bands generated with KO primers and WT primers amplified from genomic DNA. FIG. 14J includes a schematic showing that sequencing confirms successful deletion of HLA-A in HuES8 cells. Sequencing of the PCR product amplified from genomic DNA of clone 4E using KO primers demonstrates successful deletion of HLA-A in HuES8.

Figure 15A:
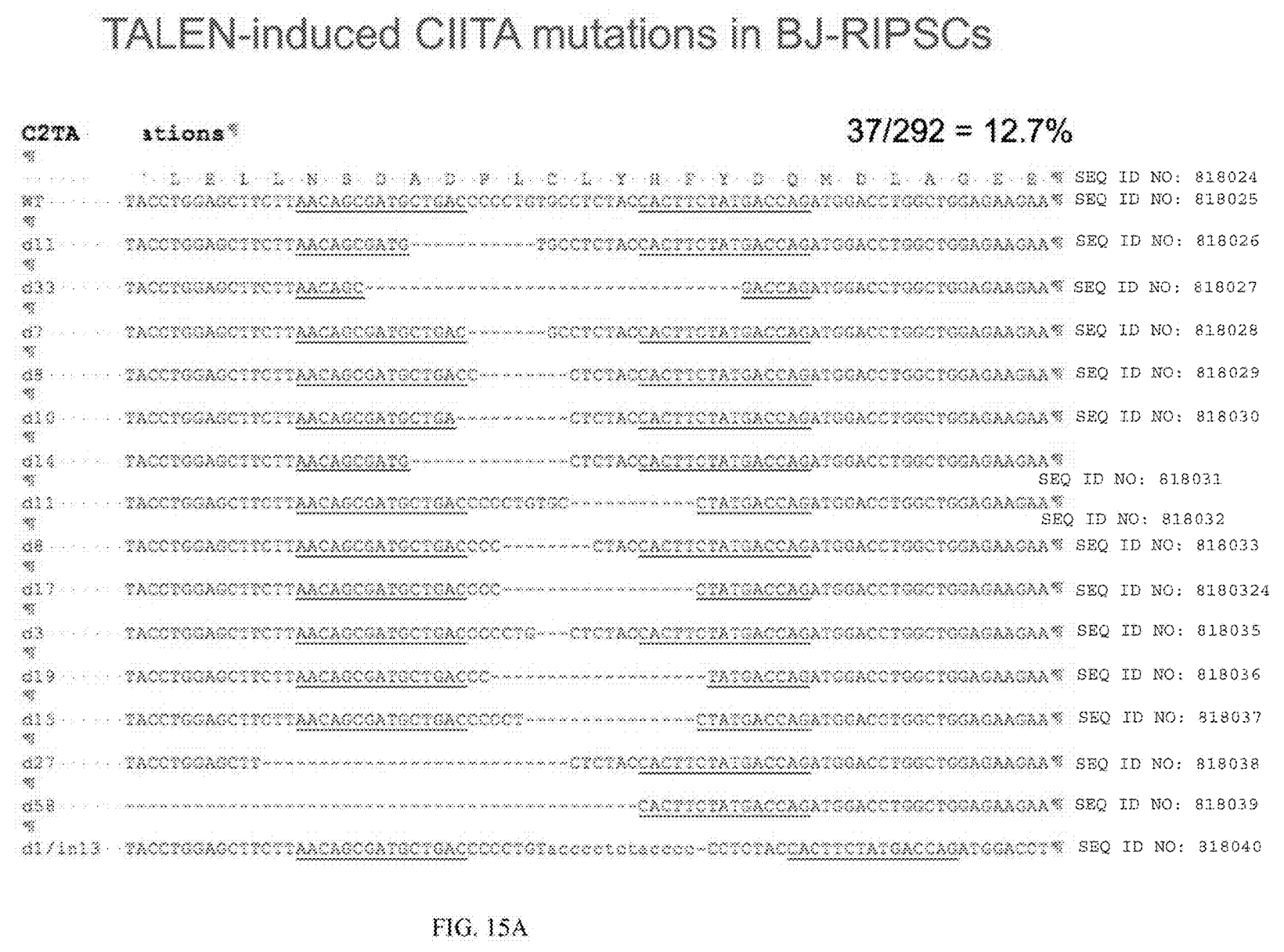
Figure 15B:
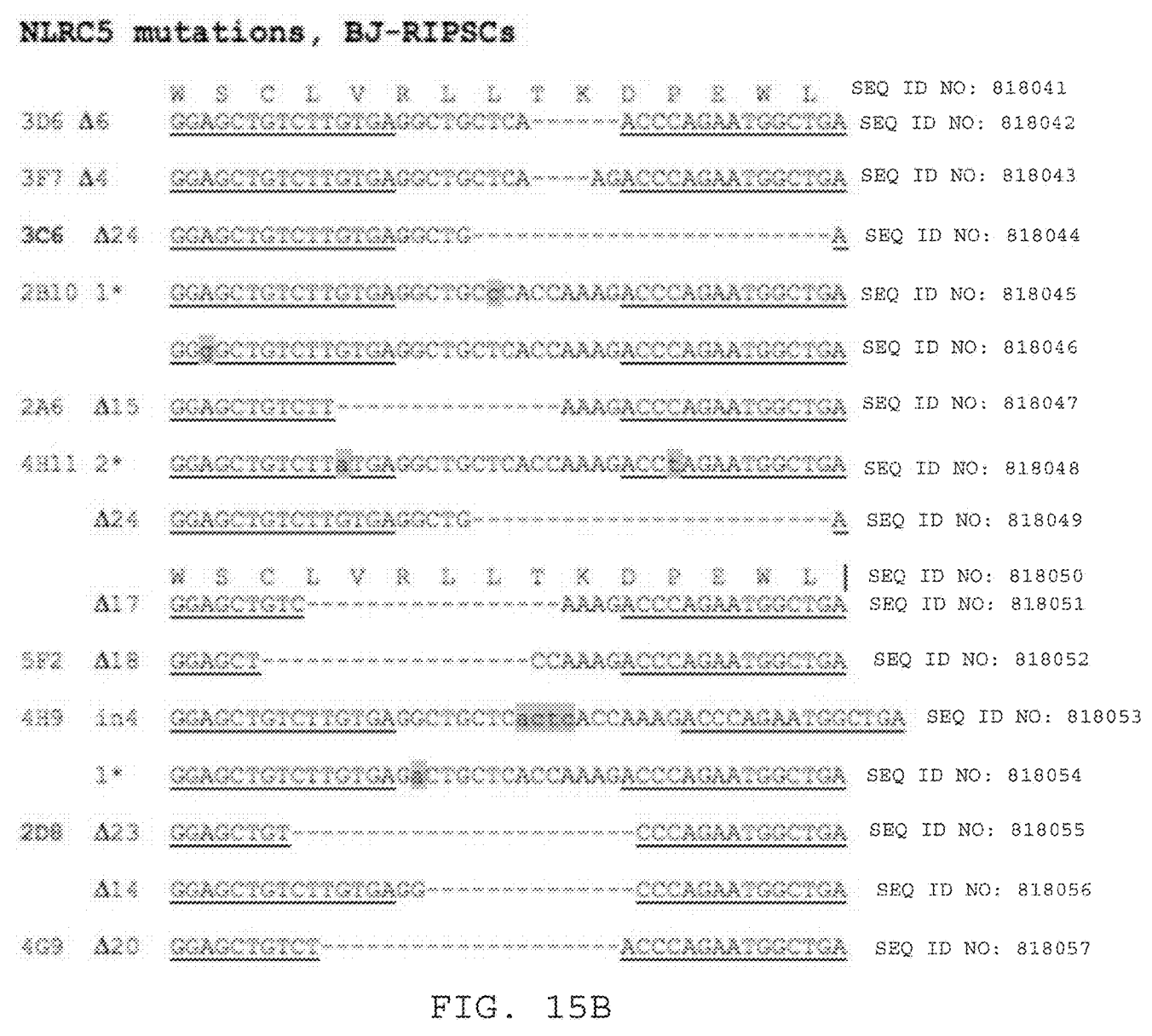
Figure 15D:
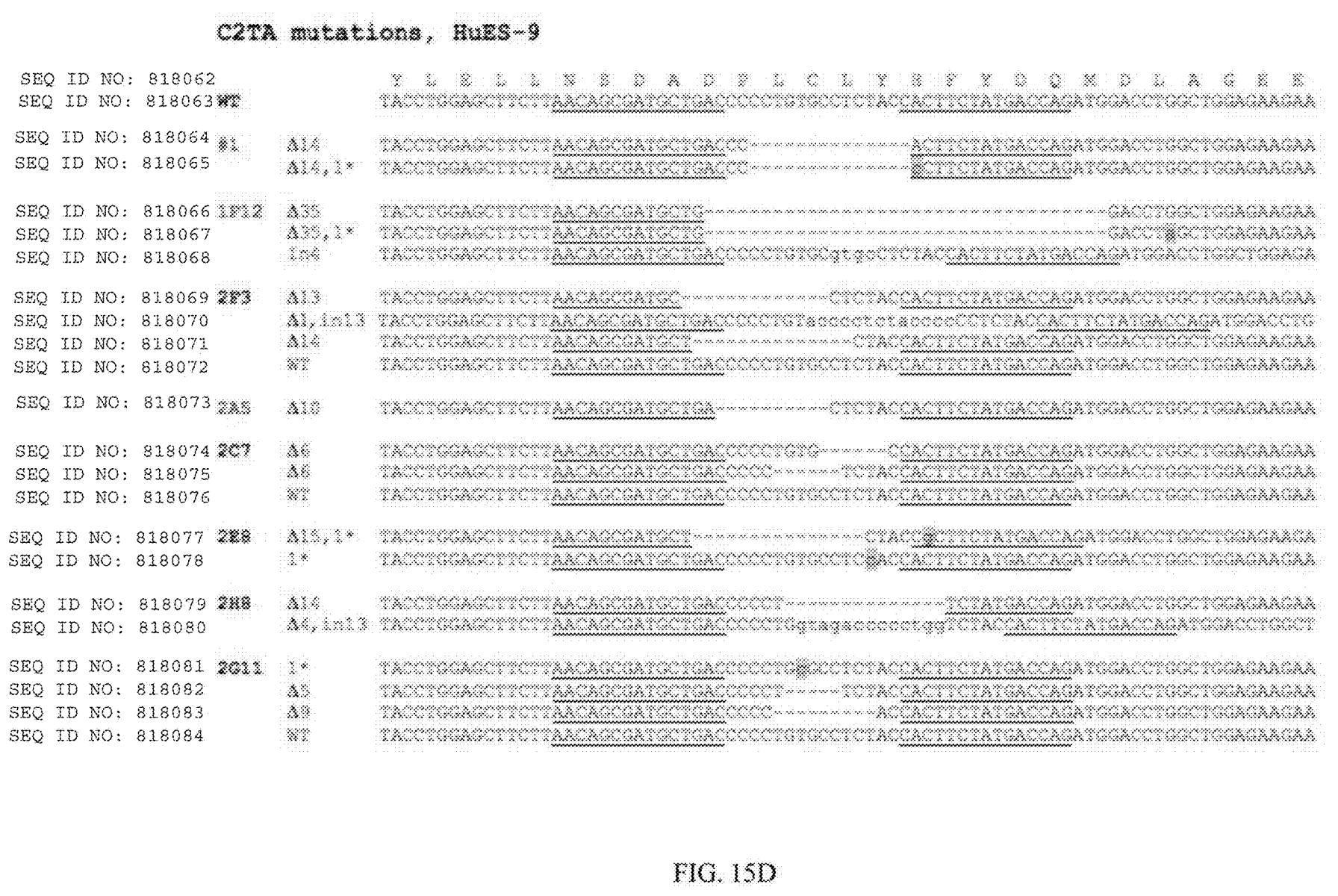

FIGS. 15A-15D show TALEN-induced CIITA and NLRC5 mutations in BJ-RIPSCs and HuES9 cells. FIG. 15A provides a schematic of TALEN-induced CIITA mutations in BJ-RIPSCs. FIG. 15B provides a schematic of TALEN-induced NLRC5 mutations in BJ-RIPSCs. FIG. 15C provides a schematic of TALEN-induced NLRC5 mutations in HuES9s. FIG. 15D provides a schematic of TALEN-induced CIITA mutations in HuES9s.

FIGS. 16A-16G demonstrate targeting of NLRC5 and CIITA utilizing a CRISPR system to achieve a reduction in MHC class I expression and complete loss of MHC class II expression. FIG. 16A shows reduced MHC-I expression in NLRC5-/- Thp1 cells, including a NLRC5 targeting strategy in Thp1 cells. The + indicates 48 hours of IFNγ stimulation. FIG. 16B provides schematics of multiple targeting strategies. FIG. 16B provides a schematic of targeting NLRC5 using CRISPR, a schematic of targeting B2M using CRISPR, a schematic of targeting CIITA using TALENs and a schematic of targeting CIITA using CRISPR. FIG. 16C shows reduced MHC class I expression in HuES9 cells following targeting with NLRC5 or B2M CRISPRs. The graph shows low basal MHC-I expression in stem cells. The MHC-I expression can be increased by IFNγ stimulation. About a 50% reduction of MHC-I expression occurs in IFNγ-treated NLRC5-/- cells. A complete loss of MHC-I surface expression is shown in B2M-/- cells. FIG. 15D shows a lentiviral transduction of Thp-1. A dual-vector lentiviral GeCKO system is used. The two component system includes *Lenti*-Cas9-Blasticidin, which acts to establish stable Thp-1 Cas9 cell line, and *Lenti*-Guide-puro, which acts to bring in the guide. FIG. 16E identifies various CRISPRs used for the lentiviral transduction of Thp-1. CRISPRs targeting CIITA, NLRC5 and IRF1 are provided. FIG. 16F shows that CIITA and NLRC5 act independently on MHC-II and MHC-I, respectively. Thp1 was transduced with lentivirus encoding NLRC5 and CIITA. A B2M CRISPR is used as a positive control. All cells were stimulated ON with 50 U IFNγ to boost HLA expression. HLA-A2 1:200; DR 1:100. FIG. 16G shows targeting of IRF1 results in loss of MHC-II expression. Thp1, 10 days post CRISPR transduction. All cells were stimulated ON with 50 U IFNγ. HLA-A2 1:200; DR 1:100.

FIGS. 17A-17K demonstrate targeting of IRF1 utilizing a CRISPR system to achieve reduced MHC class I expression in human pluripotent stem cells (HuES9) and Thp-1 cells. FIG. 17A shows a dual CRISPR strategy targeting the IRF1 locus. Three different CRISPRs are identified. FIG. 17B demonstrates the testing of different IRF1 guide combinations. Screening results of different guide combinations are provided. FIG. 17C demonstrates a 'dual guide strategy' for the targeted deletion of IRF1. Screening results of the dual guide strategy are provided. FIG. 17D provides a schematic showing sequence confirmation of IRF-1 CRISPR induced deletion. FIG. 17E provides the screening results of IRF-1 targeted HuES9 cells. The screening is of a dual CRISPR strategy using CRISPRs #2 and #3. The presence of the PCR band suggests successful targeting. FIG. 17F demonstrated reconfirmation of IRF-1 clones. Screening results using primers KYM07 and TM377 are provided. FIG. 17G demonstrates genotypes of IRF-1 clones. Screening results are provided. FIG. 17H provides a schematic showing sequence confirmation of IRF-1 CRISPR induced deletion in clone 12. FIG. 17I provides a schematic showing sequence confirmation of IRF-1 CRISPR induced deletion in clone 17. FIG. 17J provides a schematic showing sequence confirmation of IRF-1 CRISPR induced deletion in clone 21. FIG. 17K shows impaired MHC class I induction in IRF1−/− HuES9 clones following IFNγ treatment. P42 are WT; C7 are B2M KO; + identifies 48 hours IFNγ treatment.

FIGS. 18A-18H demonstrate targeting of RFX5, RFX-ANK and RFX-AP in 293T cells utilizing CRISPR results in reduced MHC class I expression. FIG. 18A demonstrates dual guide targeting of RFX5 in 293T cells. Combinations of four different CRISPRs were examined. FIG. 18B shows that the targeting of RFX5 results in reduced MHC class I expression. FIG. 18C demonstrates dual guide targeting of RFX-ANK in 293T cells. Combinations of four different CRISPRs were examined. FIG. 18D shows that the targeting of RFX-ANK results in reduced MHC class I expression. FIG. 18E shows that targeting RFX5 and RFX-ANK results in reduced MHC class I expression. FIG. 18F provides a bar graph showing that targeting RFX5 and RFX-ANK results in reduced MHC class I expression. FIG. 18G demonstrates dual guide targeting of RFX-AP in 293T cells. Combinations of four different CRISPRs were examined. FIG. 18H shows that the targeting of RFX-AP results in reduced MHC class I expression.

FIGS. 19A-19E demonstrate targeting of NFY-A, NFY-B and NFY-C utilizing CRISPR results in reduced MHC class I expression. FIG. 19A demonstrates dual guide targeting of NFY-A in 293T cells. Combinations of four different CRISPRs were examined. FIG. 19B demonstrates dual guide targeting of NFY-C in 293T cells. Combinations of four different CRISPRs were examined. FIG. 19C shows that the targeting of NFY-C and NFY-A results in reduced MHC class I expression. FIG. 19D demonstrates dual guide targeting of NFY-B in 293T cells. Combinations of four different CRISPRS were examined. FIG. 19E shows that the targeting of NFY-B results in reduced MHC class I expression.

FIGS. 20A-20D show that surface trafficking of MHC class I molecules can be suppressed by disrupting the TAP1 gene, an ER-resident peptide transporter. FIG. 20A shows TAP1 CRISPR expression reduces MHC-I surface expression in Jurkat T cells. Combinations of four different CRISPRs was examined. FIG. 20B demonstrates TAP1 CRISPR expression reduces MHC-I surface expression in Jurkat T cells. FIG. 20C demonstrates eliminating HLA surface expression in Jurkat (Cas9) T cells. The Jurkat cell line was established from the peripheral blood of a 14 year old having acute T cell leukemia by Schneider et al. FIG. 20D shows eliminating HLA surface expression in Jurkat (Cas9) T cells. The cells were treated with IFNγ for 48 hours.

FIG. 21A provides a schematic showing the targeting of a conserved sequence found in all HLAs by CRISPR or TALENs using an HLA Razor. The two violet boxes indicate the binding sites for the panHLA TALEN pair. The blue arrow indicates the pan-HLA CRISPR tested; the PAM is boxed in blue. FIG. 21B shows the expression of pan-HLA TALENs in 293T and HuES9 cells 72 hours post transfection. FIG. 21C shows HLA-Razor CRISPR blunts MHC class I expression. The 293T cells were co-transfected with Cas9-GFP. The results are shown 72 hours post transfection. FIG. 21D provides a schematic showing a comparison of the activity of two different HLA Razors. Two HLA Razor guides are identified.

FIGS. 22A-22F show the results of a PD-L1 and HLA-G knock-in strategy. FIG. 22A provides a schematic showing PD-L1 and HLA-G knock-in strategy. WT primers and knock-in (KI) primers for clone screening were designed. The amplicon with WT primers is predicted as 488 bp, and the amplicons with KI primers are predicted as 403 bp and 915 bp. FIG. 22B depicts the design of the knock-in donor plasmid. The design of the knock-in donor plasmid shows that the reading frames of PD-L1 and HLA-G are linked by T2A and their expression is driven by a CAGGS promoter. Puromycin was used as a drug resistance marker following the SA-2A gene trap element. FIG. 22C demonstrates ectopic PD-L1 and HLA-G expression in 293T cells. The expression of PD-L1 and HLA-G were examined in the donor plasmid-transfected 293T cells by FACS analysis. APC-conjugated PD-L1 antibody and FITC-conjugated HLA-G antibody were used. FIG. 22D shows ectopic HLA-G expression in JEG-3 cells. Donor plasmid was transfected into an HLA-G−/− JEG-3 cell line, and ectopic HLA-G expression was examined by FACS analysis 48 hours post-transfection. A PE-conjugated HLA-G antibody (MEM/G9) was used to detect surface HLA-G surface expression. FIG. 22E provides PCR screening results that confirm clone 1G as a heterozygous KI clone for PD-L1/HLA-G. Clone 1G was identified as a heterozygous KI clone by the presence of bands using both WT primers and KI-specific primers amplified from genomic DNA of targeted HuES8 cells. FIG. 22F shows stable PD-L1 and HLA-G expression from a safe harbor locus in HuES8. The expression of PD-L1 was verified in HuES8 KI clone 1G by FACS analysis using an APC-conjugated PD-L1 antibody.

FIG. 24 demonstrates that deletion of TRAC and TRBC in HuES9 disrupts TCR expression. A dual guide RNA approach was used to introduce deletions into the TRAC and TRBC loci in HuES9 cells. TCRA wt band is 249 bp, and is 209 bp after deletion. TCRB wt band is 162 bp, and is 140 bp after deletion. Bands identified with a * are TCRB KO in HuES9 cells; bands identified with a  are TCRA KO in HuES9 cells; and bands identified with a * are TCRA KO in HuES9 B2M−/− CIITA−/− cells. TCRA KO in HuES9 B2M−/− CIITA−/− cells is a triple knock-out stem cell line for B2M−/−, CIITA−/− and TCR−/−. Upon differentiation into T cells this triple knock out stem cell line will be devoid of MHC-I, MHC-II and TCR surface expression.

FIGS. 25A-25D demonstrate targeting of CD274/B7-H1/PD-L1 in a variety of cell lines. FIG. 25A identifies an example of a CRISPR guide sequence that may be used when targeting CD274/B7-H1/PD-L1. CD274/B7-H1/PD-L1 knock out cell lines are identified. FIG. 25B shows the screening of targeted B7-H1 colonies in JEG-3 cells. The screening identified a CRISPR cutting efficiency of 22/265 or about 8.3%. FIG. 25C demonstrates the reconfirmation of 501 melanoma knock-out clones. FIG. 25D demonstrates the reconfirmation of MalMe melanoma knock-out clones.

FIG. 26A shows co-stimulatory/co-inhibitory molecules and their receptors on T cells. FIG. 26C demonstrates dual guide targeting of TIM3 in 293T cells. All four CRISPRs were found to work. FIG. 26H demonstrates dual guide targeting of B71 in 293T cells. CRISPRs #1, #3 and #4 were found to work. FIG. 26I demonstrates dual guide targeting of CD226 in 293T cells. CRISPRs #1 and #2 were found to work. FIG. 26J demonstrates dual guide targeting of CD2 in 293T cells. CRISPRs #1, #2 and #3 were found to work. FIG. 26K demonstrates dual guide targeting of LAG3 in 293T cells. CRISPRs #2 and #3 were found to work. FIG. 26P demonstrates dual guide targeting of GITR in 293T cells. CRISPRs #1 and #3 were found to work.

FIG. 27 depicts various cell lines tested and with which targets the cell lines were tested. HuES8 and HuES9 are human ES cell lines. BJ-RiPSCs is an iPSC line. All other enhanceosome components not shown in the table (e.g., RFX and NFY) were only tested in HEK293T cells.

FIGS. 28A-28J provides that modified ES cells can be differentiated into various different cell types with reduced or absent HLA expression. FIG. 28A provides that the modified ES call can be differentiated into Mesenchymal Progenitor Cells (MPCs), endothelial cells (ECs), macrophages, hepatocytes, beta-cells and neural progenitor cells (NPCs). FIG. 28B shows reduced MHC-I expression in NLRC5−/− human ES cells. There is low basal MHC-I expression in stem cells. The expression can be increased by IFNγ stimulation. About a 50% reduction in MHC-I expression occurs in IFNγ-treated NLRC5−/− cells. FIG. 28C shows reduced MHC-I expression in NLRC5−/− human mesenchymal progenitor cells (MPCs). A comparison is provided of HuES9 cells and MPCs. FIG. 28D shows reduced MHC-I expression in stem cell-derived NLRC5−/− endothelial cells (ECs). FIG. 28E demonstrates that ECs exhibit similar differentiation efficiency. FIG. 28F shows loss of HLA expression in B2M−/− CIITA−/− ECs. N=3, 48 hours of IFNγ treatment. FIG. 28G demonstrates reduced MHC class I expression in NLRC5−/− hepatocyte-like cells. A schematic is included demonstrating the targeting strategy and CRISPR design. The HLCs are derived from BJ-RiPSCs, day 7 of final hepatocyte differentiation. FIG. 28H demonstrates that mutation of CIITA abrogates MHC class II expression in hESC-derived macrophages. A schematic is included demonstrating the targeting strategy and CRISPR design. The HuES9-derived iMos, day 5 M-CSF. FIG. 28I shows neural progenitor cell (NPC) differentiation. B2M−/− CIITA−/− HuES9 form Nestin+ neural rosettes (white arrow). FIG. 28J demonstrates the adaptation of stem cells to spin culture for beta-cell differentiation. This is the first step in the beta-cell differentiation protocol.

FIG. 29A-29B provide in vivo data in a teratoma model. FIG. 29A provides that 'hypoimmunogenic' DKO cell lines were generated. The cell lines generated include WT HuES9, NLRC5−/− CIITA−/− HuES9 and B2M−/− CIITA−/− HuES9. The WT cell lines exhibited MHC-I and MHC-II expression. The NLRC5−/− CIITA−/− cells lines exhibited reduced MHC-I expression and no MHC-II expression. The B2M−/− CIITA−/− cell lines exhibited no MHC-I and MHC-II expression. FIG. 29B shows improved engraftment of genome-edited stem cells in humanized mice. The three cell lines tested were WT HuES9, NLRC5−/− CIITA−/− HuES9 and B2M−/− CIITA−/− HuES9.

FIGS. 30A-30D demonstrates CRISPR targeting of B7-H3 in JEG-3 cells. FIG. 30A provides a CRISPR guide sequence for targeting B7-H3. FIG. 30B shows a screening of targeted B7-H3 colonies in JEG-3 cells. The CRISPR cutting efficiency is shown to be 15/80 or about 18.7%. FIG. 30C shows confirmation of B7-H3 knock-outs through sequencing. FIG. 30D demonstrates loss of B7-H3 surface expression in targeted JEG3 clones.

FIG. 32A is a schematic of gRNAs targeting B2M. FIG. 32B is a histogram of B2M surface expression in HEK293T cells. FIG. 32C shows B2M deletion efficiency with various gRNAs in HEK293T cells; n=3 (mean±SEM). FIG. 32D is a schematic of gRNAs targeting CCR5. Orange and green arrows represent primer pairs used to amplify the region for analysis. FIG. 32E shows results of Surveyor assays of each gRNA targeting CCR5 in K562 cells. % InDels is indicated under each guide. FIG. 32F illustrates B2M deletion efficiency of selected gRNAs in primary CD4+ T cells in comparison to 293T cells; n=6 (mean±SEM). FIG. 32G shows results of surveyor assay of crCCR5_A and crCCR5_B targeting CCR5 in K562 cells and HSPCs. FIG. 32H illustrates clonal deletion efficiency of crCCR5_A and crCCR5_B targeting of CCR5 in HSPCs (n=2) as determined by Sanger sequencing. (Note: crB2M_14 is not depicted in panel A schematic, as it is located 20 Kb downstream of coding sequence.).

FIG. 33A shows B2M deletion efficiency for all gRNAs targeting B2M locus in HEK293T cells as measured by flow cytometry. Pooled data from 3 independent experiments shown as mean±SEM. FIG. 33B shows B2M deletion efficiencies of selected guides in HEK293T cells, measured as % InDels by CEL Surveyor assay. FIG. 33C is a comparison of B2M surface expression in HEK293T cells and primary CD4+ T cells when transfected with Cas9 and guide crB2M_13. FIG. 33D shows B2M deletion efficiency for selected guides targeting the B2M locus in primary CD4+ T-cells, as measured by flow cytometry. FIG. 33E shows B2M deletion efficiencies of selected guides in primary CD4+ T cells, measured as % InDels by CEL Surveyor assay.

FIG. 34A is a schematic of dual gRNA approach for targeting the B2M locus. gRNA pairs are in red. The offset in base pairs between Cas9 sites for each gRNA combination (right panel). FIG. 34B shows B2M deletion efficiency in CD4+ T cells for 6 dual gRNA combinations (n=3; mean±SEM). FIG. 34C is a FACS plots showing loss of B2M expression of either crB2M_13 or crB2M_8 alone or in combination in primary CD4+ T cells. FIG. 34D is a schematic of dual gRNA approach for targeting CCR5. gRNA pairs are shown in red. Orange and green arrowheads represent primer pairs used to amplify the region. The offset between the Cas9 sites of each gRNA pair (right panel). FIG. 34E is a gel electrophoresis image of CD34+ HSPCs derived clones targeted with crCCR5_D+Q analyzed by PCR. Note the deletion of the 205 bp region between the two gRNA cutting sites (top panel; WT: wild type; ΔCCR5: deleted; green * denotes a WT clone; orange * denotes a heterozygous clone; and red * denotes a homozygous deleted clone). Clonal deletion efficiency for three dual gRNA combinations targeting CCR5 in CD34+ HSPCs (n=4; % mean±SEM; bottom panel).

FIG. 35A shows B2M deletion efficiency for 6 dual gRNA combinations from three independent donors as measured by flow cytometry. FIG. 35B are FACS plots showing loss of MHC class I surface expression (bottom panel) following B2M deletion (top panel). FIG. 35C is a schematic of the single cell nested PCR strategy for the B2M locus (left panel), black and gray arrowheads: control primer pairs, orange and green arrowheads: primer pairs flanking targeting region. % B2M null single cells is shown (right panel, n=301). FIG. 35D is a Sanger sequencing chromatogram showing predicted deletion of targeted region at B2M locus. FIG. 35E shows clonal CCR5 deletion efficiency for three dual gRNA combinations in CD34+ HSPC-mPB obtained from multiple donors. DNA isolated from individual colony was analyzed by PCR and gel electrophoresis. FIG. 35F is a schematic of the single cell nested PCR strategy (left panel) for determining deletion of CCR5 in primary CD4+ T cells. % CCR5 null single cells is shown (right panel, n=363). FIG. 35G shows Sanger sequencing chromatogram shows predicted deletion at targeted region.

FIG. 36 demonstrates B2M deletion efficiencies of selected guides in 293T cells. Arrows on the Surveyor assays show nuclease cleavage bonds.

FIG. 39 depicts Cpf1 crRNA design and cloning information.

FIGS. 40A-40G demonstrate generation and characterization of B2M KO JEG3 cells using TALENs. FIG. 40A depicts a design of B2M TALEN and induced mutations. FIG. 40B depicts an analysis of B2M at the transcript and protein levels. FIG. 40C demonstrates an analysis of B2M at the surface expression level. FIG. 40D demonstrates that ΔB2M clones are devoid of MHC-I surface expression. FIG. 40E demonstrates that ΔB2M clones are devoid of HLA-G surface expression. FIG. 40F demonstrates that ΔB2M clones are devoid of HLA-C surface expression. FIG. 40G demonstrates that ΔB2M clones are devoid of HLA-E surface expression.

FIG. 41 is a schematic illustration depicting the location of the CRISPR gRNAs targeting the first coding exons of the TCRalpha and TCRbeta chains, respectively.

FIG. 42A depicts the results of a FACS analysis employing an anti-CD3 antibody, which reveals successful TCR deletion in Jurkat T cells that stably express the Cas9 nuclease. FIG. 42B shows the results of a SURVEYOR™ assay confirming cutting at the TCRa and TCRb loci.

FIG. 43A shows the results of a SURVEYOR™ assay demonstrating CRISPR cutting at the TCRa and TCRb loci in CD3+ T cells obtained from two independent donors. FIG. 43B shows the loss of TCR surface expression demonstrated by FACS analysis.

FIG. 44A is a schematic representation of the PD-1 targeting strategy. FIG. 44B demonstrates that the double CRISPR strategy results in cutting by both CRISPRs targeting the PD-1 locus in HEK293T cells. FIG. 44C is a schematic representation of sequencing, which confirmed the predicted deletion in the PD-1 locus after transfection of two CRISPRs targeting the PD-1 gene (PDCD1).

FIG. 45A shows the results of FACS analysis, demonstrating the loss of PD-1 expression in activated Jurkat T cells. FIG. 45B shows the results of a SURVEYOR™ assay confirming cutting at the PD-1 locus.

FIG. 46A is a schematic representation of the CTLA4 targeting strategy. FIG. 46B demonstrates that the double CRISPR strategy results in cutting by both CRISPRs targeting the CTLA4 locus in HEK293T cells. FIG. 46C is a schematic representation of sequencing, which confirmed the predicted deletion in the CTLA4 locus after transfection of two CRISPRs targeting the CTLA4 gene (CTLA4).

FIG. 47A demonstrates that the double CRISPR strategy results in cutting by both CRISPRs targeting the CTLA4 locus in Jurkat T cells. FIG. 47B shows the results of a SURVEYOR™ assay, demonstrating successful cutting by both CTLA4 CRISPRs in Jurkat T cells.

Figure 1:
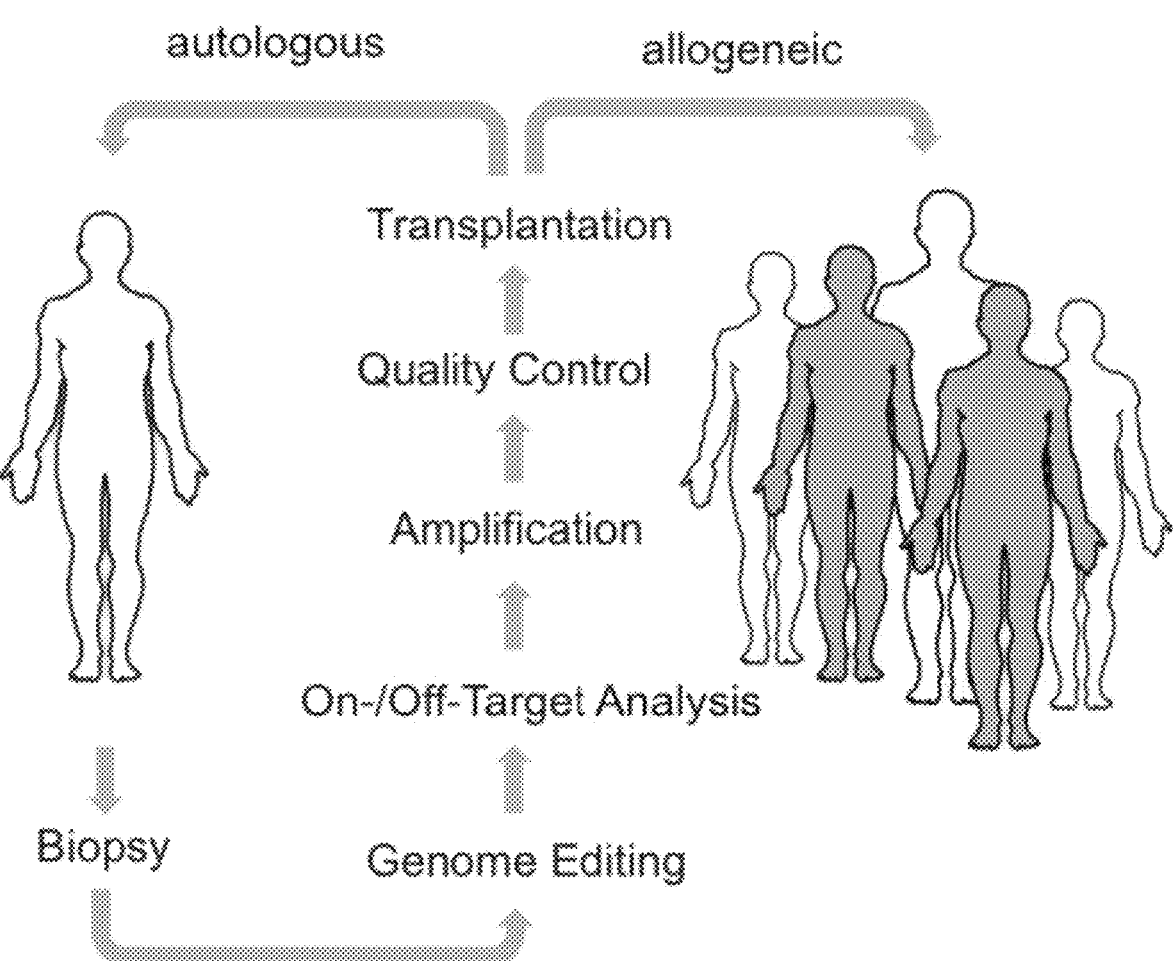
FIG. 1 illustrates the promise of regenerative medicine.

The following Tables 8-54 are submitted herewith as Appendices 1-47, respectively:

Table 8—exemplary gRNA sequences useful for targeting HLA-A;

Table 9—exemplary gRNA sequences useful for targeting HLA-B;

Table 10—exemplary gRNA sequences useful for targeting HLA-C;

Table 11—exemplary gRNA sequences useful for targeting RFX-ANK;

Table 12—exemplary gRNA sequences useful for targeting CIITA;

Table 13—exemplary gRNA sequences useful for targeting NFY-A;

Table 14—exemplary gRNA sequences useful for targeting NLRC5;

Table 15—exemplary gRNA sequences useful for targeting B2M;

Table 16—exemplary gRNA sequences useful for targeting RFX5;

Table 17—exemplary gRNA sequences useful for targeting RFX-AP;

Table 18—exemplary gRNA sequences useful for targeting HLA-G;

Table 19—exemplary gRNA sequences useful for targeting HLA-E;

Table 20—exemplary gRNA sequences useful for targeting NFY-B;

Table 21—exemplary gRNA sequences useful for targeting PD-L1;

Table 22—exemplary gRNA sequences useful for targeting NFY-C;

Table 23—exemplary gRNA sequences useful for targeting IRF1;

Table 24—exemplary gRNA sequences useful for targeting TAP1;

Table 25—exemplary gRNA sequences useful for targeting GITR;

Table 26—exemplary gRNA sequences useful for targeting 41BB;

Table 27—exemplary gRNA sequences useful for targeting CD28;

Table 28—exemplary gRNA sequences useful for targeting B7-1;

Table 29—exemplary gRNA sequences useful for targeting CD47;

Table 30—exemplary gRNA sequences useful for targeting B7-2;

Table 31—exemplary gRNA sequences useful for targeting OX40;

Table 32—exemplary gRNA sequences useful for targeting CD27;

Table 33—exemplary gRNA sequences useful for targeting HVEM;

Table 34—exemplary gRNA sequences useful for targeting SLAM;

Table 35—exemplary gRNA sequences useful for targeting CD226;

Table 36—exemplary gRNA sequences useful for targeting ICOS;

Table 37—exemplary gRNA sequences useful for targeting LAG3;

Table 38—exemplary gRNA sequences useful for targeting TIGIT;

Table 39—exemplary gRNA sequences useful for targeting TIM3;

Table 40—exemplary gRNA sequences useful for targeting CD160;

Table 41—exemplary gRNA sequences useful for targeting BTLA;

Table 42—exemplary gRNA sequences useful for targeting CD244;

Table 43—exemplary gRNA sequences useful for targeting LFA-1;

Table 44—exemplary gRNA sequences useful for targeting ST2;

Table 45—exemplary gRNA sequences useful for targeting HLA-F;

Table 46—exemplary gRNA sequences useful for targeting CD30;

Table 47—exemplary gRNA sequences useful for targeting B7-H3;

Table 48—exemplary gRNA sequences useful for targeting VISTA;

Table 49—exemplary gRNA sequences useful for targeting TLT;

Table 50—exemplary gRNA sequences useful for targeting PD-L2;

Table 51—exemplary gRNA sequences useful for targeting FOXP3;

Table 52—exemplary gRNA sequences useful for targeting CD58;

Table 53—exemplary gRNA sequences useful for targeting CD2; and

Table 54—exemplary gRNA sequences useful for targeting HELIOS.

The material submitted herewith in electronic (.txt) form and comprising Appendices 1-47 (Tables 8-54, respectively) is incorporated herein by reference, specifically:

Appendix 1 (file name: Table8.txt; date created: May 9, 2016; file size: 223,026 bytes);

Appendix 2 (file name: Table9.txt; date created: May 9, 2016; file size: 327,895 bytes);

Appendix 3 (file name: Table10.txt; date created: May 9, 2016; file size: 280,849 bytes);

Appendix 4 (file name: Table11.txt; date created: May 9, 2016; file size: 998,046 bytes);

Appendix 5 (file name: Table12.txt; date created: May 9, 2016; file size 4,717,823 bytes);

Appendix 6 (file name: Table13.txt; date created: May 9, 2016; file size 2,813,407 bytes);

Appendix 7 (file name: Table14.txt; date created: May 9, 2016; file size 6,568,742 bytes);

Appendix 8 (file name: Table15.txt; date created: May 9, 2016; file size 728,685 bytes);

Appendix 9 (file name: Table16.txt; date created: May 9, 2016; file size 766,106 bytes);

Appendix 10 (file name: Table 17.txt; date created: May 9, 2016; file size 874,435 bytes);

Appendix 11 (file name: Table 18.txt; date created: May 9, 2016; file size 232,536 bytes);

Appendix 12 (file name: Table 19.txt; date created: May 9, 2016; file size 539,932 bytes);

Appendix 13 (file name: Table20.txt; date created: May 9, 2016; file size 2,256,084 bytes);

Appendix 14 (file name: Table21.txt; date created: May 9, 2016; file size 1,303,081 bytes);

Appendix 15 (file name: Table22.txt; date created: May 9, 2016; file size 6,821,299 bytes);

Appendix 16 (file name: Table23.txt; date created: May 9, 2016; file size 1,095,386 bytes);

Appendix 17 (file name: Table24.txt; date created: May 9, 2016; file size 941,281 bytes);

Appendix 18 (file name: Table25.txt; date created: May 9, 2016; file size 378,368 bytes);

Appendix 19 (file name: Table26.txt; date created: May 9, 2016; file size 2,706,509 bytes);

Appendix 20 (file name: Table27.txt; date created: May 9, 2016; file size 3,578,977 bytes);

Appendix 21 (file name: Table28.txt; date created: May 9, 2016; file size 3,638,039 bytes);

Appendix 22 (file name: Table29.txt; date created: May 9, 2016; file size 5,083,645 bytes);

Appendix 23 (file name: Table30.txt; date created: May 9, 2016; file size 4,481,092 bytes);

Appendix 24 (file name: Table31.txt; date created: May 9, 2016; file size 393,567 bytes);

Appendix 25 (file name: Table32.txt; date created: May 9, 2016; file size 675,503 bytes);

Appendix 26 (file name: Table33.txt; date created: May 9, 2016; file size 1,002,258 bytes);

Appendix 27 (file name: Table34.txt; date created: May 9, 2016; file size 454,540 bytes);

Appendix 28 (file name: Table35.txt; date created: May 9, 2016; file size 10,463,522 bytes);

Appendix 29 (file name: Table36.txt; date created: May 9, 2016; file size 2,755,910 bytes);

Appendix 30 (file name: Table37.txt; date created: May 9, 2016; file size 733,191 bytes);

Appendix 31 (file name: Table38.txt; date created: May 9, 2016; file size 1,674,331 bytes);

Appendix 32 (file name: Table39.txt; date created: May 9, 2016; file size 2,622,419 bytes);

Appendix 33 (file name: Table40.txt; date created: May 9, 2016; file size 2,049,613 bytes);

Appendix 34 (file name: Table41.txt; date created: May 9, 2016; file size 4,016,813 bytes);

Appendix 35 (file name: Table42.txt; date created: May 9, 2016; file size 4,177,884 bytes);

Appendix 36 (file name: Table43.txt; date created: May 9, 2016; file size 4,326,759 bytes);

Appendix 37 (file name: Table44.txt; date created: May 9, 2016; file size 1,007,674 bytes);

Appendix 38 (file name: Table45.txt; date created: May 9, 2016; file size 1,690,144 bytes);

Appendix 39 (file name: Table46.txt; date created: May 9, 2016; file size 5,427,706 bytes);

Appendix 40 (file name: Table47.txt; date created: May 9, 2016; file size 3,510,941 bytes);

Appendix 41 (file name: Table48.txt; date created: May 9, 2016; file size 3,043,135 bytes);

Appendix 42 (file name: Table49.txt; date created: May 9, 2016; file size 274,899,026 bytes);

Appendix 43 (file name: Table50.txt; date created: May 9, 2016; file size 7,273,026 bytes);

Appendix 44 (file name: Table51.txt; date created: May 9, 2016; file size 2,336,524 bytes);

Appendix 45 (file name: Table52.txt; date created: May 9, 2016; file size 274,899,026 bytes);

Appendix 46 (file name: Table53.txt; date created: May 9, 2016; file size 1,820,108 bytes); and Appendix 47 (file name: Table54.txt; date created: May 9, 2016; file size 17,165,777 bytes).

DETAILED DESCRIPTION OF THE INVENTION

Recent advances in stem cell biology have made it possible to contemplate the use of a subject's own cells as an unlimited source for transplantation, as generally depicted, for example, in FIG. 1. Unfortunately, genome editing and the generation of induced pluripotent stem cells (iPSCs) followed by the differentiation of such iPSCs remains a costly, time consuming and highly variable process, with regards to pluripotency, epigenetic status, capacity for differentiation, and genomic stability. Moreover, changes occurring during genome editing and prolonged culturing have been found to trigger an adaptive immune response, resulting in immune rejection of even autologous stem cell-derived transplants. To overcome the problem of a subject's immune rejection of stem cell-derived transplants, the present inventors have developed and disclose herein a universal donor stem cell that represents a viable source for any transplantable cell type. Advantageously, the universal stem cells disclosed herein are not rejected by the recipient subject's immune system, regardless of the subject's genetic make-up.

The inventions disclosed herein employ genome editing technologies (e.g., the CRISPR/Cas or TALEN systems) to reduce or eliminate expression of critical immune genes (e.g., by deleting genomic DNA of critical immune genes) or, in certain instances, insert tolerance-inducing factors, in human ES cells and iPSCs, rendering them and the differentiated cells prepared therefrom hypoimmunogenic and less prone to immune rejection by a subject into which such cells are transplanted. As used herein to characterize a cell, the term "hypoimmunogenic" generally means that such cell is less prone to immune rejection by a subject into which such cells are transplanted. For example, relative to an unaltered wild-type cell, such a hypoimmunogenic cell may be about 2.5%, 5%, 10%, 20%, 30%, 40%, 50%, 60%, 70%, 80%, 90%, 95%, 97.5%, 99% or more less prone to immune rejection by a subject into which such cells are transplanted. In some aspects, genome editing technologies (e.g., the CRISPR/Cas or TALEN systems) are used to modulate (e.g., reduce or eliminate) the expression of MHC-I and MHC-II genes.

In certain embodiments, the inventions disclosed herein relate to a stem cell, the genome of which has been altered to reduce or delete critical components of HLA expression. Similarly, in certain embodiments, the inventions disclosed herein relate to a stem cell, the genome of which has been altered to insert one or more tolerance inducing factors. The present invention contemplates altering target polynucleotide sequences in any manner which is available to the skilled artisan, for example, utilizing a TALEN or a CRISPR/Cas system. Such CRISPR/Cas systems can employ a variety of Cas proteins (Haft et al. PLOS Comput Biol. 2005; 1 (6) e60). In some embodiments, the CRISPR/ Cas system is a CRISPR type I system. In some embodiments, the CRISPR/Cas system is a CRISPR type II system. In some embodiments, the CRISPR/Cas system is a CRISPR type V system. It should be understood that although examples of methods utilizing CRISPR/Cas (e.g., Cas9 and Cpf1) and TALEN are described in detail herein, the invention is not limited to the use of these methods/systems. Other methods of targeting polynucleotide sequences to reduce or ablate expression in target cells known to the skilled artisan can be utilized herein.

The present inventions contemplate altering, e.g., modifying or cleaving, target polynucleotide sequences in a cell for any purpose, but particularly such that the expression or activity of the encoded product is reduced or eliminated. For example, CRISPR/Cas systems may be used to target transcriptional regulators of antigen presentation to produce a hypoimmunogenic stem cell. In some embodiments, the target polynucleotide sequence in a cell (e.g., ES cells or iPSCs) is altered to produce a mutant cell. As used herein, a "mutant cell" generally refers to a cell with a resulting genotype that differs from its original genotype or the wild-type cell. In some instances, a "mutant cell" exhibits a mutant phenotype, for example when a normally functioning stem gene is altered using the CRISPR/Cas systems. In some embodiments, the target polynucleotide sequence in a cell is altered to correct or repair a genetic mutation (e.g., to restore a normal phenotype to the cell). In some embodiments, the target polynucleotide sequence in a cell is altered to induce a genetic mutation (e.g., to disrupt the function of a gene or genomic element).

In some embodiments, the alteration is an indel. As used herein, "indel" refers to a mutation resulting from an insertion, deletion, or a combination thereof. As will be appreciated by those skilled in the art, an indel in a coding region of a genomic sequence will result in a frameshift mutation, unless the length of the indel is a multiple of three. In some embodiments, the alteration is a point mutation. As used herein, "point mutation" refers to a substitution that replaces one of the nucleotides. A CRISPR/Cas system can be used to induce an indel of any length or a point mutation in a target polynucleotide sequence.

In some embodiments, the alteration results in a knock out of the target polynucleotide sequence or a portion thereof. For example, knocking out a target polynucleotide sequence in a cell can be performed in vitro, in vivo or ex vivo for both therapeutic and research purposes. Knocking out a target polynucleotide sequence in a cell can be useful for treating or preventing a disorder associated with expression of the target polynucleotide sequence (e.g., by knocking out a mutant allele in a cell ex vivo and introducing those cells comprising the knocked out mutant allele into a subject). As used herein, "knock out" includes deleting all or a portion of the target polynucleotide sequence in a way that interferes with the function of the target polynucleotide sequence or its expression product.

In some embodiments, the alteration results in reduced expression of the target polynucleotide sequence. The terms "decrease," "reduced," "reduction," and "decrease" are all used herein generally to mean a decrease by a statistically significant amount. However, for avoidance of doubt, "decreased," "reduced," "reduction," "decrease" includes a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

In some embodiments, the alteration is a homozygous alteration. In some embodiments, the alteration is a heterozygous alteration.

In some embodiments, the alteration results in correction of the target polynucleotide sequence from an undesired sequence to a desired sequence. CRISPR/Cas systems can be used to correct any type of mutation or error in a target polynucleotide sequence. For example, CRISPR/Cas systems can be used to insert a nucleotide sequence that is missing from a target polynucleotide sequence due to a deletion. CRISPR/Cas systems can also be used to delete or excise a nucleotide sequence from a target polynucleotide sequence due to an insertion mutation. In some instances, CRISPR/Cas systems can be used to replace an incorrect nucleotide sequence with a correct nucleotide sequence (e.g., to restore function to a target polynucleotide sequence that is impaired due to a loss of function mutation).

CRISPR/Cas systems can alter target polynucleotides with surprisingly high efficiency. In certain embodiments, the efficiency of alteration is at least about 5%. In certain embodiments, the efficiency of alteration is at least about 10%. In certain embodiments, the efficiency of alteration is from about 10% to about 80%. In certain embodiments, the efficiency of alteration is from about 30% to about 80%. In certain embodiments, the efficiency of alteration is from about 50% to about 80%. In some embodiments, the efficiency of alteration is greater than or equal to about 80%. In some embodiments, the efficiency of alteration is greater than or equal to about 85%. In some embodiments, the efficiency of alteration is greater than or equal to about 90%, about 91%, about 92%, about 93%, about 94%, about 95%, about 96%, about 97%, about 98%, or about 99%. In some embodiments, the efficiency of alteration is equal to about 100%.

In some embodiments, the target polynucleotide sequence is a genomic sequence. In some embodiments, the target polynucleotide sequence is a human genomic sequence. In some embodiments, the target polynucleotide sequence is a mammalian genomic sequence. In some embodiments, the target polynucleotide sequence is a vertebrate genomic sequence.

In some embodiments, CRISPR/Cas systems include a Cas protein or a nucleic acid sequence encoding the Cas protein and at least one to two ribonucleic acids (e.g., gRNAs) that are capable of directing the Cas protein to and hybridizing to a target motif of a target polynucleotide sequence. In some embodiments, CRISPR/Cas systems include a Cas protein or a nucleic acid sequence encoding the Cas protein and a single ribonucleic acid or at least one pair of ribonucleic acids (e.g., gRNAs) that are capable of directing the Cas protein to and hybridizing to a target motif of a target polynucleotide sequence. As used herein, "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Exemplary polypeptides or proteins include gene products, naturally occurring proteins, homologs, paralogs, fragments and other equivalents, variants, and analogs of the above.

In some embodiments, a Cas protein comprises one or more amino acid substitutions or modifications. In some embodiments, the one or more amino acid substitutions comprise a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In some embodiments, a Cas protein comprises a core Cas protein. Exemplary Cas core proteins include, but are not limited to Cas1, Cas2, Cas3, Cas4, Cas5, Cas6, Cas7, Cas8 and Cas9. In some embodiments, a Cas protein comprises a Cas protein of an *E. coli* subtype (also known as CASS2). Exemplary Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Exemplary Cas proteins of the Ypest subtype include, but are not limited to Csy1, Csy2, Csy3, and Csy4. In some embodiments, a Cas protein comprises a Cas protein of the Nmeni subtype (also known as CASS4). Exemplary Cas proteins of the Nmeni subtype include, but are not limited to Csn1 and Csn2. In some embodiments, a Cas protein comprises a Cas protein of the Dvulg subtype (also known as CASS1). Exemplary Cas proteins of the Dvulg subtype include Csd1, Csd2, and Cas5d. In some embodiments, a Cas protein comprises a Cas protein of the Tneap subtype (also known as CASS7). Exemplary Cas proteins of the Tneap subtype include, but are not limited to, Cst1, Cst2, Cas5t. In some embodiments, a Cas protein comprises a Cas protein of the Hmari subtype. Exemplary Cas proteins of the Hmari subtype include, but are not limited to Csh1, Csh2, and Cas5h. In some embodiments, a Cas protein comprises a Cas protein of the Apern subtype (also known as CASS5). Exemplary Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Exemplary Cas proteins of the Mtube subtype include, but are not limited to Csm1, Csm2, Csm3, Csm4, and Csm5. In some embodiments, a Cas protein comprises a RAMP module Cas protein. Exemplary RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein or a functional portion thereof. In some embodiments, the Cas protein is a *Staphylococcus aureus* Cas9 protein or a functional portion thereof. In some embodiments, the Cas protein is a *Streptococcus thermo-*

*philus* Cas9 protein or a functional portion thereof. In some embodiments, the Cas protein is a *Neisseria meningitides* Cas9 protein or a functional portion thereof. In some embodiments, the Cas protein is a *Treponema denticola* Cas9 protein or a functional portion thereof. In some embodiments, the Cas protein is Cas9 protein from any bacterial species or functional portion thereof. Cas9 protein is a member of the type II CRISPR systems which typically include a trans-coded small RNA (tracrRNA), endogenous ribonuclease 3 (rnc) and a Cas protein. Cas 9 protein (also known as CRISPR-associated endonuclease Cas9/Csn1) is a polypeptide comprising 1368 amino acids. An exemplary amino acid sequence of a Cas9 protein (SEQ ID NO: 1) is shown in FIG. 12. Cas 9 contains 2 enconuclease domains, including an RuvC-like domain (residues 7-22, 759-766 and 982-989) which cleaves target DNA that is noncomplementary to crRNA, and an HNH nuclease domain (residues 810-872) which cleave target DNA complementary to crRNA. In FIG. 12, the RuvC-like domain is highlighted in yellow and the HNH nuclease domain is underlined.

In some embodiments, the Cas protein is Cpf1 protein or a functional portion thereof. In some embodiments, the Cas protein is Cpf1 from any bacterial species or functional portion thereof. In some aspects, Cpf1 is a *Francisella novicida* U112 protein or a functional portion thereof. In some aspects, Cpf1 is a Acidaminococcus sp. BV3L6 protein or a functional portion thereof. In some aspects, Cpf1 is a Lachnospiraceae bacterium ND2006 protein or a function portion thereof. Cpf1 protein is a member of the type V CRISPR systems. Cpf1 protein is a polypeptide comprising about 1300 amino acids. Cpf1 contains a RuvC-like endonuclease domain. Cpf1 cleaves target DNA in a staggered pattern using a single ribonuclease domain. The staggered DNA double-stranded break results in a 4 or 5-nt 5' overhang.

As used herein, "functional portion" refers to a portion of a peptide which retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cpf1 protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cpf1 protein comprises a functional portion of a RuvC-like domain.

It should be appreciated that the present invention contemplates various ways of contacting a target polynucleotide sequence with a Cas protein (e.g., Cas9). In some embodiments, exogenous Cas protein can be introduced into the cell in polypeptide form. In certain embodiments, Cas proteins can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of molecule into a cell. The cell-penetrating polypeptides can contain a detectable label.

In certain embodiments, Cas proteins can be conjugated to or fused to a charged protein (e.g., that carries a positive, negative or overall neutral electric charge). Such linkage may be covalent. In some embodiments, the Cas protein can be fused to a superpositively charged GFP to significantly increase the ability of the Cas protein to penetrate a cell (Cronican et al. ACS Chem Biol.2010; 5 (8): 747-52). In certain embodiments, the Cas protein can be fused to a protein transduction domain (PTD) to facilitate its entry into a cell. Exemplary PTDs include Tat, oligoarginine, and penetratin. In some embodiments, the Cas9 protein comprises a Cas9 polypeptide fused to a cell-penetrating peptide. In some embodiments, the Cas9 protein comprises a Cas9 polypeptide fused to a PTD. In some embodiments, the Cas9 protein comprises a Cas9 polypeptide fused to a tat domain. In some embodiments, the Cas9 protein comprises a Cas9 polypeptide fused to an oligoarginine domain. In some embodiments, the Cas9 protein comprises a Cas9 polypeptide fused to a penetratin domain. In some embodiments, the Cas9 protein comprises a Cas9 polypeptide fused to a superpositively charged GFP. In some embodiments, the Cpf1 protein comprises a Cpf1 polypeptide fused to a cell-penetrating peptide. In some embodiments, the Cpf1 protein comprises a Cpf1 polypeptide fused to a PTD. In some embodiments, the Cpf1 protein comprises a Cpf1 polypeptide fused to a tat domain. In some embodiments, the Cpf1 protein comprises a Cpf1 polypeptide fused to an oligoarginine domain. In some embodiments, the Cpf1 protein comprises a Cpf1 polypeptide fused to a penetratin domain. In some embodiments, the Cpf1 protein comprises a Cpf1 polypeptide fused to a superpositively charged GFP.

In some embodiments, the Cas protein can be introduced into a cell containing the target polynucleotide sequence in the form of a nucleic acid encoding the Cas protein (e.g., Cas9 or Cpf1). The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

In some embodiments, nucleic acids encoding Cas protein and nucleic acids encoding the at least one to two ribonucleic acids are introduced into a cell via viral transduction (e.g., lentiviral transduction).

In some embodiments, the Cas protein is complexed with one to two ribonucleic acids. In some embodiments, the Cas protein is complexed with two ribonucleic acids. In some embodiments, the Cas protein is complexed with one ribonucleic acid. In some embodiments, the Cas protein is encoded by a modified nucleic acid, as described herein (e.g., a synthetic, modified mRNA).

The methods of the present invention contemplate the use of any ribonucleic acid that is capable of directing a Cas protein to and hybridizing to a target motif of a target polynucleotide sequence. In some embodiments, at least one of the ribonucleic acids comprises tracrRNA. In some embodiments, at least one of the ribonucleic acids comprises CRISPR RNA (crRNA). In some embodiments, a single ribonucleic acid comprises a guide RNA that directs the Cas protein to and hybridizes to a target motif of the target polynucleotide sequence in a cell. In some embodiments, at least one of the ribonucleic acids comprises a guide RNA that directs the Cas protein to and hybridizes to a target motif of the target polynucleotide sequence in a cell. In some embodiments, both of the one to two ribonucleic acids comprise a guide RNA that directs the Cas protein to and hybridizes to a target motif of the target polynucleotide sequence in a cell. The ribonucleic acids of the present invention can be selected to hybridize to a variety of different target motifs, depending on the particular CRISPR/Cas system employed, and the sequence of the target polynucleotide, as will be appreciated by those skilled in the art. The one to two ribonucleic acids can also be selected to minimize hybridization with nucleic acid sequences other than the target polynucleotide sequence. In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

In some embodiments, at least one of the one to two ribonucleic acids comprises a sequence selected from the group consisting of the ribonucleic acid sequences of SEQ ID NOs: 2-817976. In some embodiments, at least one ribonucleic acid comprises a sequence selected from the group consisting of the ribonucleic acid sequences of SEQ ID NOs: 2-817976.

In some embodiments, at least one of the one to two ribonucleic acids comprises a sequence with a single nucleotide mismatch to a sequence selected from the group consisting of the ribonucleic acid sequences of SEQ ID NOs: 2-817976. In some embodiments, at least one ribonucleic acid comprises a sequence with a single nucleotide mismatch to a sequence selected from the group consisting of the ribonucleic acid sequences of SEQ ID NOs: 2-817976.

In some embodiments, each of the one to two ribonucleic acids comprises guide RNAs that directs the Cas protein to and hybridizes to a target motif of the target polynucleotide sequence in a cell. In some embodiments, one or two ribonucleic acids (e.g., guide RNAs) are complementary to and/or hybridize to sequences on the same strand of a target polynucleotide sequence. In some embodiments, one or two ribonucleic acids (e.g., guide RNAs) are complementary to and/or hybridize to sequences on the opposite strands of a target polynucleotide sequence. In some embodiments, the one or two ribonucleic acids (e.g., guide RNAs) are not complementary to and/or do not hybridize to sequences on the opposite strands of a target polynucleotide sequence. In some embodiments, the one or two ribonucleic acids (e.g., guide RNAs) are complementary to and/or hybridize to overlapping target motifs of a target polynucleotide sequence. In some embodiments, the one or two ribonucleic acids (e.g., guide RNAs) are complementary to and/or hybridize to offset target motifs of a target polynucleotide sequence.

In some embodiments, the target motif is a 17 to 23 nucleotide DNA sequence. In some embodiments, the target motif is at least 20 nucleotides in length. In some embodiments, the target motif is a 20-nucleotide DNA sequence. In some embodiments, the target motif is a 17 to 23-nucleotide DNA sequence and immediately precedes an NRG motif. In some aspects, the NRG motif is NGG or NAG. In some embodiments, the target motif is a 20-nucleotide DNA sequence and immediately precedes an NGG motif recognized by the Cas protein. In some embodiments, the target motif is a 20-nucleotide DNA sequence and immediately precedes an NAG motif recognized by the Cas protein. In some embodiments, the target motif is a 20-nucleotide DNA sequence beginning with G and immediately precedes an NGG motif recognized by the Cas protein. In some embodiments, the target motif is G (N) 19NGG. In some embodiments, the target motif is (N) 20NGG.

In some embodiments, the target motif is a 17 to 23-nucleotide DNA sequence and immediately precedes an NNGRRT motif. In some embodiments, the target motif is a 20 nucleotide DNA sequence and immediately precedes an NNGRRT motif. In some embodiments, the target motif is a 17 to 23-nucleotide DNA sequence and immediately precedes an NNNRRT motif. In some embodiments, the target motif is a 20 nucleotide DNA sequence and immediately precedes an NNNRRT motif. In some embodiments, the target motif is a 17 to 23-nucleotide DNA sequence and immediately precedes an NNAGAAW motif. In some embodiments, the target motif is a 20 nucleotide DNA sequence and immediately precedes an NNAGAAW motif. In some embodiments, the target motif is a 17 to 23-nucleotide DNA sequence and immediately precedes an NNNN-GATT motif. In some embodiments, the target motif is a 20 nucleotide DNA sequence and immediately precedes an NNNNGATT motif. In some embodiments, the target motif is a 17 to 23-nucleotide DNA sequence and immediately precedes an NAAAAC motif. In some embodiments, the target motif is a 20 nucleotide DNA sequence and immediately precedes an NAAAAC motif. In some embodiments, the target motif is a 17 to 23-nucleotide DNA sequence having a 5' T-rich region (e.g., TTTN motif). In some embodiments, the target motif is a 20 nucleotide DNA sequence having a 5' T-rich region (e.g., TTTN motif).

In some embodiments, the target motif is a 17 to 23-nucleotide DNA sequence and immediately precedes an NRG motif (e.g., NGG or NAG) recognized by a *S. pyogenes* Cas9 protein. In some embodiments, the target motif is a 17 to 23-nucleotide DNA sequence and immediately precedes an NNGRRT motif recognized by a *S. aureus* Cas9 protein. In some embodiments, the target motif is a 17 to 23-nucleotide DNA sequence and immediately precedes an NNNRRT motif recognized by a *S. aureus* Cas9 protein. In some embodiments, the target motif is a 17 to 23-nucleotide DNA sequence and immediately precedes an NNAGAAW motif recognized by a *S. thermophilus* Cas9 protein. In some embodiments, the target motif is a 17 to 23-nucleotide DNA sequence and immediately precedes an NNNNGATT motif recognized by *N. meningitides* Cas9 protein. In some embodiments, the target motif is a 17 to 23-nucleotide DNA sequence and immediately precedes an NAAAAC motif recognized by *T. denticola* Cas9 protein. In some embodiments, the target motif is a 17 to 23-nucleotide DNA sequence having a 5' T-rich region (e.g., TTTN motif) recognized by Acidaminococcus or Lachnospiracede Cpf1 protein.

In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. Those skilled in the art will appreciate that a variety of techniques can be used to select suitable target motifs for minimizing off-target effects (e.g., bioinformatics analyses). In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

In some aspects, the target polynucleotide sequence in a cell is altered to reduce or eliminate expression and/or activity of one or more critical immune genes in the cell using a genetic editing system (e.g., TALENs, CRISPR/Cas, etc.). In some embodiments, the present disclosure provides that the target polynucleotide sequence in a cell is altered to delete a contiguous stretch of genomic DNA (e.g., delete one or more critical immune genes) from one or both alleles of the cell (e.g., using a CRISPR/Cas system). In some embodiments, the target polynucleotide sequence in a cell is altered to insert a genetic mutation in one or both alleles of the cell (e.g., using a CRISPR/Cas system). In still other embodiments, the universal stem cells disclosed herein may be subject to complementary genome editing approaches (e.g., using a CRISPR/Cas system), whereby such stem cells are modified to both delete contiguous stretches of genomic DNA (e.g., critical immune genes) from one or both alleles of the cell, as well as to insert one or more tolerance-inducing factors, such as HLA-G or PD-L1, into one or both alleles of the cells to locally suppress the immune system and improve transplant engraftment.

The universal stem cells disclosed herein may be differentiated into relevant cell types to assess HLA expression, as well as the evaluation of immunogenicity of the universal stem cell lines, for example, in a pre-clinical humanized mouse model. For example, the universal stem cells disclosed herein may be incubated under appropriate conditions and differentiated into mesenchymal progenitors cells (MPCs), hypoimmunogenic cardiomyocytes, endothelial cells (ECs), macrophages, hepatocytes, beta cells (e.g., pancreatic beta cells), or neural progenitor cells (NPCs).

The universal stem cells and methods disclosed herein will have an enormous impact on regenerative medicine by leading the way to rigorously tested universal donor stem cell lines that could be grown up and differentiated into a very large numbers of cells, made widely available to all medical institutions, and used on demand to treat patients suffering from degenerative illnesses, and thereby make it unnecessary to use a patient's own cells on a case-by-case basis as a source for autologous transplantation. Moreover, as the resulting cell products will be protected from immune attack, they will represent a new form of treatment for autoimmune diseases such as MS (multiple sclerosis) and diabetes, where autologous cells would still be prone to immune attack. Immunoprivileged universal donor stem cell-derived cell products, however, will be protected from autoimmune rejection.

The universal stem cells disclosed herein may be used, for example, to diagnose, monitor, treat and/or cure the presence or progression of a disease or condition in a subject. As used herein, a "subject" means a human or animal. In certain embodiments, the subject is a human. In certain embodiments, the subject is an adolescent. In certain embodiments, the subject is treated in vivo, in vitro and/or in utero. In certain aspects, a subject in need of treatment in accordance with the methods disclosed herein has a condition or is suspected or at increased risk of developing such condition.

Figure 2A:
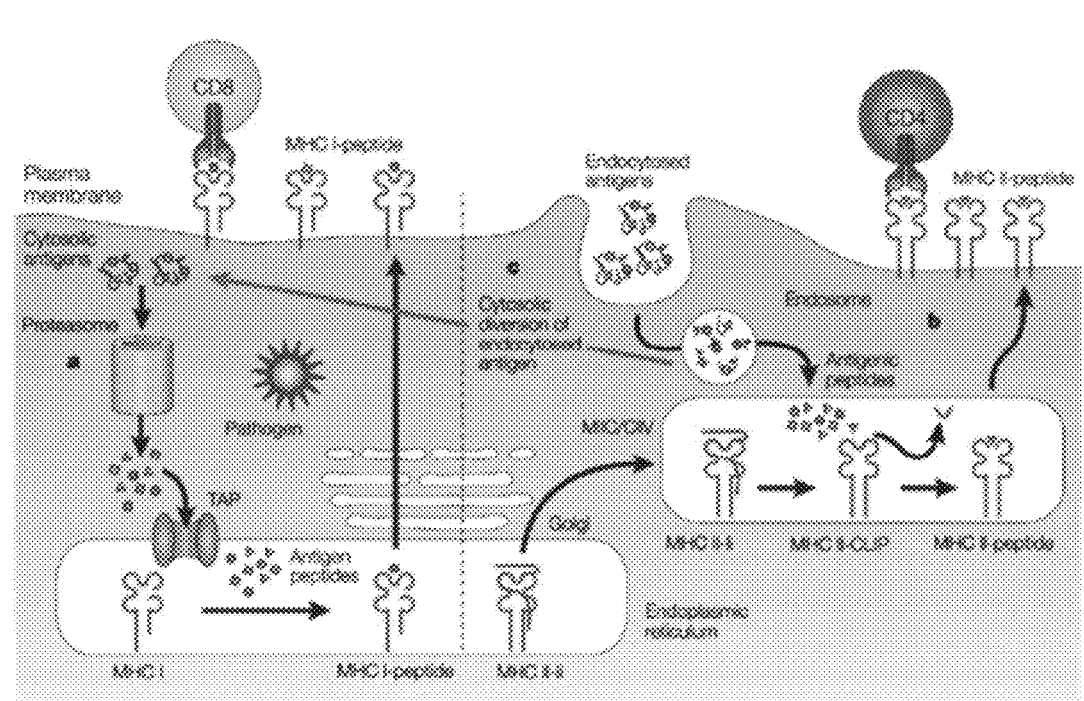
FIGS. 2A-2B graphically depict the HLA barrier in transplantation.
Figure 2B:
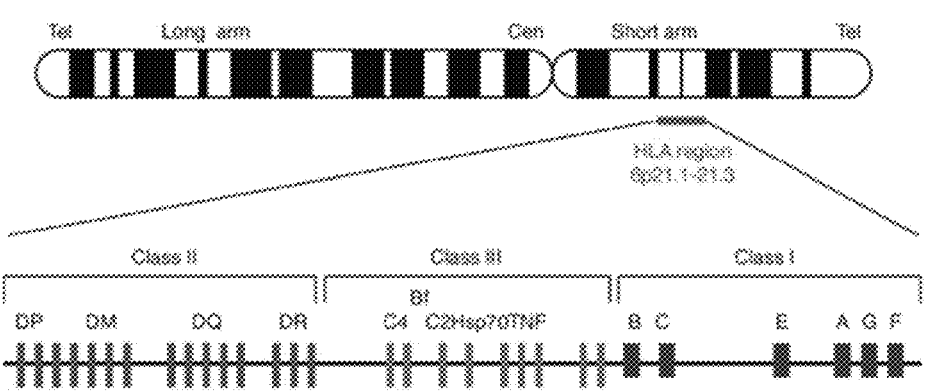
Figure 13:
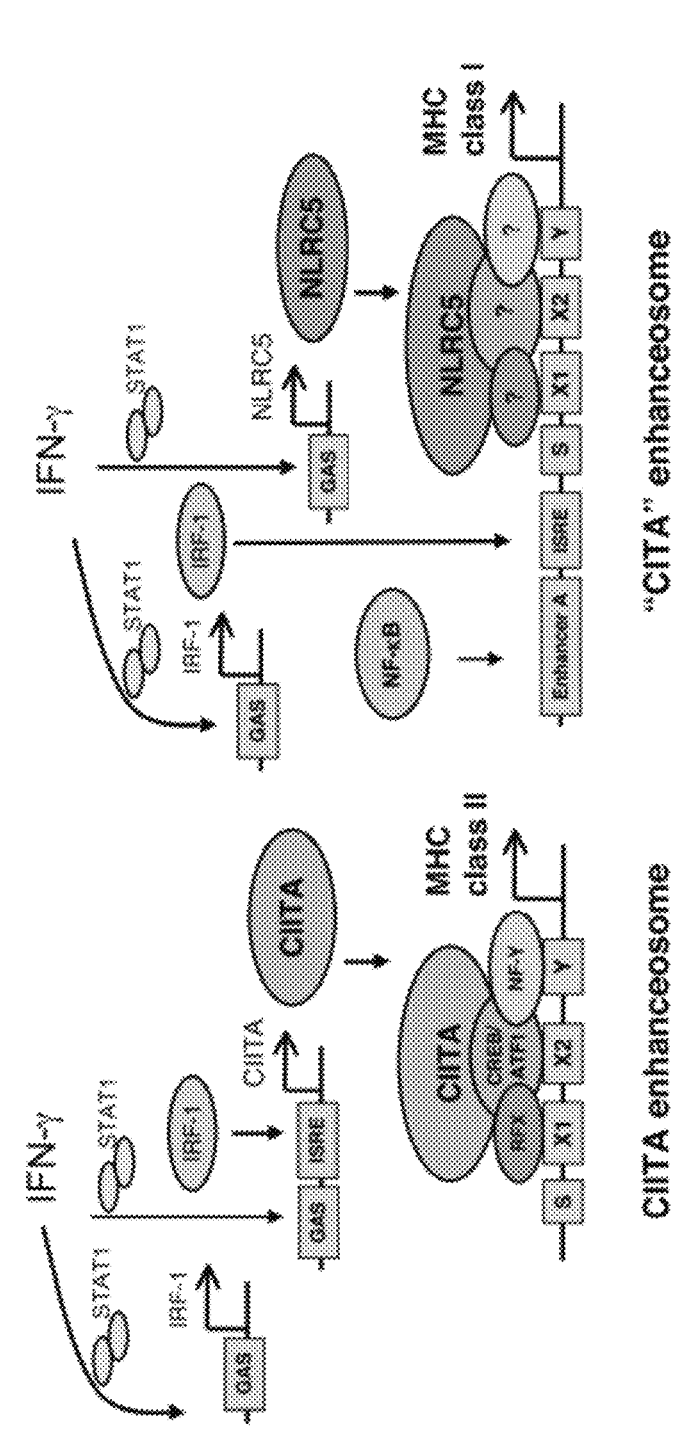
FIG. 13 illustrates a comparison of the MHC-II and MHC-I enhanceosomes.

As depicted in FIG. 2A, HLA represents an immunologic barrier to the successful transplantation of stem cells or differentiated stem cells in a subject. Disclosed herein are novel compositions, cells and related methods that are useful for overcoming the HLA immunologic barrier to transplantation. As illustrated in FIG. 2B, major histocompatibility complex (MHC) is a locus on human Chr. 6p21, which encodes a highly polymorphic gene family of surface molecules that define donor compatibility during organ transplantation. MHC class I (MHC-I) and MHC class II (MHC-II) play essential roles in the activation of adaptive immune responses by presenting antigens to T lymphocytes. A comparison of the MHC-II and MHC-I enhanceosomes is provided in FIG. 13. Humans have three classical MHC-Ia molecules (HLA-A, HLA-B, and HLA-C), which are vital to the detection and elimination of viruses, cancerous cells, and transplanted cells. In addition, there are three non-classical MHC-Ib molecules (HLA-E, HLA-F, and HLA-G), which have immune regulatory functions. While MHC's serve a vital cellular function, in certain contexts, such as cell-based transplantation therapies, they may also contribute to immune rejection. Provided herein are novel cells, compositions and methods that are useful for addressing such HLA-based immune rejection of transplanted cells.

Knock-Outs

In certain aspects, the inventions disclosed herein relate to genomic modifications of one or more targeted polynucleotide sequences of the stem cell genome that regulates the expression of MHC-I and/or MHC-II. In some aspects, a genetic editing system is used to modify one or more targeted polynucleotide sequences. In some aspects, a CRISPR/Cas system is used to delete the one or more targeted polynucleotide sequences. MHC-I molecules are composed of MHC-encoded heavy chains and the invariant subunit β2-microglobulin (B2M). Antigen-derived peptides are presented by MHC-I-B2M complexes at the cell surface to CD8 T cells carrying an antigen-specific T cell receptor. Peptides are mostly produced from the degradation of cytoplasmic proteins by a specialized proteasome or immunoproteasome, which is optimized to generate MHC class I peptides and contains several IFN-γ-inducible subunits. Unlike MHC-II, which is found mainly in antigen-presenting cells, MHC-Ia is ubiquitously expressed in almost all nucleated cells (Pamer, et al., Annu Rev Immunol (1998) 16:323-358.). Both MHC-I and MHC-II genes are highly inducible by IFN-γ stimulation.

The efficient removal of the HLA barrier can be accomplished by one or more of the following: (1) targeting the polymorphic HLA alleles (HLA-A,-B,-C) and MHC-II genes directly; (2) removal of B2M, which will prevent surface trafficking of all MHC-I molecules; and/or (3) deletion of components of the MHC enhanceosomes, such as NLRC5, RFX-5,-ANK, and -AP, IRF1, NF-Y, and CIITA that are critical for HLA expression.

In certain embodiments, HLA expression is interfered with. In some aspects, HLA expression is interfered with by targeting individual HLAs (e.g., knocking out expression of HLA-A, HLA-B and/or HLA-C), targeting transcriptional regulators of HLA expression (e.g., knocking out expression of NLRC5, CIITA, RFX5, RFXAP, RFXANK, NFY-A, NFY-B, NFY-C and/or IRF-1), blocking surface trafficking of MHC class I molecules (e.g., knocking out expression of B2M and/or TAP1), and/or targeting HLA-Razor.

In certain aspects, the stem cells disclosed herein do not express one or more human leukocyte antigens (e.g., HLA-A, HLA-B and/or HLA-C) corresponding to MHC-I and/or MHC-II and are thus characterized as being hypoimmunogenic. For example, in certain aspects, the stem cells disclosed herein have been modified such that the stem cell or a differentiated stem cell prepared therefrom do not express or exhibit reduced expression of one or more of the following MHC-I molecules: HLA-A, HLA-B and HLA-C. In some aspects, one or more of HLA-A, HLA-B and HLA-C may be "knocked-out" of a cell. A cell that has a knocked-out HLA-A gene, HLA-B gene, and/or HLA-C gene may exhibit reduced or eliminated expression of each knocked-out gene. See FIGS. 13A-J.

In some aspects, the present disclosure provides a stem cell (e.g., hypoimmunogenic stem cell) or population thereof comprising a genome in which the HLA-A gene has been edited to delete a contiguous stretch of genomic DNA, thereby reducing or eliminating surface expression of MHC class I molecules in the cell or population thereof. The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 2-1418.

In certain aspects, the present disclosure provides a method for altering a target HLA-A sequence in a cell comprising contacting the HLA-A sequence with a clustered regularly interspaced short palindromic repeats-associated (Cas) protein and at least one ribonucleic acid or at least one pair of ribonucleic acids, wherein the ribonucleic acids direct Cas protein to and hybridize to a target motif of the target HLA-A polynucleotide sequence, wherein the target HLA-A polynucleotide sequence is cleaved, and wherein the at least one ribonucleic acid or the at least one pair of ribonucleic acids is selected from the group consisting of SEQ ID NOs: 2-1418.

In some aspects, the present disclosure provides a stem cell (e.g., hypoimmunogenic stem cell) or population thereof comprising a genome in which the HLA-B gene has been edited to delete a contiguous stretch of genomic DNA, thereby reducing or eliminating surface expression of MHC class I molecules in the cell or population thereof. The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 1419-3277.

In certain aspects, the present disclosure provides a method for altering a target HLA-B sequence in a cell comprising contacting the HLA-B sequence with a clustered regularly interspaced short palindromic repeats-associated (Cas) protein and at least one ribonucleic acid or at least one pair of ribonucleic acids, wherein the ribonucleic acids direct Cas protein to and hybridize to a target motif of the target HLA-B polynucleotide sequence, wherein the target HLA-B polynucleotide sequence is cleaved, and wherein the at least one ribonucleic acid or the at least one pair of ribonucleic acids is selected from the group consisting of SEQ ID NOs: 1419-3277.

In some aspects, the present disclosure provides a stem cell (e.g., hypoimmunogenic stem cell) or population thereof comprising a genome in which the HLA-C gene has been edited to delete a contiguous stretch of genomic DNA, thereby reducing or eliminating surface expression of MHC class I molecules in the cell or population thereof. The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 3278-5183.

In certain aspects, the present disclosure provides a method for altering a target HLA-C sequence in a cell comprising contacting the HLA-C sequence with a clustered regularly interspaced short palindromic repeats-associated (Cas) protein and at least one ribonucleic acid or at least one pair of ribonucleic acids, wherein the ribonucleic acids direct Cas protein to and hybridize to a target motif of the target HLA-C polynucleotide sequence, wherein the target HLA-C polynucleotide sequence is cleaved, and wherein the at least one ribonucleic acid or the at least one pair of ribonucleic acids is selected from the group consisting of SEQ ID NOs: 3278-5183.

In certain embodiments, the expression of MHC-I or MHC-II is modulated by targeting and deleting a contiguous stretch of genomic DNA thereby reducing or eliminating expression of a target gene, for example, NLRC5. As used herein, the term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. In certain aspects, the target gene is NLRC5, CIITA, RFX5, RFXAP, RFXANK, NFY-A, NFY-B, NFY-C or IRF-1.

In certain aspects, the inventions disclosed herein modulate (e.g., reduce or eliminate) the expression of MHC-II genes by targeting and modulating (e.g., reducing or eliminating) Class II transactivator (CIITA) expression. In some aspects, the modulation occurs using a CRISPR/Cas system. CIITA is a member of the NLR or nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-γ in most cell types. Aside from CIITA, NLR proteins are localized in the cytoplasm and contribute to the innate immune response by recognizing microbial products and exogenous danger signals, leading to inflammation and/or cell death.

In some aspects, the present disclosure provides a stem cell (e.g., hypoimmunogenic stem cell) or population thereof comprising a genome in which the Class II transactivator (CIITA) gene has been edited to delete a contiguous stretch of genomic DNA, thereby reducing or eliminating surface expression of MHC class II molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 5184-36352.

The present invention contemplates genomically editing human cells to cleave CIITA gene sequences, as well as editing the genome of such cells to alter one or more additional target polynucleotide sequences (e.g., NLRC5 and/or B2M). It should be appreciated that cleaving a CIITA genomic sequence using one or more gRNAs or gRNA pairs described herein and a Cas protein could result in partial or complete deletion of the target CIITA genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the CIITA gene has been edited to delete a contiguous stretch of genomic DNA, thereby reducing or eliminating MHC Class II molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 5184-36352.

In some aspects, the invention provides a method for altering a target CIITA polynucleotide sequence in a cell comprising contacting the CIITA polynucleotide sequence with a clustered regularly interspaced short palindromic repeats-associated (Cas) protein and from one to two ribonucleic acids, wherein the ribonucleic acids direct Cas protein to and hybridize to a target motif of the target CIITA polynucleotide sequence, wherein the target CIITA polynucleotide sequence is cleaved, and wherein at least one of the one to two ribonucleic acids are selected from the group consisting of SEQ ID NOs: 5184-36352.

In some aspects, the invention provides a stem cell (e.g., hypoimmunogenic stem cell) or population thereof, each cell comprising a modified genome comprising: a genomic modification in which the CIITA gene has been edited to reduce or eliminate CIITA surface expression and/or activity in the cell by contacting the cell with a Cas protein or a nucleic acid encoding the Cas protein and at least one ribonucleic acid having a sequence selected from the group consisting of SEQ ID NOs: 5184-36352.

In some aspects, the invention provides a method for altering a target CIITA polynucleotide sequence in a cell comprising contacting the CIITA polynucleotide sequence with a clustered regularly interspaced short palindromic repeats-associated (Cas) protein and at least one ribonucleic acid, wherein the ribonucleic acid directs Cas protein to and hybridizes to a target motif of the target CIITA polynucleotide sequence, wherein the target CIITA polynucleotide sequence is cleaved, and wherein the at least one ribonucleic acid is selected from the group consisting of SEQ ID NOS: 5184-36352.

In certain aspects, the inventions disclosed herein modulate (e.g., reduce or eliminate) the expression of MHC-I genes by targeting and modulating (e.g., reducing or eliminating) expression of the NLR family, CARD domain containing 5/NOD27/CLR16.1 (NLRC5). In some aspects, the modulation occurs using a CRISPR/Cas system. NLRC5 is a critical regulator of MHC-I-mediated immune responses and, similar to CIITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some aspects, the present disclosure provides a stem cell (e.g., hypoimmunogenic stem cell) or population thereof comprising a genome in which the NLRC5 gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 36353-81239.

The present invention contemplates genomically editing human cells to cleave NLRC5 gene sequences, as well as editing the genome of such cells to alter one or more additional target polynucleotide sequences (e.g., CIITA and/or B2M). It should be appreciated that cleaving a NLRC5 genomic sequence using one or more gRNAs or gRNA pairs described herein and a Cas protein could result in partial or complete deletion of the target NLRC5 genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the NLRC5 gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 36353-81239.

In some aspects, the invention provides a method for altering a target NLRC5 polynucleotide sequence in a cell comprising contacting the NLRC5 polynucleotide sequence with a clustered regularly interspaced short palindromic repeats-associated (Cas) protein and from one to two ribonucleic acids, wherein the ribonucleic acids direct Cas protein to and hybridize to a target motif of the target NLRC5 polynucleotide sequence, wherein the target NLRC5 polynucleotide sequence is cleaved, and wherein at least one of the one to two ribonucleic acids are selected from the group consisting of SEQ ID NOs: 36353-81239.

In some aspects, the invention provides a stem cell (e.g., hypoimmunogenic stem cell) or population thereof, each cell comprising a modified genome comprising: a genomic modification in which the NLRC5 gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 36353-81239.

In some aspects, the invention provides a method for altering a target NLRC5 polynucleotide sequence in a cell comprising contacting the NLRC5 polynucleotide sequence with a clustered regularly interspaced short palindromic repeats-associated (Cas) protein and at least one ribonucleic acid, wherein the ribonucleic acid directs Cas protein to and hybridizes to a target motif of the target NLRC5 polynucleotide sequence, wherein the target NLRC5 polynucleotide sequence is cleaved, and wherein the at least one ribonucleic acid is selected from the group consisting of SEQ ID NOs: 36353-81239.

In certain embodiments, the inventions disclosed herein modulate (e.g., reduce or eliminate) the expression of MHC-I genes by targeting and modulating (e.g., reducing or eliminating) expression of the accessory chain B2M. In some aspects, the modulation occurs using a CRISPR/Cas system. By modulating (e.g., reducing or deleting) expression of B2M, surface trafficking of MHC-I molecules is blocked and the cell rendered hypoimmunogenic.

In some aspects, the present disclosure provides a stem cell (e.g., hypoimmunogenic stem cell) or population thereof comprising a genome in which the B2-microglobulin (B2M) gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 81240-85644.

The present invention contemplates genomically editing human cells to cleave B2M gene sequences, as well as editing the genome of such cells to alter one or more additional target polynucleotide sequences (e.g., NLRC5 and/or CIITA). It should be appreciated that cleaving a B2M genomic sequence using one or more gRNAs or gRNA pairs described herein and a Cas protein could result in partial or complete deletion of the target B2M genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the B2M gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 81240-85644.

In some aspects, the invention provides a method for altering a target B2M polynucleotide sequence in a cell comprising contacting the B2M polynucleotide sequence with a clustered regularly interspaced short palindromic repeats-associated (Cas) protein and from one to two ribonucleic acids, wherein the ribonucleic acids direct Cas protein to and hybridize to a target motif of the target B2M polynucleotide sequence, wherein the target B2M polynucleotide sequence is cleaved, and wherein at least one of the one to two ribonucleic acids are selected from the group consisting of SEQ ID NOs: 81240-85644.

In some aspects, the invention provides a stem cell (e.g., hypoimmunogenic stem cell) or population thereof, each cell comprising a modified genome comprising: a genomic modification in which the B2M gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 81240-85644.

In some aspects, the invention provides a method for altering a target B2M polynucleotide sequence in a cell comprising contacting the B2M polynucleotide sequence with a clustered regularly interspaced short palindromic repeats-associated (Cas) protein and at least one ribonucleic acid, wherein the ribonucleic acid directs Cas protein to and hybridizes to a target motif of the target B2M polynucleotide sequence, wherein the target B2M polynucleotide sequence is cleaved, and wherein the at least one ribonucleic acid is selected from the group consisting of SEQ ID NOS: 81240-85644.

In certain aspects, the inventions disclosed herein modulate (e.g., reduce or eliminate) the expression of MHC-I genes by targeting and modulating (e.g., reducing or eliminating) expression of one or more of RFX5. In some aspects, the modulation occurs using a CRISPR/Cas system.

In some aspects, the present disclosure provides a stem cell (e.g., hypoimmunogenic stem cell) or population thereof comprising a genome in which the RFX5 gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 85645-90115.

The present invention contemplates genomically editing human cells to cleave RFX5 gene sequences, as well as editing the genome of such cells to alter one or more additional target polynucleotide sequences. It should be appreciated that cleaving a RFX5 genomic sequence using one or more gRNAs or gRNA pairs described herein and a Cas protein could result in partial or complete deletion of the target RFX5 genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the RFX5 gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 85645-90115.

In some aspects, the invention provides a method for altering a target RFX5 polynucleotide sequence in a cell comprising contacting the RFX5 polynucleotide sequence with a clustered regularly interspaced short palindromic repeats-associated (Cas) protein and from one to two ribonucleic acids, wherein the ribonucleic acids direct Cas protein to and hybridize to a target motif of the target RFX5 polynucleotide sequence, wherein the target RFX5 polynucleotide sequence is cleaved, and wherein at least one of the one to two ribonucleic acids are selected from the group consisting of SEQ ID NOs: 85645-90115.

In some aspects, the invention provides a stem cell (e.g., hypoimmunogenic stem cell) or population thereof, each cell comprising a modified genome comprising: a genomic modification in which the RFX5 gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 85645-90115.

In some aspects, the invention provides a method for altering a target RFX5 polynucleotide sequence in a cell comprising contacting the RFX5 polynucleotide sequence with a clustered regularly interspaced short palindromic repeats-associated (Cas) protein and at least one ribonucleic acid, wherein the ribonucleic acid directs Cas protein to and hybridizes to a target motif of the target RFX5 polynucleotide sequence, wherein the target RFX5 polynucleotide sequence is cleaved, and wherein the at least one ribonucleic acid is selected from the group consisting of SEQ ID NOs: 85645-90115.

In certain aspects, the inventions disclosed herein modulate (e.g., reduce or eliminate) the expression of MHC-I genes by targeting and modulating (e.g., reducing or eliminating) expression of one or more of RFXAP. In some aspects, the modulation occurs using a CRISPR/Cas system.

In some aspects, the present disclosure provides a stem cell (e.g., hypoimmunogenic stem cell) or population thereof comprising a genome in which the RFXAP gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 90116-95635.

The present invention contemplates genomically editing human cells to cleave RFXAP gene sequences, as well as editing the genome of such cells to alter one or more additional target polynucleotide sequences. It should be appreciated that cleaving a RFXAP genomic sequence using one or more gRNAs or gRNA pairs described herein and a Cas protein could result in partial or complete deletion of the target RFXAP genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the RFXAP gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 90116-95635.

In some aspects, the invention provides a method for altering a target RFXAP polynucleotide sequence in a cell comprising contacting the RFXAP polynucleotide sequence with a clustered regularly interspaced short palindromic repeats-associated (Cas) protein and from one to two ribonucleic acids, wherein the ribonucleic acids direct Cas protein to and hybridize to a target motif of the target RFXAP polynucleotide sequence, wherein the target RFXAP polynucleotide sequence is cleaved, and wherein at least one of the one to two ribonucleic acids are selected from the group consisting of SEQ ID NOs: 90116-95635.

In some aspects, the invention provides a stem cell (e.g., hypoimmunogenic stem cell) or population thereof, each cell comprising a modified genome comprising: a genomic modification in which the RFXAP gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 90116-95635.

In some aspects, the invention provides a method for altering a target RFXAP polynucleotide sequence in a cell comprising contacting the RFXAP polynucleotide sequence with a clustered regularly interspaced short palindromic repeats-associated (Cas) protein and at least one ribonucleic acid, wherein the ribonucleic acid directs Cas protein to and hybridizes to a target motif of the target RFXAP polynucleotide sequence, wherein the target RFXAP polynucleotide sequence is cleaved, and wherein the at least one ribonucleic acid is selected from the group consisting of SEQ ID NOS: 90116-95635.

In certain aspects, the inventions disclosed herein modulate (e.g., reduce or eliminate) the expression of MHC-I genes by targeting and modulating (e.g., reducing or eliminating) expression of one or more of RFXANK. In some aspects, the modulation occurs using a CRISPR/Cas system.

In some aspects, the present disclosure provides a stem cell (e.g., hypoimmunogenic stem cell) or population thereof comprising a genome in which the RFXANK gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 95636-102318.

The present invention contemplates genomically editing human cells to cleave RFXANK gene sequences, as well as editing the genome of such cells to alter one or more additional target polynucleotide sequences. It should be appreciated that cleaving a RFXANK genomic sequence using one or more gRNAs or gRNA pairs described herein and a Cas protein could result in partial or complete deletion of the target RFXANK genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the RFXAP gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 95636-102318.

In some aspects, the invention provides a method for altering a target RFXANK polynucleotide sequence in a cell comprising contacting the RFXANK polynucleotide sequence with a clustered regularly interspaced short palindromic repeats-associated (Cas) protein and from one to two ribonucleic acids, wherein the ribonucleic acids direct Cas protein to and hybridize to a target motif of the target RFXANK polynucleotide sequence, wherein the target RFXANK polynucleotide sequence is cleaved, and wherein at least one of the one to two ribonucleic acids are selected from the group consisting of SEQ ID NOs: 95636-102318.

In some aspects, the invention provides a stem cell (e.g., hypoimmunogenic stem cell) or population thereof, each cell comprising a modified genome comprising: a genomic modification in which the RFXANK gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 95636-102318.

In some aspects, the invention provides a method for altering a target RFXANK polynucleotide sequence in a cell comprising contacting the RFXANK polynucleotide sequence with a clustered regularly interspaced short palindromic repeats-associated (Cas) protein and at least one ribonucleic acid, wherein the ribonucleic acid directs Cas protein to and hybridizes to a target motif of the target RFXANK polynucleotide sequence, wherein the target RFXANK polynucleotide sequence is cleaved, and wherein the at least one ribonucleic acid is selected from the group consisting of SEQ ID NOs: 95636-102318.

In certain aspects, the inventions disclosed herein modulate (e.g., reduce or eliminate) the expression of MHC-I genes by targeting and modulating (e.g., reducing or eliminating) expression of one or more of NFY-A. In some aspects, the modulation occurs using a CRISPR/Cas system.

In some aspects, the present disclosure provides a stem cell (e.g., hypoimmunogenic stem cell) or population thereof comprising a genome in which the NFY-A gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 102319-121796.

The present invention contemplates genomically editing human cells to cleave NFY-A gene sequences, as well as editing the genome of such cells to alter one or more additional target polynucleotide sequences. It should be appreciated that cleaving a NFY-A genomic sequence using one or more gRNAs or gRNA pairs described herein and a Cas protein could result in partial or complete deletion of the target NFY-A genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the NFY-A gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 102319-121796.

In some aspects, the invention provides a method for altering a target NFY-A polynucleotide sequence in a cell comprising contacting the NFY-A polynucleotide sequence with a clustered regularly interspaced short palindromic repeats-associated (Cas) protein and from one to two ribonucleic acids, wherein the ribonucleic acids direct Cas protein to and hybridize to a target motif of the target NFY-A polynucleotide sequence, wherein the target NFY-A polynucleotide sequence is cleaved, and wherein at least one of the one to two ribonucleic acids are selected from the group consisting of SEQ ID NOs: 102319-121796.

In some aspects, the invention provides a stem cell (e.g., hypoimmunogenic stem cell) or population thereof, each cell comprising a modified genome comprising: a genomic modification in which the NFY-A gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 102319-121796.

In some aspects, the invention provides a method for altering a target NFY-A polynucleotide sequence in a cell comprising contacting the NFY-A polynucleotide sequence with a clustered regularly interspaced short palindromic repeats-associated (Cas) protein and at least one ribonucleic acid, wherein the ribonucleic acid directs Cas protein to and hybridizes to a target motif of the target NFY-A polynucleotide sequence, wherein the target NFY-A polynucleotide sequence is cleaved, and wherein the at least one ribonucleic acid is selected from the group consisting of SEQ ID NOS: 102319-121796.

In certain aspects, the inventions disclosed herein modulate (e.g., reduce or eliminate) the expression of MHC-I genes by targeting and modulating (e.g., reducing or eliminating) expression of one or more of NFY-B. In some aspects, the modulation occurs using a CRISPR/Cas system.

In some aspects, the present disclosure provides a stem cell (e.g., hypoimmunogenic stem cell) or population thereof comprising a genome in which the NFY-B gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 121797-135112.

The present invention contemplates genomically editing human cells to cleave NFY-B gene sequences, as well as editing the genome of such cells to alter one or more additional target polynucleotide sequences. It should be appreciated that cleaving a NFY-B genomic sequence using one or more gRNAs or gRNA pairs described herein and a Cas protein could result in partial or complete deletion of the target NFY-B genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the NFY-B gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 121797-135112.

In some aspects, the invention provides a method for altering a target NFY-B polynucleotide sequence in a cell comprising contacting the NFY-B polynucleotide sequence with a clustered regularly interspaced short palindromic repeats-associated (Cas) protein and from one to two ribonucleic acids, wherein the ribonucleic acids direct Cas protein to and hybridize to a target motif of the target NFY-B polynucleotide sequence, wherein the target NFY-B polynucleotide sequence is cleaved, and wherein at least one of the one to two ribonucleic acids are selected from the group consisting of SEQ ID NOs: 121797-135112.

In some aspects, the invention provides a stem cell (e.g., hypoimmunogenic stem cell) or population thereof, each cell comprising a modified genome comprising: a genomic modification in which the NFY-B gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 121797-135112.

In some aspects, the invention provides a method for altering a target NFY-B polynucleotide sequence in a cell comprising contacting the NFY-B polynucleotide sequence with a clustered regularly interspaced short palindromic repeats-associated (Cas) protein and at least one ribonucleic acid, wherein the ribonucleic acid directs Cas protein to and hybridizes to a target motif of the target NFY-B polynucleotide sequence, wherein the target NFY-B polynucleotide sequence is cleaved, and wherein the at least one ribonucleic acid is selected from the group consisting of SEQ ID NOS: 121797-135112.

In certain aspects, the inventions disclosed herein modulate (e.g., reduce or eliminate) the expression of MHC-I genes by targeting and modulating (e.g., reducing or eliminating) expression of one or more of NFY-C. In some aspects, the modulation occurs using a CRISPR/Cas system.

In some aspects, the present disclosure provides a stem cell (e.g., hypoimmunogenic stem cell) or population thereof comprising a genome in which the NFY-C gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 135113-176601.

The present invention contemplates genomically editing human cells to cleave NFY-C gene sequences, as well as editing the genome of such cells to alter one or more additional target polynucleotide sequences. It should be appreciated that cleaving a NFY-C genomic sequence using one or more gRNAs or gRNA pairs described herein and a Cas protein could result in partial or complete deletion of the target NFY-C genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the NFY-C gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 135113-176601.

In some aspects, the invention provides a method for altering a target NFY-C polynucleotide sequence in a cell comprising contacting the NFY-C polynucleotide sequence with a clustered regularly interspaced short palindromic repeats-associated (Cas) protein and from one to two ribonucleic acids, wherein the ribonucleic acids direct Cas protein to and hybridize to a target motif of the target NFY-C polynucleotide sequence, wherein the target NFY-C polynucleotide sequence is cleaved, and wherein at least one of the one to two ribonucleic acids are selected from the group consisting of SEQ ID NOs: 135113-176601.

In some aspects, the invention provides a stem cell (e.g., hypoimmunogenic stem cell) or population thereof, each cell comprising a modified genome comprising: a genomic modification in which the NFY-C gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 135113-176601.

In some aspects, the invention provides a method for altering a target NFY-C polynucleotide sequence in a cell comprising contacting the NFY-C polynucleotide sequence with a clustered regularly interspaced short palindromic repeats-associated (Cas) protein and at least one ribonucleic acid, wherein the ribonucleic acid directs Cas protein to and hybridizes to a target motif of the target NFY-C polynucleotide sequence, wherein the target NFY-C polynucleotide sequence is cleaved, and wherein the at least one ribonucleic acid is selected from the group consisting of SEQ ID NOS: 135113-176601.

In certain aspects, the inventions disclosed herein modulate (e.g., reduce or eliminate) the expression of MHC-I genes by targeting and modulating (e.g., reducing or eliminating) expression of one or more of IRF-1. In some aspects, the modulation occurs using a CRISPR/Cas system.

In some aspects, the present disclosure provides a stem cell (e.g., hypoimmunogenic stem cell) or population thereof comprising a genome in which the IRF-1 gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 176602-182813.

The present invention contemplates genomically editing human cells to cleave IRF-1 gene sequences, as well as editing the genome of such cells to alter one or more additional target polynucleotide sequences. It should be appreciated that cleaving a IRF-1 genomic sequence using one or more gRNAs or gRNA pairs described herein and a Cas protein could result in partial or complete deletion of the target IRF-1 genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the IRF-1 gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 176602-182813.

In some aspects, the invention provides a method for altering a target IRF-1 polynucleotide sequence in a cell comprising contacting the IRF-1 polynucleotide sequence with a clustered regularly interspaced short palindromic repeats-associated (Cas) protein and from one to two ribonucleic acids, wherein the ribonucleic acids direct Cas protein to and hybridize to a target motif of the target IRF-1 polynucleotide sequence, wherein the target IRF-1 polynucleotide sequence is cleaved, and wherein at least one of the one to two ribonucleic acids are selected from the group consisting of SEQ ID NOs: 176602-182813.

In some aspects, the invention provides a stem cell (e.g., hypoimmunogenic stem cell) or population thereof, each cell comprising a modified genome comprising: a genomic modification in which the IRF-1 gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 176602-182813.

In some aspects, the invention provides a method for altering a target IRF-1 polynucleotide sequence in a cell comprising contacting the IRF-1 polynucleotide sequence with a clustered regularly interspaced short palindromic repeats-associated (Cas) protein and at least one ribonucleic acid, wherein the ribonucleic acid directs Cas protein to and hybridizes to a target motif of the target IRF-1 polynucleotide sequence, wherein the target IRF-1 polynucleotide sequence is cleaved, and wherein the at least one ribonucleic acid is selected from the group consisting of SEQ ID NOs: 176602-182813.

In some aspects, the present disclosure provides a stem cell (e.g., hypoimmunogenic stem cell) or population thereof comprising a genome in which the TAP1 gene has been edited to delete a contiguous stretch of genomic DNA, thereby reducing or eliminating surface expression of MHC class I molecules in the cell or population thereof.

The contiguous stretch of genomic DNA can be deleted by contacting the cell or population thereof with a Cas protein or a nucleic acid encoding the Cas protein and at least one ribonucleic acid or at least one pair of ribonucleic acids selected from the group consisting of SEQ ID NOs: 182814-188371.

The present invention contemplates genomically editing human cells to cleave TAP1 gene sequences, as well as editing the genome of such cells to alter one or more additional target polynucleotide sequences. It should be appreciated that cleaving a TAP1 genomic sequence using one or more gRNAs or gRNA pairs described herein and a Cas protein could result in partial or complete deletion of the target TAP1 genomic sequence, depending on the number of gRNAs or gRNA pairs selected, as well as their targets.

In some aspects, the invention provides a stem cell (e.g., hypoimmunogenic stem cell) or population thereof, each cell comprising a modified genome comprising a genomic modification in which the TAP1 gene has been edited to delete a contiguous stretch of genomic DNA, thereby reducing or eliminating MHC Class I molecule surface expression and/or activity in the cell. In some embodiments, the contiguous stretch of genomic DNA has been deleted by contacting the cell with a Cas protein or a nucleic acid encoding the Cas protein and a pair of ribonucleic acids having sequences selected from the group consisting of SEQ ID NOs: 182814-188371.

In some aspects, the invention provides a method for altering a target TAP1 polynucleotide sequence in a cell comprising contacting the TAP1 polynucleotide sequence with a clustered regularly interspaced short palindromic repeats-associated (Cas) protein and from one to two ribonucleic acids, wherein the ribonucleic acids direct Cas protein to and hybridize to a target motif of the target TAP1 polynucleotide sequence, wherein the target TAP1 polynucleotide sequence is cleaved, and wherein at least one of the one to two ribonucleic acids are selected from the group consisting of SEQ ID NOs: 182814-188371.

In some aspects, the invention provides a stem cell (e.g., hypoimmunogenic stem cell) or population thereof, each cell comprising a modified genome comprising: a genomic modification in which the TAP1 gene has been edited to reduce or eliminate MHC Class I molecule surface expression and/or activity in the cell by contacting the cell with a Cas protein or a nucleic acid encoding the Cas protein and at least one ribonucleic acid having a sequence selected from the group consisting of SEQ ID NOs: 182814-188371.

In some aspects, the invention provides a method for altering a target TAP1 polynucleotide sequence in a cell comprising contacting the TAP1 polynucleotide sequence with a clustered regularly interspaced short palindromic repeats-associated (Cas) protein and at least one ribonucleic acid, wherein the ribonucleic acid directs Cas protein to and hybridizes to a target motif of the target TAP1 polynucleotide sequence, wherein the target TAP1 polynucleotide sequence is cleaved, and wherein the at least one ribonucleic acid is selected from the group consisting of SEQ ID NOS: 182814-188371.

Figure 21A:
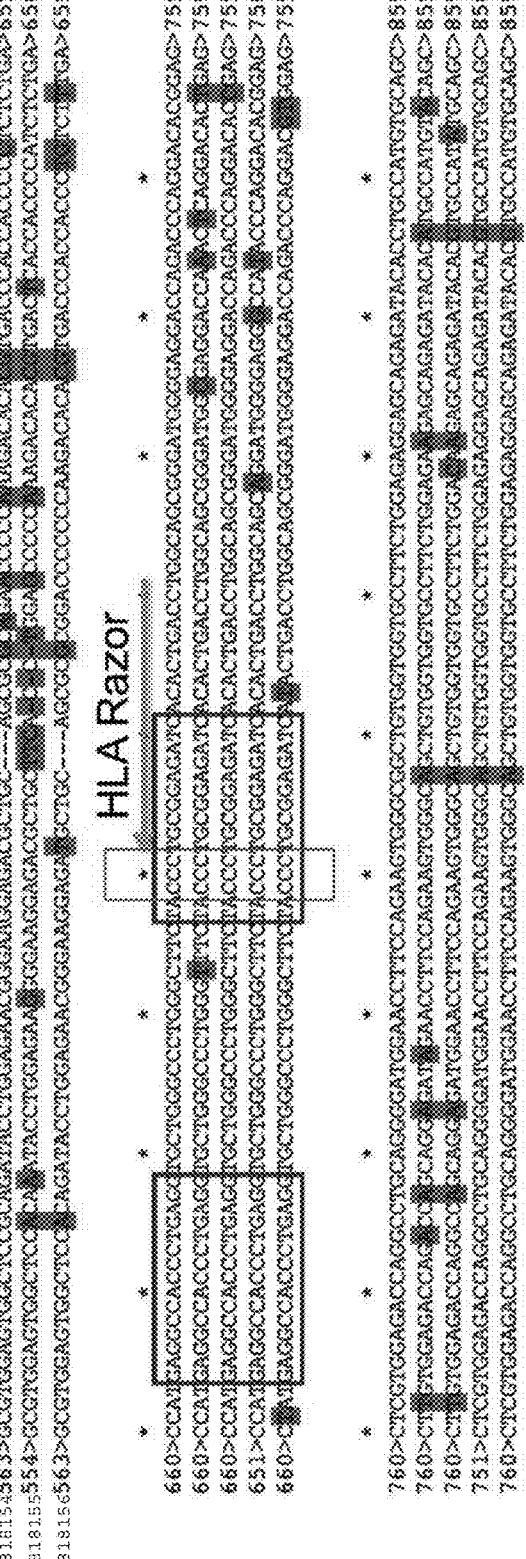
FIGS. 21A-21D demonstrate the use of a CRISPR gRNA identified as an HLA Razor that allows simultaneous deletion of all MHC class I alleles by targeting a conserved region in the HLA genes.

In certain embodiments, gRNAs that allow simultaneous deletion of all MHC class I alleles by targeting a conserved region in the HLA genes are identified as HLA Razors. In some aspects, the gRNAs are part of a CRISPR system. In alternative aspects, the gRNAs are part of a TALEN system. In one aspect, an HLA Razor targeting an identified conserved region in HLAs is depicted in FIG. 21A. In other aspects, multiple HLA Razors targeting identified conserved regions are utilized. It is generally understood that any guide that targets a conserved region in HLAs can act as an HLA Razor.

Knock-in

In certain embodiments, tolerogenic factors can be inserted or reinserted into genome-edited stem cell lines to create immune-privileged universal donor stem cell lines. In certain embodiments, the universal stem cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, C1-inhibitor, and IL-35.

Figures 11A, 11B, 11C:
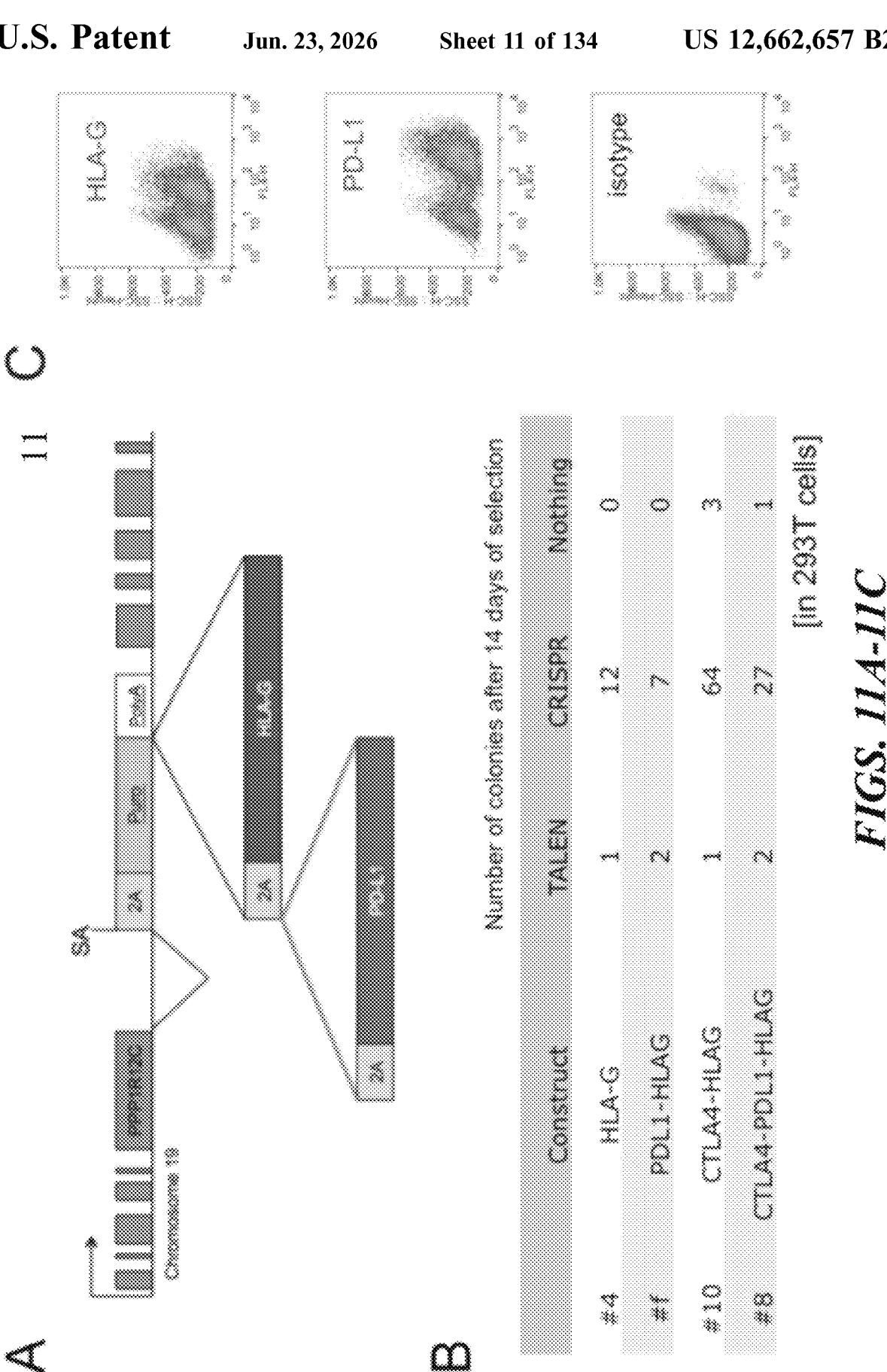
FIGS. 11A-11C demonstrate that tolerogenic factors, such as PD-L1 and HLA-G, can be expressed from a safe harbor locus.

The present inventors have used genome editing systems, such as the CRISPR/Cas system, to facilitate the insertion of tolerogenic factors, such as the tolerogenic factors shown in Table 2 below, into a safe harbor locus, such as the AAVS1 locus, to actively inhibit immune rejection. As evidenced in FIGS. 11A-11C, the present inventors have successfully expressed tolerogenic factors, such as PD-L1 and HLA-G, from a safe harbor locus.

TABLE 2

Tolerogenic factors that can be (re)introduced into genome edited stem cell lines to create immune-privileged universal donor stem cell lines.

| Gene | Receptor | Target Cell |
|---|---|---|
| HLA-G* | KIR2DL4 | NK cells |
| HLA-C* | KIR2DS1/L1 | NK cells |
| HLA-E* | NKG2A/C | NK cells |
| PD-L1 | PD-1 | T cells |
| CTLA4-Ig | CD28 | APC/T cells |
| CD47 | SIRPα | Macrophages |
| C1-inhibitor | Complement | |
| IL-35 | IL35R | T reg |

*in the form of a peptide-B2M-HLA fusion construct, when (re)introduced into a B2M$^{-/-}$ cell line In some aspects, the present disclosure provides a stem cell (e.g., hypoimmunogenic stem cell) or population thereof comprising a genome in which the stem cell genome has been modified to express HLA-G. In some aspects, the present disclosure provides a method for altering a stem cell genome to express HLA-G. In certain aspects at least one ribonucleic acid or at least one pair of ribonucleic acids may be utilized to facilitate the insertion of HLA-G into a stem cell line. In certain embodiments, the at least one ribonucleic acid or the at least one pair of ribonucleic acids is selected from the group consisting of SEQ ID NOs: 188372-189858.

In some aspects, the present disclosure provides a stem cell (e.g., hypoimmunogenic stem cell) or population thereof comprising a genome in which the stem cell genome has been modified to express HLA-C. In some aspects, the present disclosure provides a method for altering a stem cell genome to express HLA-C. In certain aspects at least one ribonucleic acid or at least one pair of ribonucleic acids may be utilized to facilitate the insertion of HLA-C into a stem cell line. In certain embodiments, the at least one ribonucleic acid or the at least one pair of ribonucleic acids is selected from the group consisting of SEQ ID NOs: 3278-5183.

In some aspects, the present disclosure provides a stem cell (e.g., hypoimmunogenic stem cell) or population thereof comprising a genome in which the stem cell genome has been modified to express HLA-E. In some aspects, the present disclosure provides a method for altering a stem cell genome to express HLA-E. In certain aspects at least one ribonucleic acid or at least one pair of ribonucleic acids may be utilized to facilitate the insertion of HLA-E into a stem cell line. In certain embodiments, the at least one ribonucleic acid or the at least one pair of ribonucleic acids is selected from the group consisting of SEQ ID NOs: 189859-193183.

In some aspects, the present disclosure provides a stem cell (e.g., hypoimmunogenic stem cell) or population thereof comprising a genome in which the stem cell genome has been modified to express PD-L1. In some aspects, the present disclosure provides a method for altering a stem cell genome to express PD-L1. In certain aspects at least one ribonucleic acid or at least one pair of ribonucleic acids may be utilized to facilitate the insertion of PD-L1 into a stem cell line. In certain embodiments, the at least one ribonucleic acid or the at least one pair of ribonucleic acids is selected from the group consisting of SEQ ID NOs: 193184-200783.

In some aspects, the present disclosure provides a stem cell (e.g., hypoimmunogenic stem cell) or population thereof comprising a genome in which the stem cell genome has been modified to express CD-47. In some aspects, the present disclosure provides a method for altering a stem cell genome to express CD-47. In certain aspects at least one ribonucleic acid or at least one pair of ribonucleic acids may be utilized to facilitate the insertion of CD-47 into a stem cell line. In certain embodiments, the at least one ribonucleic acid or the at least one pair of ribonucleic acids is selected from the group consisting of SEQ ID NOs: 200784-231885.

In some aspects, the present disclosure provides a stem cell (e.g., hypoimmunogenic stem cell) or population thereof comprising a genome in which the stem cell genome has been modified to express HLA-F. In some aspects, the present disclosure provides a method for altering a stem cell genome to express HLA-F. In certain aspects at least one ribonucleic acid or at least one pair of ribonucleic acids may be utilized to facilitate the insertion of HLA-F into a stem cell line. In certain embodiments, the at least one ribonucleic acid or the at least one pair of ribonucleic acids is selected from the group consisting of SEQ ID NOs: 688808-399754.

Other Target Modifications

In some embodiments, additional targets can be modified and/or deleted in universal cells, such as universal T cells, to improve their function and/or tailor them to a specific therapeutic approach.

In some aspects, genes encoding for co-stimulatory molecules/receptors that engage cytotoxic T cells can be deleted by genome editing (Table 3). Deletion of co-stimulatory molecules/receptors may occur to prevent autoimmunity. In other aspects, genes encoding for co-inhibitory molecules/receptors can be deleted by genome editing (Table 4). Deletion of co-inhibitory molecules/receptors may occur to prevent T cell inhibition by cancer cells, and may be useful in T cell-based cancer immunotherapy.

TABLE 3

Co-stimulatory molecules that will be deleted to prevent autoimmunity
(e.g., to block interaction of transplanted cells with T cells).

| Ligand on Cancer cells | Receptor on T cells |
|---|---|
| Ox40L | Ox40 |
| GITRL | GITR |
| 4-1BBL | 4-1BB |
| CD58 | CD2 |
| B7-1, −2 | CD28 |
| B2-2 | ICOS |
| CD70 | CD27 |
| LIGHT | HVEM |
| SLAM | SLAM |
| CD155, CD112 | CD226 |

TABLE 4

Co-inhibitory molecules/receptors that will be deleted to prevent
T cell inhibition by cancer cells. Useful in T cell-based cancer immunotherapy

| Ligand on Cancer cells | Receptor on T cells |
|---|---|
| B7/H1PD-L1 | PD1 |
| B7-1/B7-2 | CTLA4 |
| MHC | LAG3 |
| CD155, CD112, CD113 | TIGIT |
| Galectin 9 | TIM3 |
| B7-1 | B7-H1/PD-L1 |
| PD-L2 | PD-1 |
| B7-H3 | TLT-2 |
| CD153 | CD30 |
| VISTA | ? |
| HVEM | CD160 |
| HVEM | BTLA |
| Collagen | LAIR1 |
| CD48 | 2B4/CD244 |

In some aspects, the present disclosure provides a stem cell or population thereof comprising a genome in which the OX40 gene has been edited to modify (e.g., delete) a contiguous stretch of genomic DNA. In certain aspects, the present disclosure provides a method for altering a target OX40 sequence in a cell. The contiguous stretch of genomic DNA can be modified (e.g., deleted) by contacting the cell or population thereof with a Cas protein or a nucleic acid encoding the Cas protein and at least one ribonucleic acid or at least one pair of ribonucleic acids selected from the group consisting of SEQ ID NOs: 231886-234210.

In some aspects, the present disclosure provides a stem cell or population thereof comprising a genome in which the GITR gene has been edited to modify a contiguous stretch of genomic DNA. In certain aspects, the present disclosure provides a method for altering a target GITR sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 234211-236445.

In some aspects, the present disclosure provides a stem cell or population thereof comprising a genome in which the 4-1BB gene has been edited to modify a contiguous stretch of genomic DNA. In certain aspects, the present disclosure provides a method for altering a target 4-1BB sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 234211-236445.

In some aspects, the present disclosure provides a stem cell or population thereof comprising a genome in which the CD28 gene has been edited to modify a contiguous stretch of genomic DNA. In certain aspects, the present disclosure provides a method for altering a target CD28 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 252807-274181.

In some aspects, the present disclosure provides a stem cell or population thereof comprising a genome in which the B7-1 gene has been edited to modify a contiguous stretch of genomic DNA. In certain aspects, the present disclosure provides a method for altering a target B7-1 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 274182-295529.

In some aspects, the present disclosure provides a stem cell or population thereof comprising a genome in which the B7-2 gene has been edited to modify a contiguous stretch of genomic DNA. In certain aspects, the present disclosure provides a method for altering a target B7-2 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 295530-324177.

In some aspects, the present disclosure provides a stem cell or population thereof comprising a genome in which the ICOS gene has been edited to modify a contiguous stretch of genomic DNA. In certain aspects, the present disclosure provides a method for altering a target ICOS sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 324178-339974.

In some aspects, the present disclosure provides a stem cell or population thereof comprising a genome in which the CD27 gene has been edited to modify a contiguous stretch of genomic DNA. In certain aspects, the present disclosure provides a method for altering a target CD27 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 339975-344266.

In some aspects, the present disclosure provides a stem cell or population thereof comprising a genome in which the HVEM gene has been edited to modify a contiguous stretch of genomic DNA. In certain aspects, the present disclosure provides a method for altering a target HVEM sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 344267-350722.

In some aspects, the present disclosure provides a stem cell or population thereof comprising a genome in which the SLAM gene has been edited to modify a contiguous stretch of genomic DNA. In certain aspects, the present disclosure provides a method for altering a target SLAM sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 350723-353590.

In some aspects, the present disclosure provides a stem cell or population thereof comprising a genome in which the CD226 gene has been edited to modify a contiguous stretch of genomic DNA. In certain aspects, the present disclosure provides a method for altering a target CD226 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 353591-416840.

In some aspects, the present disclosure provides a stem cell or population thereof comprising a genome in which the PD1 gene has been edited to modify a contiguous stretch of genomic DNA. In certain aspects, the present disclosure provides a method for altering a target PD1 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of sequences numbered 196-531 and 4047-9101 in U.S. application Ser. No. 15/083,021, which is incorporated herein by reference.

In some aspects, the present disclosure provides a stem cell or population thereof comprising a genome in which the CTLA4 gene has been edited to modify a contiguous stretch of genomic DNA. In certain aspects, the present disclosure provides a method for altering a target CTLA4 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of sequences numbered 1-195 and 797-4046 in U.S. application Ser. No. 15/083,021, which is incorporated herein by reference.

In some aspects, the present disclosure provides a stem cell or population thereof comprising a genome in which the LAG3 gene has been edited to modify a contiguous stretch of genomic DNA. In certain aspects, the present disclosure provides a method for altering a target LAG3 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 416841-421195.

In some aspects, the present disclosure provides a stem cell or population thereof comprising a genome in which the TIGIT gene has been edited to modify a contiguous stretch of genomic DNA. In certain aspects, the present disclosure provides a method for altering a target TIGIT sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 421196-432039.

In some aspects, the present disclosure provides a stem cell or population thereof comprising a genome in which the TIM3 gene has been edited to modify a contiguous stretch of genomic DNA. In certain aspects, the present disclosure provides a method for altering a target TIM3 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 432040-447610.

In some aspects, the present disclosure provides a stem cell or population thereof comprising a genome in which the CD160 gene has been edited to modify a contiguous stretch of genomic DNA. In certain aspects, the present disclosure provides a method for altering a target CD160 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 447611-459294.

In some aspects, the present disclosure provides a stem cell or population thereof comprising a genome in which the BTLA gene has been edited to modify a contiguous stretch of genomic DNA. In certain aspects, the present disclosure provides a method for altering a target BTLA sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 459295-482454.

In some aspects, the present disclosure provides a stem cell or population thereof comprising a genome in which the CD244 gene has been edited to modify a contiguous stretch of genomic DNA. In certain aspects, the present disclosure provides a method for altering a target CD244 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 482455-504169.

In some aspects, the present disclosure provides a stem cell or population thereof comprising a genome in which the CD244 gene has been edited to modify a contiguous stretch of genomic DNA. In certain aspects, the present disclosure provides a method for altering a target CD244 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 482455-504169.

In some aspects, the present disclosure provides a stem cell or population thereof comprising a genome in which the CD30 gene has been edited to modify a contiguous stretch of genomic DNA. In certain aspects, the present disclosure provides a method for altering a target CD30 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 699755-731993.

In some aspects, the present disclosure provides a stem cell or population thereof comprising a genome in which the TLT gene has been edited to modify a contiguous stretch of genomic DNA. In certain aspects, the present disclosure provides a method for altering a target TLT sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 731994-739957.

In some aspects, the present disclosure provides a stem cell or population thereof comprising a genome in which the VISTA gene has been edited to modify a contiguous stretch of genomic DNA. In certain aspects, the present disclosure provides a method for altering a target VISTA sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 739958-757515.

In some aspects, the present disclosure provides a stem cell or population thereof comprising a genome in which the B7-H3 gene has been edited to modify a contiguous stretch of genomic DNA. In certain aspects, the present disclosure provides a method for altering a target B7-H3 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 757516-777888.

In some aspects, the present disclosure provides a stem cell or population thereof comprising a genome in which the PD-L2 gene has been edited to modify a contiguous stretch of genomic DNA. In certain aspects, the present disclosure provides a method for altering a target PD-L2 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 777889-817976.

In some embodiments, lymphocyte adhesion is blocked to prevent autoimmunity. In certain aspects, target genes can be edited by genome editing to block lymphocyte adhesion (Table 5).

TABLE 5

| Blocking lymphocyte adhesion to prevent autoimmunity. | |
| --- | --- |
| Ligand on Cancer cells | Receptor on T cells |
| ICAM-1, ICAM-2 | LFA-1 |
| CD58/LFA-3 | CD2 |
| CD-SIGN | ICAM-3 |

In some aspects, the present disclosure provides a stem cell or population thereof comprising a genome in which the LFA-1 gene has been edited to modify a contiguous stretch of genomic DNA. In certain aspects, the present disclosure provides a method for altering a target LFA-1 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 504170-526670.

In some aspects, the present disclosure provides a stem cell or population thereof comprising a genome in which the CD2 gene has been edited to modify a contiguous stretch of genomic DNA. In certain aspects, the present disclosure provides a method for altering a target CD2 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 526671-536704.

In some aspects, the present disclosure provides a stem cell or population thereof comprising a genome in which the CD58 gene has been edited to modify a contiguous stretch of genomic DNA. In certain aspects, the present disclosure provides a method for altering a target CD58 sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 536705-570967.

In some embodiments, genes encoding for T cell receptors can be deleted by genome editing. Deletion of T cell receptor genes may occur to prevent autoimmune attack in T cell therapy. In some aspects, the gene encoding the T cell receptor is a T cell receptor alpha locus (TCRA), or a homolog, ortholog, or variant thereof (Gene ID: 5133, also known as IMD7, TCRD, TRA@, TRAC, and referred to herein as TCRa, TCRA, TCRalpha, and the like). In some aspects, the gene encoding the T cell receptor is a T cell receptor alpha locus (TCRB), or a homolog, ortholog, or variant thereof (Gene ID: 6957, also known as TCRB; TRB@, and referred to herein as TCRb, TCRB, TCRbeta, and the like). In some aspects, the T cell receptor gene is modified by genome editing as described in U.S. application Ser. No. 15/083,021 and PCT Application No. PCT/US2016/024554, both of which are incorporated herein by reference.

In some aspects, the present disclosure provides a stem cell or population thereof comprising a genome in which the TRAC gene has been edited to modify a contiguous stretch of genomic DNA. In certain aspects, the present disclosure provides a method for altering a target TRAC sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of sequences numbered 532-609 and 9102-9797, as described in U.S. application Ser. No. 15/083,021, incorporated herein by reference.

In some aspects, the present disclosure provides a stem cell or population thereof comprising a genome in which the TRBC gene has been edited to modify a contiguous stretch of genomic DNA. In certain aspects, the present disclosure provides a method for altering a target TRBC sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of sequences numbered 610-765 and 9798-10573, as described in U.S. application Ser. No. 15/083,021 and incorporated herein by reference.

In some embodiments, genes involved in regulatory T cell (T reg) function can be deleted by genome editing (Table 6). Deletion of genes involved in regulatory T cell (T reg) function may occur to break tolerance in T cell therapy.

TABLE 6

Deletion of genes involved in regulatory T cell
(T reg) function to break tolerance in T cell therapy.

| Gene | Function |
|---|---|
| FOXP3 | T reg development |
| HELIOS | T reg maintenance |
| ST2 | IL-33 receptor |

In some aspects, the present disclosure provides a stem cell or population thereof comprising a genome in which the FOXP3 gene has been edited to modify (e.g., delete) a contiguous stretch of genomic DNA. In certain aspects, the present disclosure provides a method for altering a target FOXP3 sequence in a cell. The contiguous stretch of genomic DNA can be modified (e.g., deleted) by contacting the cell or population thereof with a Cas protein or a nucleic acid encoding the Cas protein and at least one ribonucleic acid or at least one pair of ribonucleic acids selected from the group consisting of SEQ ID NOs: 570968-584068.

In some aspects, the present disclosure provides a stem cell or population thereof comprising a genome in which the HELIOS gene has been edited to modify a contiguous stretch of genomic DNA. In certain aspects, the present disclosure provides a method for altering a target HELIOS sequence in a cell. The contiguous stretch of genomic DNA can be modified by contacting the cell or population thereof with a Cas protein or a nucleic acid encoding the Cas protein and at least one ribonucleic acid or at least one pair of ribonucleic acids selected from the group consisting of SEQ ID NOs: 683033-688807.

The capacity of the CRISPR/Cas system for multiplexing also allows the generation of disease-specific universal donor cell lines that harbor one or more genomic alterations that will improve their applicability to treat a certain disease or condition. A list of potential diseases that can be addressed can be found in Table 7.

TABLE 7

Additional targets that can be modified using the
CRISPR/Cas system in order to generate universal
donor cell lines tailored to a specific disease or application.

| Gene | Disease |
|---|---|
| TCR | T cell therapy |
| PD-1 | T cell therapy |
| CTLA4 | T cell therapy |
| LAG-3 | T cell therapy |
| TIGIT | T cell therapy |
| TIM3 | T cell therapy |
| CCR5 | HIV resistance |
| PCSK9 | Cardiovascular disease |
| APOC3 | Cardiovascular disease |

It is to be understood that the inventions disclosed herein are not limited in their application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compositions, methods and assays of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Cell Lines

The inventors have targeted various genes in a variety of cell lines. The various cell lines utilized include HuES8, HuES9, BJ-RiPSCs, Thp1, Jurkat, Primary T cells and HEK293T cells (FIG. 27). HuES8 and HuES9 are human ES cell lines. BJ-RiPSC is an iPSC line.

Knock-Out of HLA-A, HLA-B, and HLA-C

Figure 14A:
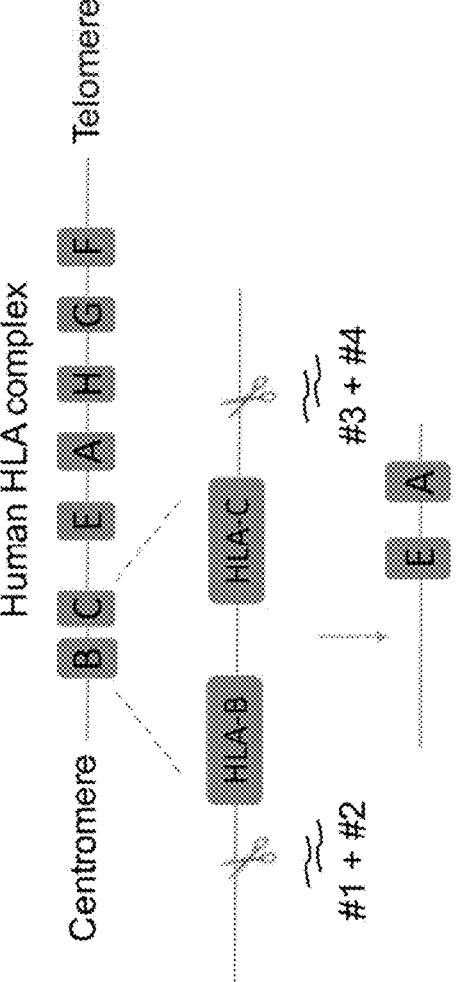
FIGS. 14A-14J demonstrates the targeting of HLA-A, HLA-B and HLA-C.

Knock-out targeting of HLAs was examined. Initially, an HLA-B and HLA-C knock-out strategy was examined. Two short guide RNAs (sgRNAs) were designed upstream of the HLA-B locus and downstream of HLA-C, which allowed for excision of the HLA-B and HLA-C genes (FIG. 14A).

sgRNA #1 and sgRNA #2 target the HLA-B upstream region, and sgRNA #3 and sgRNA #4 target the HLA-C downstream region.

Figure 14B:
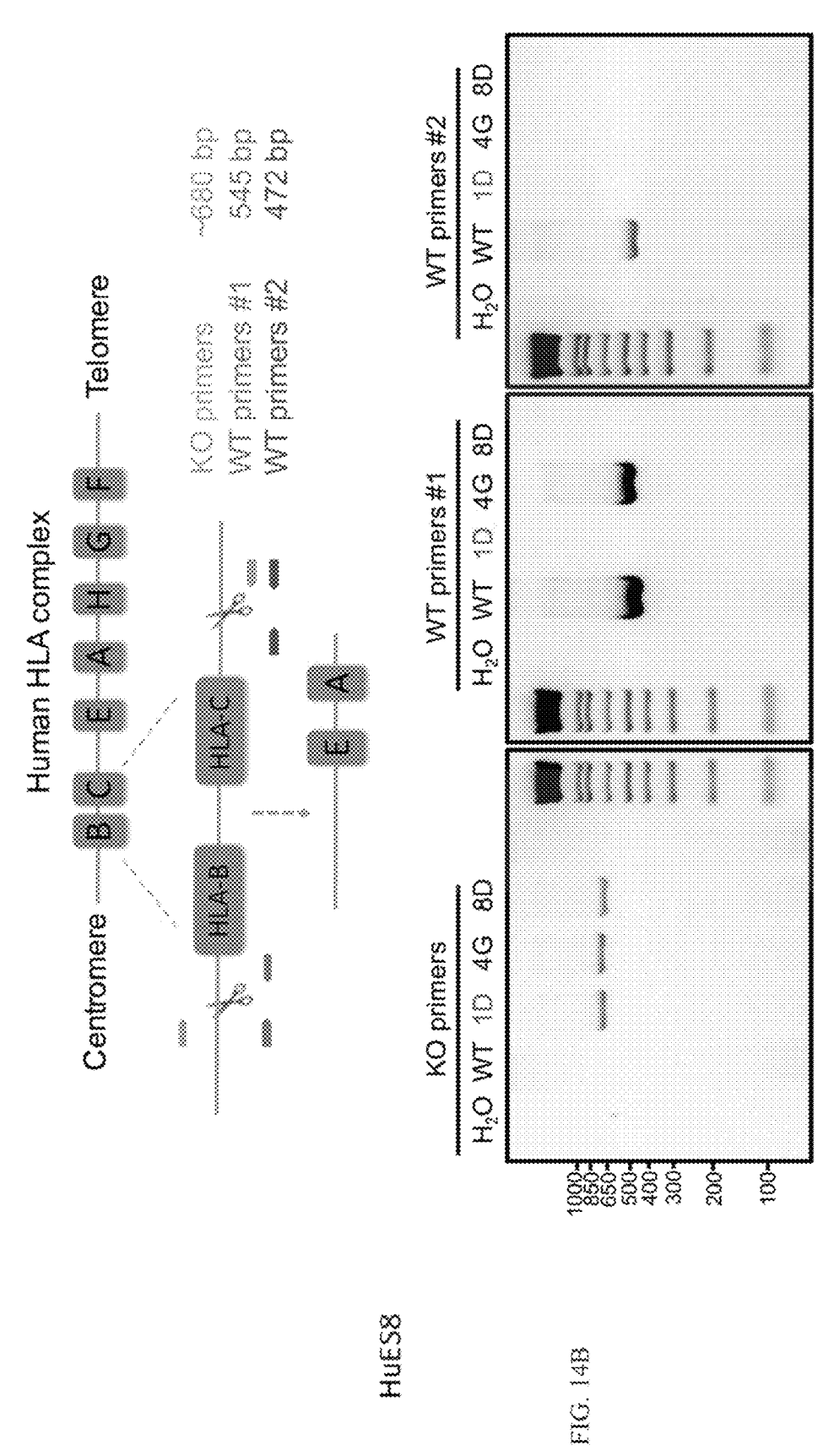
Figure 14C:
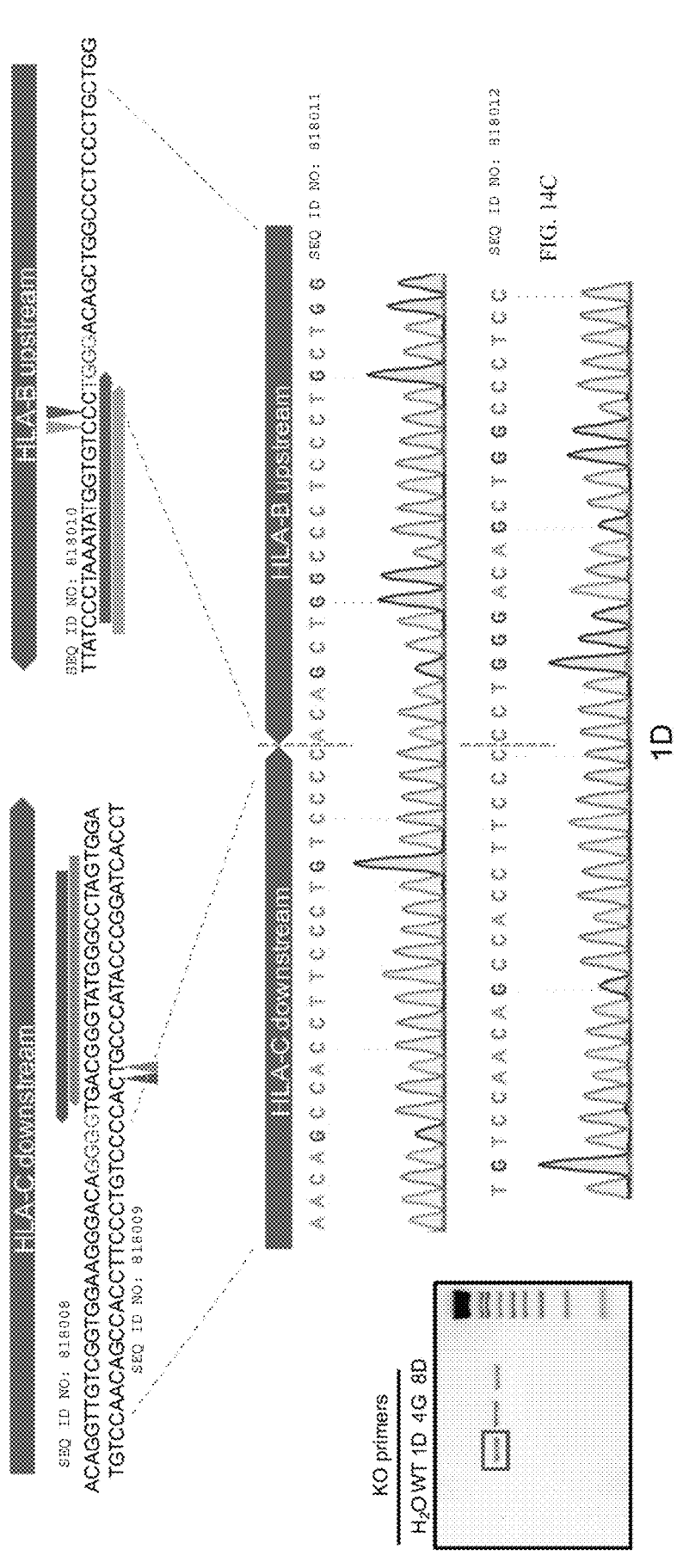

PCR screening was performed and confirmed that clone 1D was a homozygous knock-out clone. A schematic showing the PCR verification strategy for successful deletion of HLA-B and HLA-C is shown in FIG. 13B. Two pairs of wild-type (WT) primers were designed flanking each cutting site, with predicted amplicons sizes of 545 bp and 472 bp. Clone 1D was identified as a homozygous knock-out clone by the presence of ~680 pb PCR band generated with KO primers and the absence of bands using the two different sets of WT primers (FIG. 14B). In addition, genomic DNA was isolated from the indicated targeted HuES8 clones. Sequencing results of the clone 1D PCR product demonstrated successful deletion of HLA-B and HLA-C genes in HuES9 (FIG. 14C).

Figure 14D:
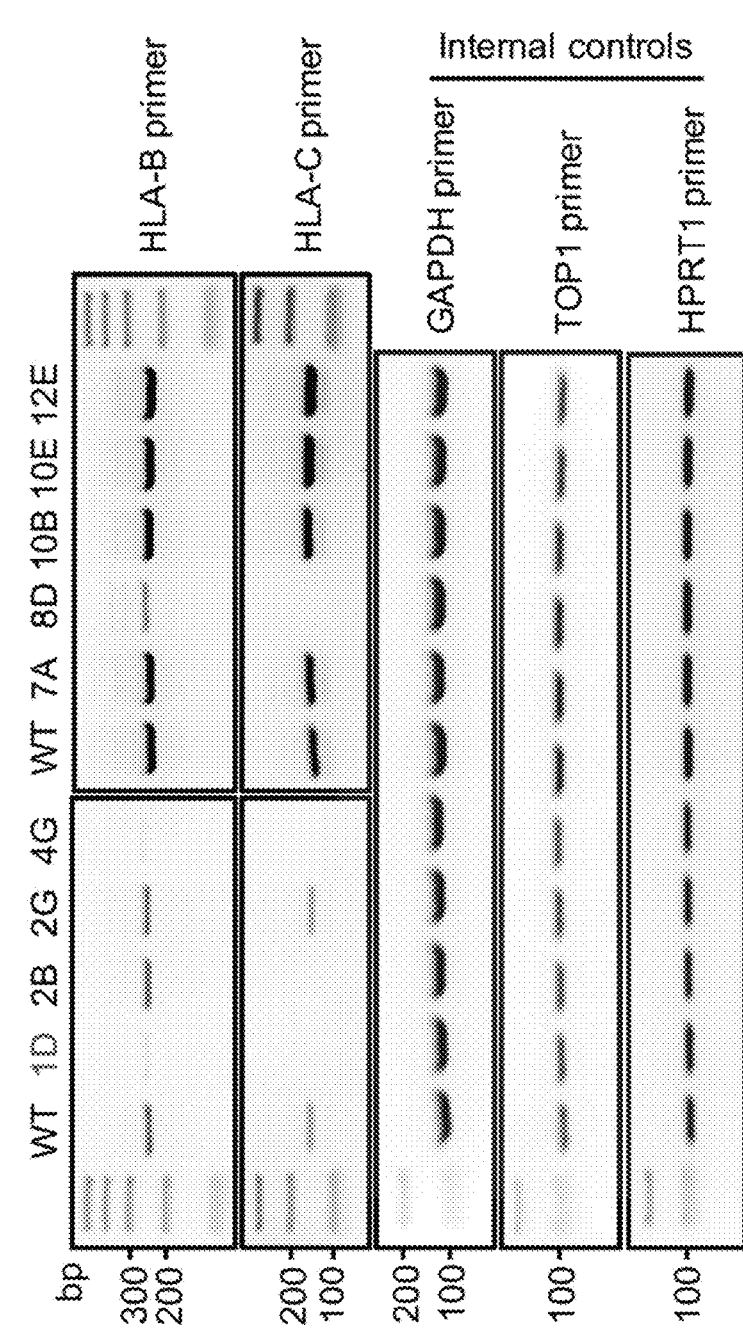
Figure 14E:
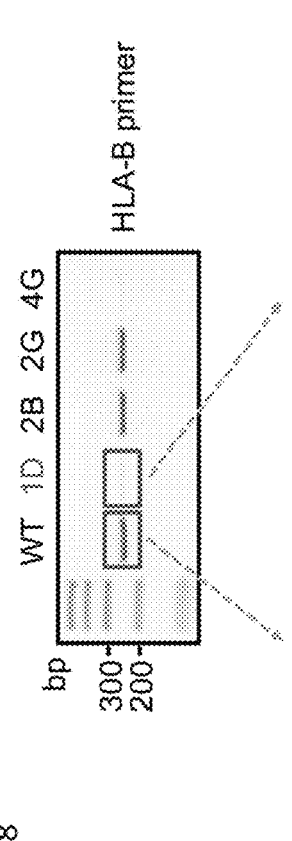
Figure 14F:
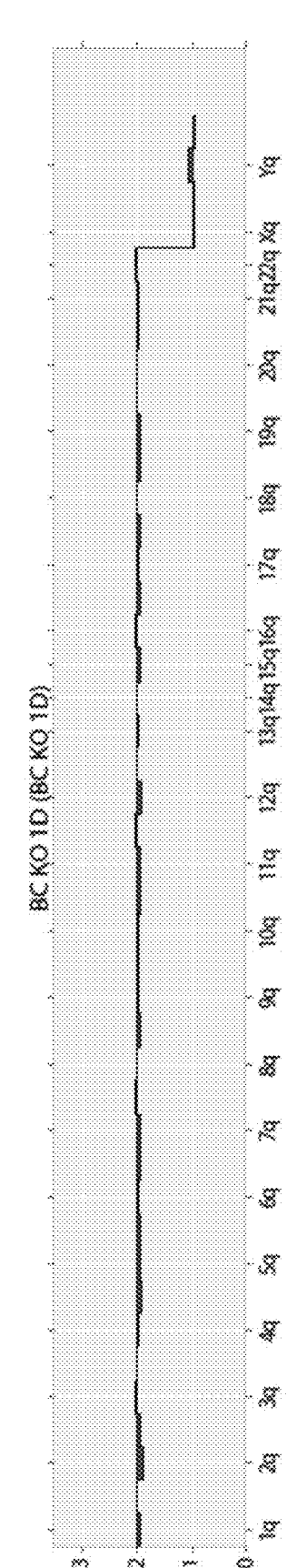

Further, RT-PCR with HLA-B and HLA-C specific primers demonstrated the mRNA expression of HLA-B and HLA-C in clone 1D was eliminated (FIG. 14D). GAPDH, TOP1 and HPRT1 were used as internal controls. WT and clone 1D RT-PCR products amplified with HLA-B primers were sequenced and identified as HLA-B and HLA-A mRNAs, respectively using BLAST (FIG. 14E). These results demonstrated that in the absence of the HLA-B gene, the HLA-B specific primers will amplify HLA-A mRNA in HuES8 clone 1D. HuES8 clone 1D displays a normal karyotype as assessed by NanoString nCounter set (FIG. 14F).

Figure 14G:
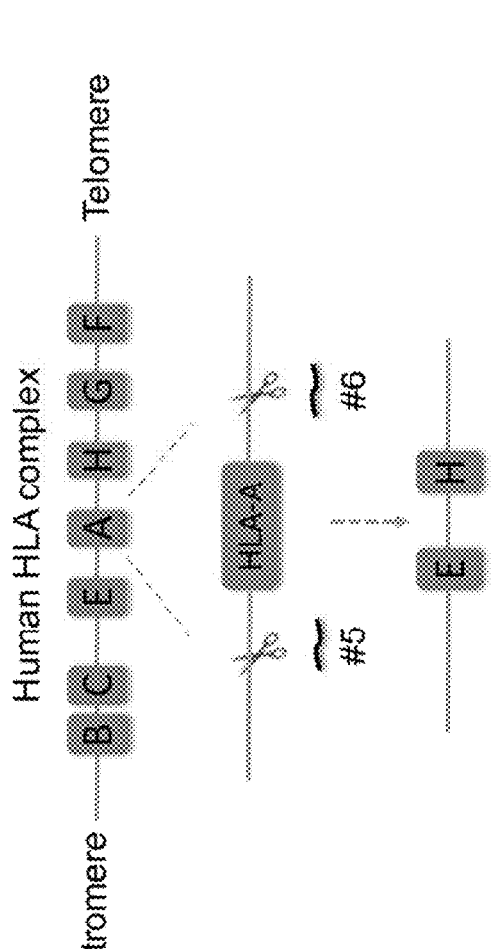
Figure 14H:
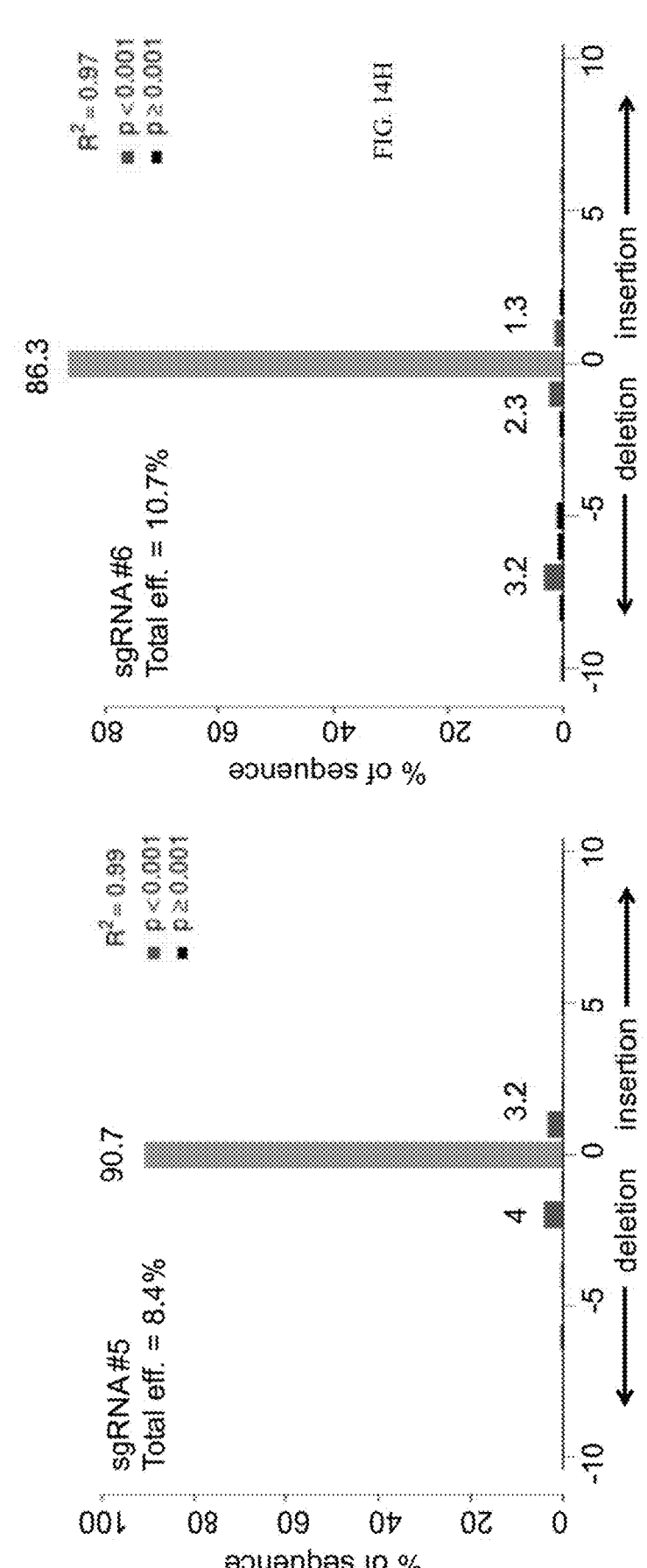

A schematic demonstrating an HLA-A knockout strategy using the dual sgRNA approach is provided in FIG. 14G. The schematic shows the position of the two sgRNAs (#5 and #6) that were designed to bind upstream and downstream of HLA-A. The on-target cutting efficiency of sgRNA #5 and #6 was determined in 293T cells using TIDE (FIG. 14H).

Figure 14I:
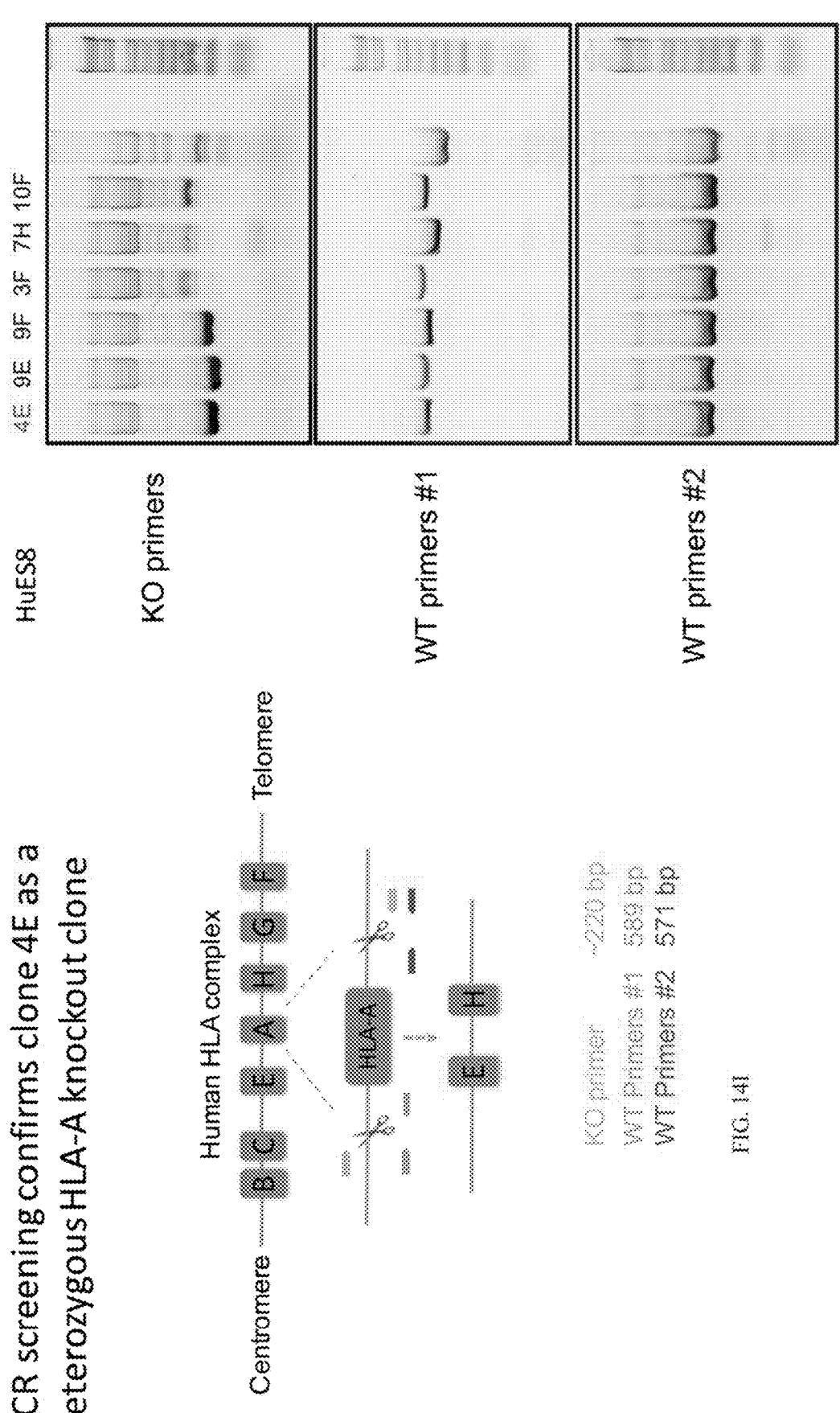
Figure 14J:
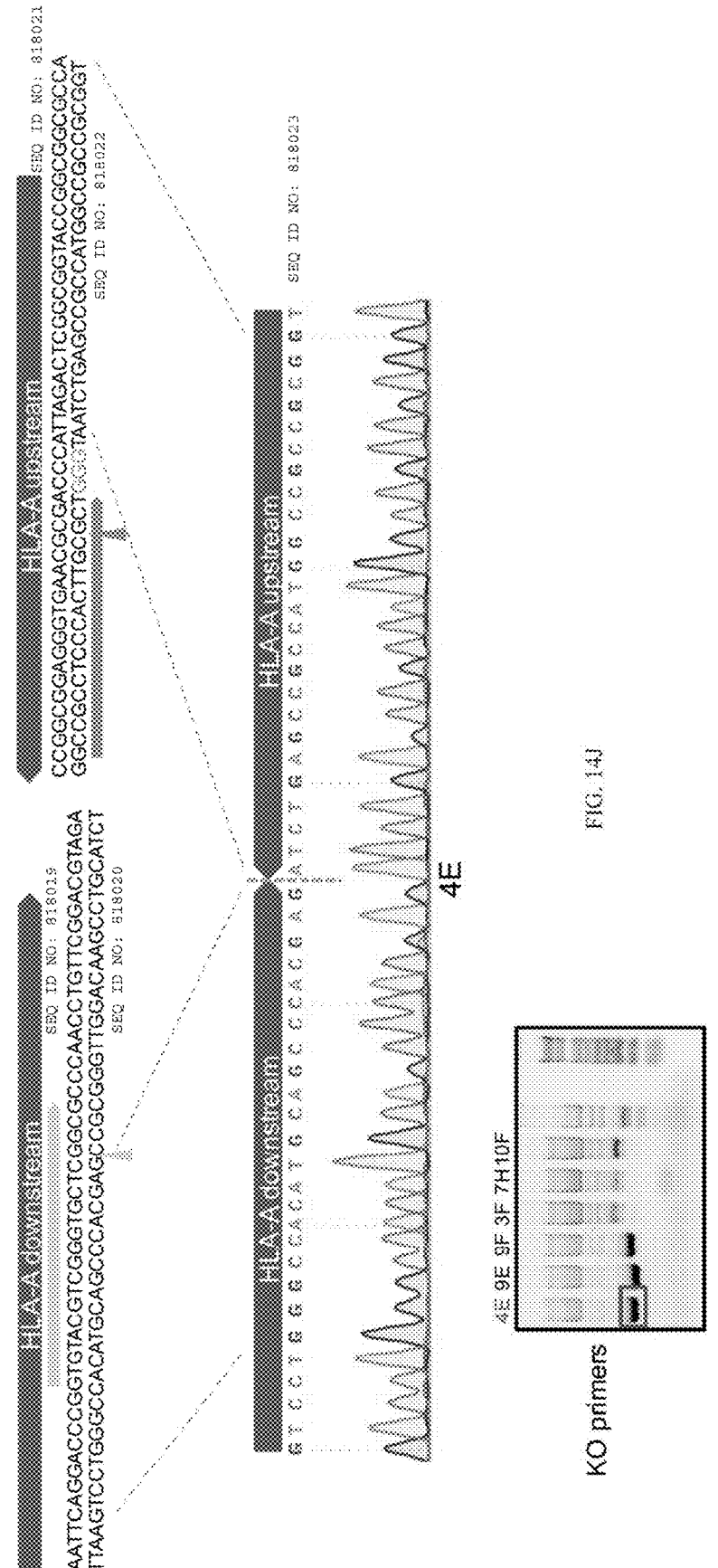

PCR screening confirmed that clone 4E was a heterozygous HLA-A knockout clone (FIG. 14I). The PCR screening strategy confirmed deletion of HLA-A in HuES8. KO primers were designed with one primer annealing upstream and one primer annealing downstream of the cutting sites. Upon HLA-A deletion, the resulting amplicon was observed as 220 bp on a 2% agarose gel. Two pairs of WT primers were designed flanking each cutting site, with predicted amplicon sizes of 589 bp and 571 bp. Clone 4E was identified as a heterozygous clone due to the presence of bands generated with KO primers and WT primers amplified from genomic DNA (FIG. 14I). Sequencing of the PCR product amplified from the genomic DNA of clone 4E using KO primers demonstrated successful deletion of HLA-A in HuES8 (FIG. 14J).

Knock-Out of Transcriptional Regulators

Figures 3A, 3B:
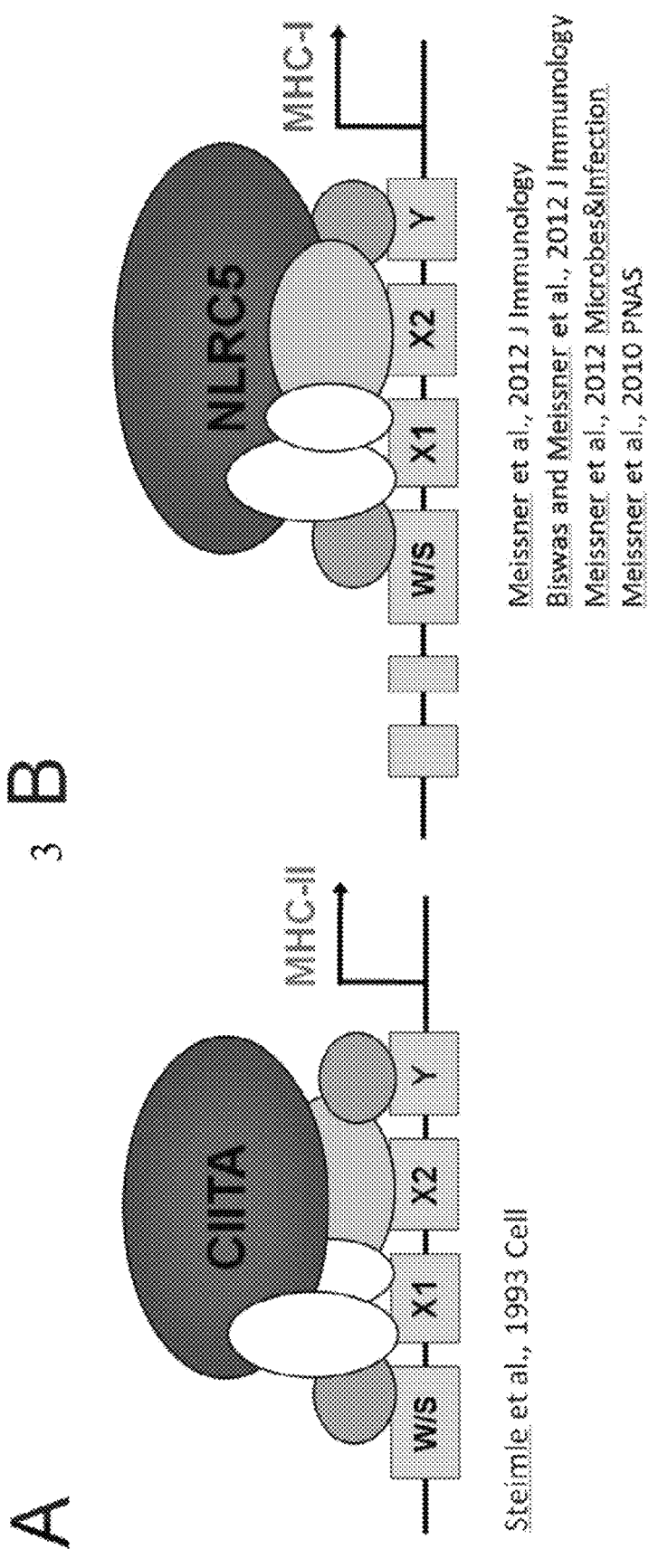
FIGS. 3A-3B illustrate targeting of transcriptional regulators of antigen presentation.
Figure 4:
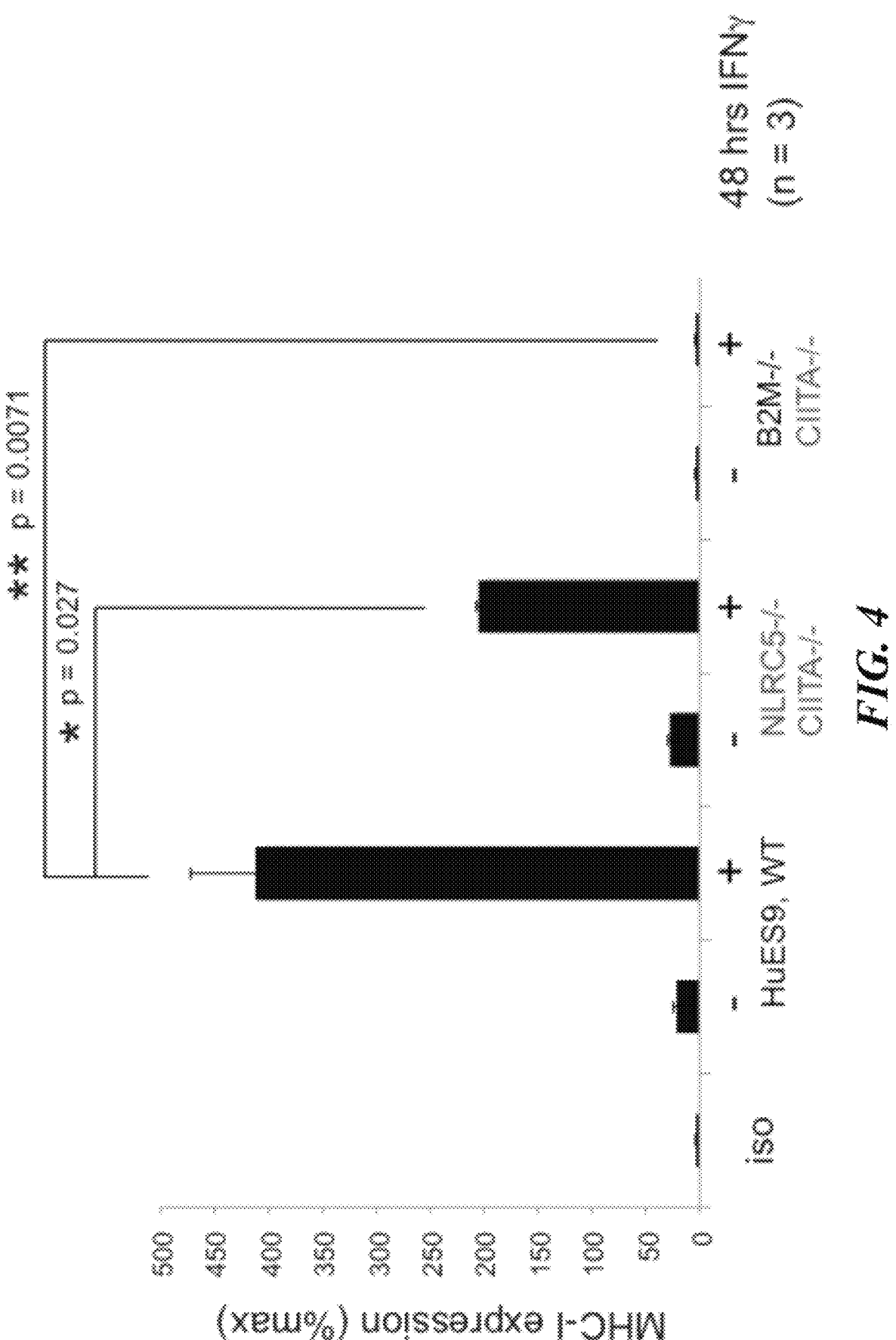
FIG. 4 illustrates MHC-I expression in WT HuES9 and the indicated modified mutant cell lines. Cells were stimulated for 48 hrs. with IFNγ and MHC-I expression was assessed by FACS.

As illustrated in FIGS. 3A-3B, in certain aspects, the inventions disclosed herein target the transcriptional regulators of antigen presentation (e.g., CIITA and/or NLRC5). The inventors have discovered that targeting and/or modulating the expression of such transcriptional regulators of antigen presentation provides a means to efficiently modulate (e.g., reduce or eliminate) the expression of the three classical MHC-Ia molecules, HLA-A, HLA-B, and HLA-C, and thereby produce hypoimmunogenic universal stem cell lines that are useful for cell replacement therapy. As evidenced in FIG. 4, the present inventors have demonstrated that such genome-edited cells are characterized by reduced MHC-I expression relative to the WT HuES9 cells, as assessed by FACS. Reduced or eliminated MHC-I surface expression was observed in those stem cells in which the expression of NLRC5, CIITA and B2M was modulated using the CRISPR/Cas system. In particular, FIG. 4 evidences low basal MHC-I expression in stem cells which can be increased by IFN-Y, that an approximately 50% reduction of MHC-I surface expression was observed in the IFN-γ-treated NLRC5−/− stem cells and that a complete loss of MHC-I surface expression was observed in the B2M−/− stem cells.

Figures 5A, 5B, 5C:
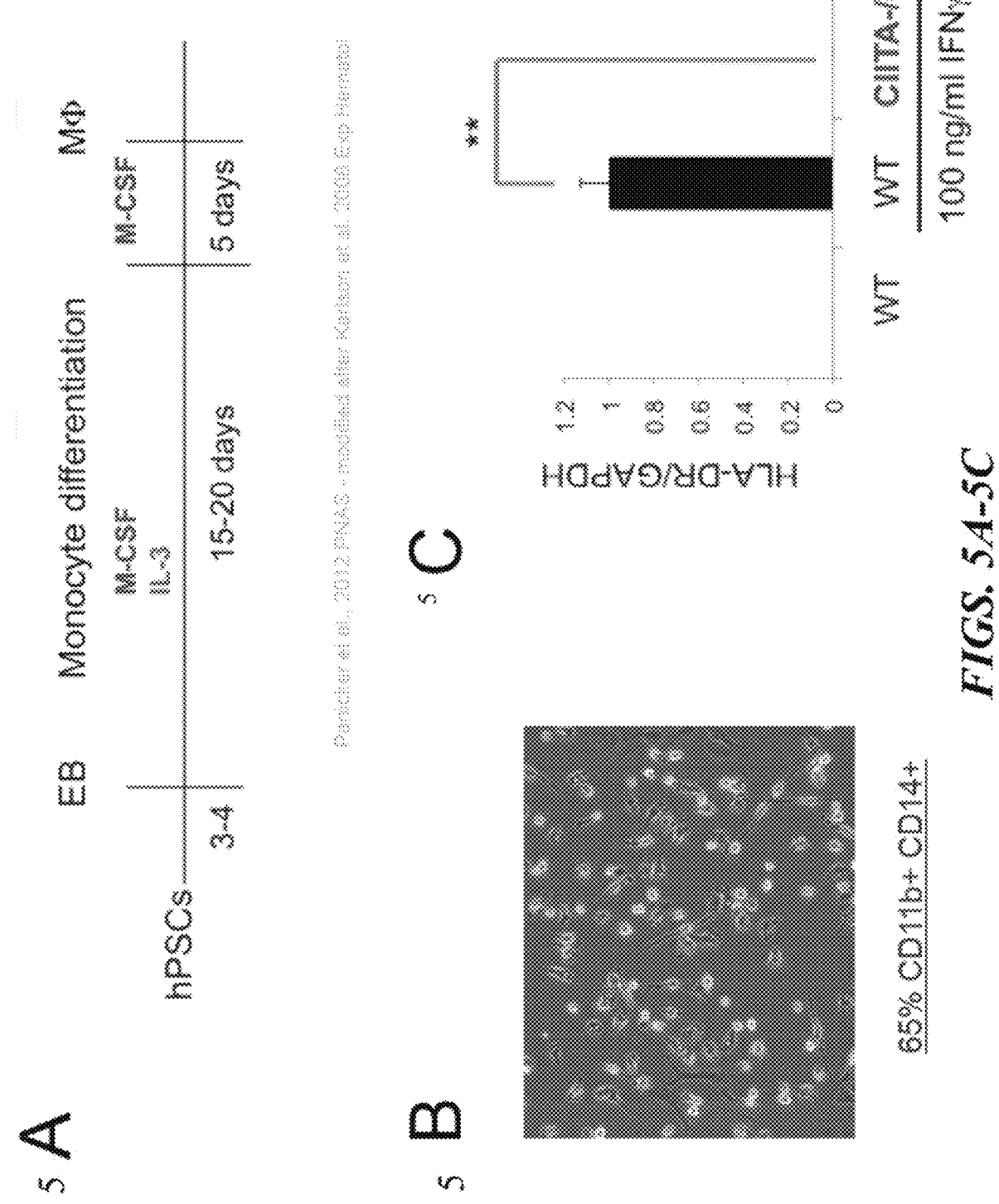
FIGS. 5A-5C illustrate that CIITA-deficient stem cell-derived macrophage lack MHC-II expression.
Figures 10A, 10B:
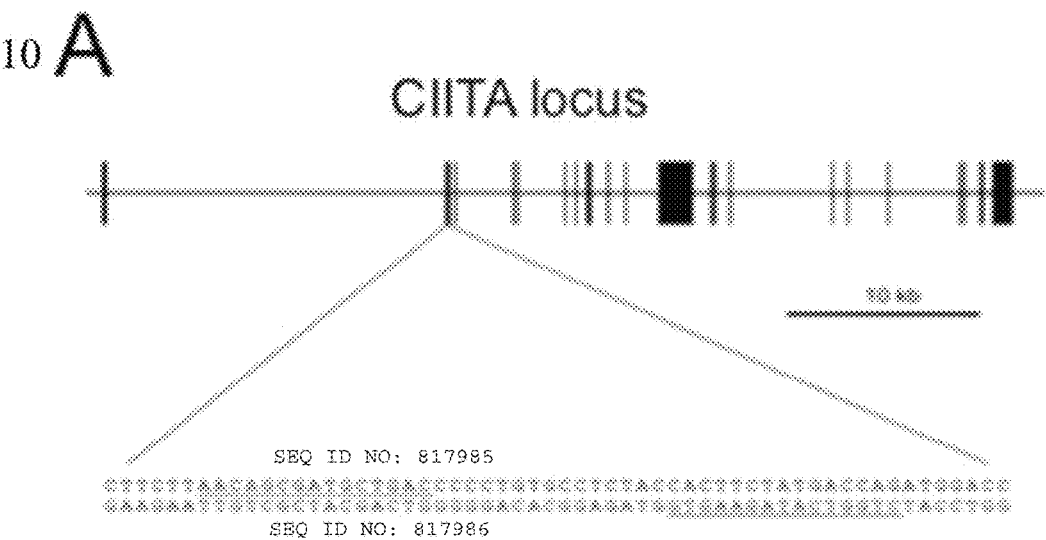
FIGS. 10A-10B illustrate targeting of the first coding exon of the CIITA gene.

Similar results were observed on MHC-II expression following modulation of the expression of CIITA. The present inventors differentiated the genome-edited CIITA−/− stem cell line into macrophage, which are antigen presenting cells. As depicted in FIG. 5C, the CIITA-deficient stem cell-derived macrophage lacked MHC-II expression, thus clearly showcasing the expected phenotype. In particular, by targeting the first coding exon of the CIITA gene (FIGS. 10A-10B), the foregoing results evidence that MHC-II expression can be efficiently abrogated.

Figure 6:
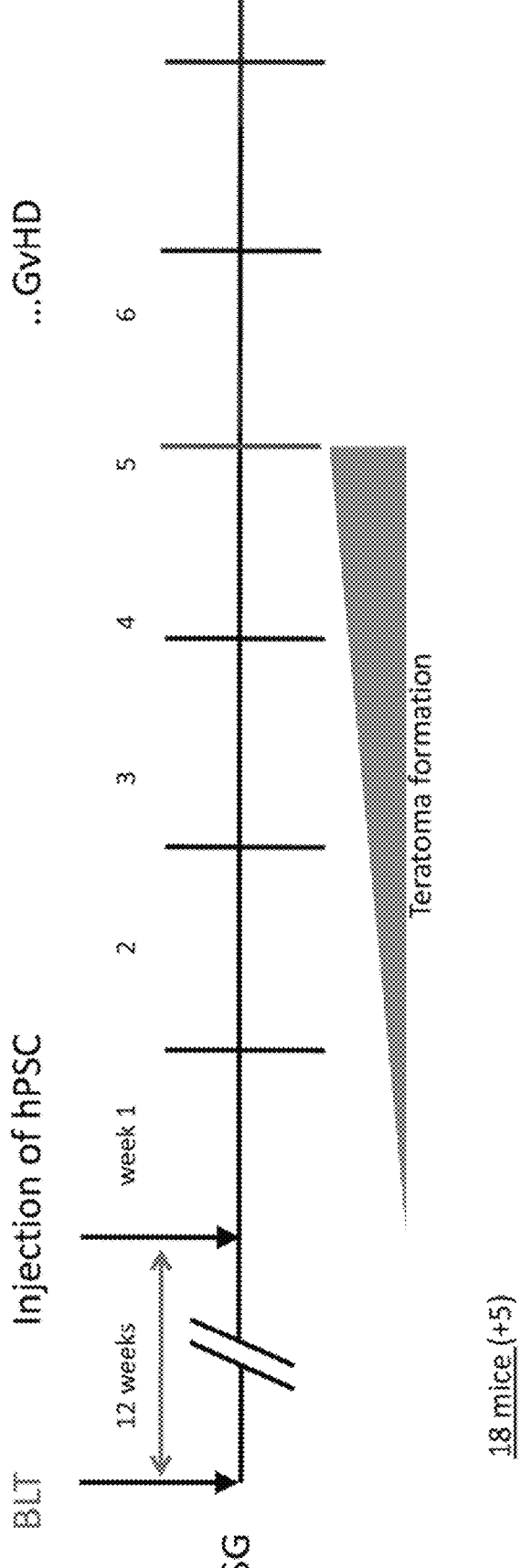
FIG. 6 illustrates a time line of the teratoma rejection study disclosed herein in which humanized NSG mice-BLT mice are given 3 months to fully reconstitute a human immune system before injection of the indicated genome-edited stem cell lines.
Figure 7:
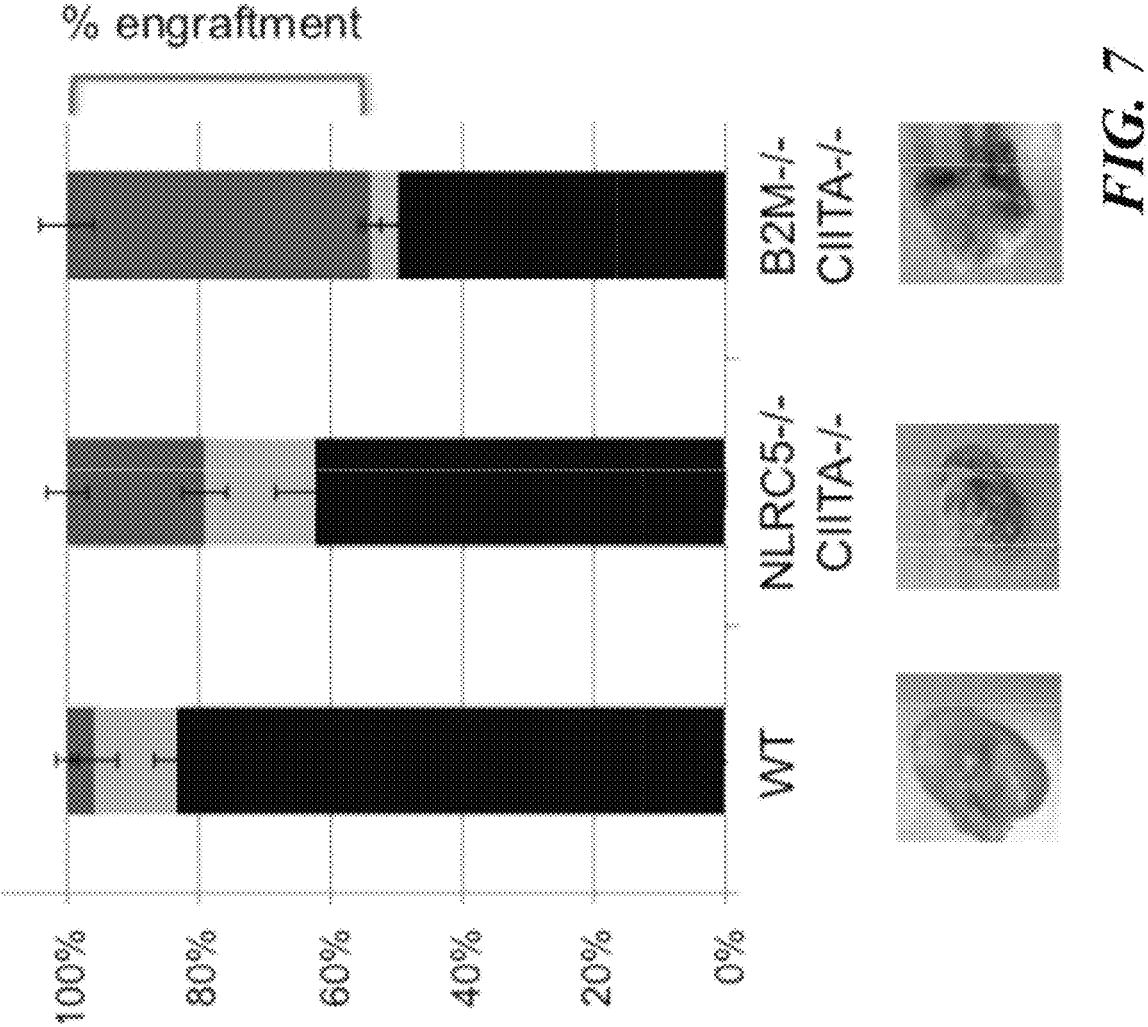
FIG. 7 demonstrates improved engraftment of genome-edited stem cells in humanized mice. Illustrated are the quantification of teratoma type observed following the teratoma rejection study depicted in FIG. 6. Upon review of the morphology of the teratoma samples, a clear phenotype that correlates with the levels of MHC-I expression was observed.
Figures 8A, 8B, 8C:
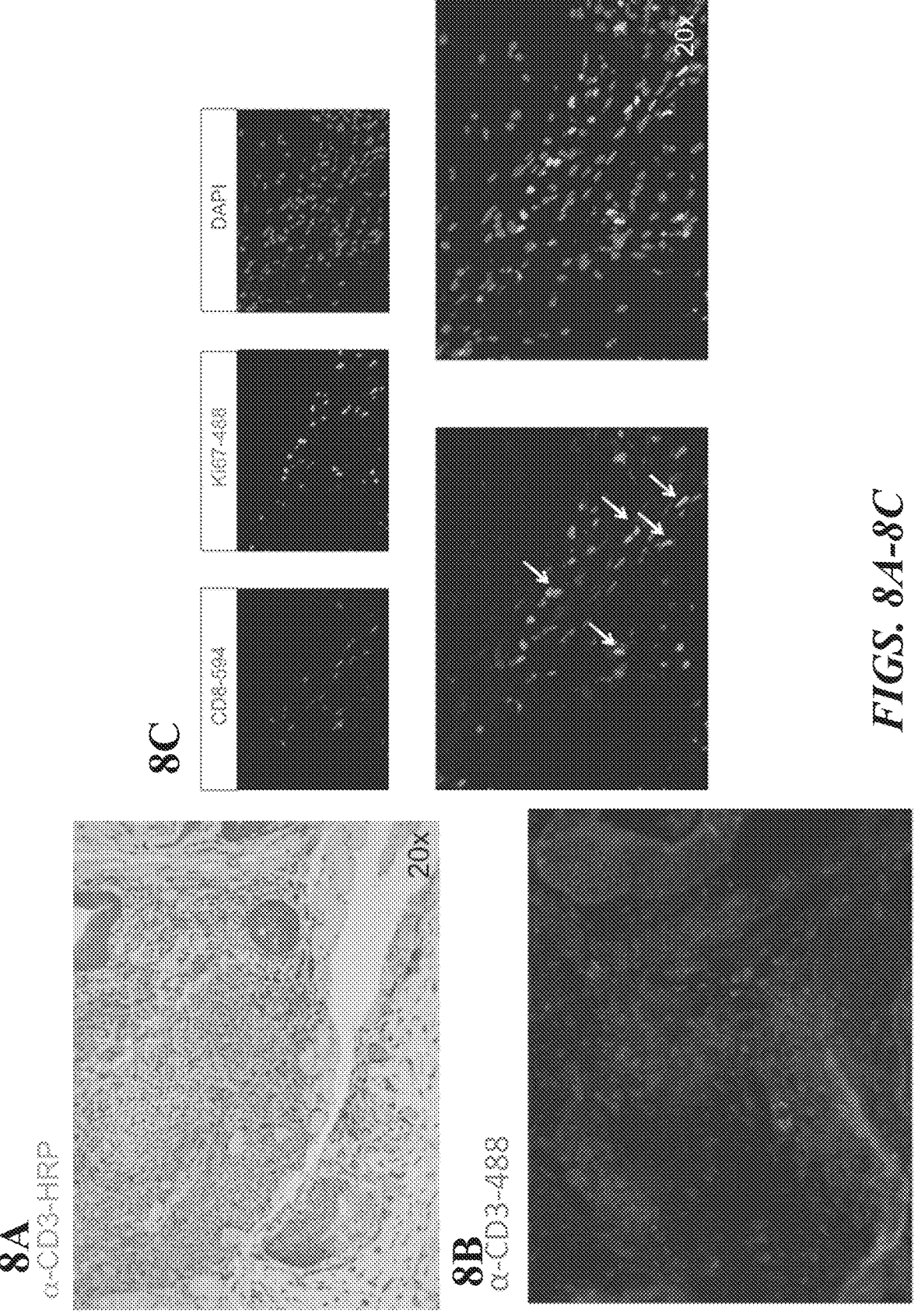
FIGS. 8A-8C demonstrate that proliferation of infiltrating CD8+ T cell indicates immune rejection.
Figures 9A, 9B, 9C, 9D:
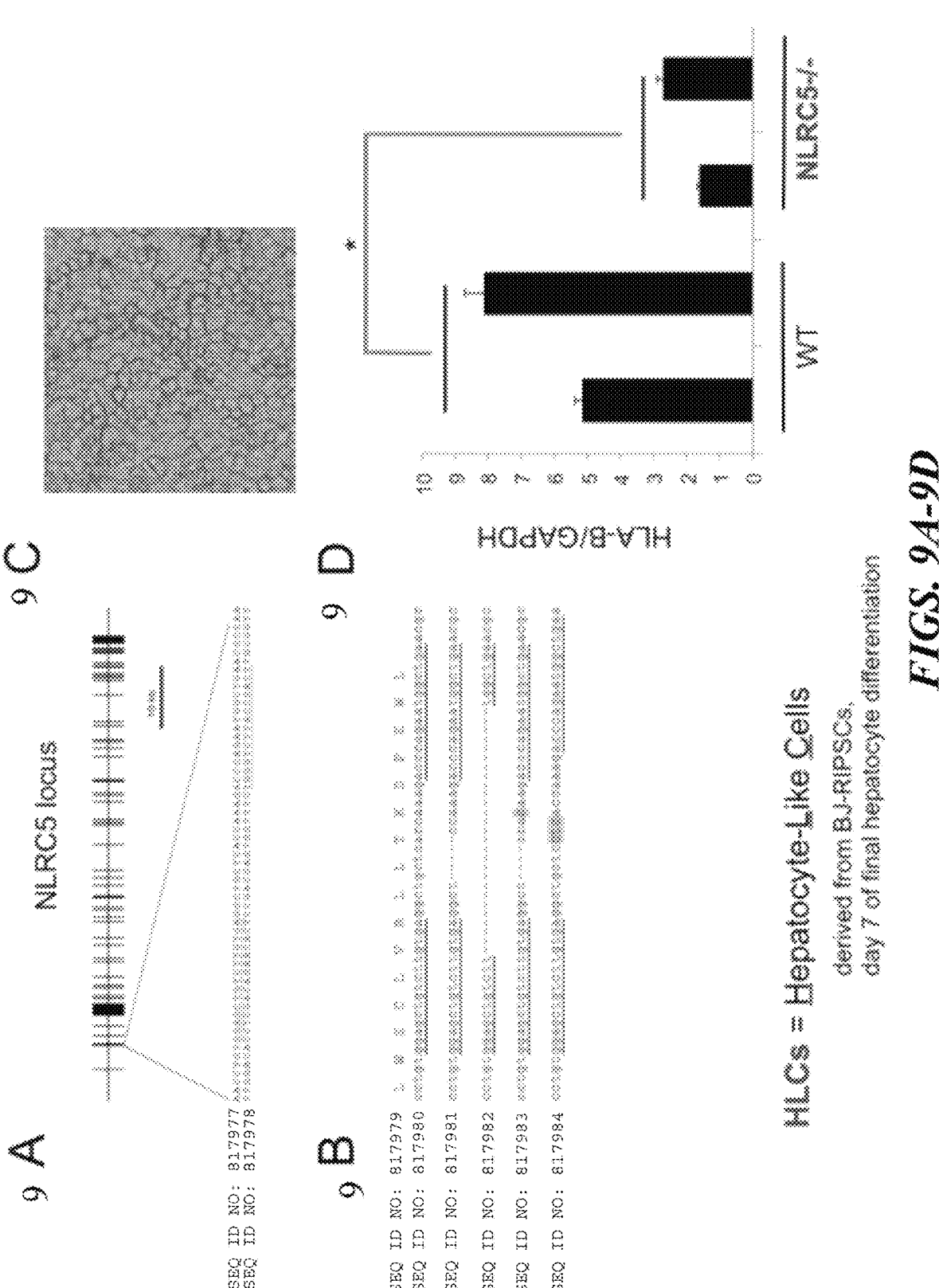
FIGS. 9A-9D demonstrate that the deletion of NLRC5 using TALENs results in reduced MHC-I expression in induced pluripotent stem cell-derived hepatocyte-like cells (HLCs).

The functional consequences of reduced HLA expression in the genome-edited cells were next evaluated in a humanized mouse model that was prepared by reconstituting an immunocompromised mice model with a human immune system (FIG. 6). As illustrated in Table 1 below, a comparable number of teratomas formed in all cases, irrespective of the genotype and the whole colony had to be sacrificed. Similarly, no differences in the failure rates of teratoma formation was observed. The inventors looked more closely at the overall morphology of the teratoma samples and a clear cut phenotype that correlates with the levels of MHC-I expression was identified. NLRC5, reduced, B2M absent MHC-I on the surface. FIG. 7 illustrates the quantification of the resulting teratoma types. FIGS. 8A-8C further demonstrate CD8+ T cell proliferation in wild-type cells and suggests immune rejection of the wild-type teratomas and improved engraftment of the genome-edited cells in the humanized mouse model.

TABLE 1

| | Genotype | #tumors (injections) |
|---|---|---|
| p42 | WT | 21 (24) |
| E4 | NLRC5−/−CIITA−/− | 21 (24) |
| C7 | B2M−/−CIITA−/− | 20 (24) |
| C6 | NLRC5−/−CIITA−/− | 18 (20) |

The foregoing results therefore demonstrate successful targeting of NLRC5, CIITA and B2M in HuES9 and BJ RiPSCs and further evidence that genome-edited cells can be differentiated into a variety of different cell types that are characterized by reduced HLA expression.

The inventors have used both a TALENs system and a CRISPR/Cas system to facilitate the targeting of transcriptional regulators of HLA expression (i.e., the MHC enhanceosome). TALEN-induced CIITA and NLRC5 mutations in BJ-RIPSCs and HuES9 are illustrated in FIGS. 15A-D. In addition, NLRC5 and CIITA can also be targeted utilizing CRISPRs to achieve a reduction in MHC class I expression and complete loss of MHC class II expression, respectively.

Figure 16A:
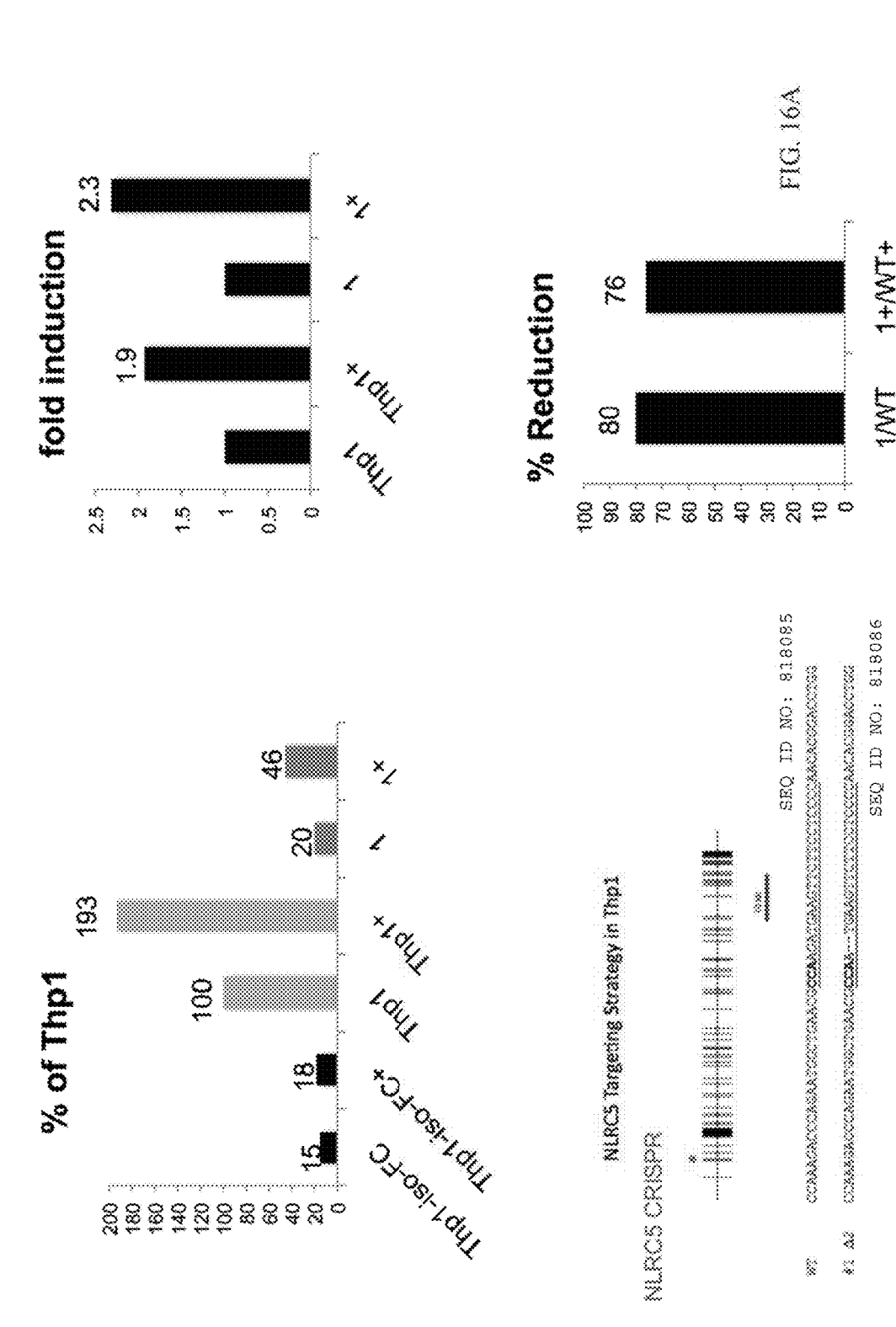
Figure 16B:
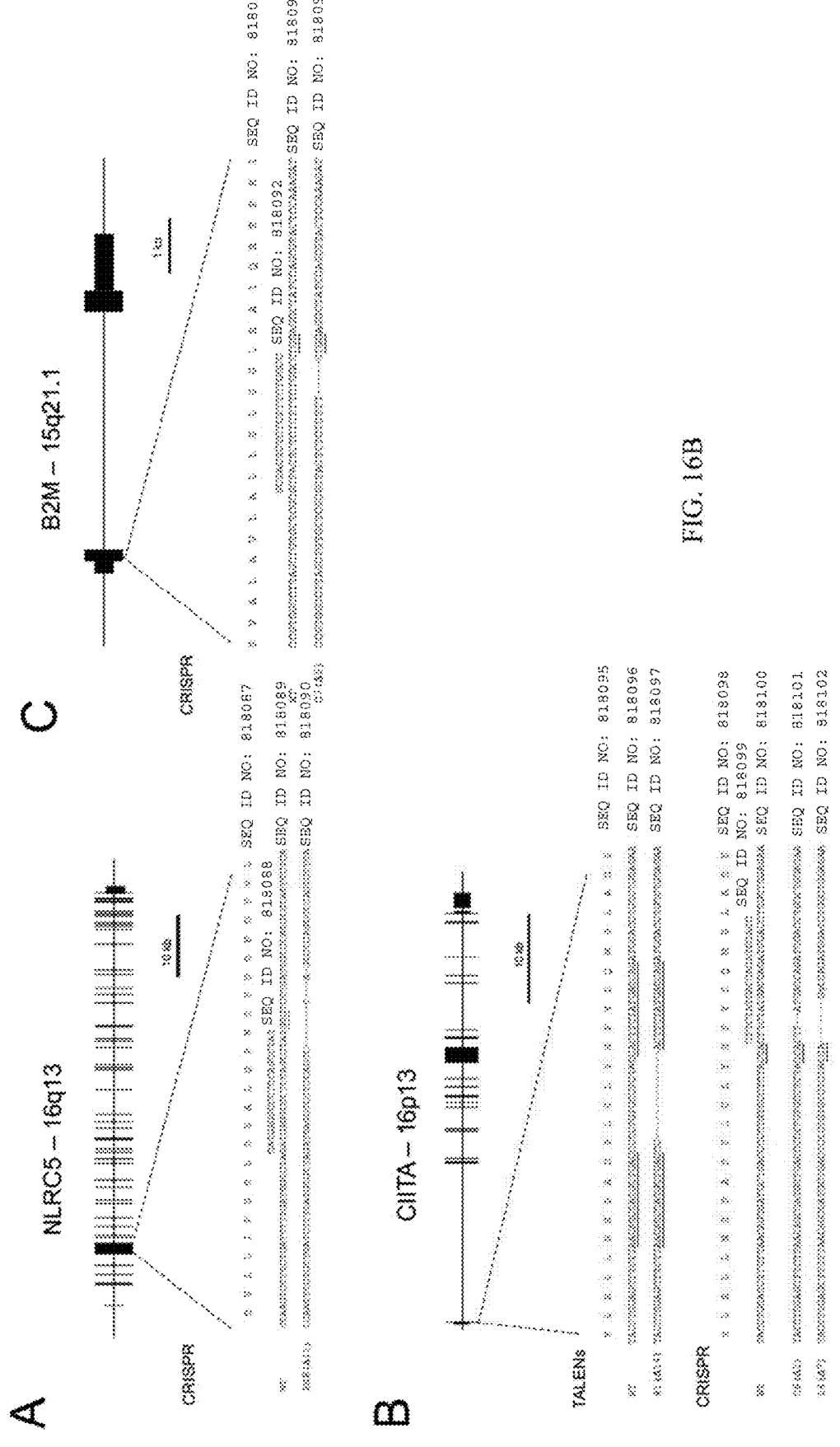
Figure 16C:
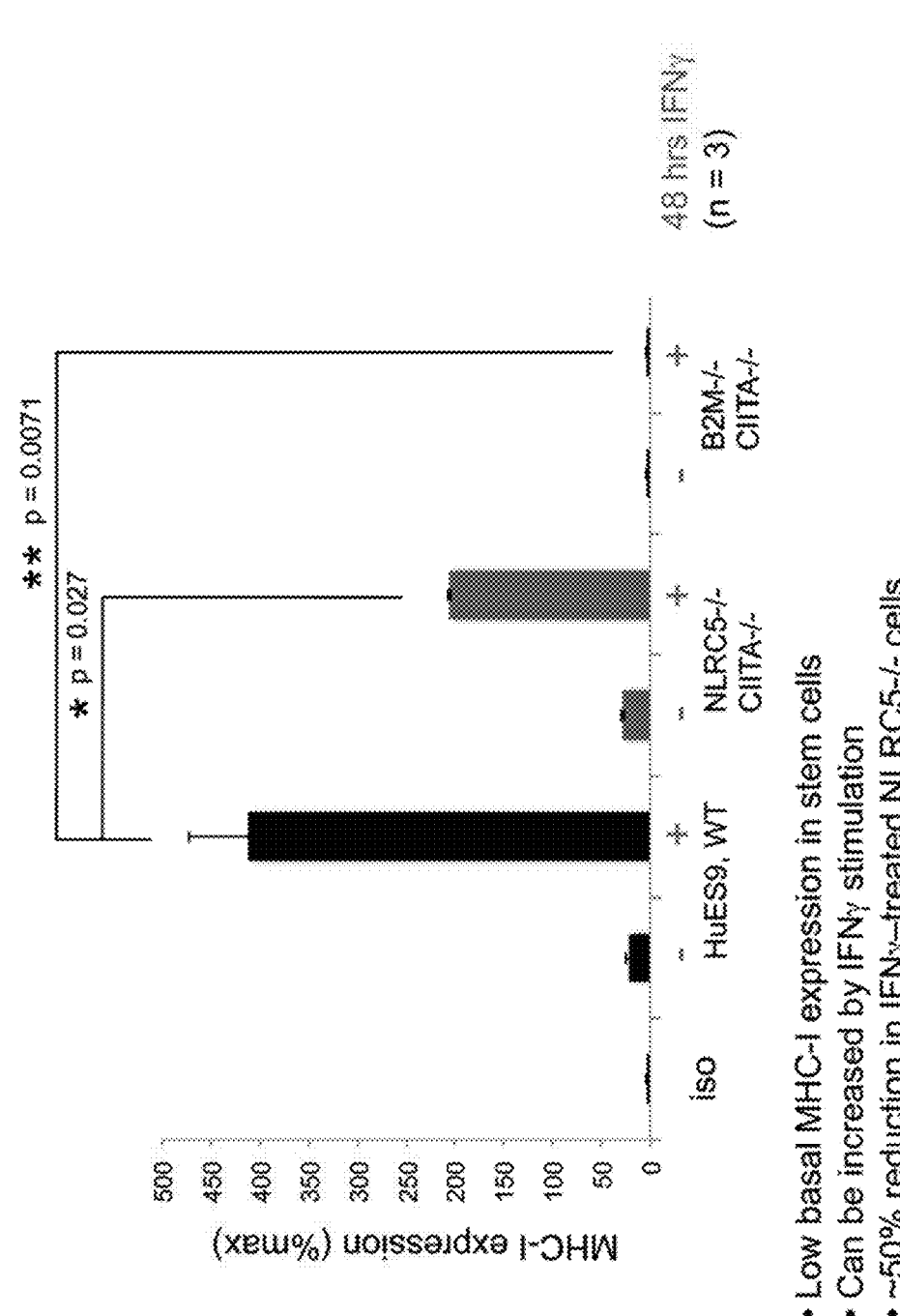

NLRC5 was targeted in Thp1 cells using CRISPR and it was demonstrated that MHC-I expression in NLRC5−/− Thp1 cells was reduced (FIG. 16A). Examples of CRISPR and/or TALENs systems targeting NLRC5, CIITA and B2M are provided in FIG. 16B. Reduced MHC class I expression in HuES9 was shown following targeting with NLRC5 or B2M CRISPRs. For example, about 50% reduction was shown in IFNγ-treated NLRC5–/– cells and complete loss of MHC-I surface expression was shown in B2M–/– cells (FIG. 16C).

Figure 16D:
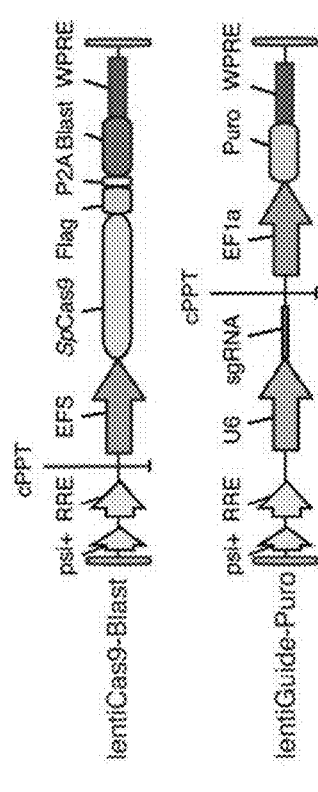
Figure 16F:
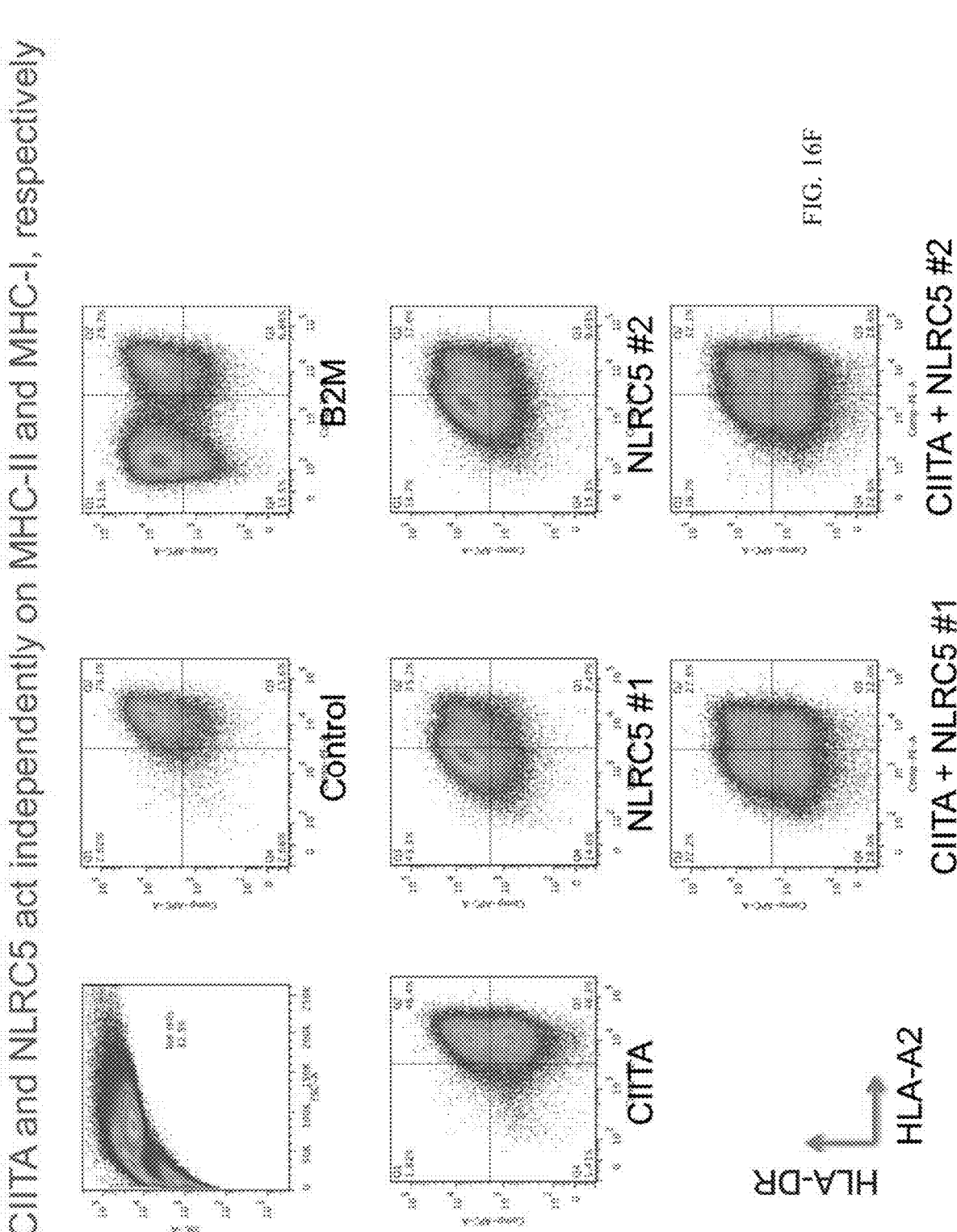
Figure 16G:
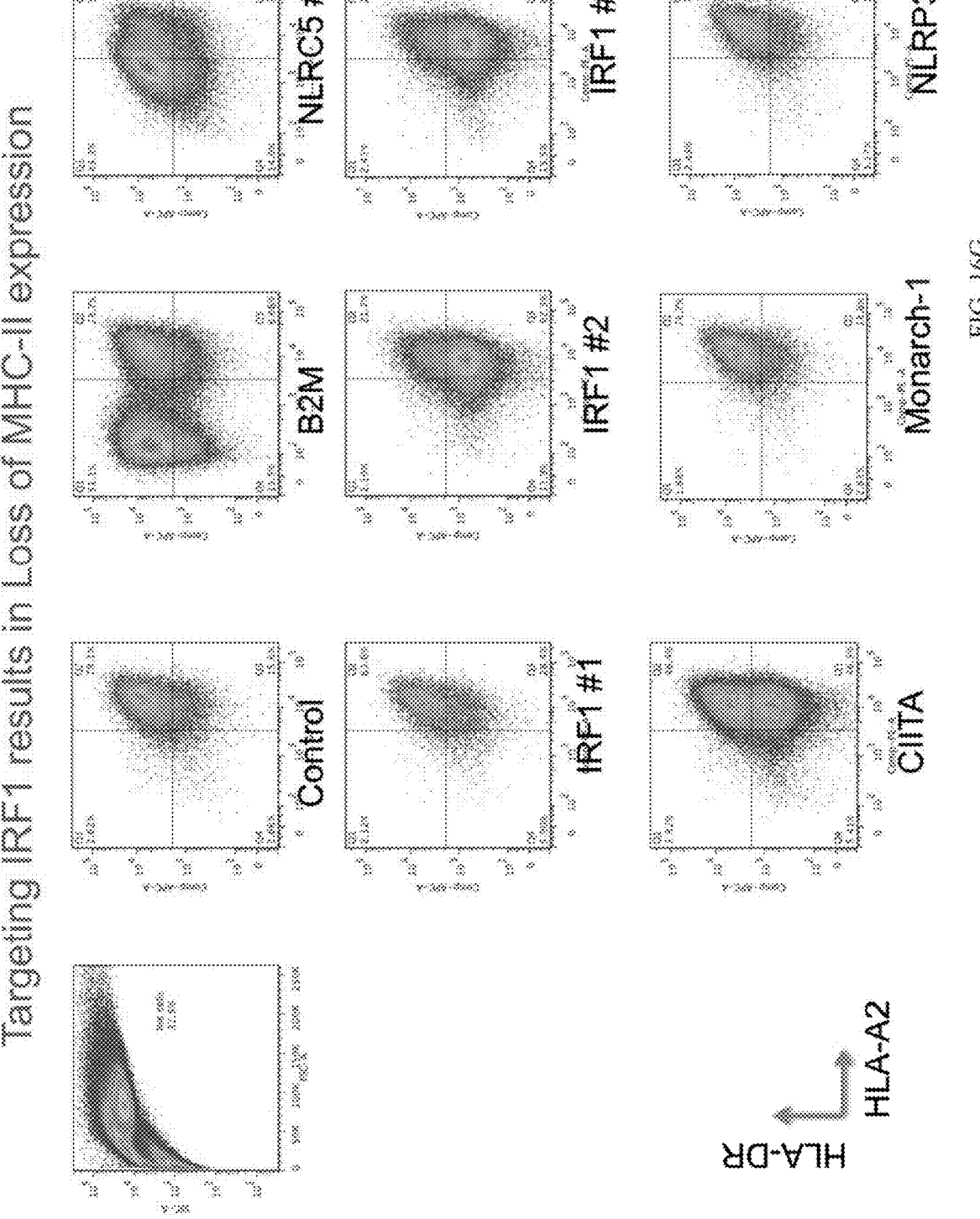

A lentiviral transduction of Thp-1 was conducted using a two component (e.g., dual vector) system (FIG. 16D). The two component system included *Lenti*-Cas9-Blasticidin and *Lenti*-Guide-puro. Examples of the different CRISPRs used for the lentiviral transduction of Thp-1 are provided in FIG. 16E. Thp-1 was transduced with lentivirus encoding NLRC5 and CIITA. A B2M CRISPR was used as a positive control. All of the cells were stimulated ON with 50 U IFNγ to boost HLA expression (HLA-A2 was 1:200 and HLA-DR was 1:100). It was demonstrated that CIITA and NLRC5 act independently on MHC-II and MHC-I, respectively (FIG. 16F). At ten days post CRISPR transduction, when the Thp1 cells were all stimulated ON with 5OU IFNγ (HLA-A2 is 1:200 and HLA-DR is 1:100), it was demonstrated that targeting IRF1 results in a loss of MHC-II expression (FIG. 16G).

Figure 17A:
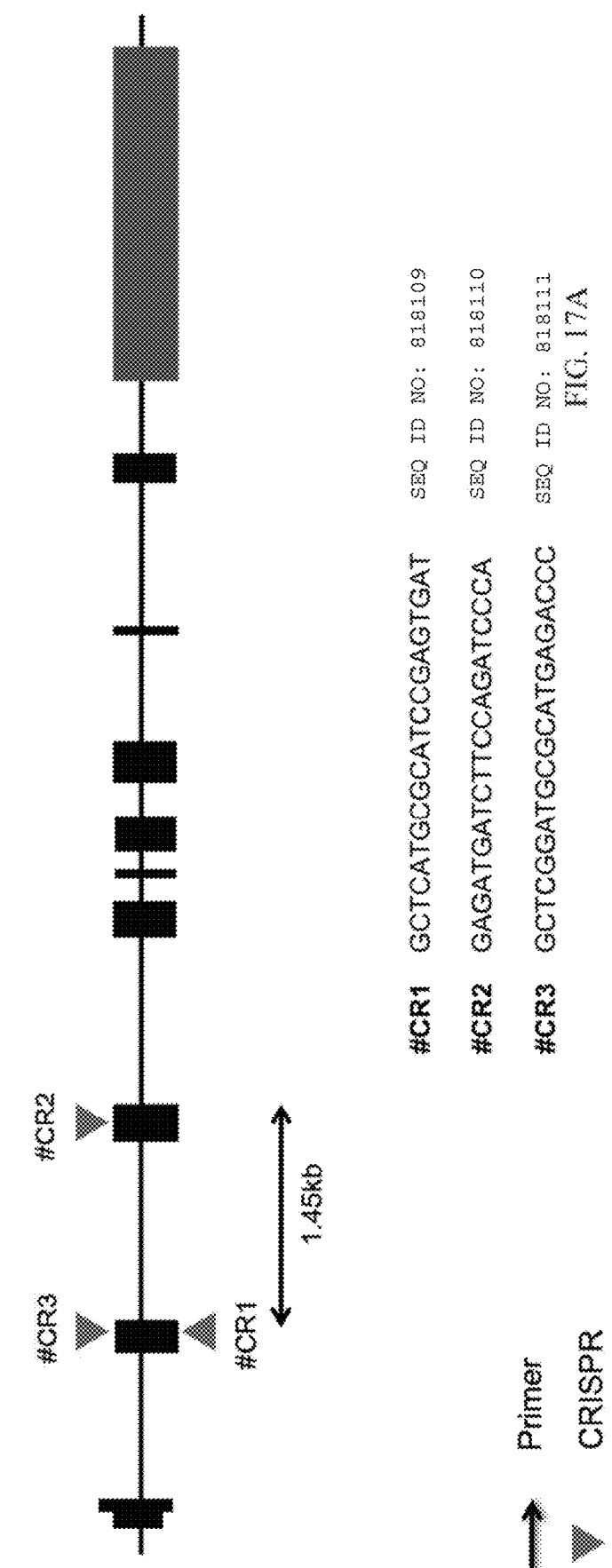
Figure 17B:
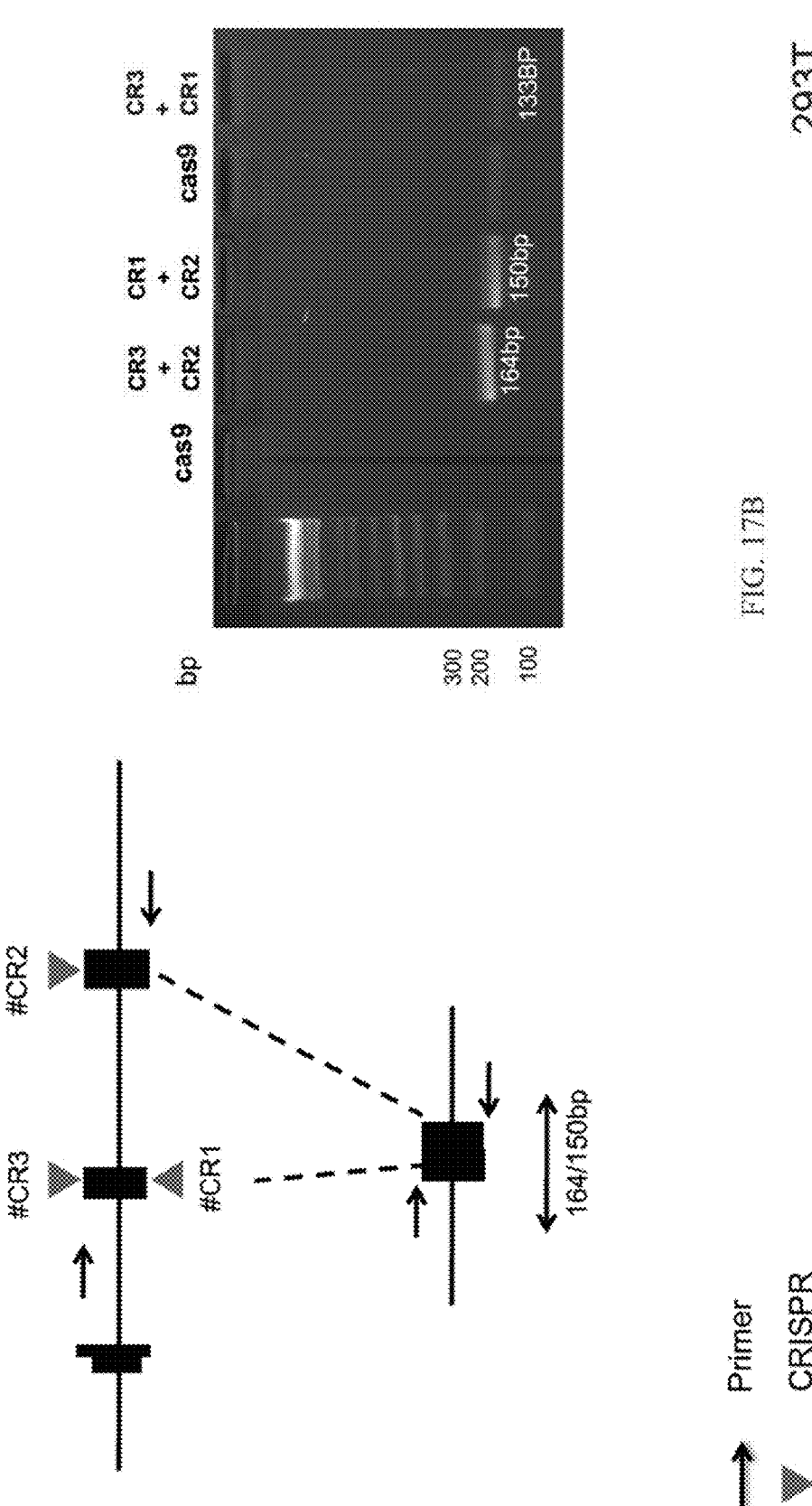
Figure 17D:
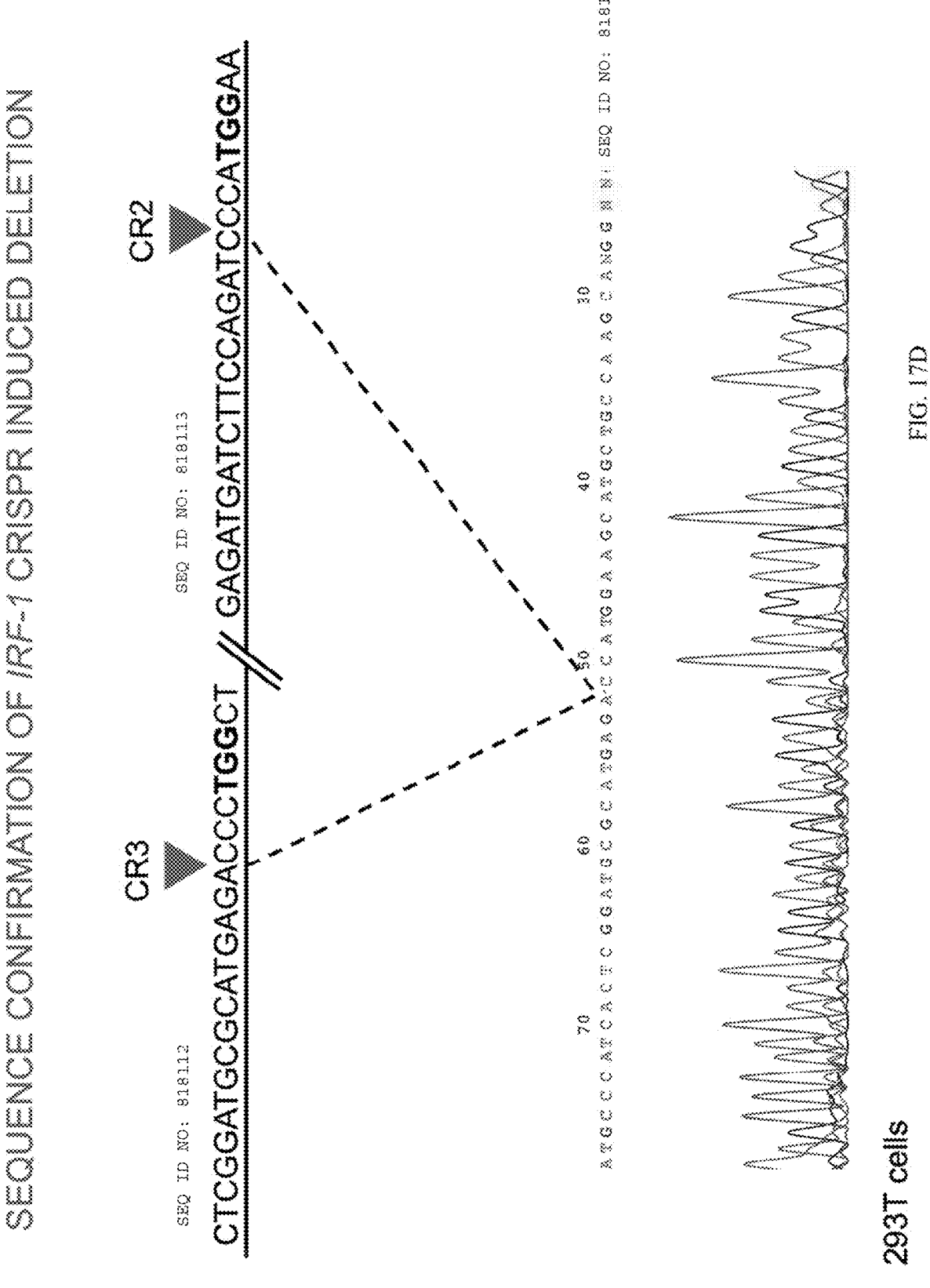
Figure 17E:
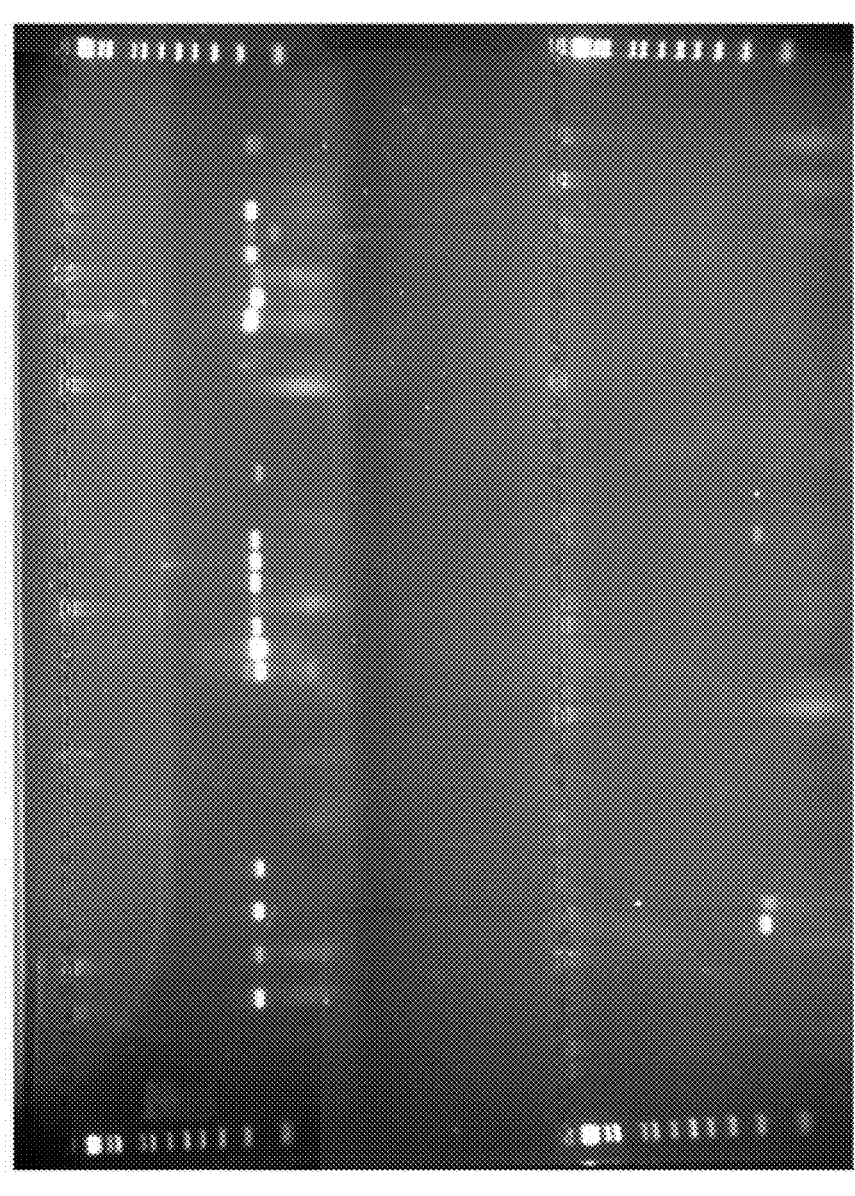

The inventors further examined targeting of IRF1 and the resultant reduced MHC class I expression in human pluripotent stem cells (HuES9) and Thp-1 cells. A schematic demonstrating a dual CRISPR strategy for targeting the IRF1 locus is provided in FIG. 17A. Testing of different IRF1 guide combinations was conducted (FIG. 17B) and a 'dual guide strategy' for the targeted deletion of IRF1 was identified (FIG. 17C). After the dual guide strategy for the targeted deletion of IRF1 was applied, a sequence confirmation of IRF1 CRISPR induced deletion was provided (FIG. 17D), followed by screening of IRF-1 targeted HuES9 cells (FIG. 17E). The presence of the PCR bands suggests successful targeting using the dual CRISPR strategy.

Figure 17F:
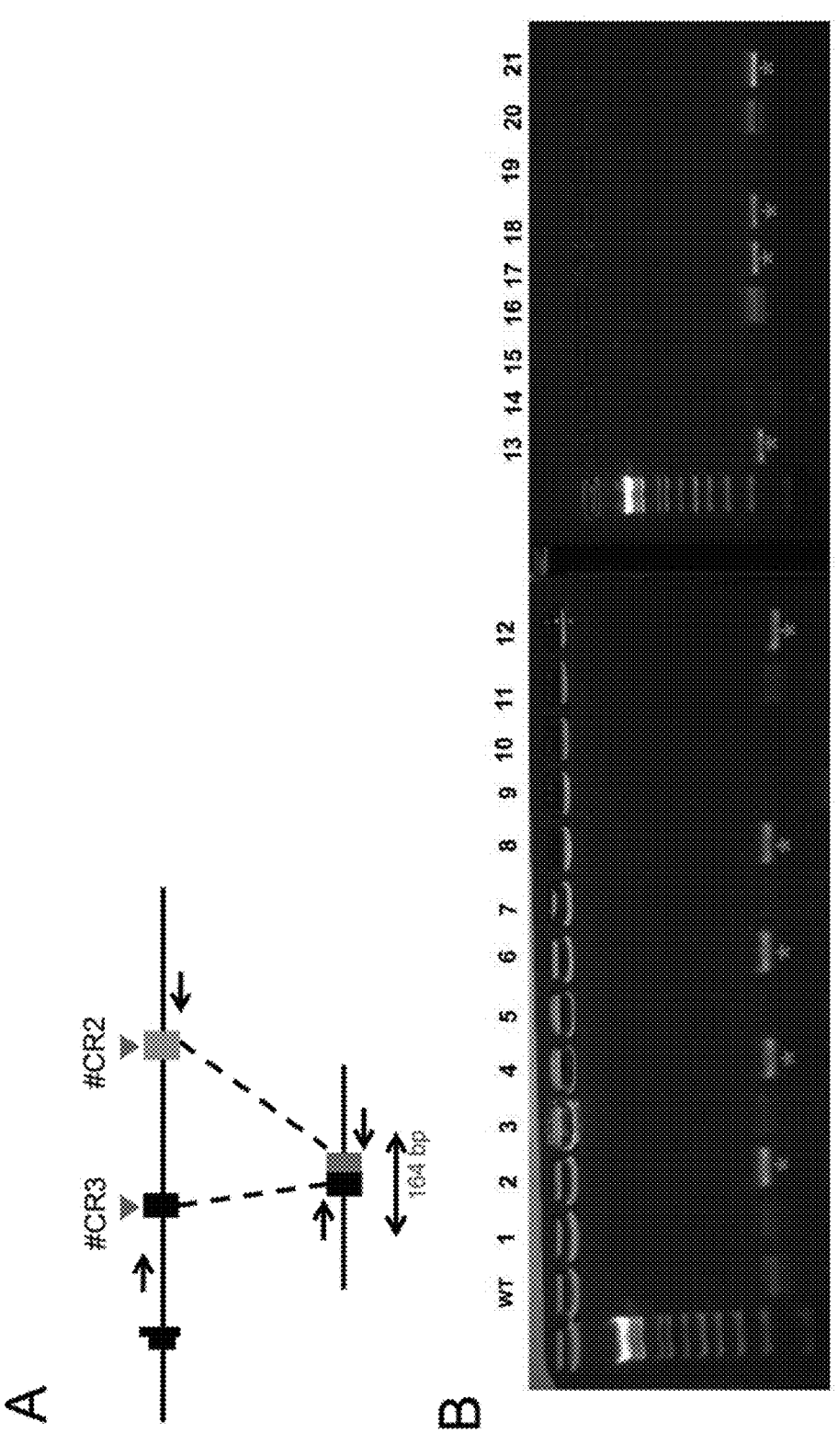
Figure 17G:
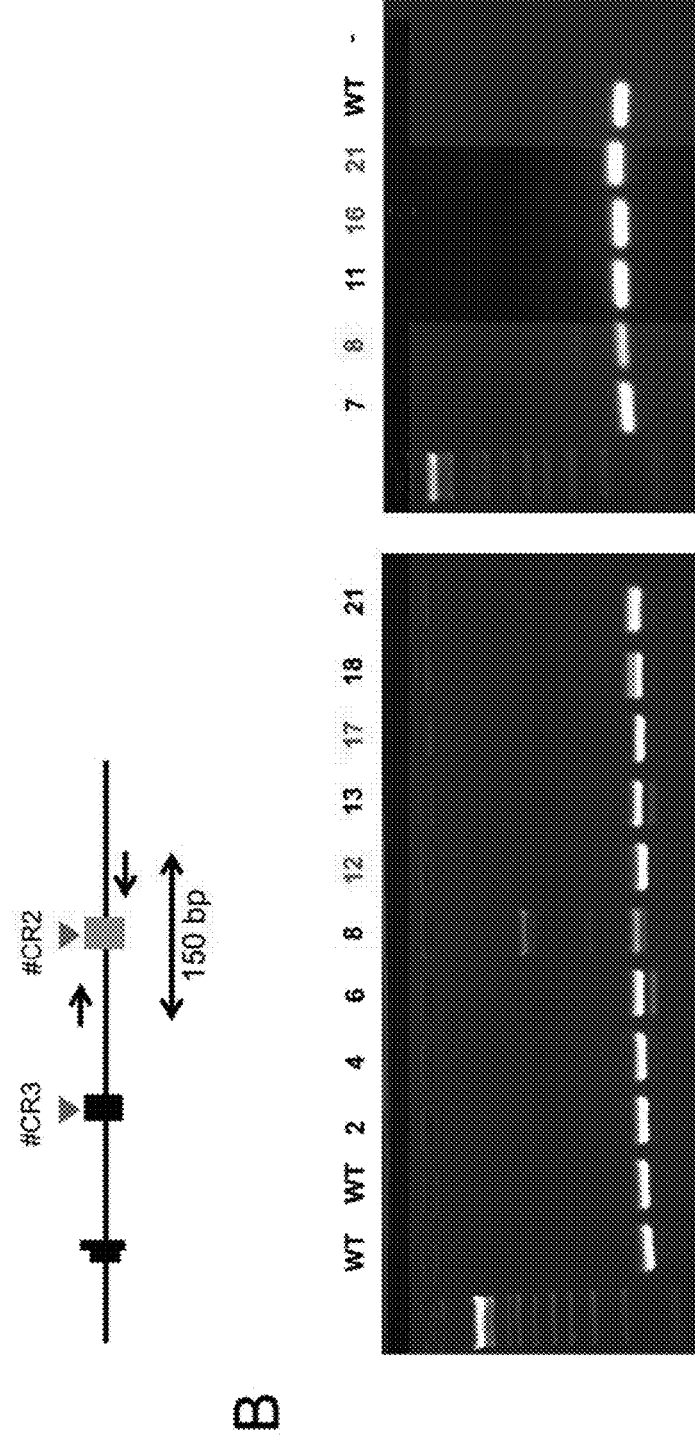
Figure 17H:
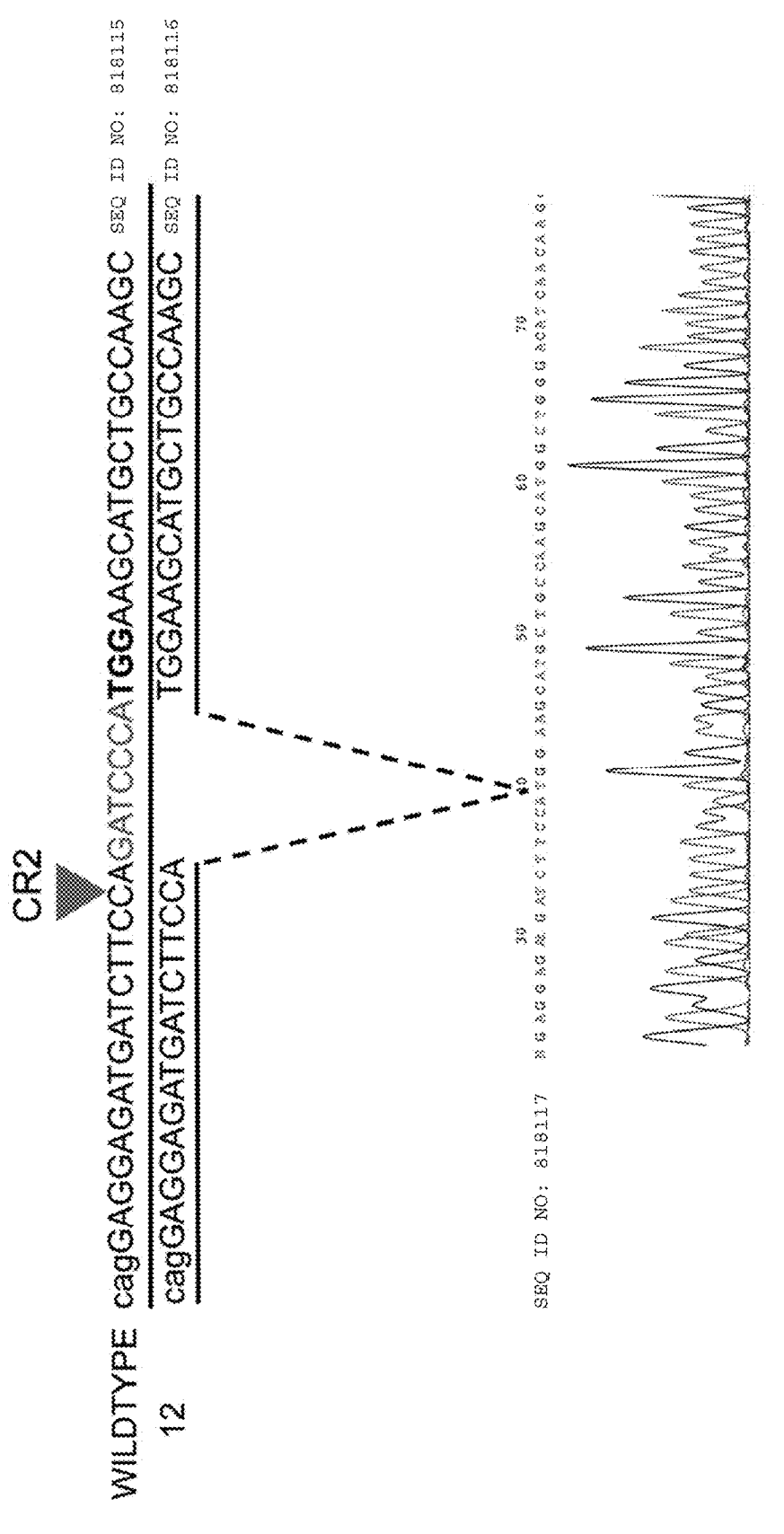
Figure 17I:
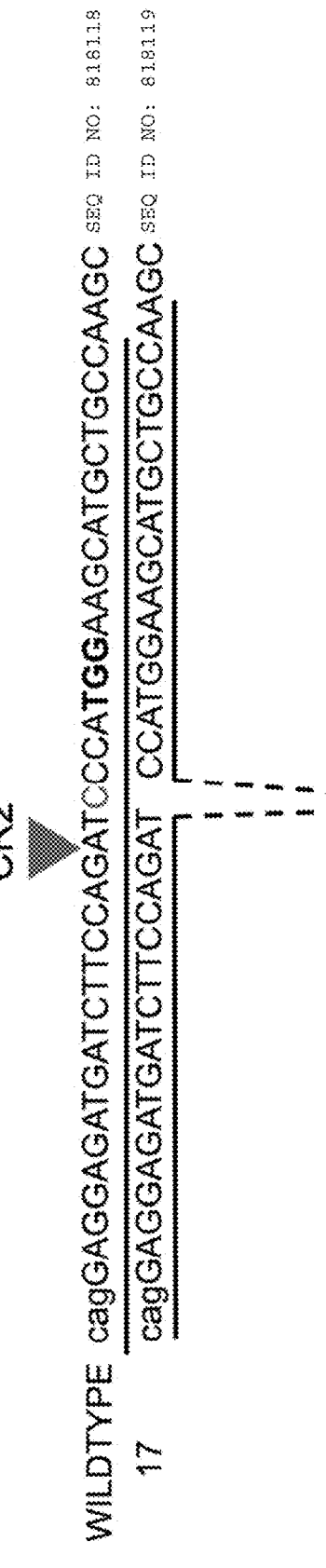
Figure 17J:
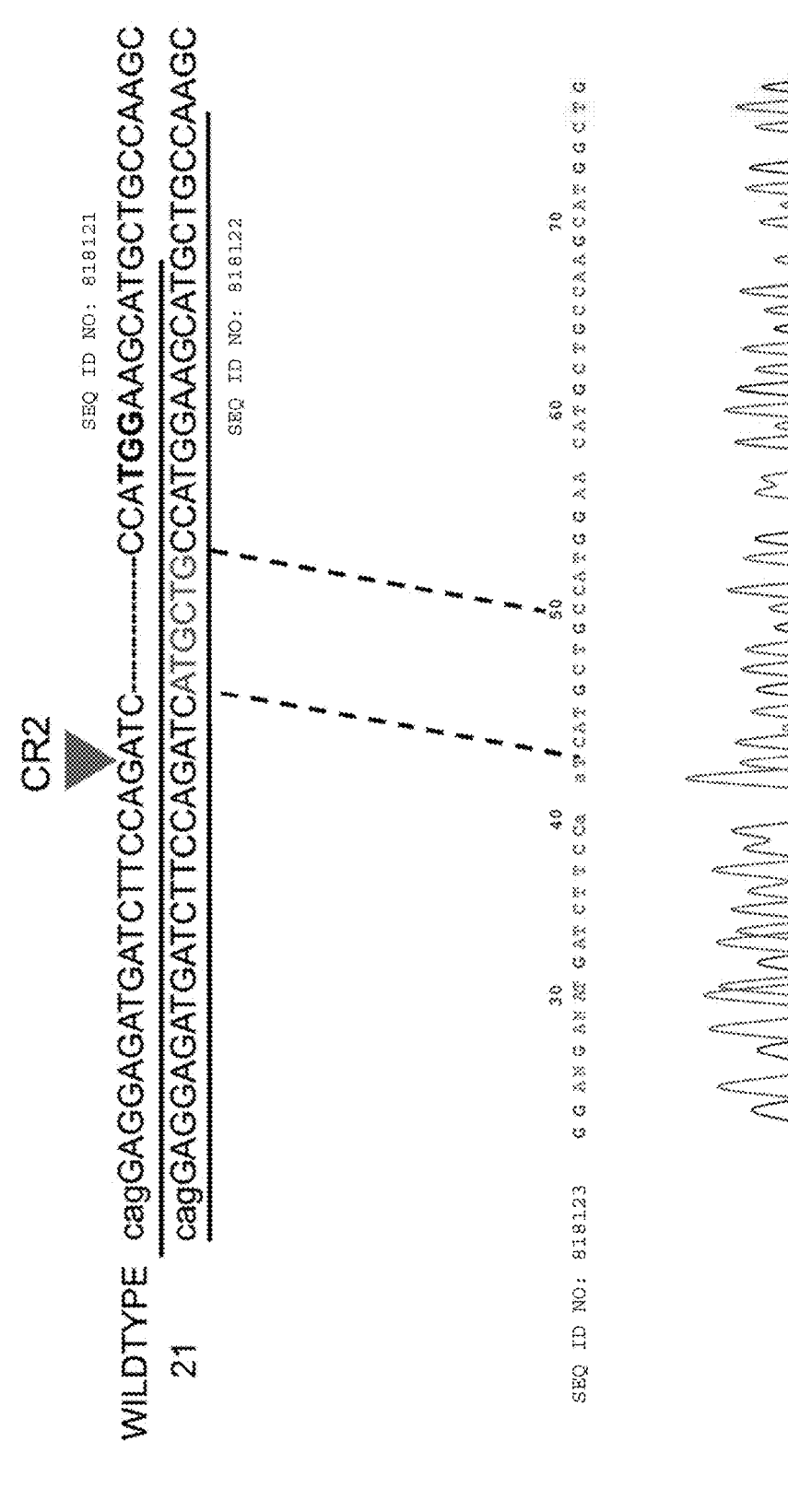

The inventors then reconfirmed (FIG. 17F) and genotyped (FIG. 17G) the IRF1 clones. Sequencing confirmed IRF1 CRISPR induced deletion in clone 12 (FIG. 17H), clone 17 (FIG. 17I) and clone 21 (FIG. 17J). The IRF1–/– HuES9 clones exhibited impaired MHC class I induction following IFNγ treatment for 48 hours (FIG. 17K).

Figure 18A:
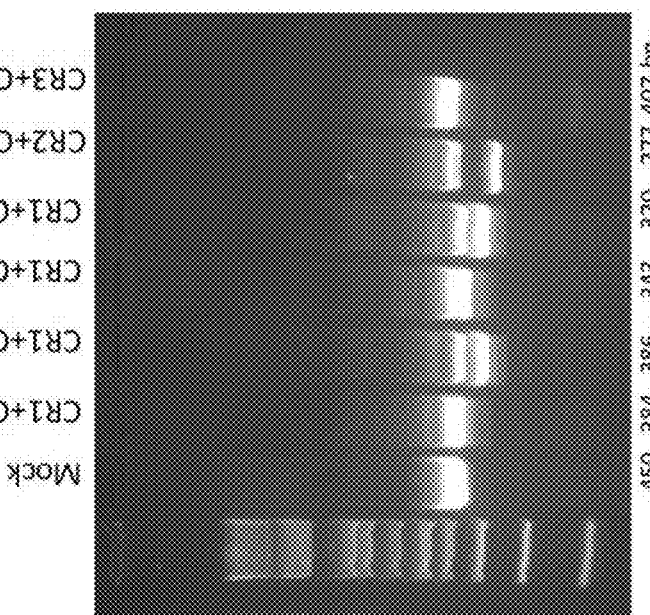
Figure 18C:
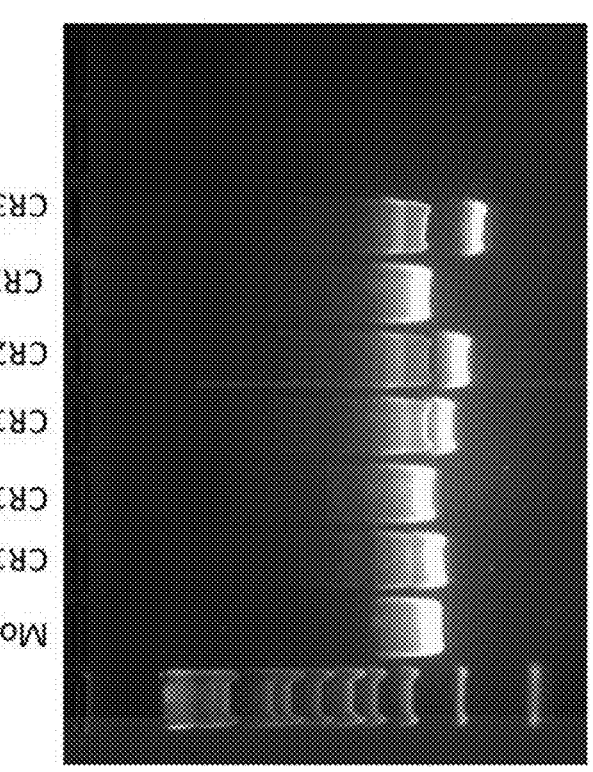
Figure 18D:
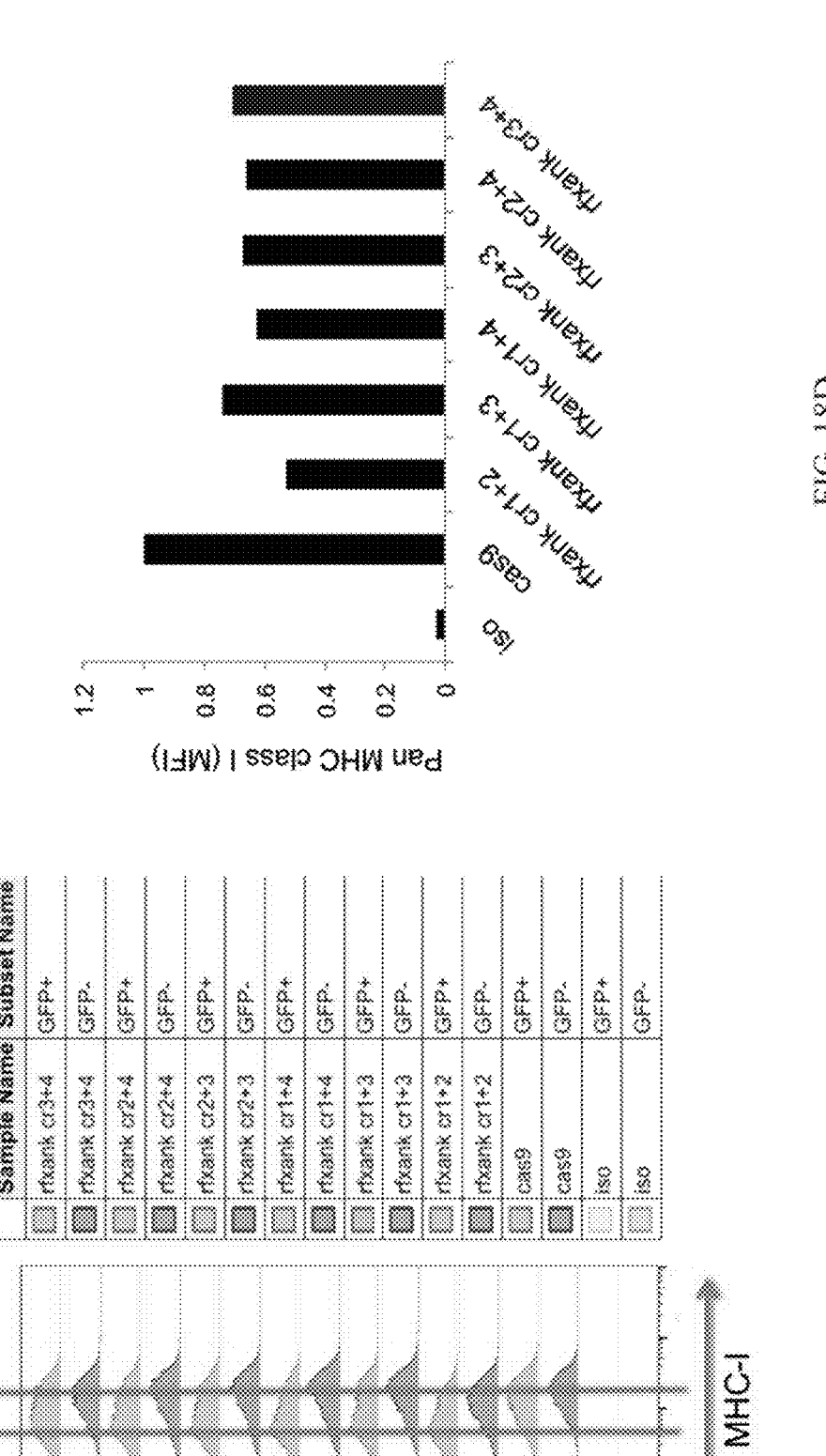
Figure 18F:
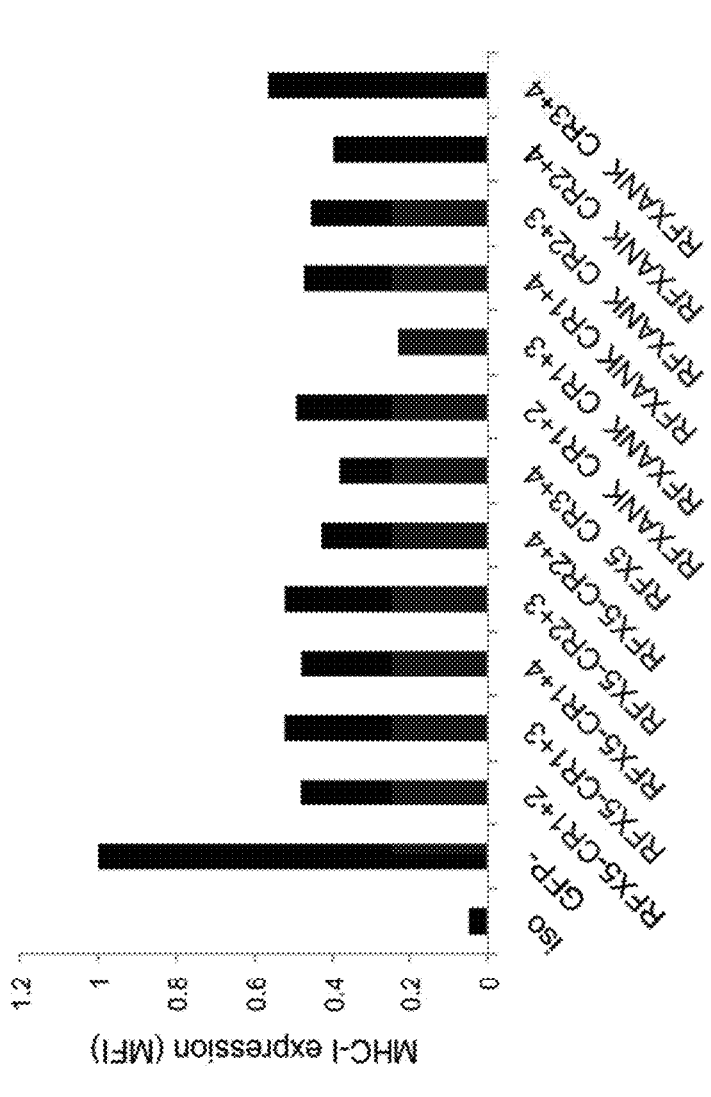
Figure 18G:
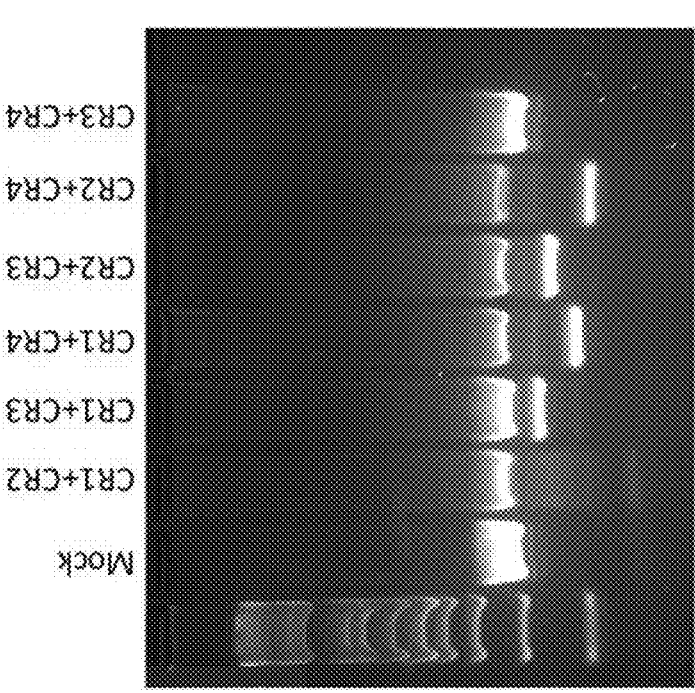
Figure 19A:
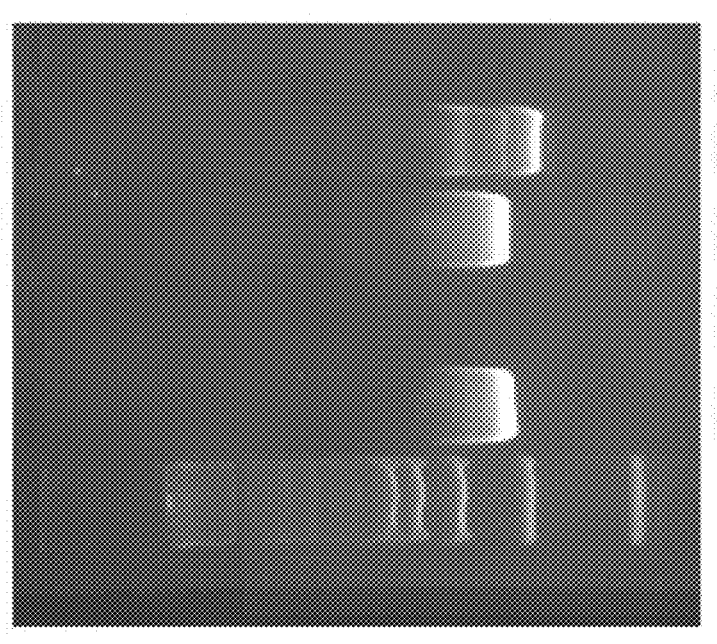

The inventors also examined targeting of additional enhanceosome components. The impact on MHC-I expression by targeting additional enhanceosome components in 293T cells was examined, but it is expected that the targeting of these additional enhanceosome components will also affect MHC-II levels in cells that actually express it, e.g., Thp1 cells or other APCs. For example, the inventors examined CRISPR targeting of RFX5 (FIG. 18A), RFX-ANK (FIG. 18C) and RFK-AP (FIG. 18G) in 293T cells using a dual guide strategy. The targeting results demonstrated reduced MHC class I expression of RFX5 (FIG. 18B, FIGS. 18E-18F), RFK-ANK (FIG. 18D, FIGS. 18E-F) and RFK-AP (FIG. 18H). The inventors also examined CRISPR dual guide targeting of NFY-A (FIG. 19A), NFY-B (FIG. 19D) and NFY-C (FIG. 19B) in 293T cells. The targeting results demonstrated reduced MHC class I expression of NFY-A (FIG. 19C), NFY-B (FIG. 19E) and NFY-C (FIG. 19C).

Blocking Surface Trafficking of MHC Class I

Figure 31:
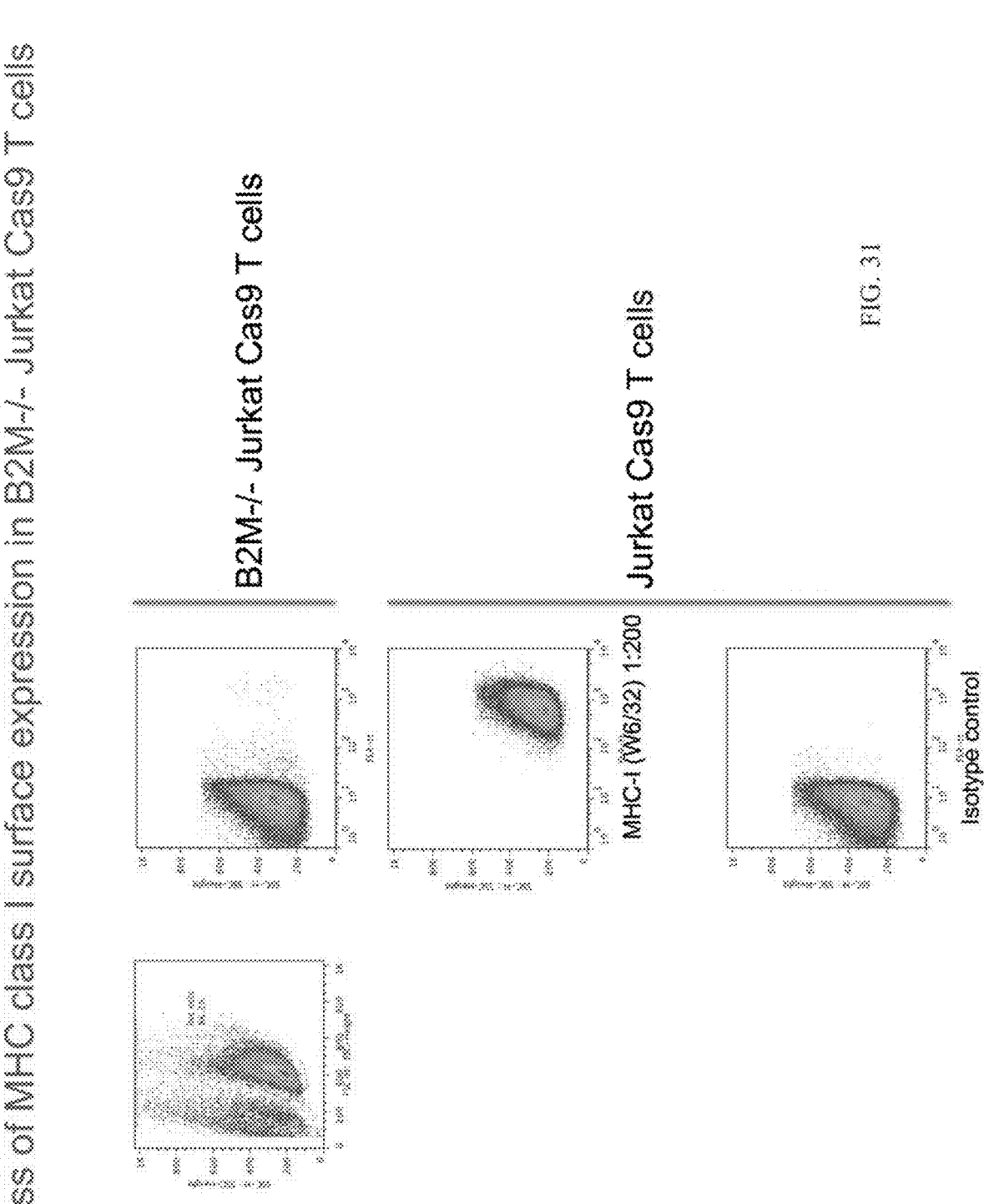
FIG. 31 shows loss of MHC class I surface expression in B2M−/− Jurkat Cas9 T cells. The B2M−/− Jurkat Cas9 T cells are compared to Jurkat Cas9 T cells that do not include a knock out of B2M.
Figures 32A, 32B, 32C, 32D, 32E, 32F, 32G, 32H:
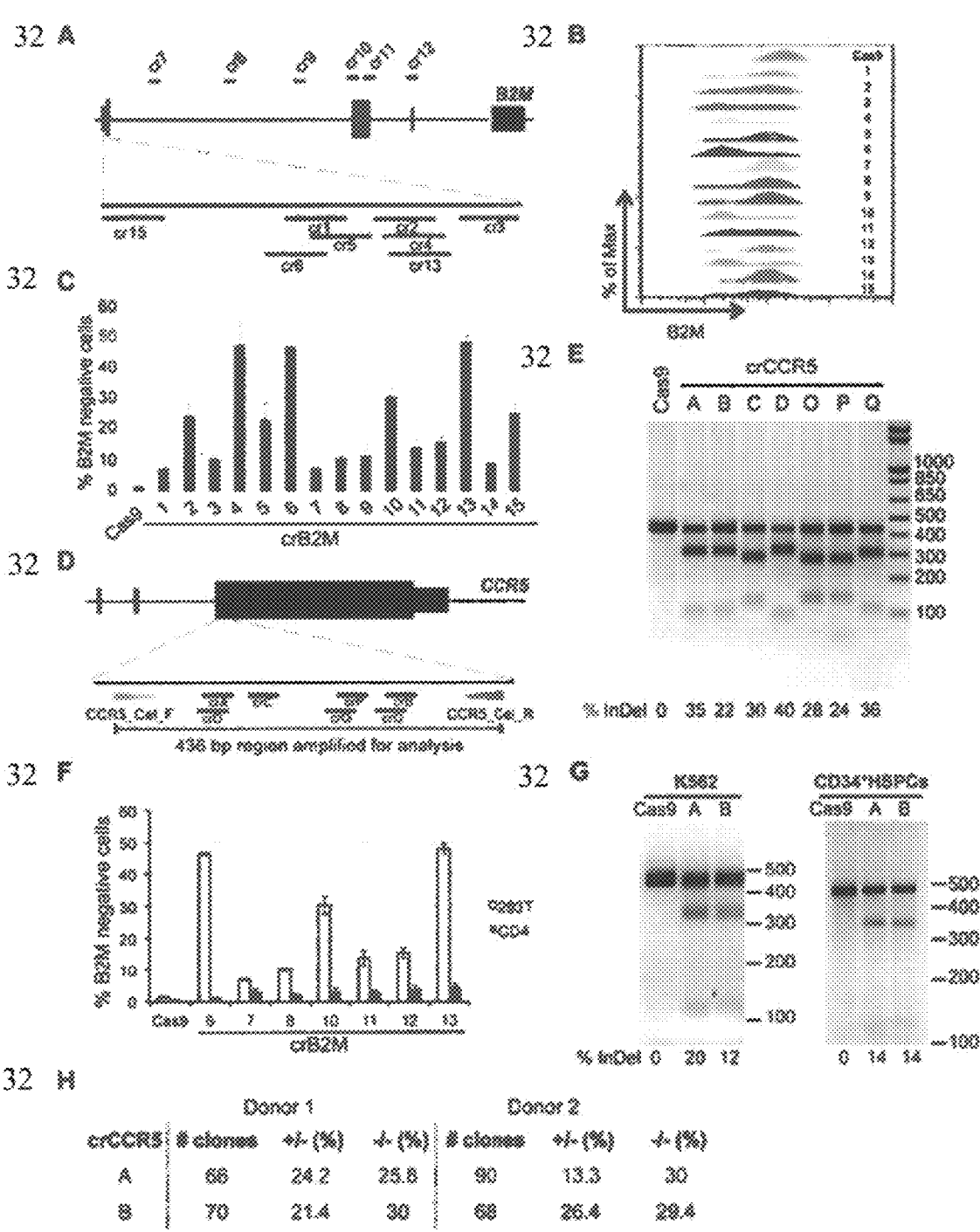
FIGS. 32A-32H demonstrate targeting clinically relevant loci in human cells using CRISPR/Cas9.
Figures 33A, 33B, 33C, 33D, 33E:
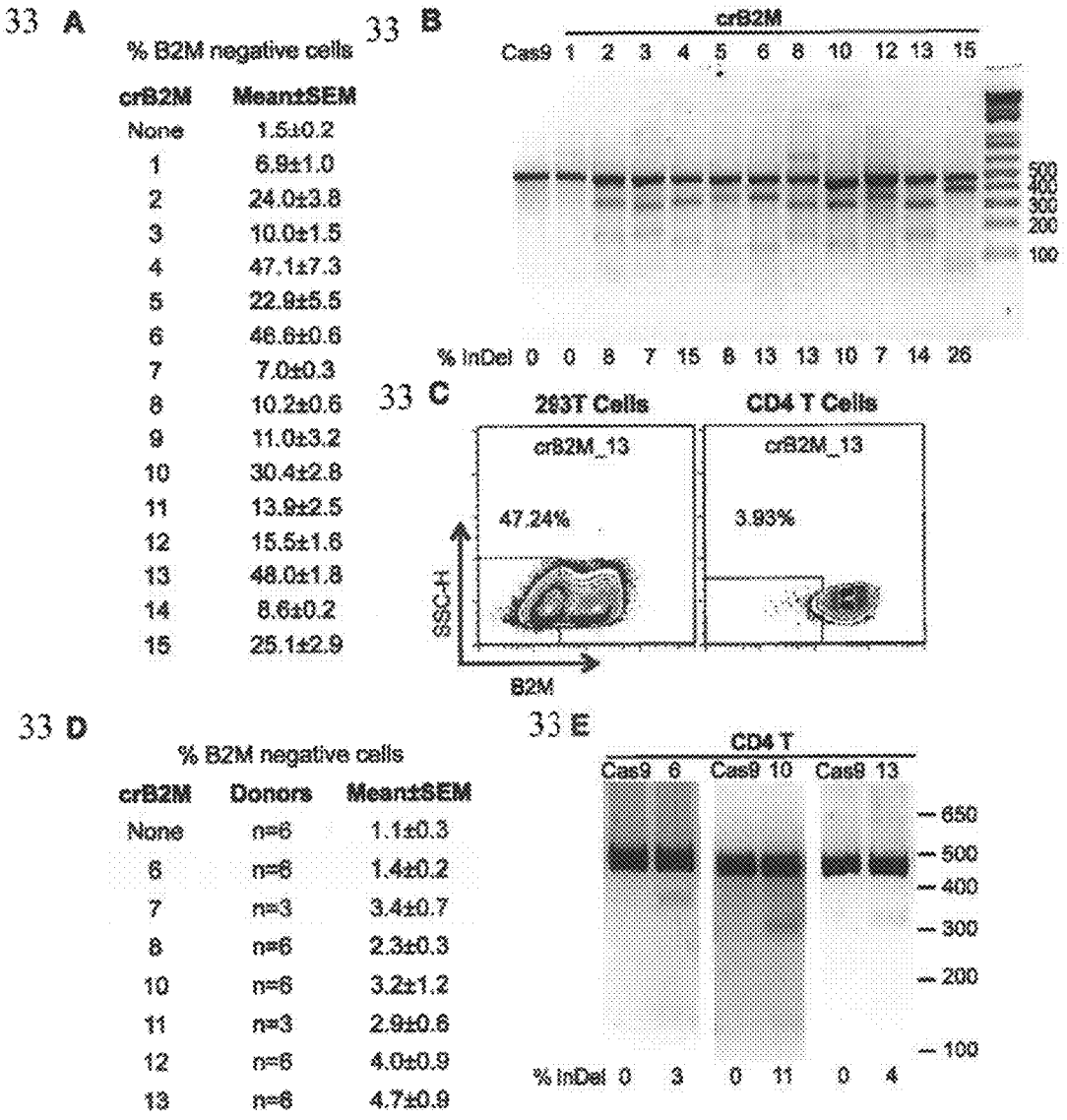
FIGS. 33A-33E demonstrate an evaluation of on target mutational efficiencies of various gRNAs targeting B2M.
Figures 34A, 34B, 34C, 34D, 34E:
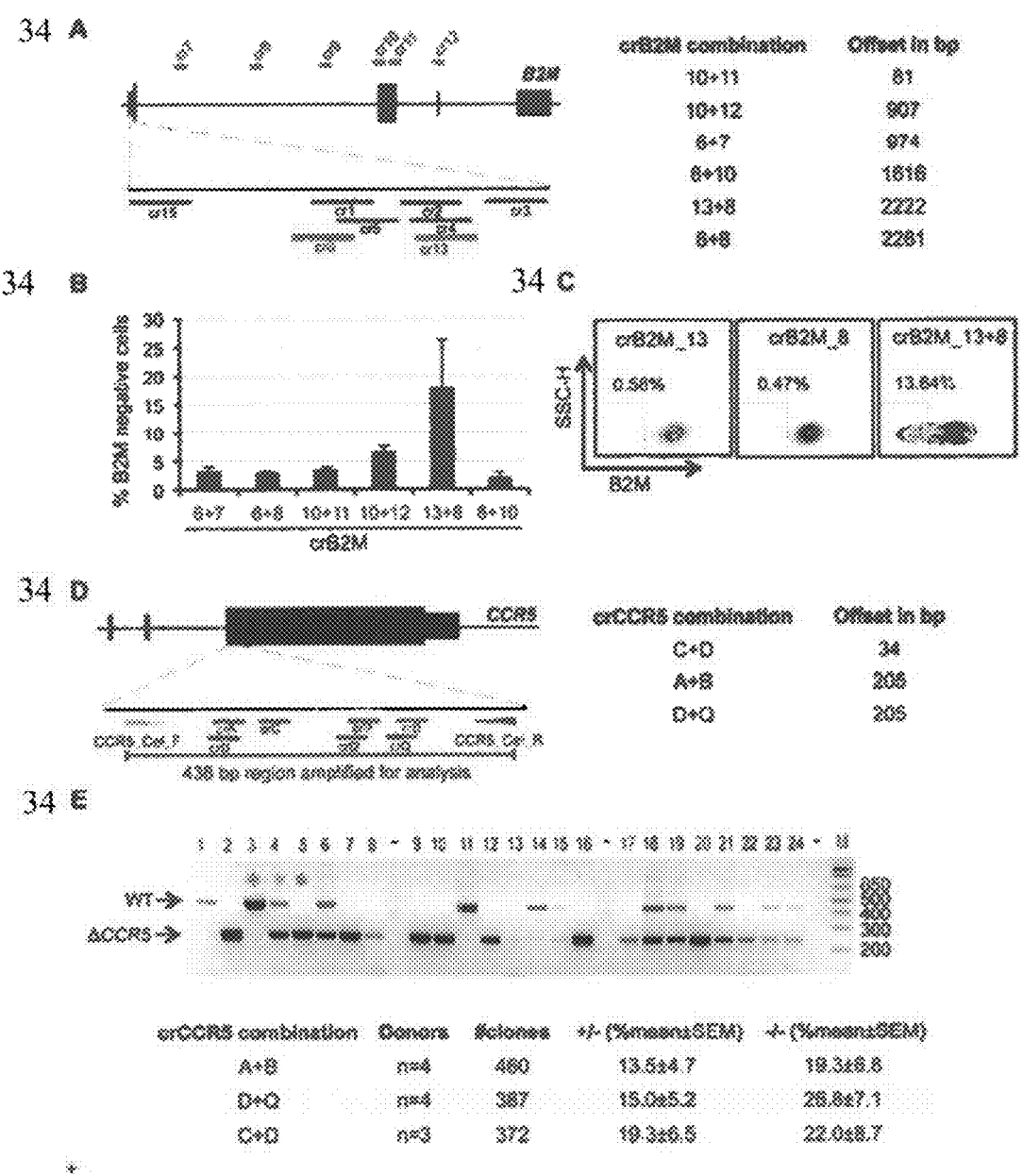
FIGS. 34A-34E depict a dual gRNA approach for CRISPR/Cas9 genome editing in primary human hematopoietic stem and effector cells.
Figures 35A, 35B, 35C, 35D, 35E, 35F, 35G:
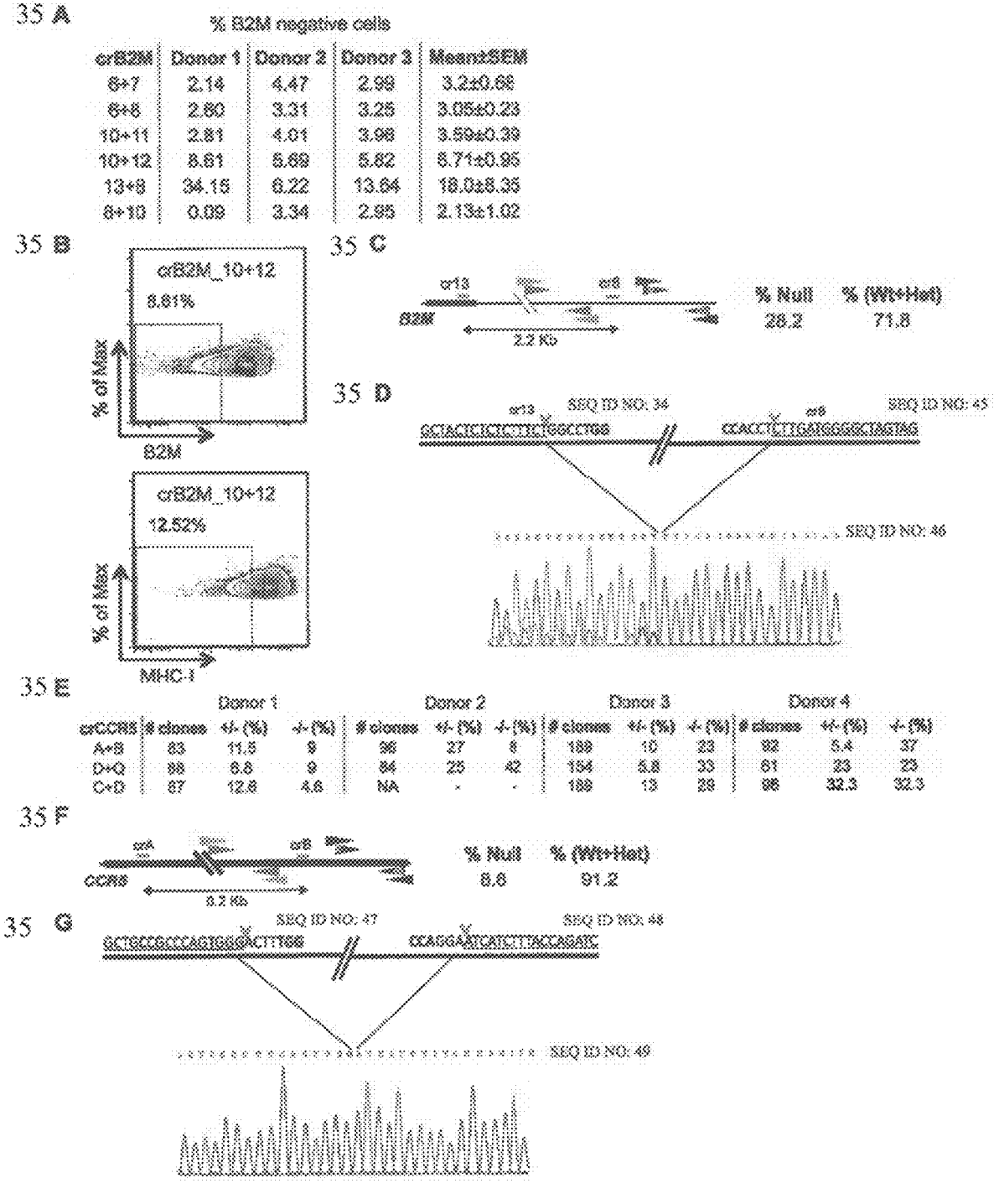
FIGS. 35A-35G demonstrate the targeting efficiency of dual gRNA combinations.
Figure 37:
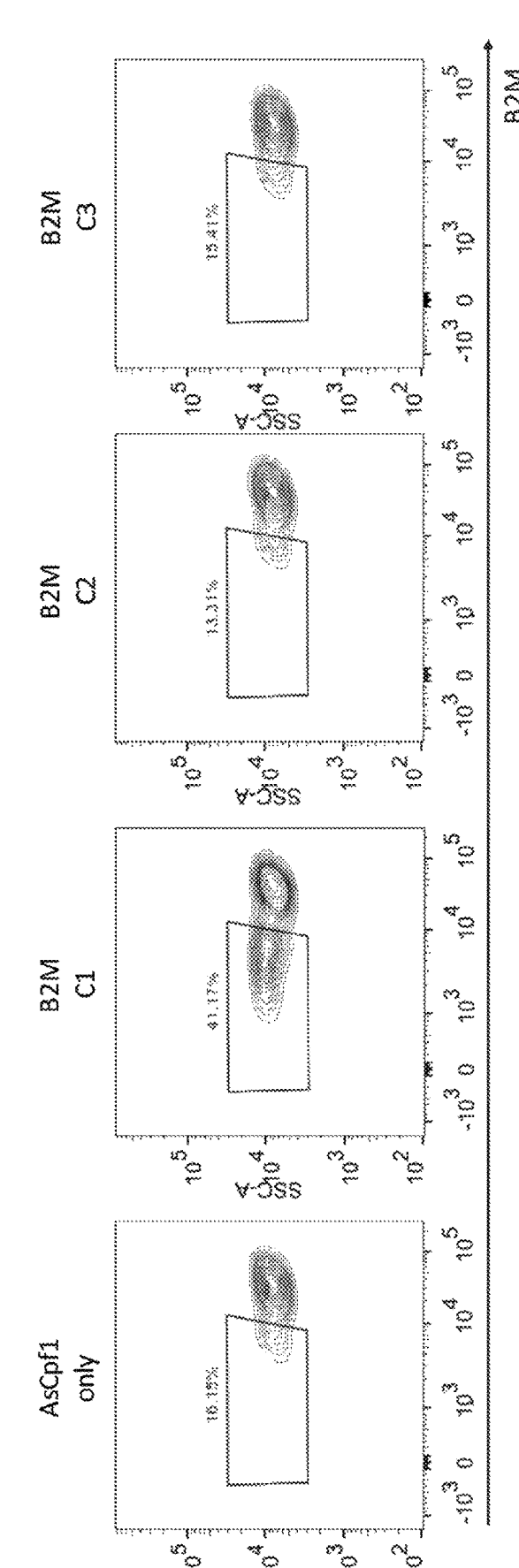
FIG. 37 demonstrates a comparison of B2M surface expression in 293T cells when transfected with AsCpf1 and guide crB2M.
Figure 38:
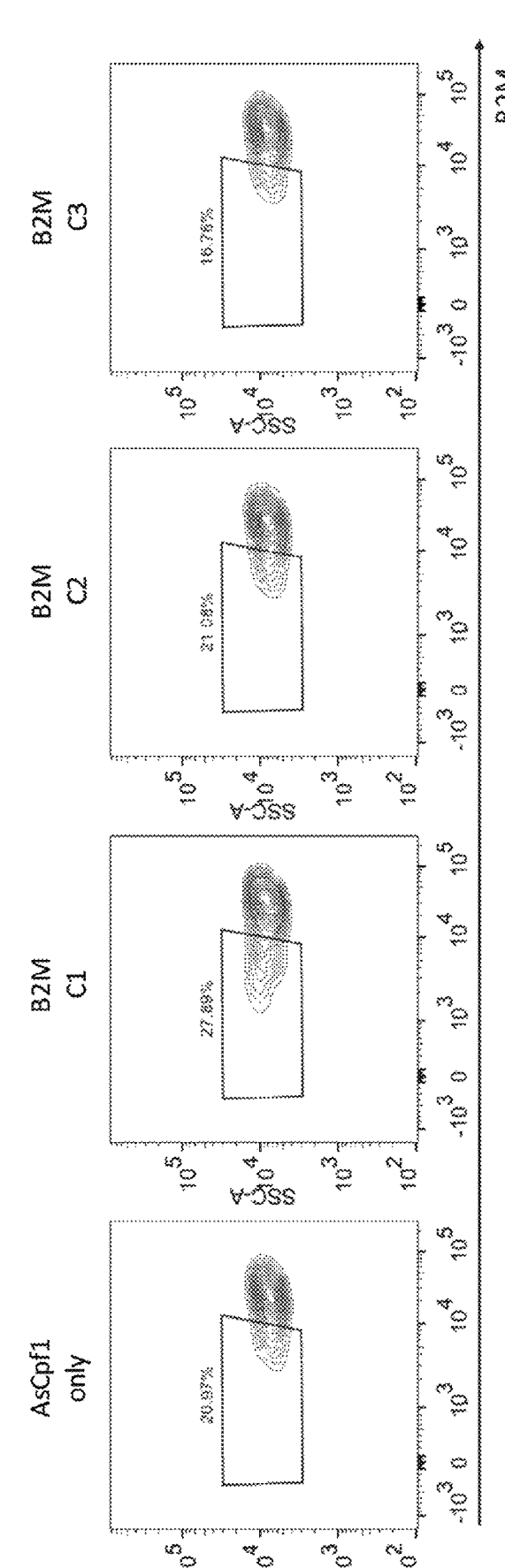
FIG. 38 demonstrates a comparison of B2M surface expression in 293T cells when transfected with LbCpf1 and guide crB2M.
Figure 40A:
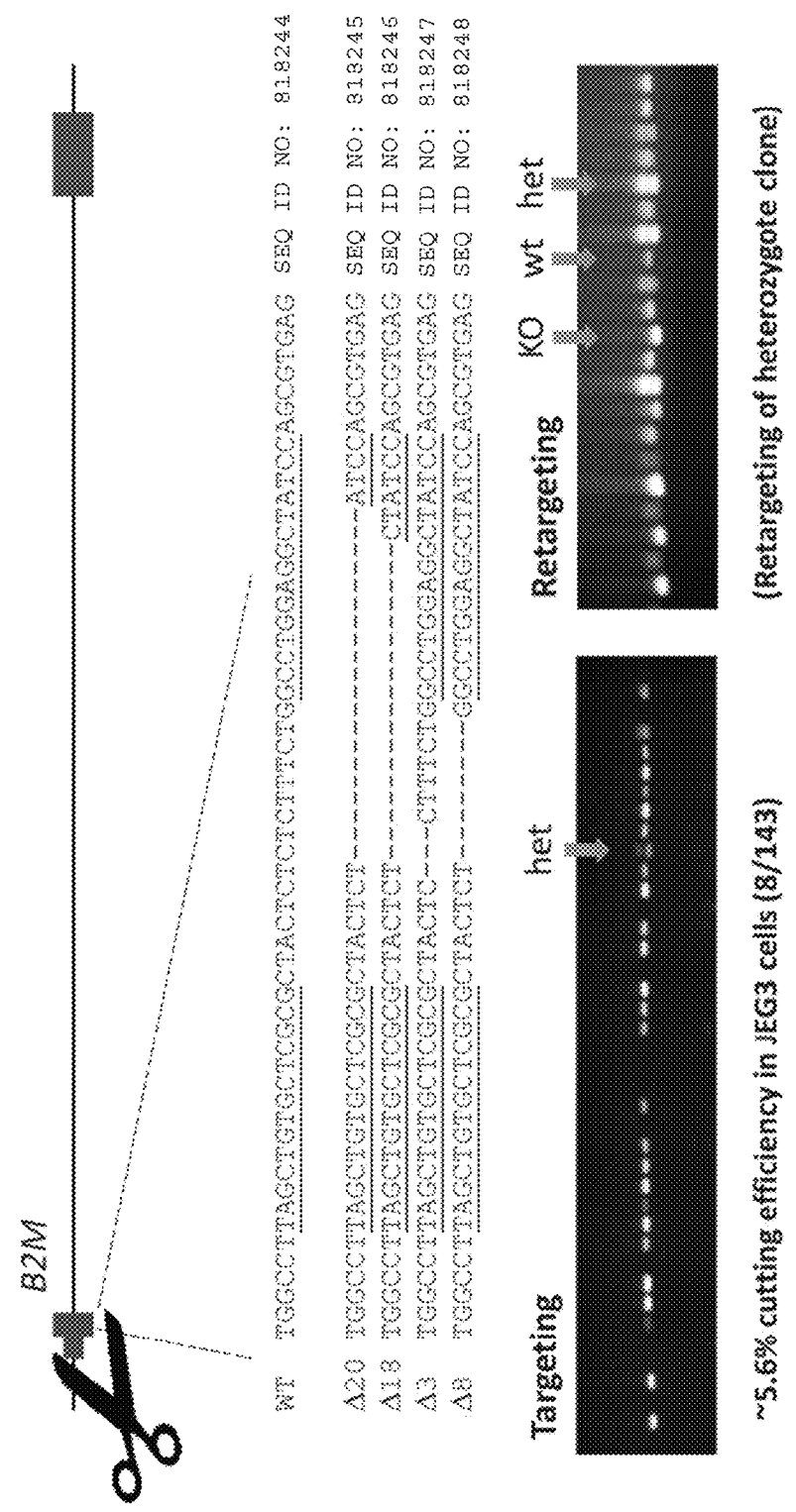
Figure 40B:
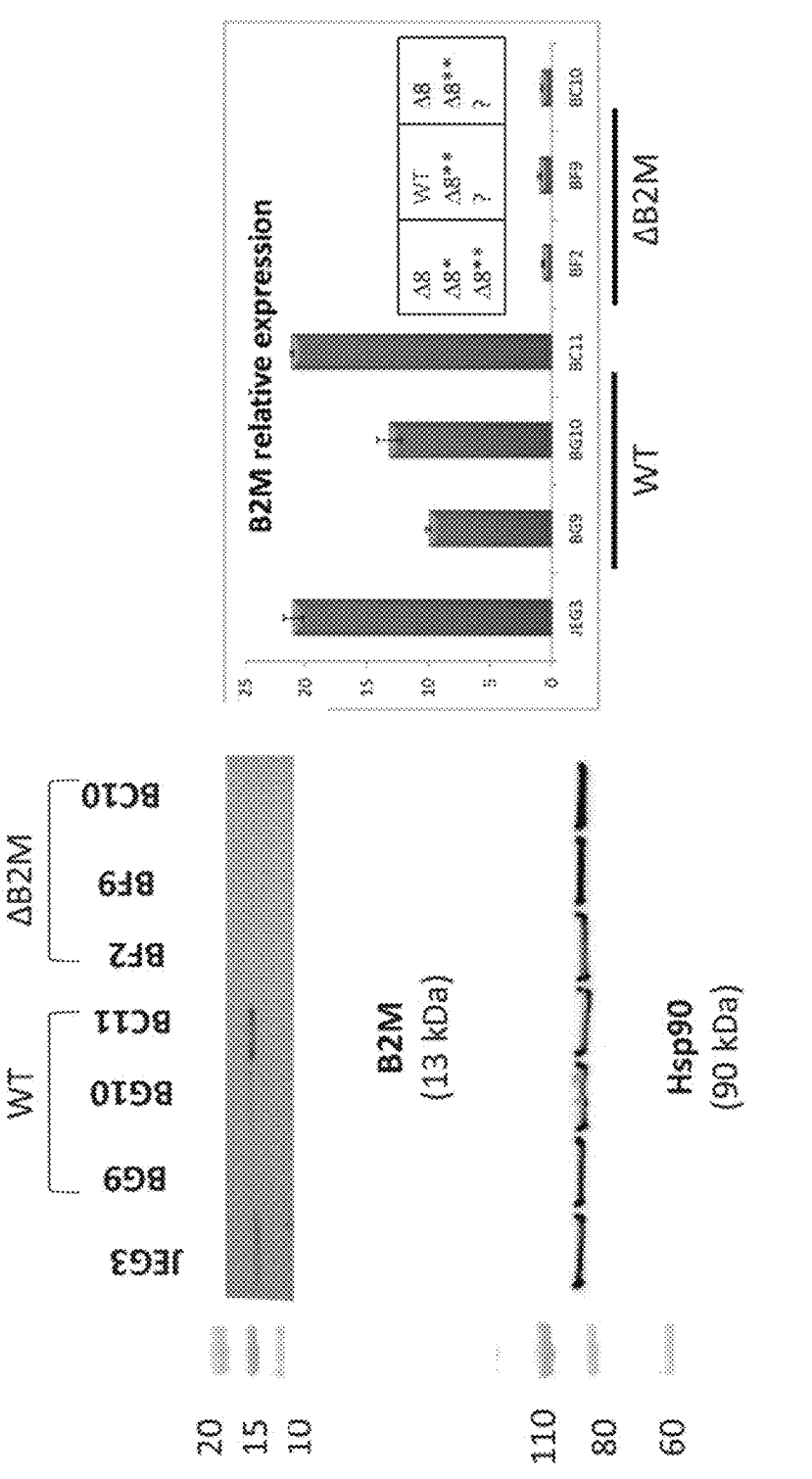
Figure 40C:
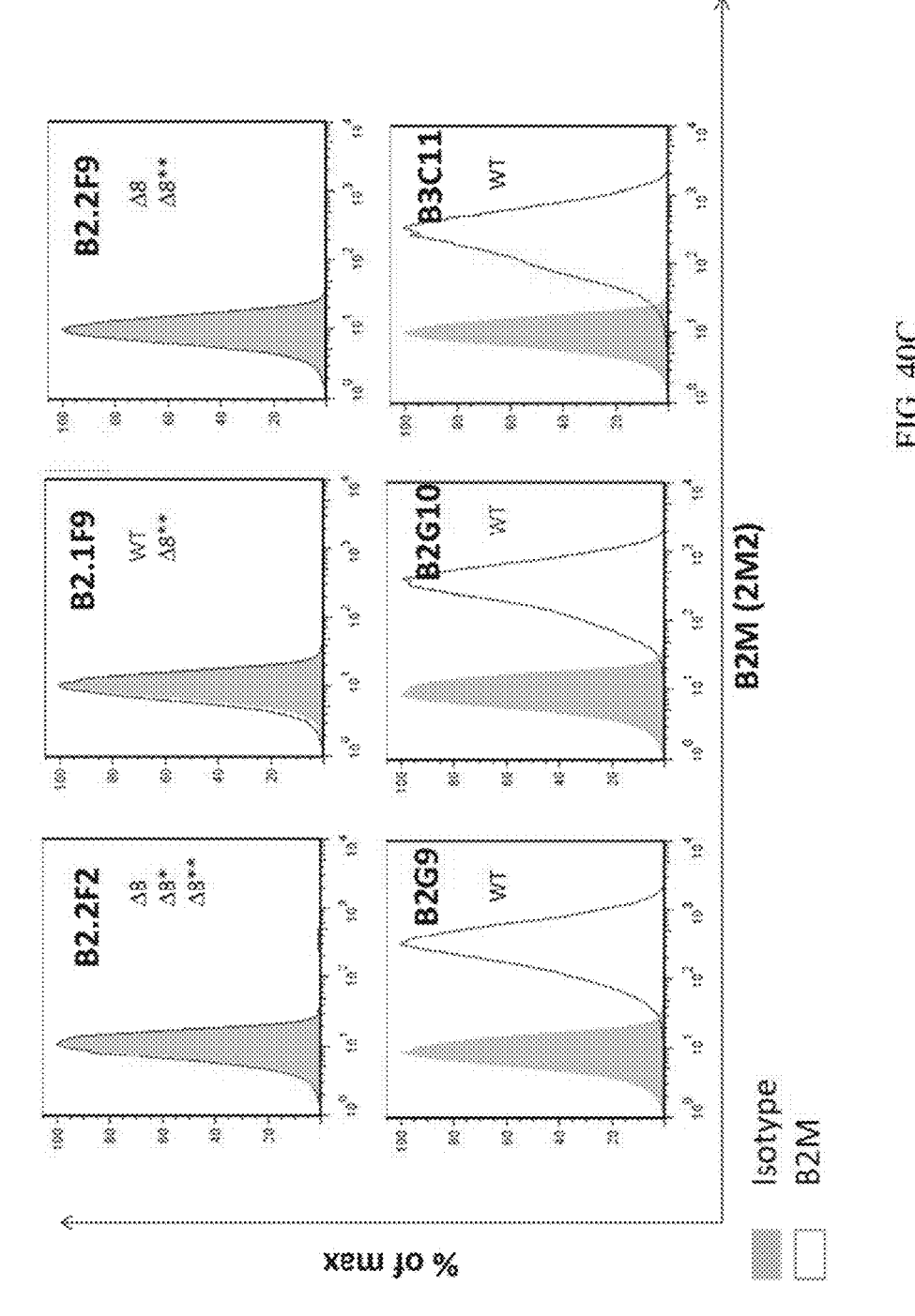
Figure 40D:
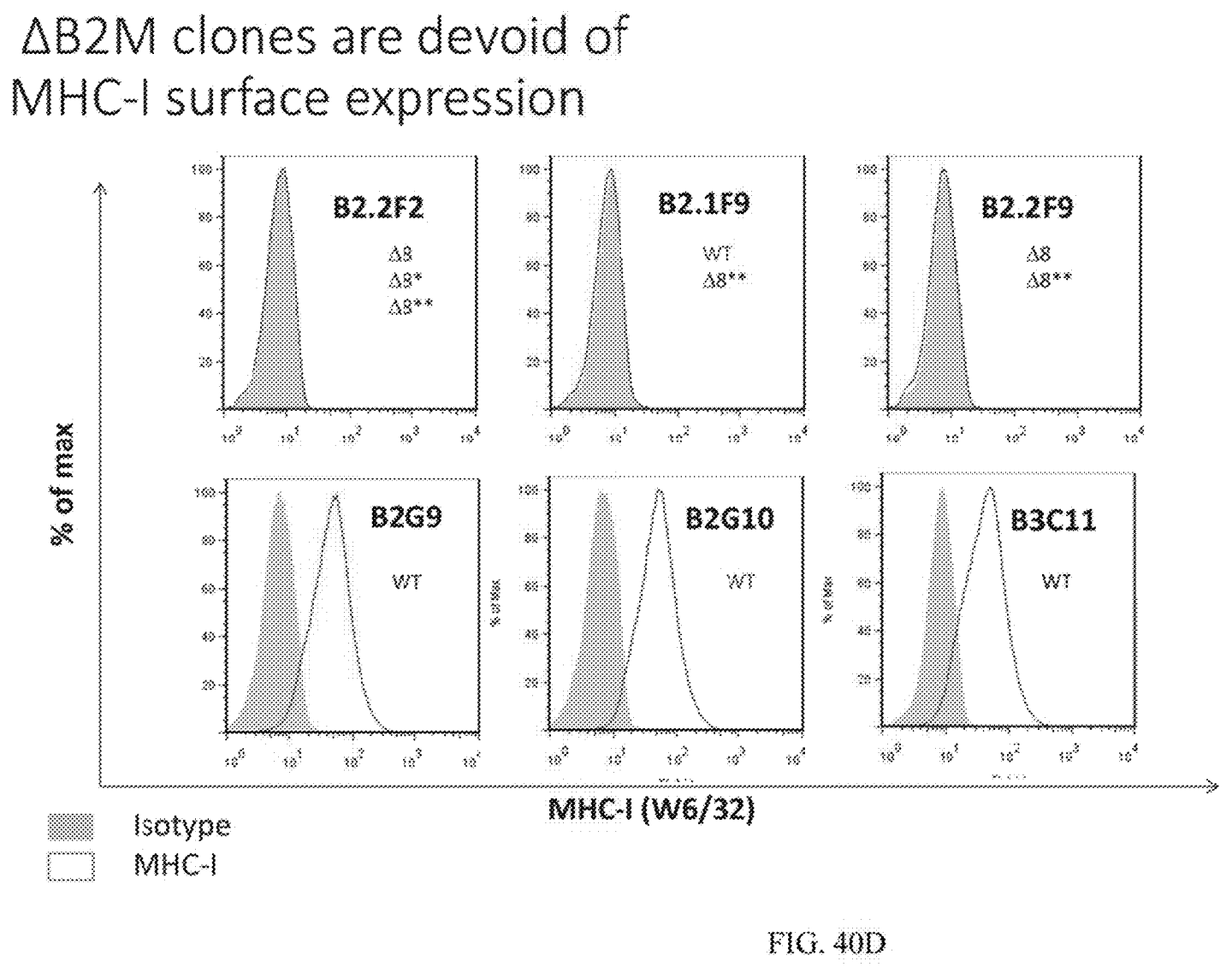
Figure 40E:
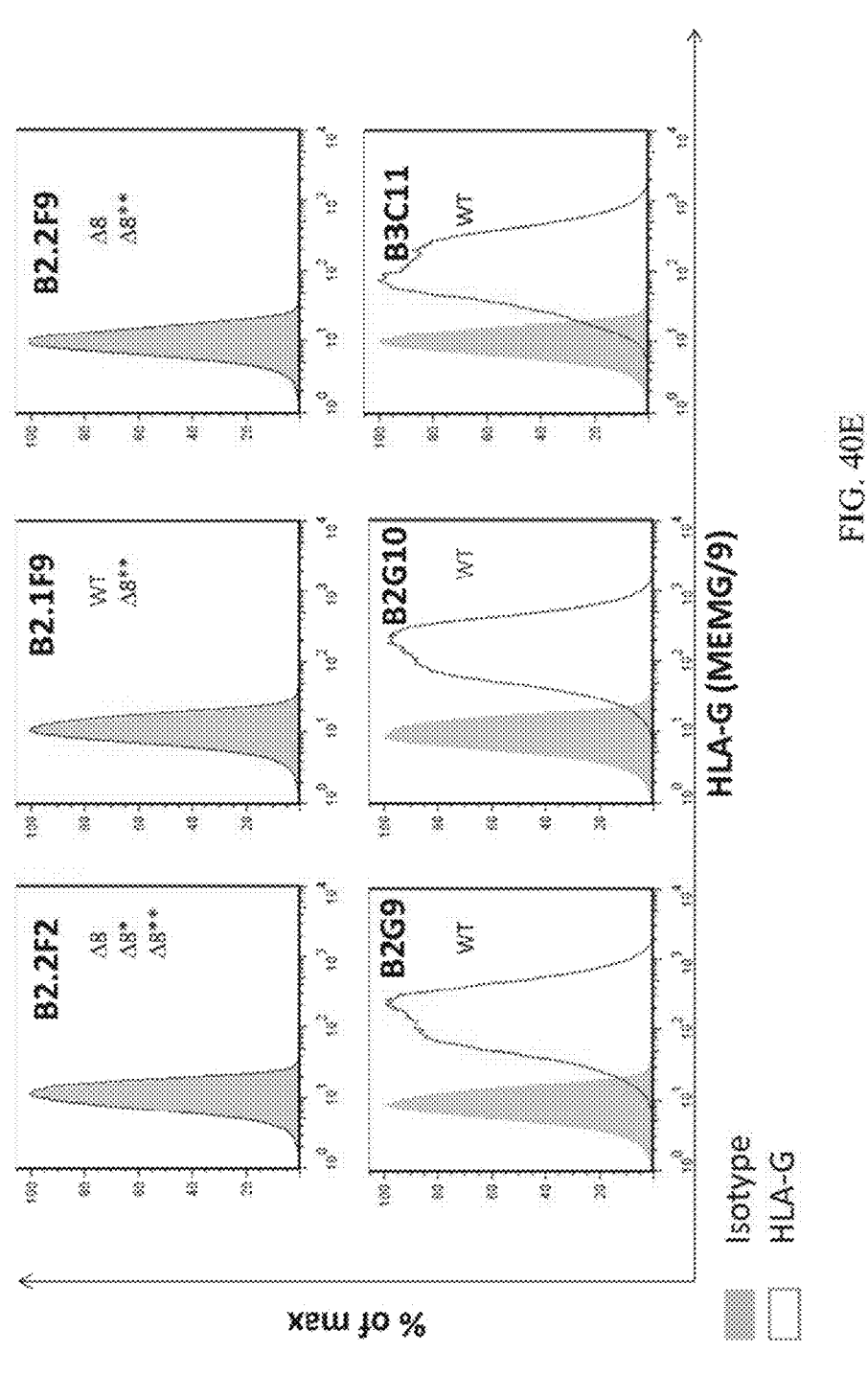
Figure 40F:
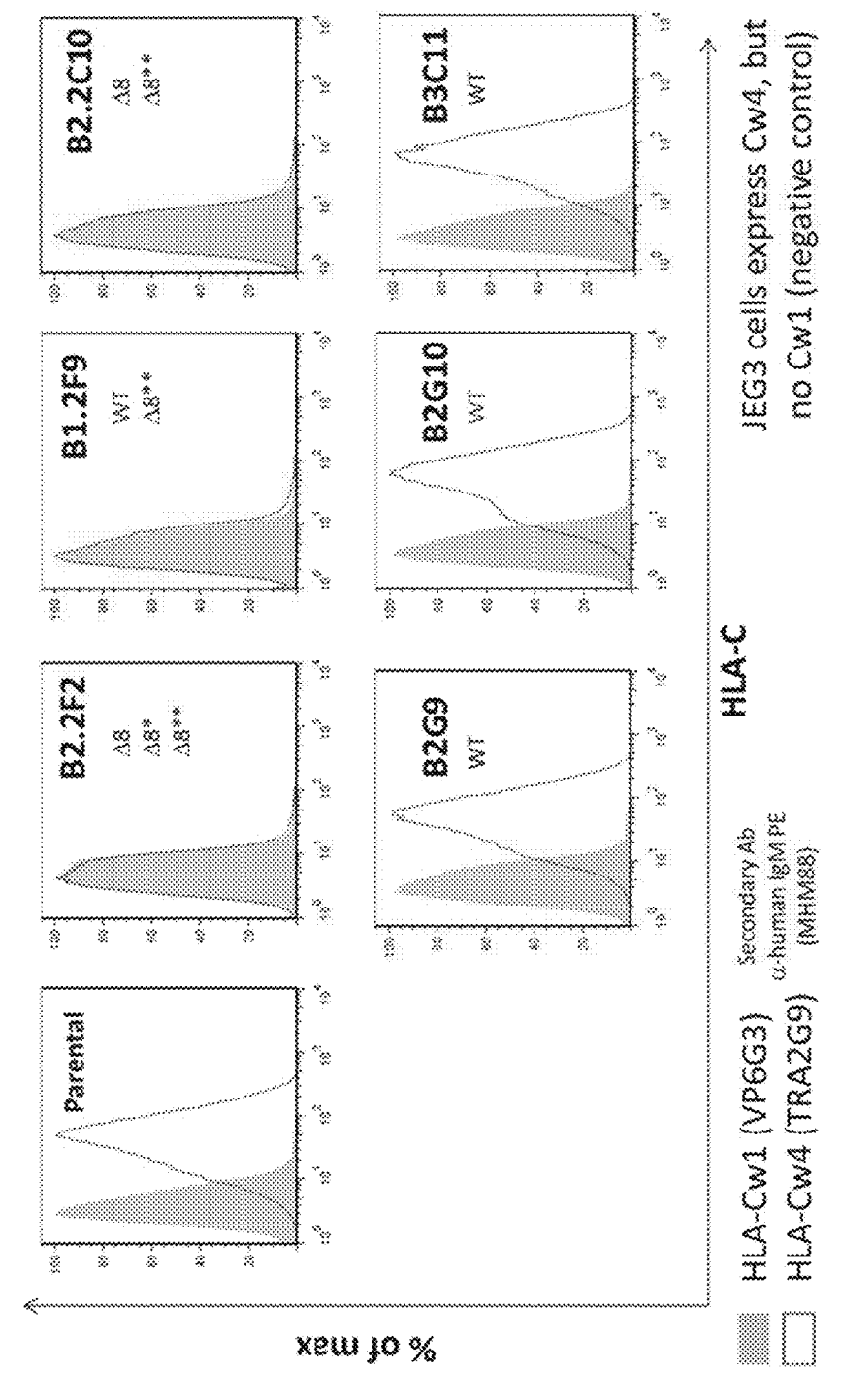
Figure 40G:
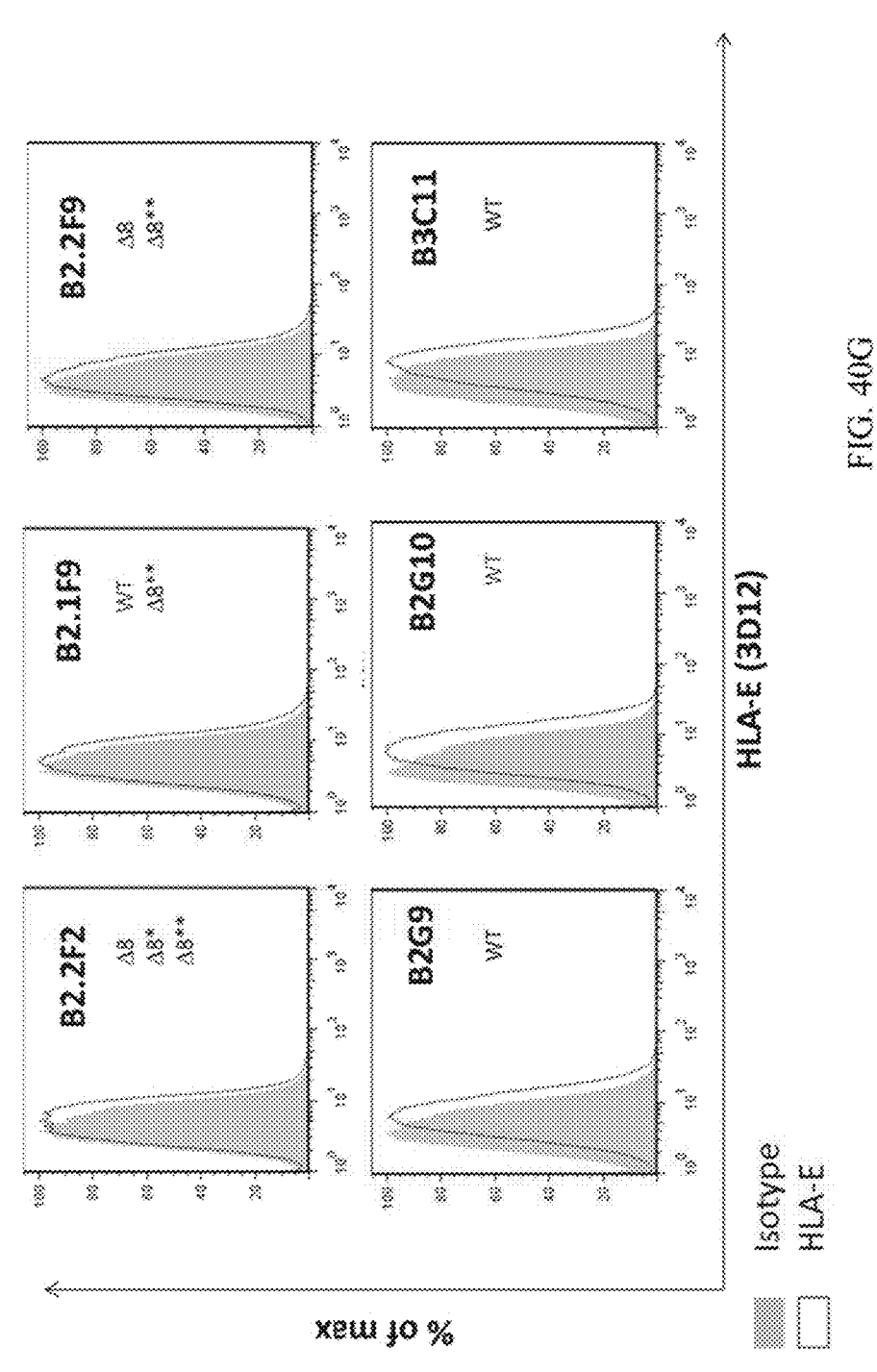
Figure 41:
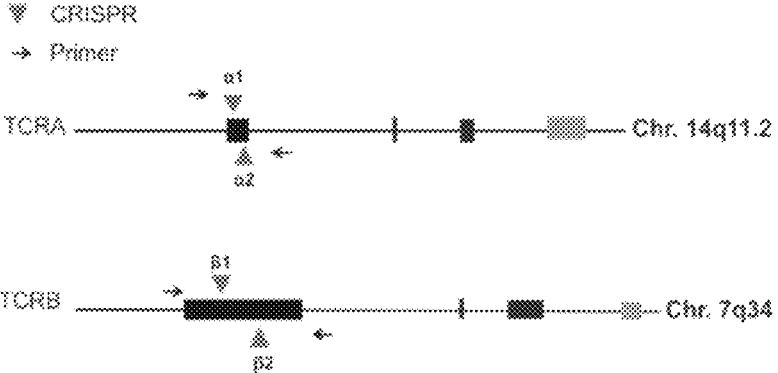
FIG. 41 demonstrates an exemplary TCR targeting strategy of the present invention.
Figures 42A, 42B:
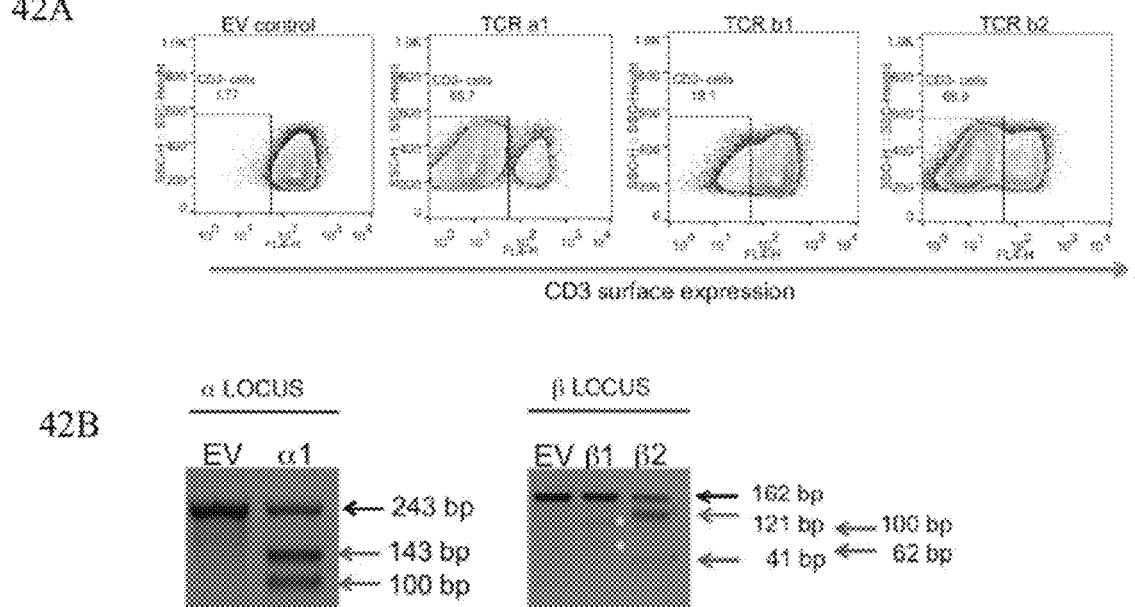
FIGS. 42A-42B demonstrate deletion of T cell receptor in Jurkat T cells.
Figure 43A:
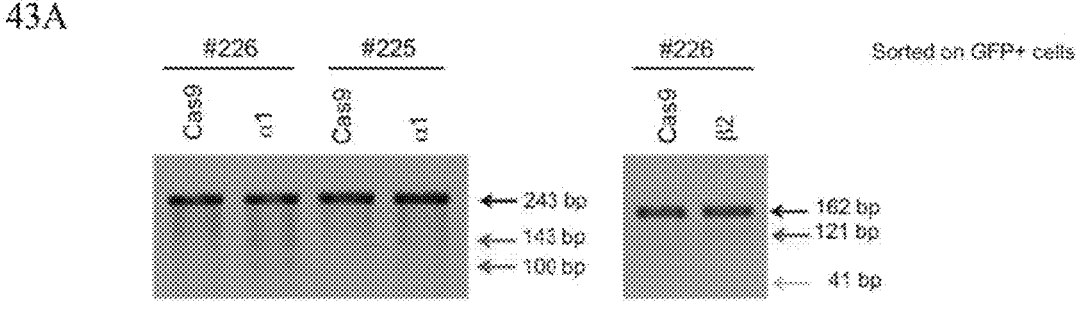
FIGS. 43A-43B demonstrate TCR Deletion in Primary Human CD3+ T Cells.
Figure 43B:
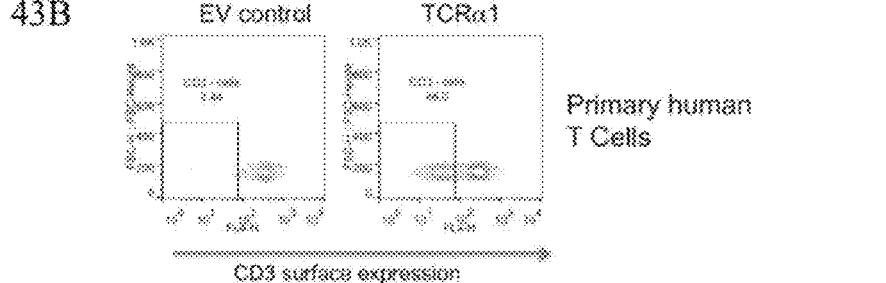
Figures 44A, 44B, 44C:
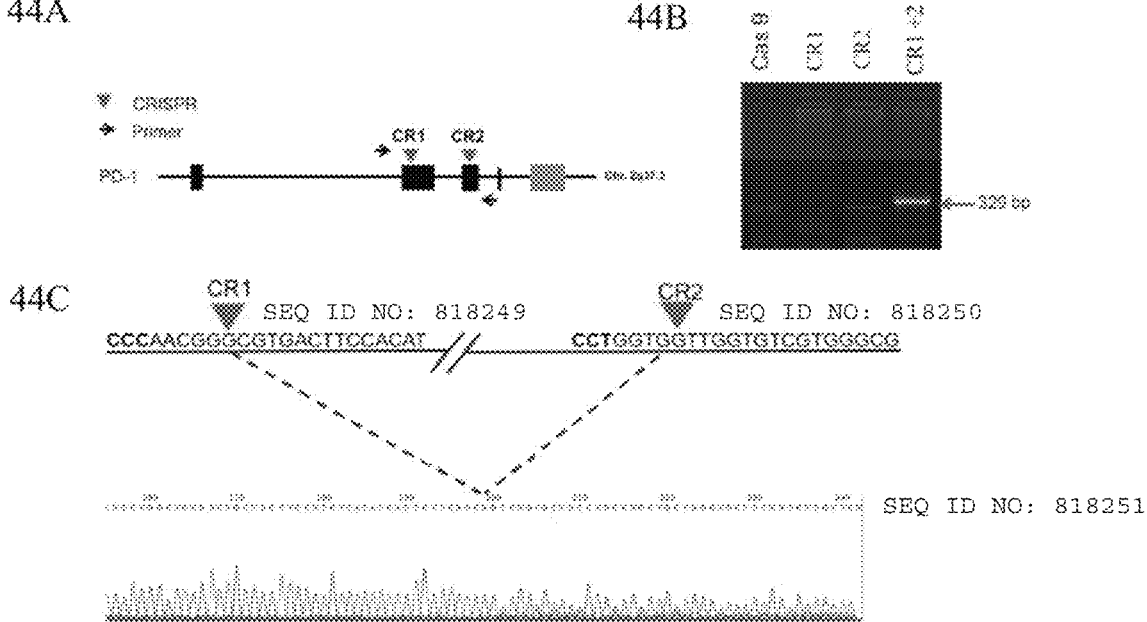
FIGS. 44A-44C demonstrate an exemplary PD-1 locus targeting strategy of the present invention.
Figures 45A, 45B:
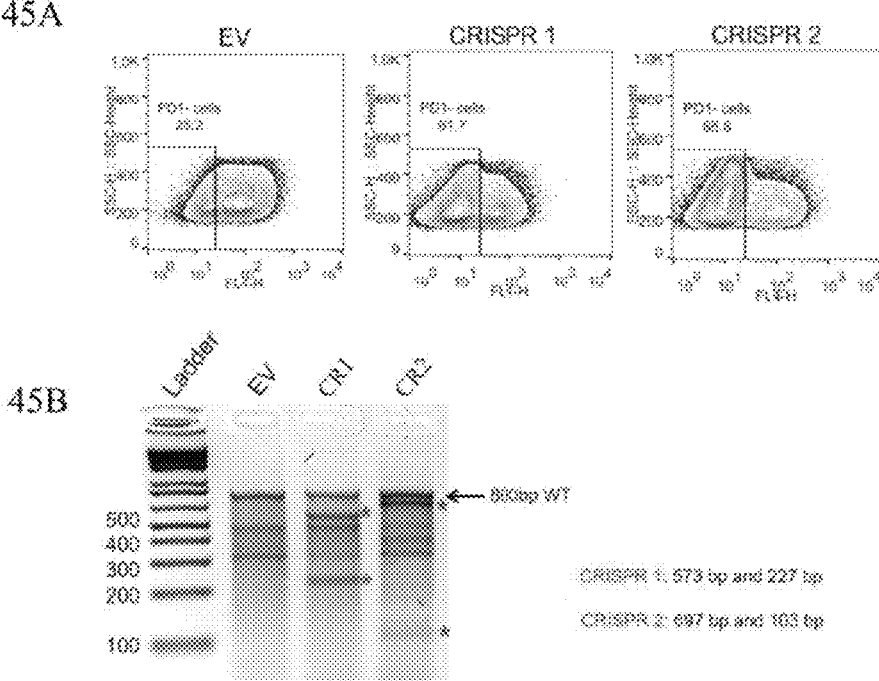
FIGS. 45A-45B demonstrate the loss of PD-1 expression in Jurkat T cells.
Figures 46A, 46B, 46C:
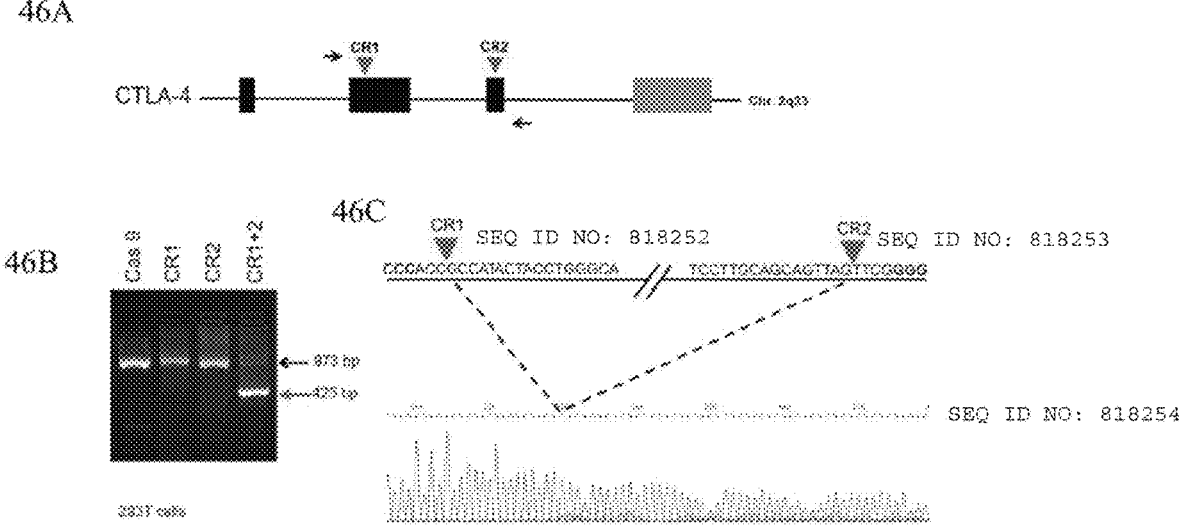
FIGS. 46A-46C demonstrate an exemplary CTLA4 locus targeting strategy of the present invention.
Figures 47A, 47B:
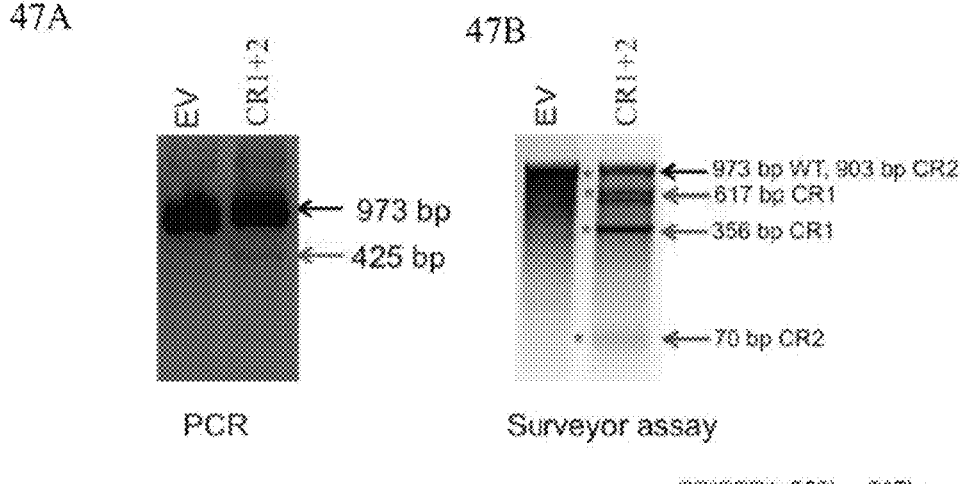
FIGS. 47A-47B demonstrate cutting at the CTLA-4 locus in Jurkat T cells.

The successful targeting of B2M utilizing TALENs and/or CRISPR has previously been described in PCT Patent Application No. PCT/US2015/059621, which is incorporated herein by reference and is shown in FIGS. 32-40. It has further been demonstrated that surface expression of MHC class I molecules is reduced or eliminated, thereby blocking the surface trafficking of MHC-I molecules. For example, loss of MHC class I surface expression in B2M–/– Jurkat Cas9 T cells was shown in comparison to MHC class I surface expression in Jurkat Cas9 T cells in FIG. 31.

Figure 20B:
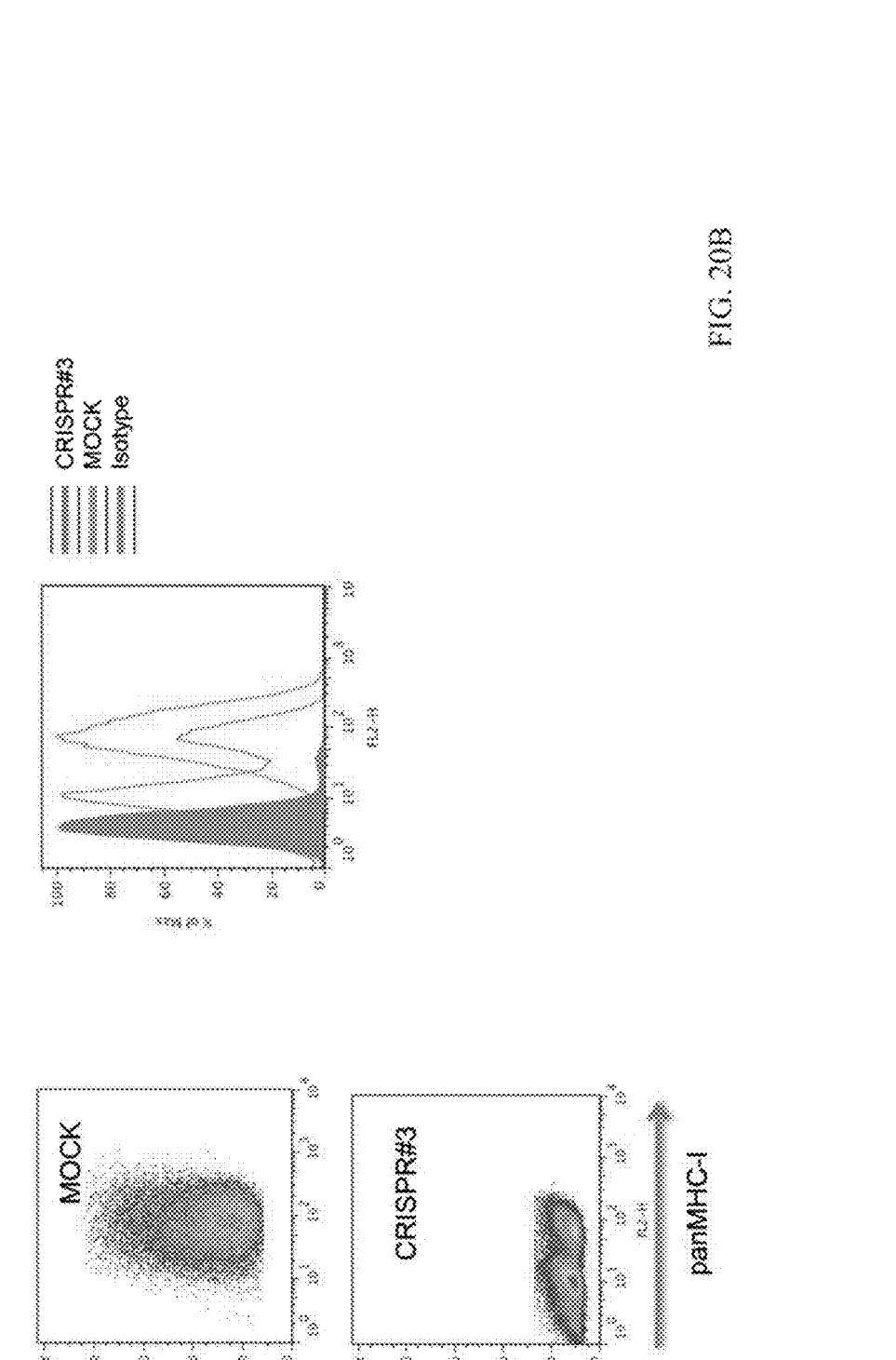
Figure 20C:
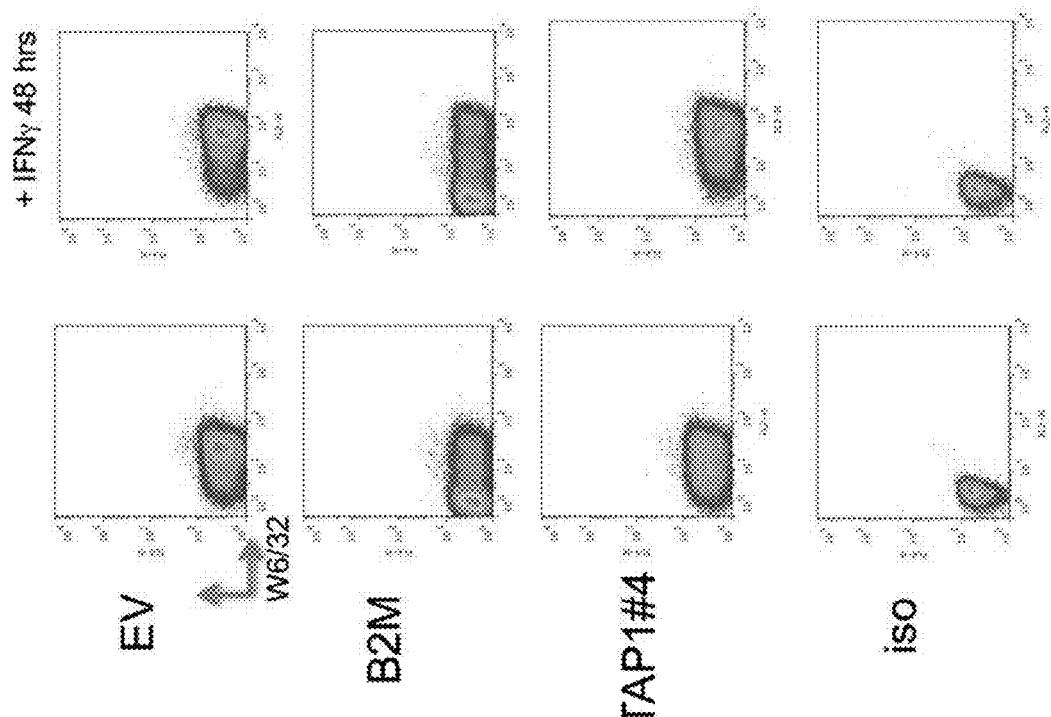
Figure 20D:
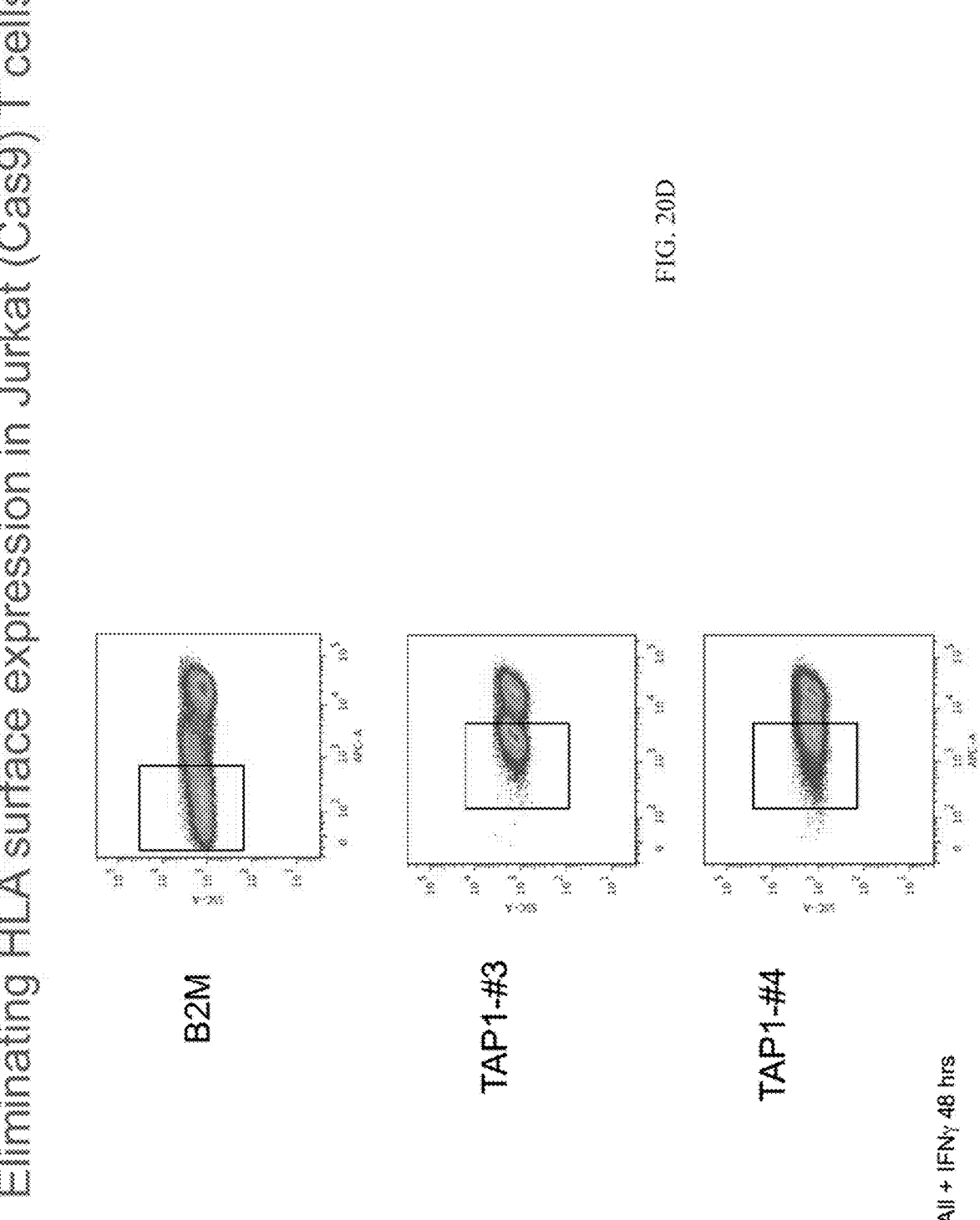

In addition, the inventors have demonstrated that surface trafficking of MHC class I molecules can be suppressed but disrupting the TAP1 gene, an ER-resident peptide transporter. For example, TAP1 CRISPR expression reduces MHC-I surface expression in Jurkat cells (FIG. 20A), as well as in Jurkat T cells (FIG. 20B), following 48 hour treatment with IFNγ. It was further demonstrated that HLA surface expression in Jurkat (Cas9) T cells could be eliminated (FIG. 20C and FIG. 20D). The Jurkat T cells were established from the peripheral blood of a 14 year old boy who had acute T cell leukemia.

HLA Razor

Figure 21B:
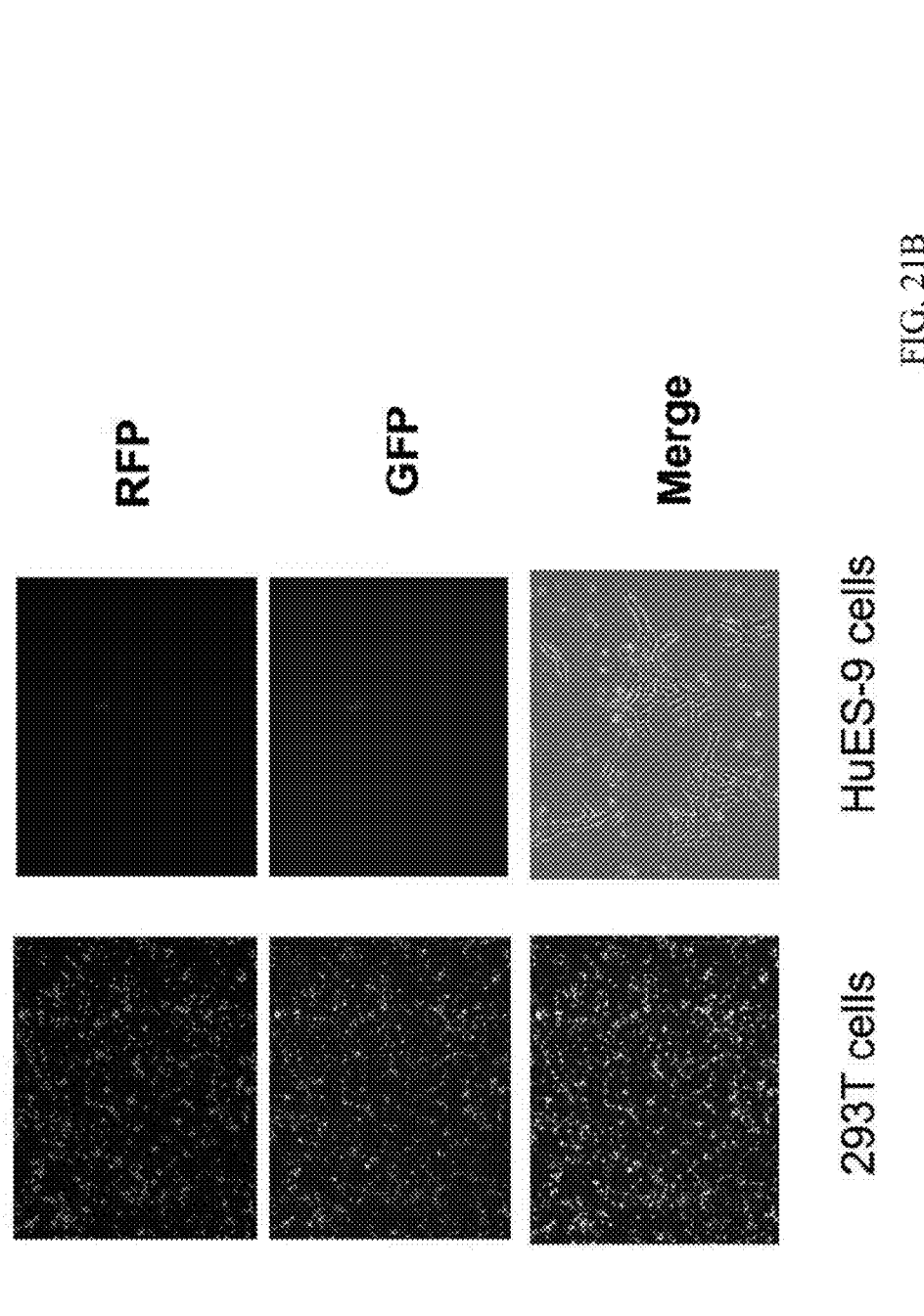
Figure 21C:
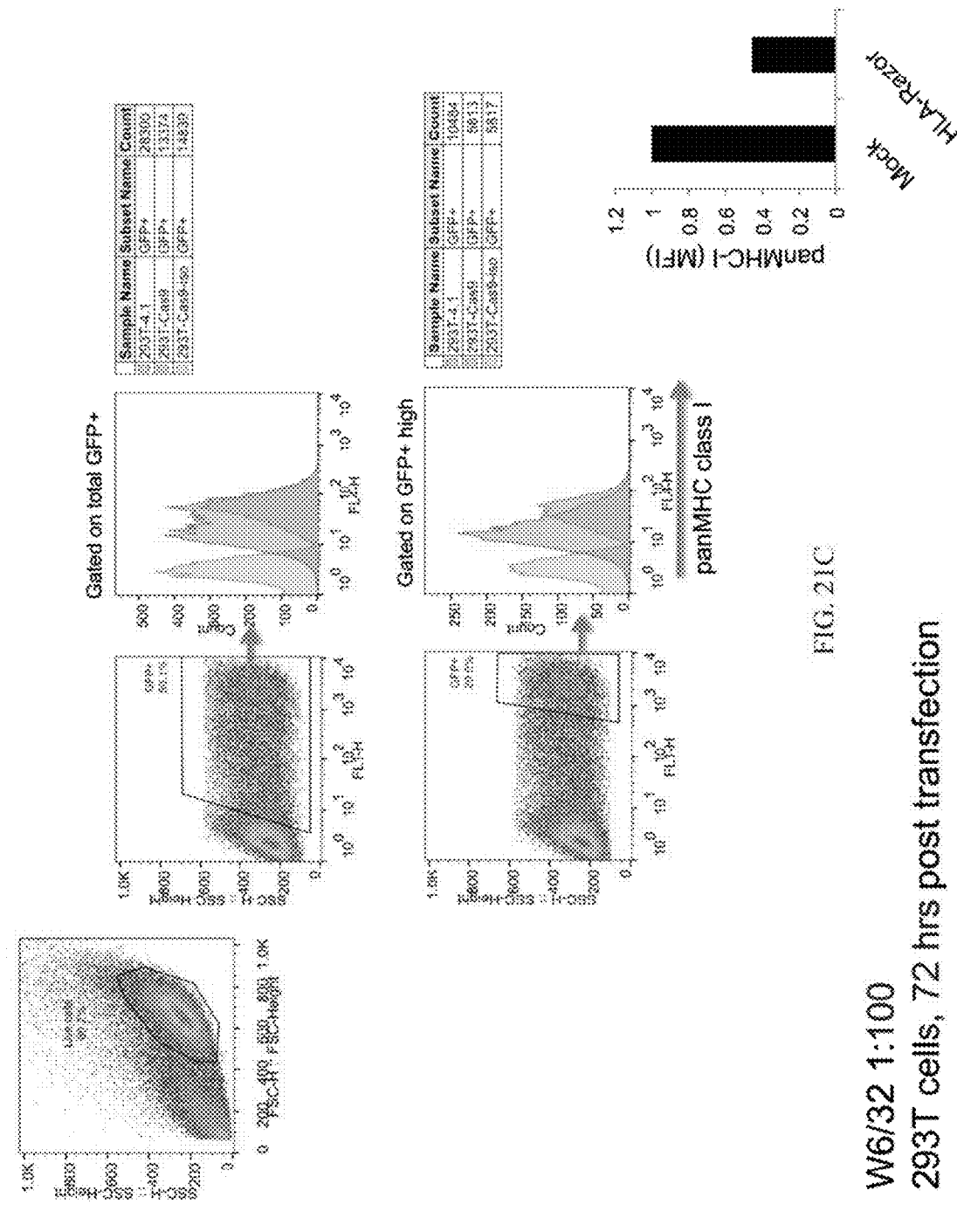
Figure 21D:
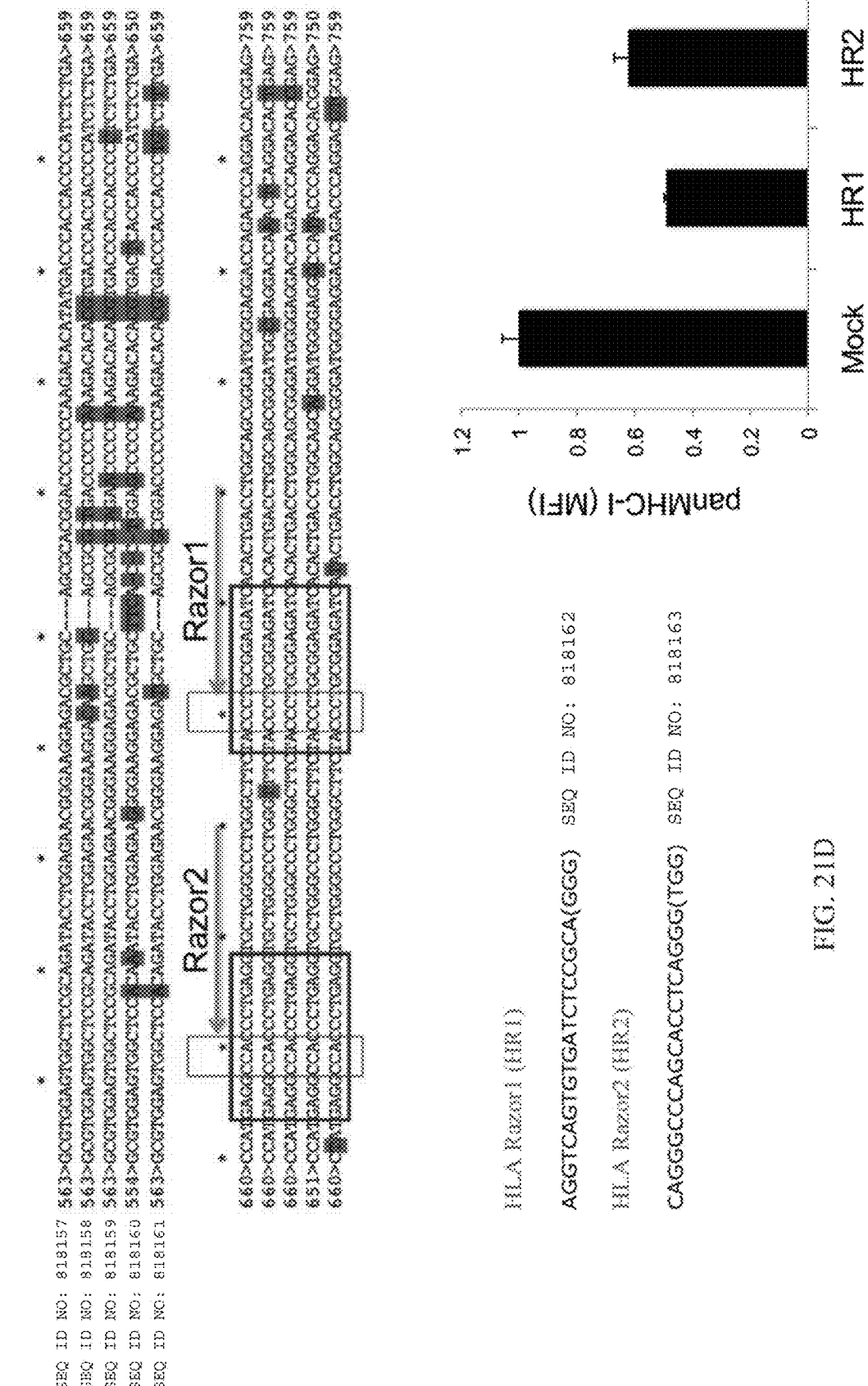

The inventors examined CRISPR guide RNAs that allow simultaneous deletion of all MHC class I alleles by targeting a conserved region in the HLA genes. A TALEN pair of guides that target the same conserved region in MHC class I genes were also identified. Any guide that targets the conserved regions may be identified or classified as an HLA Razor. The targeting of a conserved sequence found in all HLAs by CRISPR or TALENS was demonstrated in FIG. 21A. The two violet boxes indicate the binding sites for the pan-HLA TALEN pair. The blue arrow indicates the pan-HLA CRISPR tested pair, with the PAM being boxed in blue. The expression of pan-HLA-TALENs in 293T and HuES9 cells was shown in FIG. 21B at 72 hours post transfection. The HLA-Razor CRISPR blunts MHC class I expression in 293T cells as demonstrated in FIG. 21C. The 293T cells were also co-transfected with Cas9-GFP. FIG. 21D provides a comparison of the activity of two different HLA Razors targeting two different conserved regions of the HLAs.

Knock-In of PD-L1 and HLA-G

The present inventors have used a CRISPR/Cas system to facilitate the insertion of tolerogenic factors, such as the tolerogenic factors shown in Table 2, into an AAVS1 locus, to actively inhibit immune rejection. As evidenced in FIGS. 11A-11C, tolerogenic factors, such as PD-L1 and HLA-G, have been successfully expressed from the AAVS1 locus.

Figure 22A:
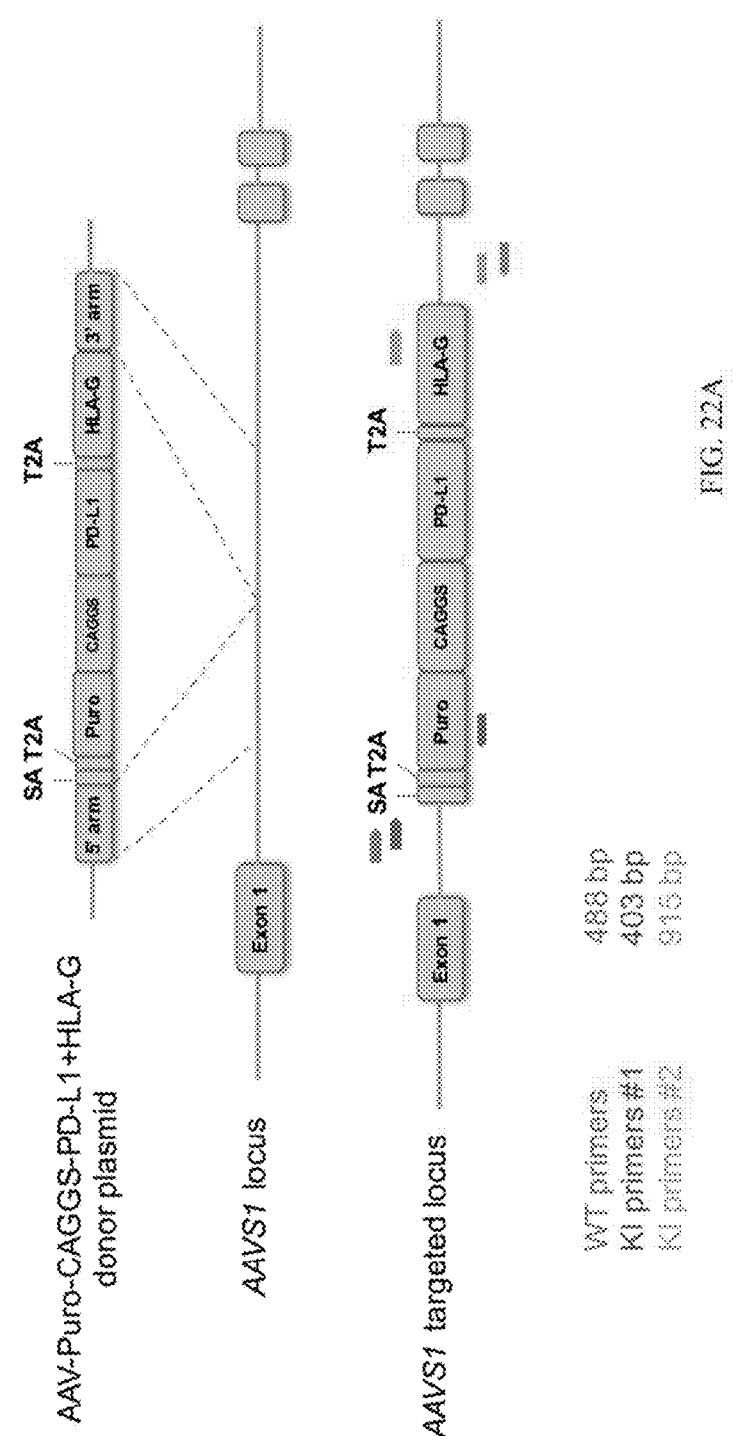

A schematic of the PD-L1 and HLA-G knock-in strategy is shown in FIG. 22A. Wild type (WT) and knock-in (KI) primers for clone screening were designed. The amplicon with WT primers is predicted as 488 bp, and the amplicons with KI primers are predicted as 403 bp and 915 bp. A design of a knock-in donor plasmid (FIG. 22B) shows that the reading frames of PD-L1 and HLA-G are linked by T2A and their expression is driven by a CAGGS promoter. Puromycin was used as a drug resistance marker following the SA-2A gene trap element.

Figure 22C:
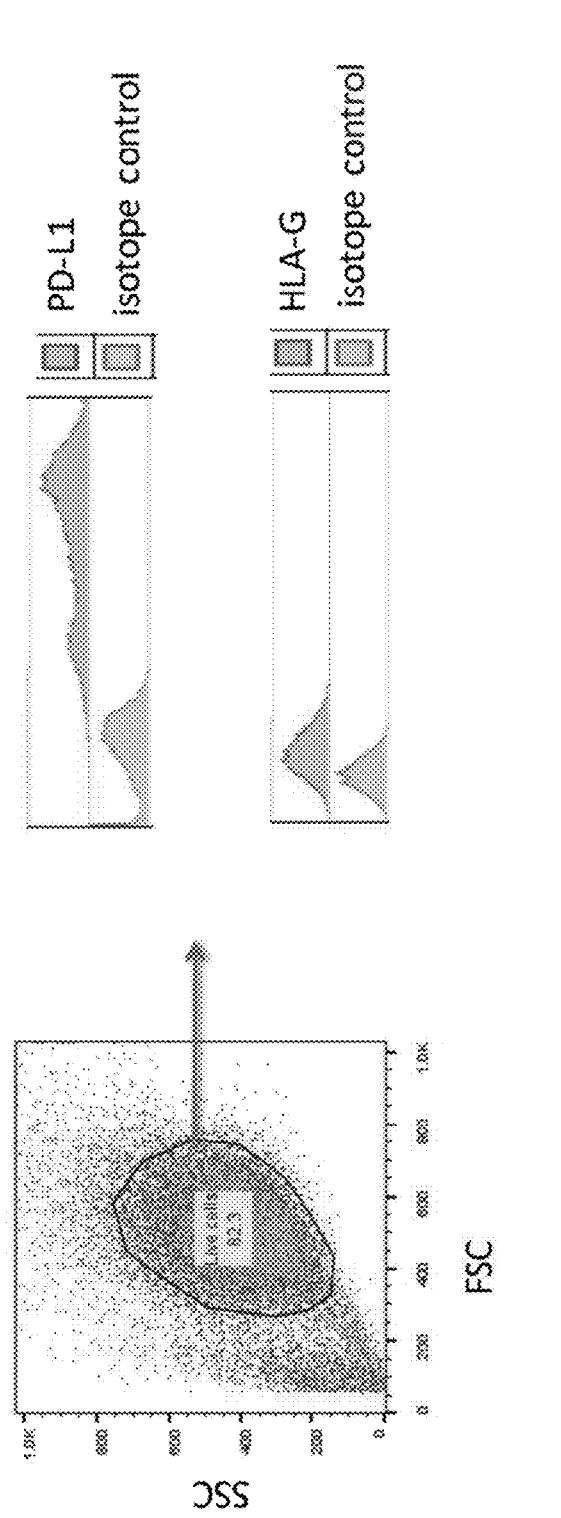
Figure 22D:
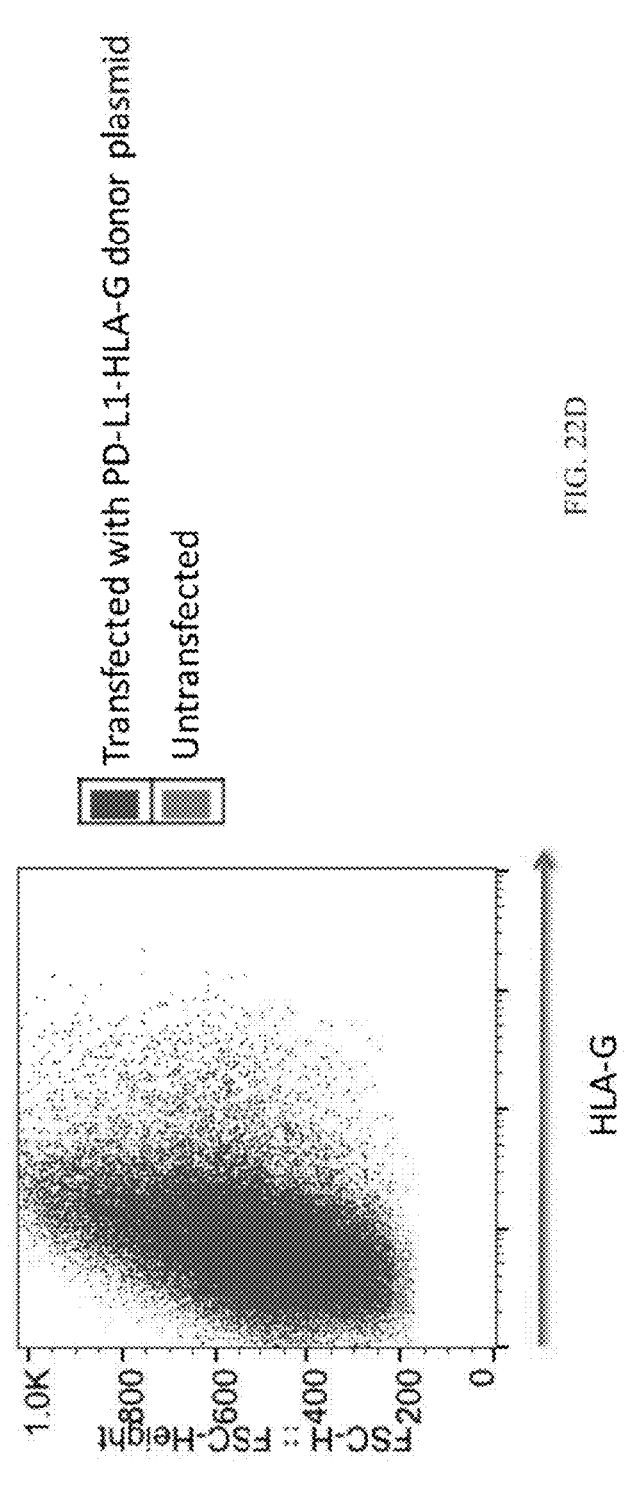

The expression of PD-L1 and HLA-G was examined in the donor plasmid-transfected 293T cells by FACS analysis. FIG. 22C shows the ectopic PD-L1 and HLA-G expression in 293T cells. APC-conjugated PD-L1 antibody and FITC-conjugated HLA-G antibody were used. In addition, the expression of ectopic HLA-G expression in JEG-3 cells is shown in FIG. 22D. The donor plasmid was transfected into an HLA-G–/– JEG-3 cell line, and ectopic HLA-G expression was examined by FACS analysis 48 hours post-transfection. A PE-conjugated HLA-G antibody (MEM/G9) was used to detect surface HLA-G surface expression.

Figure 22F:
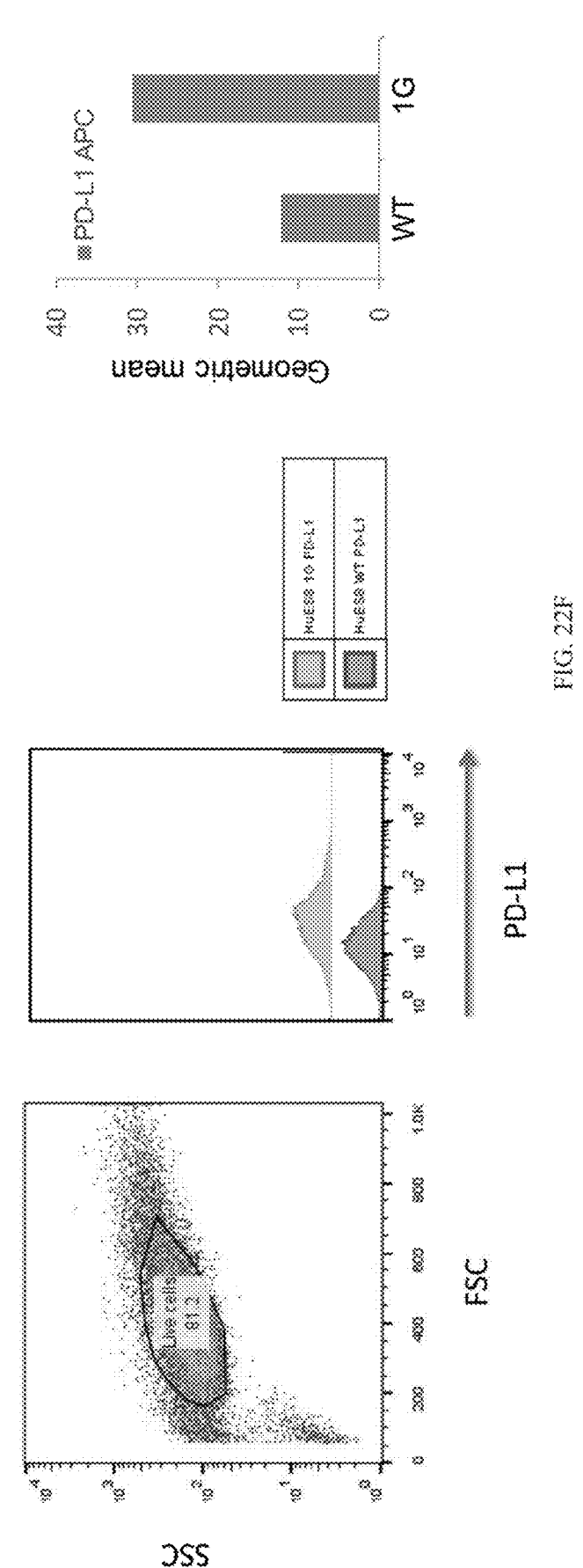

PCR screening was performed, which confirmed that clone 1G was a heterozygous KI clone for PD-L1/HLA-G (FIG. 22E). Clone 1G was identified as a heterozygous KI clone by the presence of bands using both WT primers and KI-specific primers amplified from genomic DNA of targeted HuES8. The expression of PD-L1 was verified in HuES8 KI clone 1G by FACS analysis using an APC-conjugated PD-L1 antibody (FIG. 22F).

Knock-In of CD-47

Figure 23:
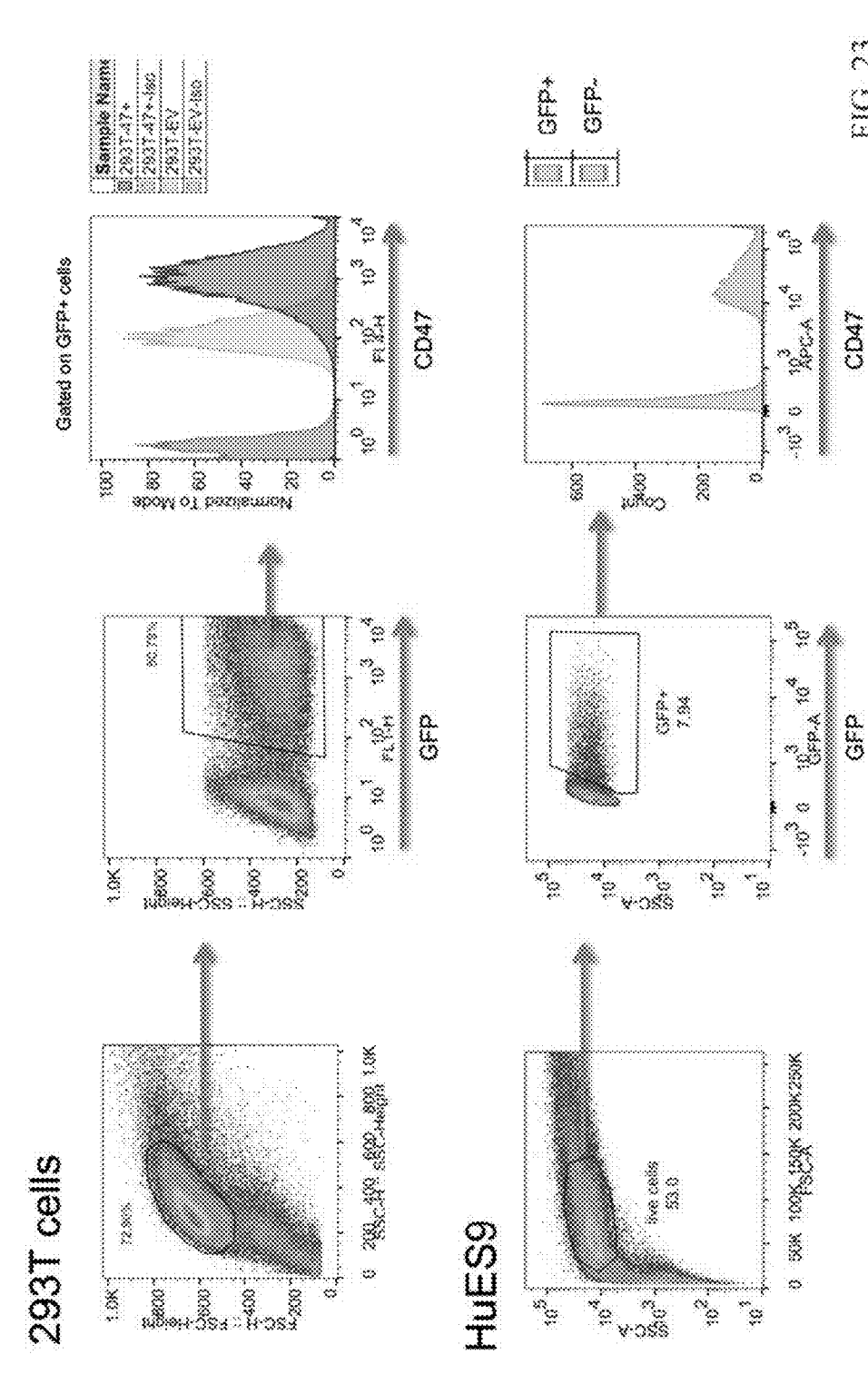
FIG. 23 demonstrates expression of CD47 in 293T cells and hPSCs using a knock-in strategy. Human CD47 was cloned into an expression plasmid driven by a CAG promoter, which in addition contains an IRES-GFP. 293T cells already express high levels of CD47, the human 'don't eat me' signal, which prevents engulfment of cells from macrophages. Expression can be increased by overexpression of CD47 in both 293T cells, as well as in human pluripotent stem cells (HuES9), as detected by FACS using a CD47-specific antibody. Overexpression of CD47 will assist engraftment of stem cell-derived transplants by protecting cells from macrophage engulfment.

In addition, a CD47 knock-in strategy was also examined. Human CD47 was cloned into an expression plasmid driven by a CAG promoter, which also contained an IRES-GFP. 293T cells already express high levels of CD47 (the human "don't eat me" signal), which prevents engulfment of cells from macrophages. Expression can be increased by overexpression of CD47 in both 293T cells, as well as in human pluripotent stem cells (HuES9), as detected by FACS using a CD47-specific antibody (FIG. 23). It is expected that overexpression of CD47 will assist engraftment of stem cell-derived transplants by protecting cells from macrophage engulfment.

Additional Targets to be Modified in Universal Donor Cells

Additional targets may be modified in universal donor cells to tailor them to a specific application. For example, additional targets may be modified in universal donor cells to tailor them to be used as universal CAR T cells. In one instance, the inventors deleted TRAC and TRBC in HuES9 to disrupt TCR expression (FIG. 24). A dual guide RNA approach was used to introduce deletions into the TRAC and TRBC loci in HuES9 cells. The TCRA wild type band is 249 bp and after deletion is 209 bp. The TCRB wild type band is 162 bp and after deletion is 140 bp. The inventors additionally targeted TCRA in HuES9 B2M–/– CIITA–/– to create a triple knock-out stem cell line for B2M–/–, CIITA–/– and TCR–/–, which upon differentiation into T cells will be devoid of MHC-I and -II and exhibit no TCR surface expression.

Figure 25B:
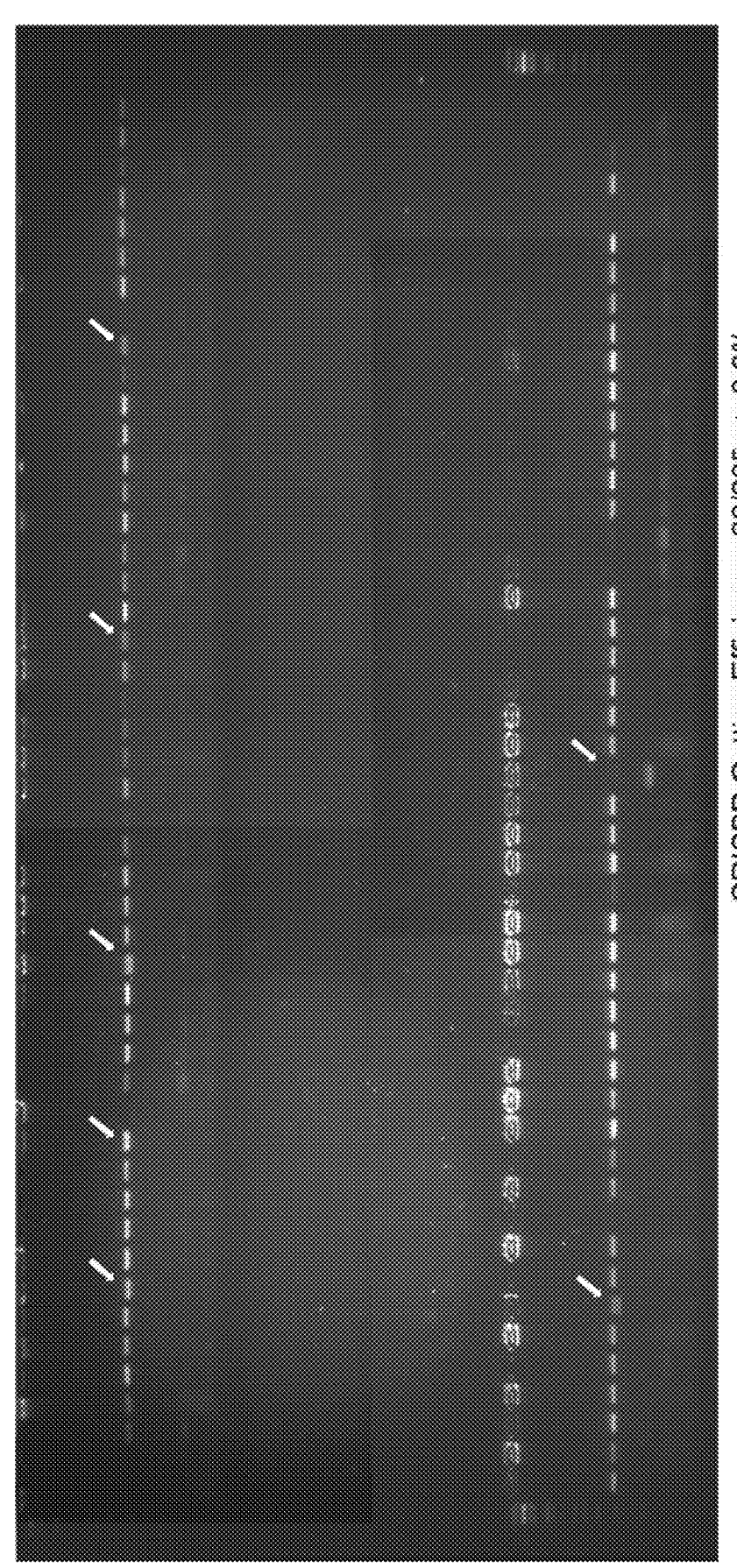

In another instance, the inventors targeted PD-L1 (FIG. 25A). It was identified that CRISPRs targeting Cd274/B7-H1/PD-L1 were very useful in breaking tolerance in cancer immunotherapy. PD-L1 knock out was demonstrated in multiple cell types, including JEG-3, a choriocarcinoma cell line, and in two melanoma cell lines, 501 and MalMe (FIGS. 25B-25D). Screening of targeted B7-H1 colonies was conducted, and it was identified that there was an 8.3% CRISPR cutting efficiency in JEG-3 cells (FIG. 25B). Additionally, reconfirmation of 501 melanoma knock out clones was shown in FIG. 25C, and reconfirmation of MalMe melanoma knock out clones was shown in FIG. 25D.

Targeting Co-Inhibitor/Co-Stimulatory Receptors or their Ligands

Figure 26A:
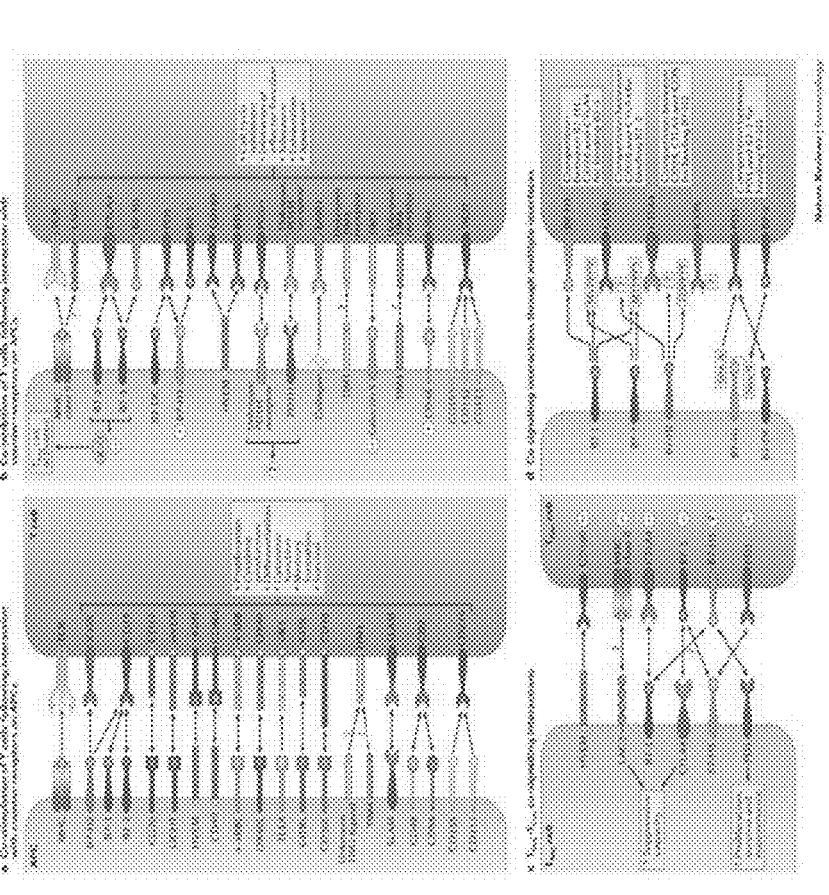
FIGS. 26A-26P demonstrate targeting of co-inhibitory/co-stimulatory receptors or their ligands. For each target, the indicated four CRISPRs have been cloned and tested for on-target activity in 293T cells. The expected size of the PCR band, when cutting of both CRISPRs occurs, is indicated below the gel picture.
Figure 26B:
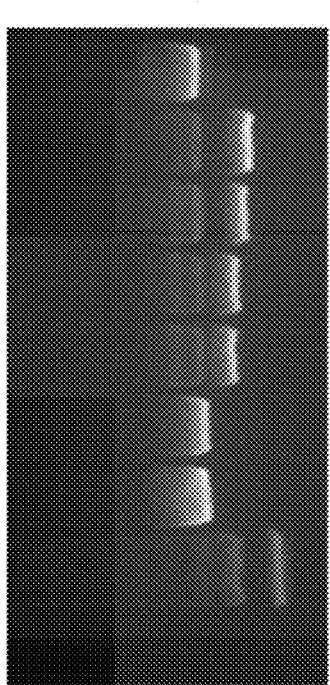
FIG. 26B demonstrates dual guide targeting of TIGIT in 293T cells. All four CRISPRS were found to work.
Figure 26D:
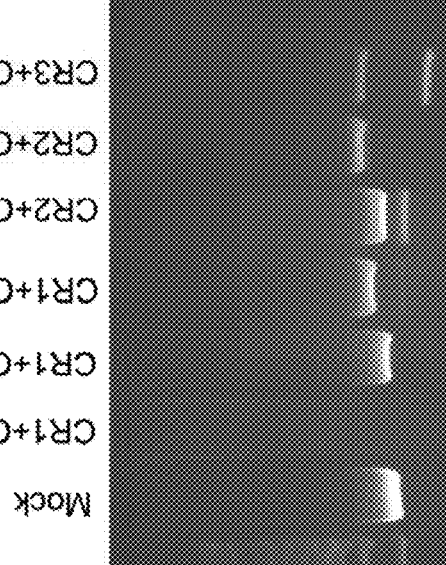
FIG. 26D demonstrates dual guide targeting of HVEM in 293T cells. All four CRISPRs were found to work.
Figure 26E:
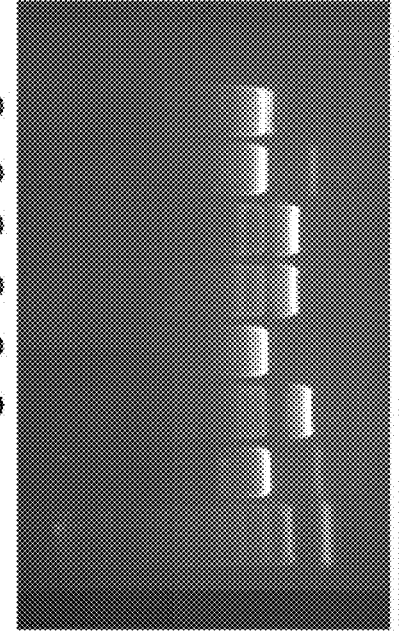
FIG. 26E demonstrates dual guide targeting of 2B4/CD244 in 293T cells. All four CRISPRs were found to work.
Figure 26F:
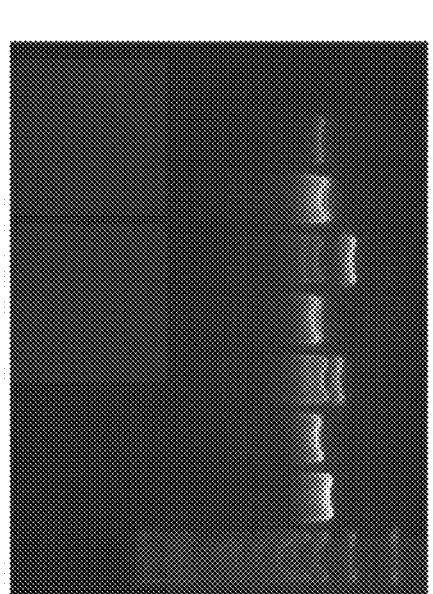
FIG. 26F demonstrates dual guide targeting of CD28 in 293T cells. CRISPRs #1, #2 and #3 were found to work.
Figure 26G:
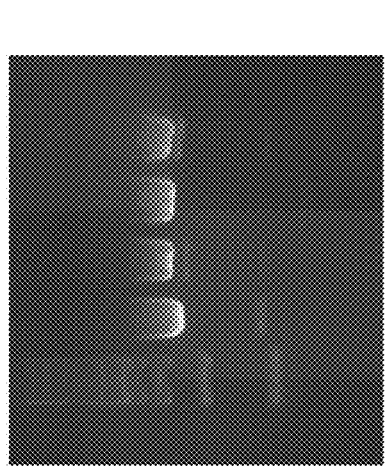
FIG. 26G demonstrates dual guide targeting of OX40 in 293T cells. CRISPRs #1, #2 and #4 were found to work.
Figure 26H:
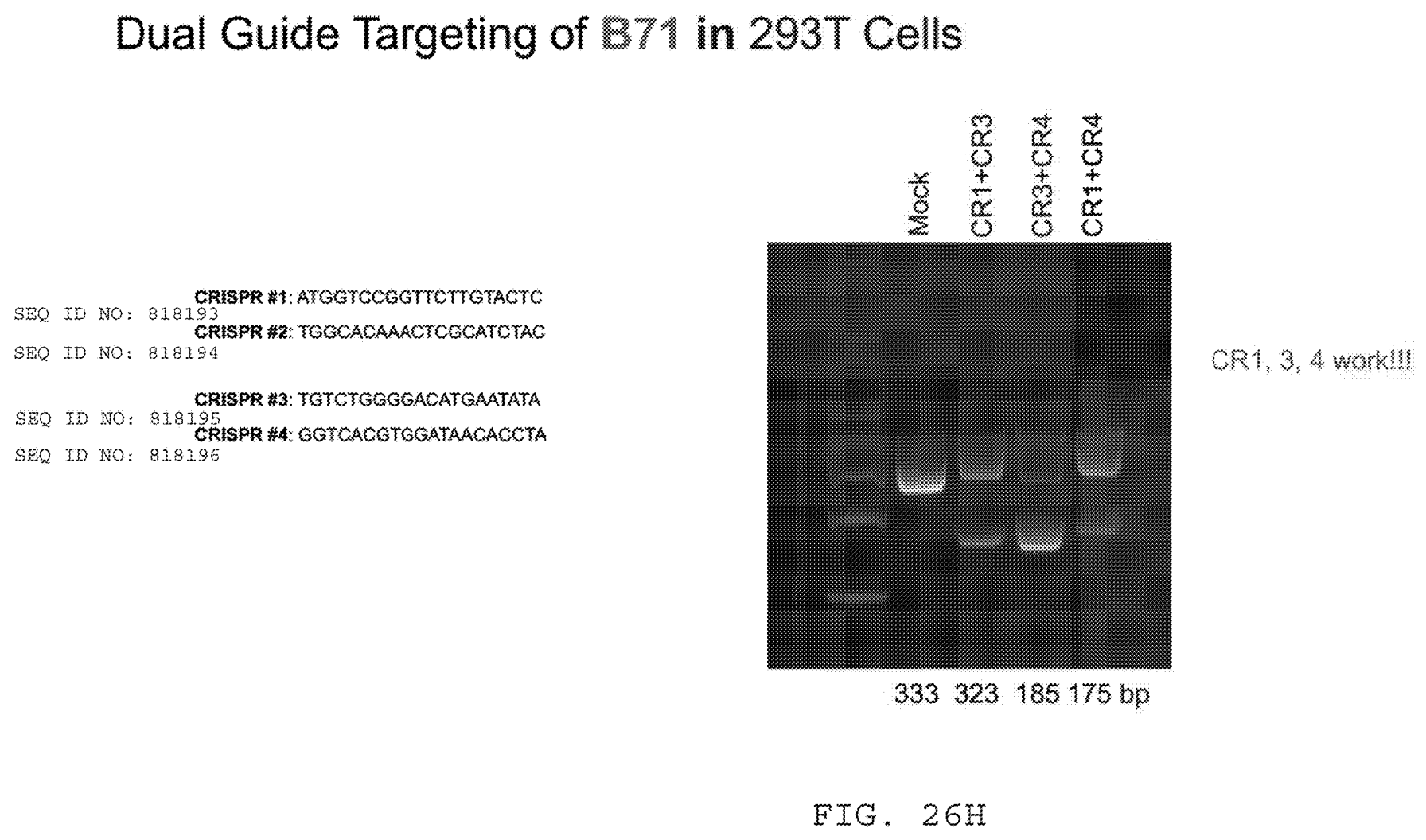
Figure 263:
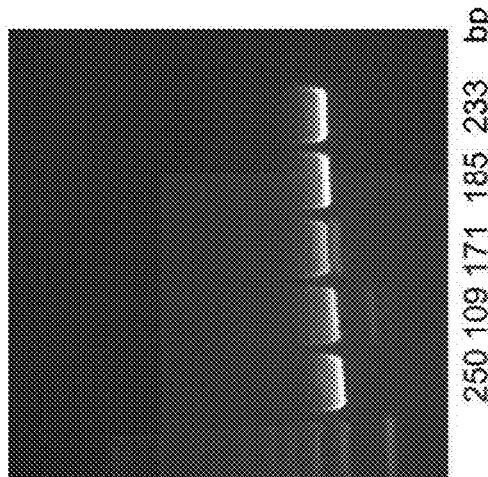
Figure 26L:
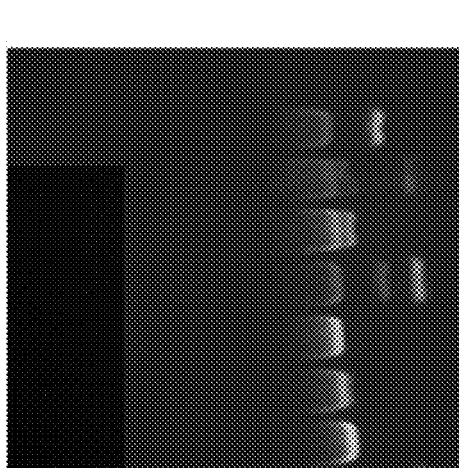
FIG. 26L demonstrates dual guide targeting of BTLA in 293T cells. All four CRISPRs were found to work.
Figure 26M:
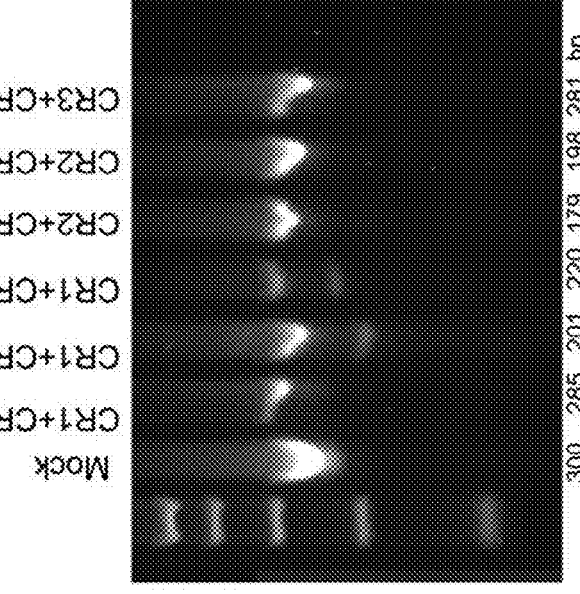
FIG. 26M demonstrates dual guide targeting of ICOS in 293T cells. CRISPRs #2, #3 and #4 were found to work.
Figure 26N:
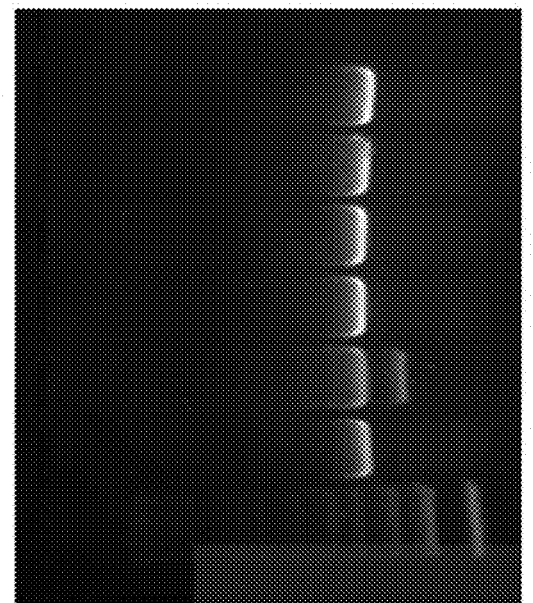
FIG. 26N demonstrates dual guide targeting of CD27 in 293T cells. CRISPRs #1 and #2 were found to work.
Figure 26O:
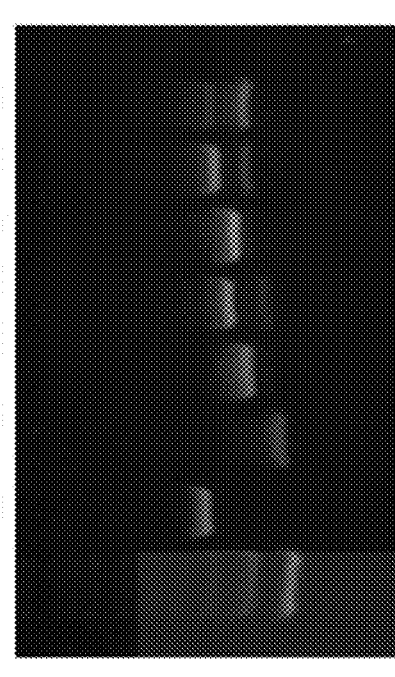
FIG. 26O demonstrates dual guide targeting of ST2 in 293T cells. All four CRISPRs were found to work.
Figure 26P:
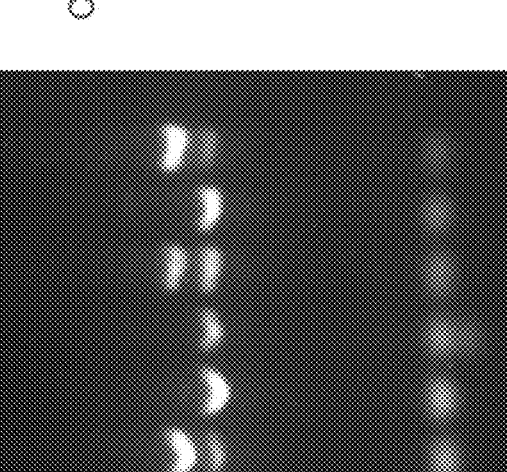

The inventors examined multiple targets utilizing CRISPR. An illustration of co-stimulatory/inhibitory molecules and their receptors on T cells is provided in FIG. 26A. For each target examined, the indicated four CRISPRs have been cloned and tested for on-target activity in 293T cells. The expected size of the PCR band, when cutting of both CRISPRs occurs, is indicated below each individual gel picture (FIGS. 26B-26P). Dual guide targeting in 293T cells was demonstrated for TIGIT (FIG. 26B), TIM3 (FIG. 26C), HVEM (FIG. 26D), 2B4/CD244 (FIG. 26E), CD28 (FIG. 26F), OX40 (FIG. 26G), B71 (FIG. 26H), CD226 (FIG.

26I), CD2 (FIG. 26J), LAG3 (FIG. 26K), BTLA (FIG. 26L), ICOS (FIG. 26M), CD27 (FIG. 26N), ST2 (FIG. 26O) and GITR (FIG. 26P).

Figure 30B:
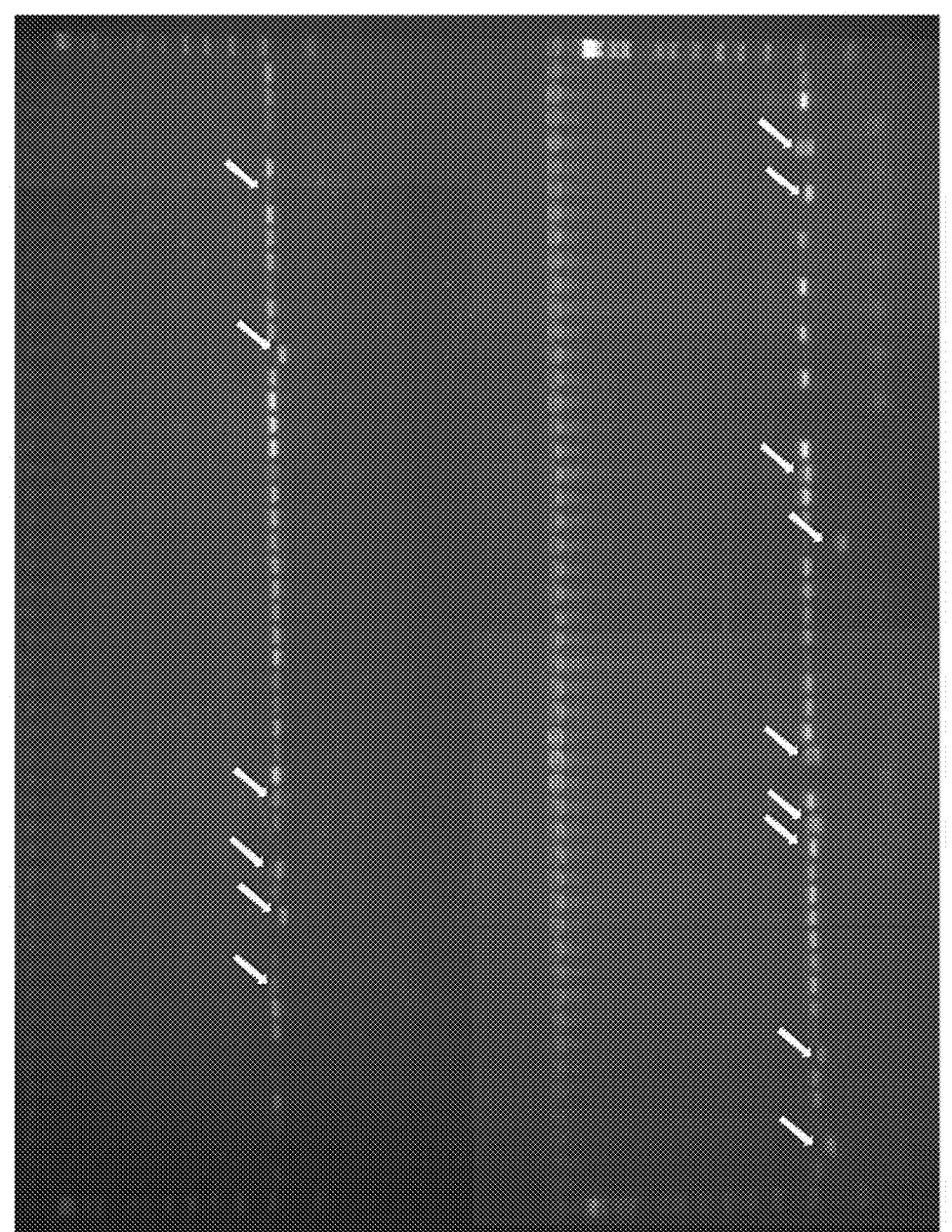
Figure 30C:
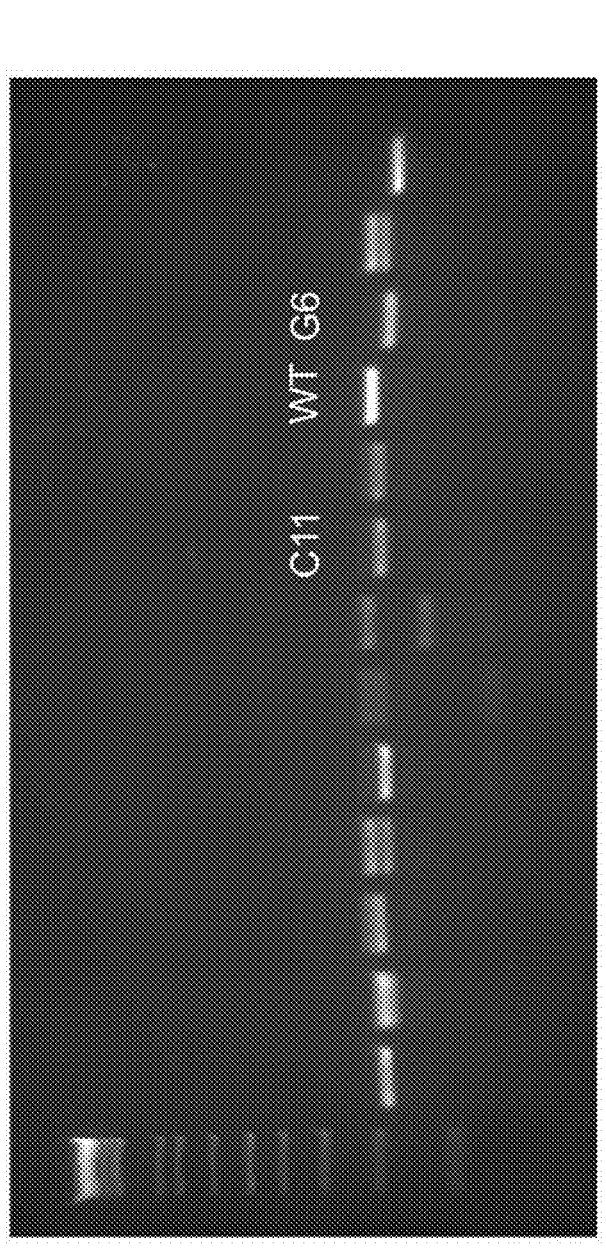
Figure 30D:
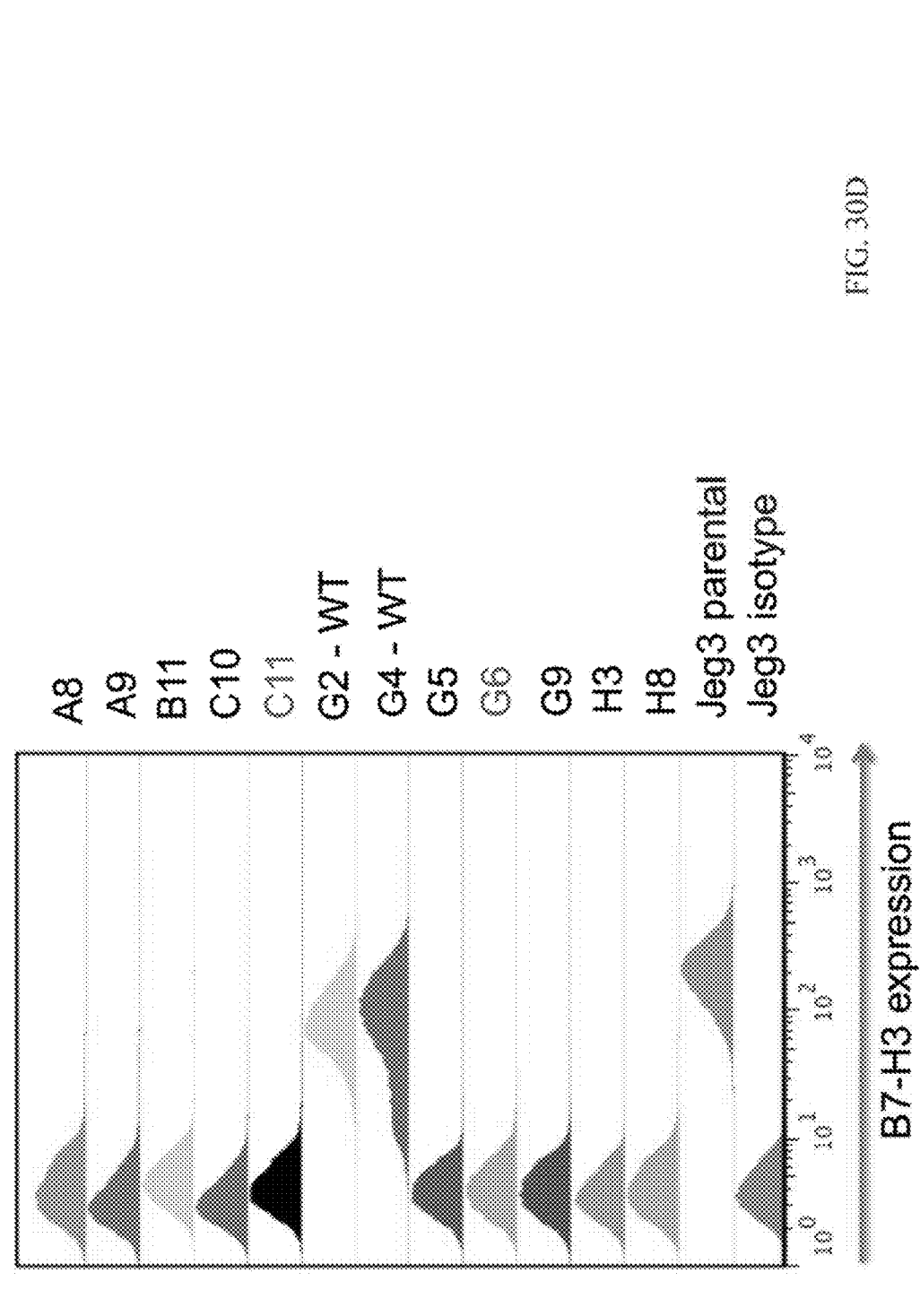

CRISPR targeting of B7-H3 was examined in JEG-3 cells (FIGS. 30A-30D). FIG. 30B shows a screening of targeted B7-H3 colonies in JEG-3 cells and identifies a CRISPR cutting efficiency of 15/80 or about 18.7%. Confirmation of the B7-H3 knock-outs through sequencing was performed (FIG. 30C) and the loss of B7-H3 surface expression in targeted Jeg3 clones was provided in FIG. 30D.

Differentiation of Modified Embryonic Stem Cells

Modified embryonic stem cells may be differentiated into a variety of different cell types, with reduced or absent HLA expression (FIG. 28A). Examples of such cell types include mesenchymal progenitors cells (MPCs), hypoimmunogenic cardiomyocytes, endothelial cells (ECs), macrophages, hepatocytes, beta cells (e.g., pancreatic beta cells), or neural progenitor cells (NPCs).

Figure 28B:
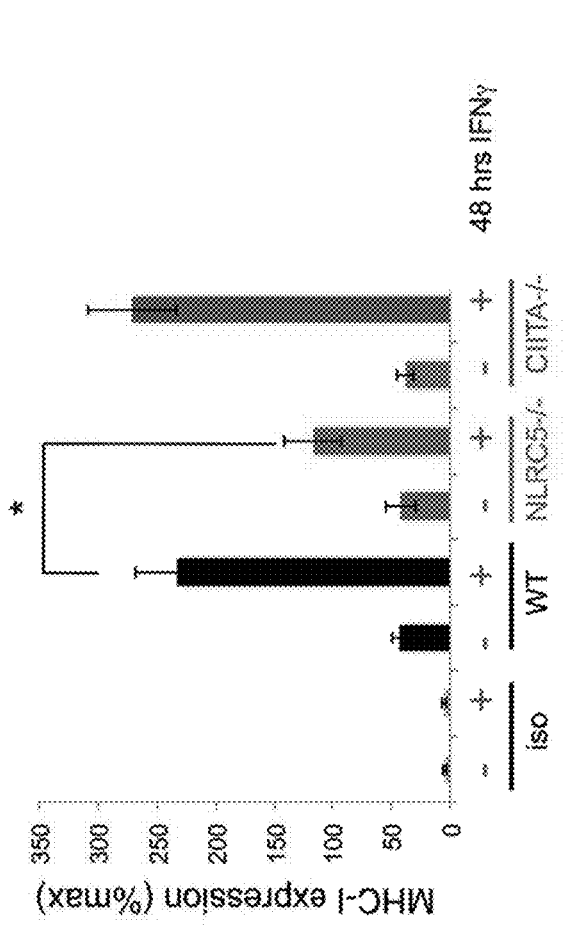

Initially, the inventors demonstrated reduced MHC-I expression in NLRC5–/– human ES cells in FIG. 28B. Low basal MHC-I expression was seen in stem cells, but expression could be increased by IFNγ stimulation. There is about a 50% reduction in IFNγ-treated NLRC5–/– cells.

Figure 28C:
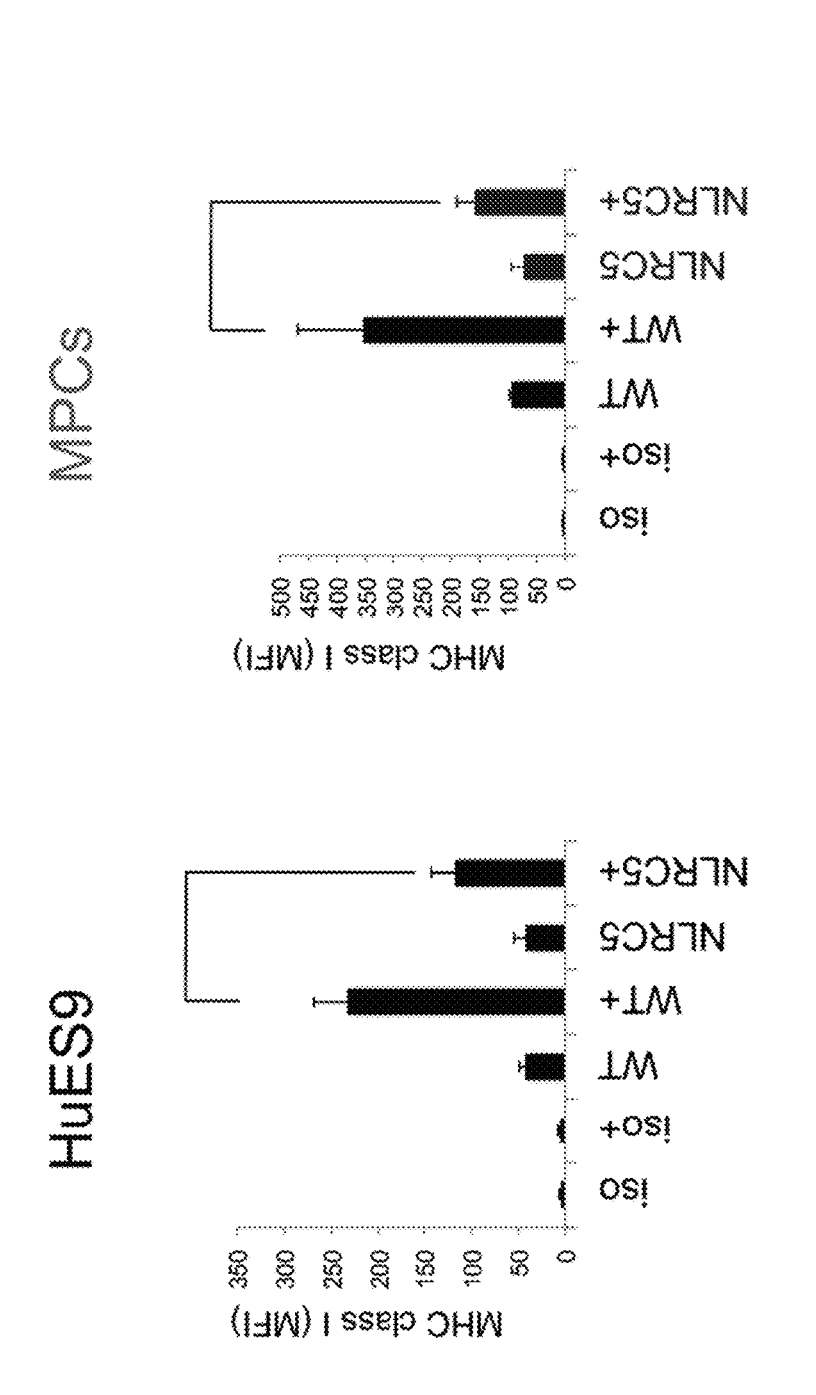
Figure 28D:
Figure 28F:
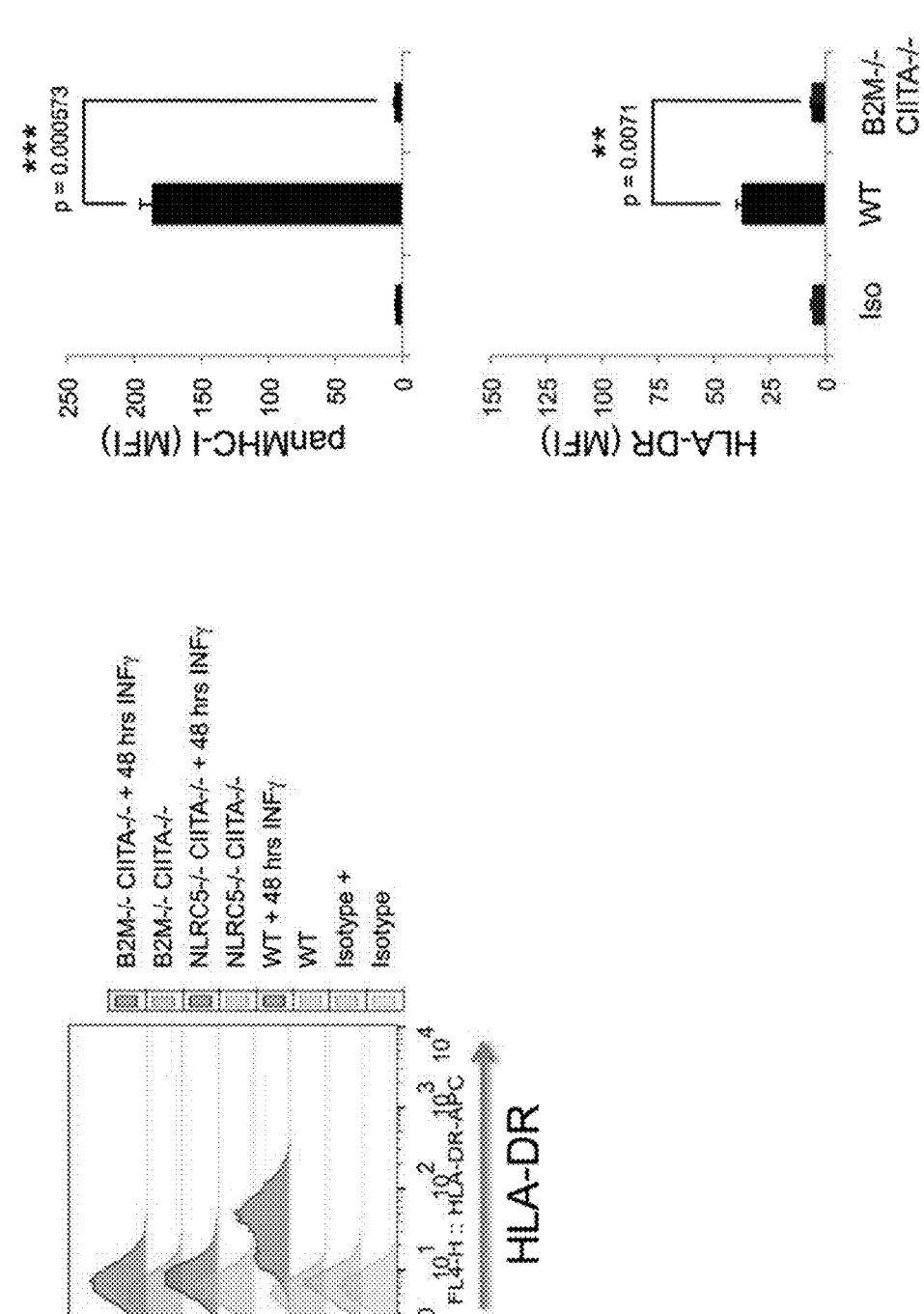
Figure 28G:
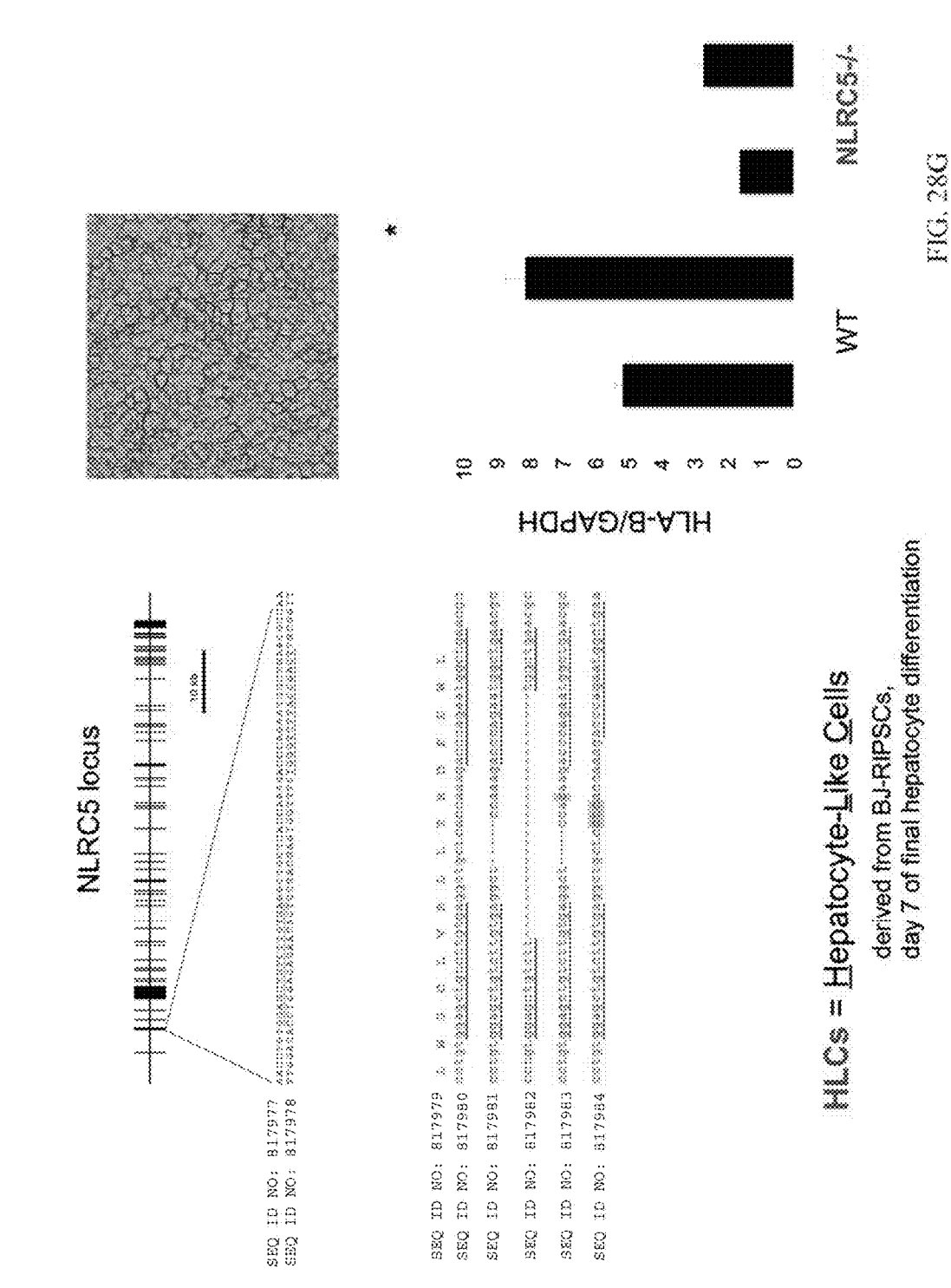

The inventors then examined MHC-I expression in various differentiated cell types. For example, FIG. 28C shows reduced MHC-I expression in NLRC5–/– human mesenchymal progenitor cells (MPCs). The graphs included in FIG. 28C demonstrate the differences between MHC-I expression in HuES9 cells and MPC cells. FIG. 28D shows reduced MHC-I expression in stem cell-derived NLRC5–/– endothelial cells (ECs). Similar differentiation efficiency for ECs was shown in FIG. 28E, and a loss of HLA expression in B2M–/– CIITA–/– ECs was shown in FIG. 28F. Next, reduced MHC class I expression in NLRC5–/– hepatocyte-like cells (HLCs) was provided (FIG. 28G). The HLCs were derived from BJ-RIPSCs.

Figure 28H:
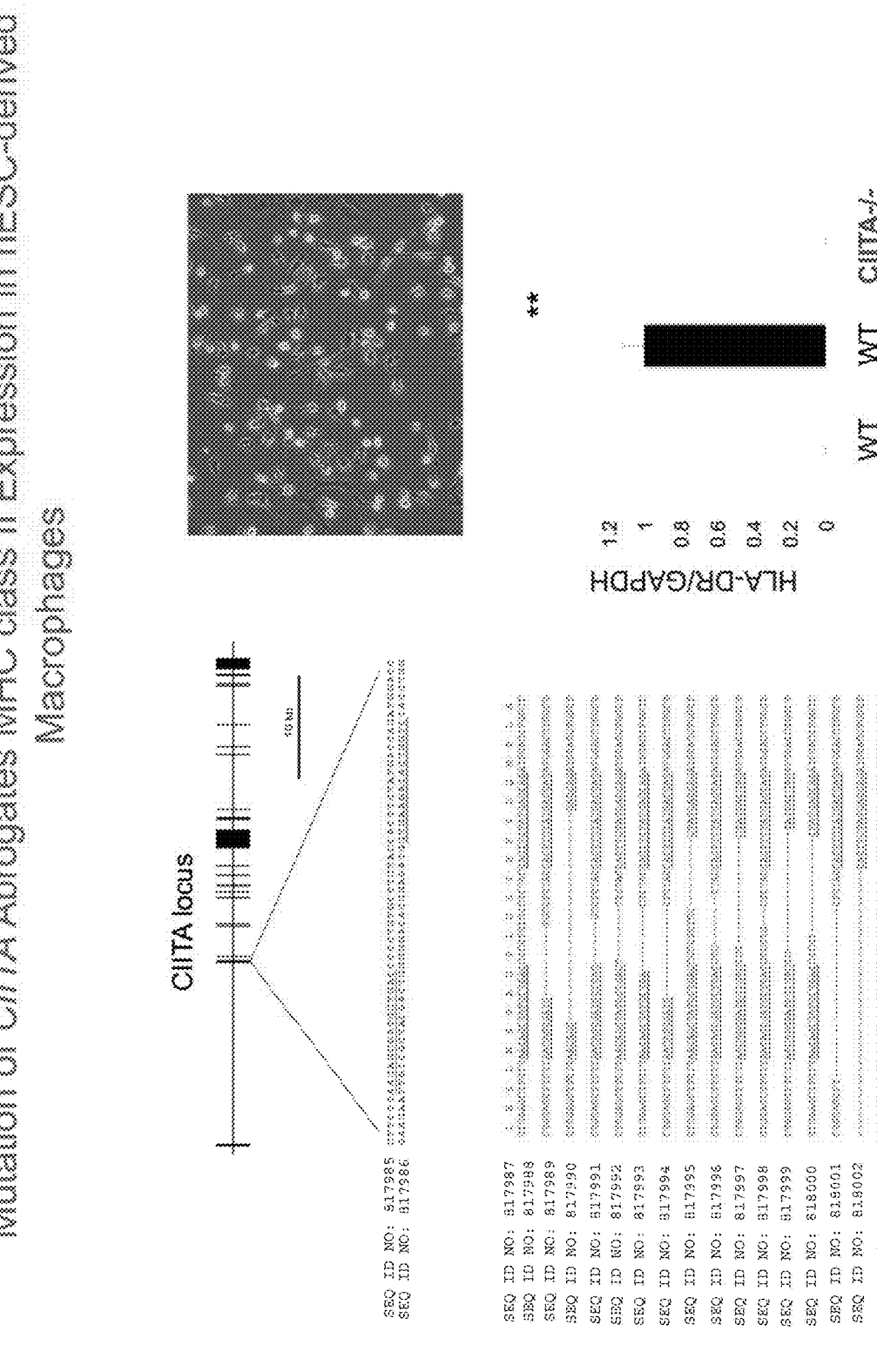
Figure 28I:
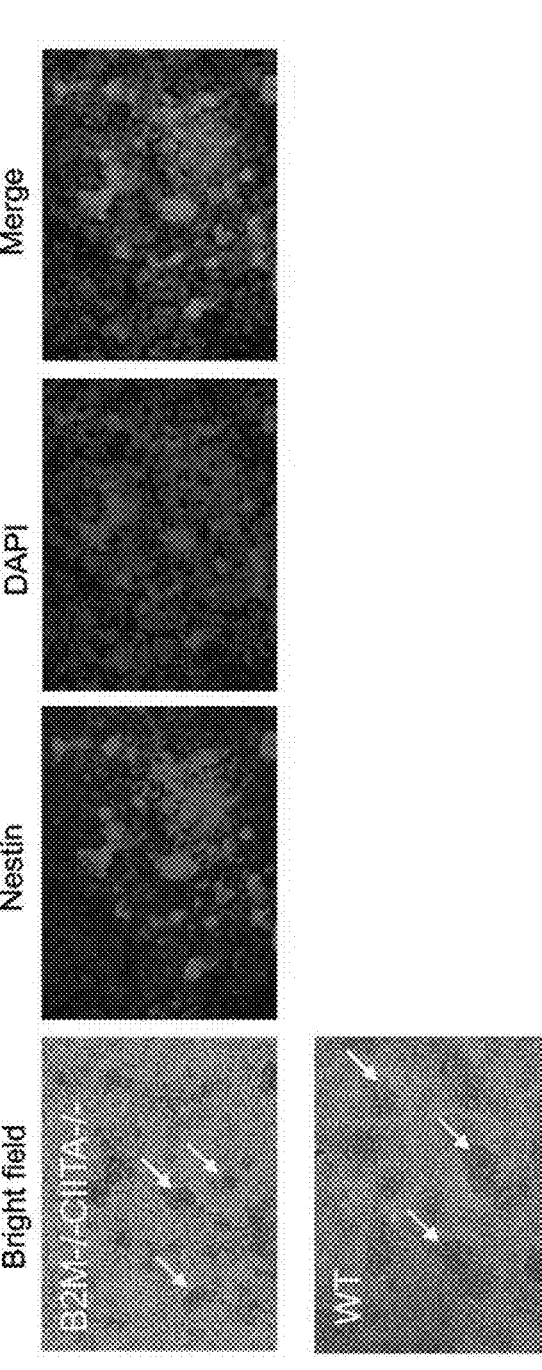

At FIG. 28H it is shown that a mutation of CIITA abrogates MHC class II expression in hESC-derived macrophages. Additionally, neural progenitor cells (NPCs) are differentiated from an embryonic stem cell (FIG. 28I). It was shown that B2M–/– CIITA–/– HuES9 cells form Nestin+ neural rosettes (white arrows in figure) as a result of differentiation. Finally, the inventors have adapted modified embryonic stem cells to spin culture so as to be utilized for beta-cell differentiation (FIG. 28J).

In Vivo Data

Figure 29B:
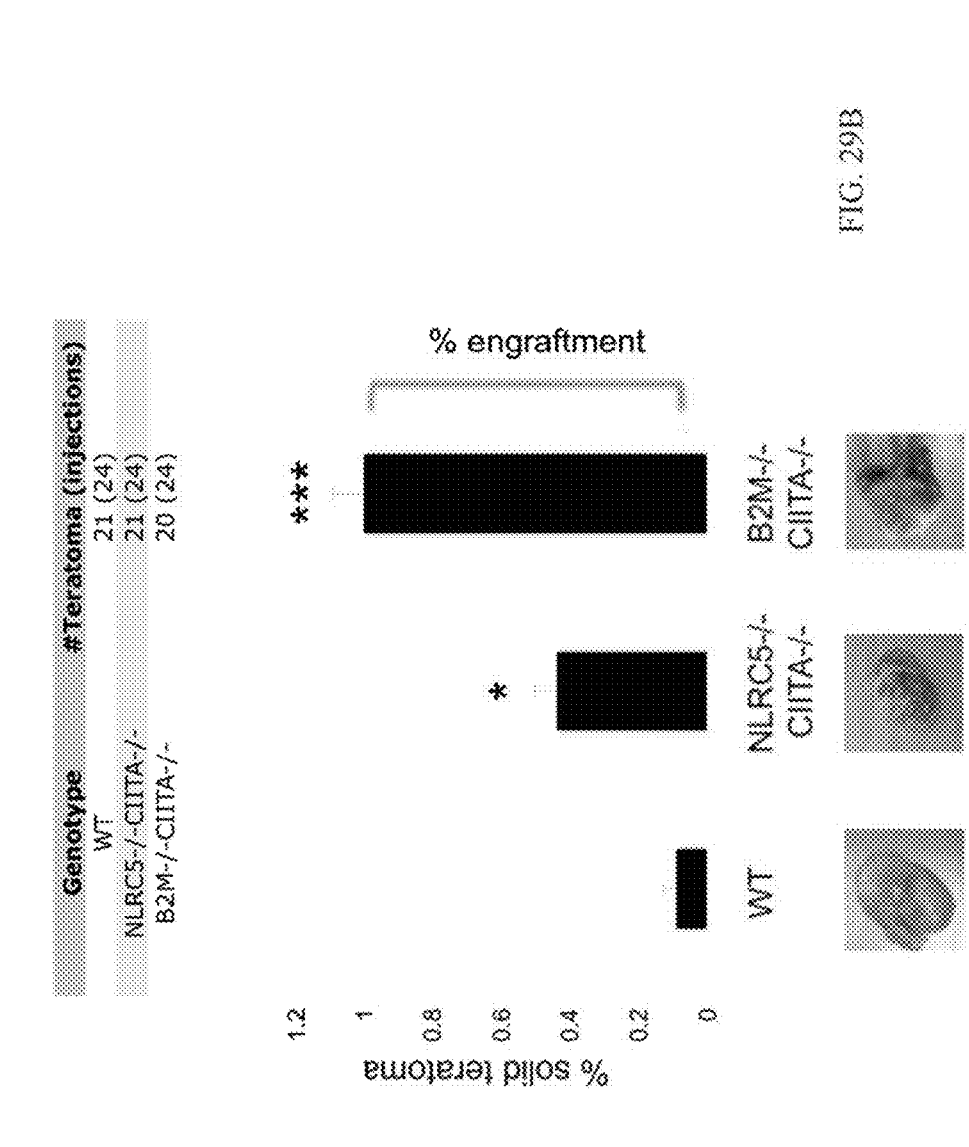

Finally, the inventors have generated 'hypoimmunogenic' DKO cell lines (FIG. 29A). The cells lines examined were WT HuES9 cells, NLRC5–/–C2TA–/– HuES9 cells and B2M–/–C2TA–/– HuES9 cells. The different cells lines showed 5 different levels of MHC-I and MHC-II expression (FIG. 29A). For example, WT HuES9 cells exhibited expression of MHC-I and MHC-II. The NLRC5–/– C2TA–/– HuES9 cells exhibited reduced MHC-I expression and no MHC-II expression. The B2M–/–C2TA–/– HuES9 cells exhibited no MHC-I and MHC-II expression. These cells lines were then examined in humanized mice and improved engraftment of genome-edited stem cells in humanized mice was shown in FIG. 29B.

SEQUENCE LISTING

The patent contains a lengthy sequence listing. A copy of the sequence listing is available in electronic form from the USPTO web site (https://seqdata.uspto.gov/docdetail?docId=US12662657B2). An electronic copy of the sequence listing will also be available from the USPTO upon request and payment of the fee set forth in 37 CFR 1.19(b)(3).

What is claimed is:

1. A method of generating a genetically modified stem cell comprising:

(i) introducing one or more genetic modifications into a stem cell that reduce cell surface expression of one or more MHC-I human leukocyte antigen molecules relative to an unmodified cell of the same type and/or one or more genetic modifications that reduce cell surface expression of one or more MHC-II human leukocyte antigen molecules relative to an unmodified cell of the same type, and (ii) introducing a nucleic acid encoding CD47 into the stem cell, wherein the stem cell is an embryonic stem cell or an induced pluripotent stem cell, and wherein the genetically modified stem cell comprises one or more genetic modifications that reduce cell surface expression of one or more MHC-I human leukocyte antigen molecules relative to an unmodified cell of the same type and/or one or more genetic modifications that reduce cell surface expression of one or more MHC-II human leukocyte antigen molecules relative to an unmodified cell of the same type, and comprise a nucleic acid encoding CD47.

2. The method of claim 1, wherein the introduction of the one or more genetic modifications comprises introducing one or more indels in one or more genes encoding an MHC-I human leukocyte antigen molecule, thereby resulting in the reduced cell surface expression of the one or more MHC-I human leukocyte antigen molecules relative to an unmodified cell of the same type.

3. The method of claim 2, wherein the introduction of the one or more genetic modifications comprises introducing one or more indels in an HLA-A gene, an HLA-B gene, an HLA-C gene, or a combination thereof in the genome of the genetically modified cell, thereby resulting in the reduced cell surface expression of the one or more MHC-I human leukocyte antigen molecules relative to an unmodified cell of the same type.

4. The method of claim 2, wherein the introduction of the one or more genetic modifications comprises introducing one or more indels in a β2M gene in the genome of the genetically modified cell, thereby resulting in the reduced cell surface expression of the one or more MHC-I human leukocyte antigen molecules relative to an unmodified cell of the same type.

5. The method of claim 4, wherein the one or more indels comprises a β2M gene knock out.

6. The method of claim 5, wherein the genetically modified stem cell is a β2M$^{-/-}$ genetically modified stem cell.

7. The method of claim 1, wherein the introduction of the one or more genetic modifications comprises introducing one or more indels in one or more genes encoding a transcriptional regulator of an MHC-I human leukocyte antigen molecule, thereby resulting in the reduced cell surface expression of the one or more MHC-I human leukocyte antigen molecules relative to an unmodified cell of the same type.

8. The genetically modified cell of claim 7, wherein the introduction of the one or more genetic modifications comprise introducing one or more indels in a TAP1 gene, an NLRC5 gene, an RFX5 gene, an RFXAP gene, an RFXANK gene, an NFY-A gene, an NFY-B gene, an NFY-C gene, an IRF-1 gene, or a combination thereof.

9. The method of claim 1, wherein the introduction of the one or more genetic modifications comprises introducing one or more indels in one or more genes encoding an MHC-II human leukocyte antigen molecule, thereby resulting in the reduced cell surface expression of the one or more MHC-II human leukocyte antigen molecules.

10. The method of claim 1, wherein the introduction of the one or more genetic modifications comprises introducing one or more indels in one or more genes encoding a transcriptional regulator of an MHC-II human leukocyte antigen molecule, thereby resulting in the reduced cell surface expression of the one or more MHC-II human leukocyte antigen molecules relative to an unmodified cell of the same type.

11. The method of claim 10, wherein the introduction of the one or more genetic modifications comprises introducing one or more indels in a class II major histocompatibility complex transactivator (CIITA) gene in the genome of the genetically modified cell, thereby resulting in the reduced cell surface expression of the one or more MHC-II human leukocyte antigen molecules.

12. The method of claim 11, wherein the one or more indels comprises a CIITA gene knock out.

13. The method of claim 12, wherein the genetically modified stem cell is a CIITA$^{-/-}$ genetically modified stem cell.

14. The method of claim 1, wherein the genetically modified stem cell is a β2M$^{-/-}$ CIITA$^{-/-}$ genetically modified stem cell.

15. The method of claim 1, wherein the nucleic acid encoding CD47 is inserted into at least one allele of a safe harbor locus of the genetically modified stem cell.

16. The method of claim 15, wherein the safe harbor locus comprises an AAVS1 locus.

17. The method of claim 1, wherein the introduction of the one or more genetic modifications comprise introducing one or more indels in a TAP1 gene, an NLRC5 gene, an RFX5 gene, an RFXAP gene, an RFXANK gene, an NFY-A gene, an NFY-B gene, an NFY-C gene, an IRF-1 gene, or any combination thereof.

18. The method of claim 1, further comprising differentiating the genetically modified stem cell into a cardiomyocyte, an endothelial cell, a hepatocyte, a hepatocyte-like cell, a beta cell, a mesenchymal progenitor cell, a neural progenitor cell, a macrophage, or a T cell.

19. The method of claim 1, further comprising differentiating wherein the genetically modified stem cell into a T cell.

20. The method of claim 1, further comprising differentiating the genetically modified stem cell into a CD8+ T cell.

21. The method of claim 1, further comprising differentiating the genetically modified stem cell into a beta cell.

* * * * *